United States Patent
Yamamoto et al.

(10) Patent No.: US 9,630,924 B2
(45) Date of Patent: *Apr. 25, 2017

(54) HETEROCYCLIC COMPOUND

(71) Applicant: Takeda Pharmaceutical Company Limited, Osaka-shi, Osaka (JP)

(72) Inventors: Satoshi Yamamoto, Kanagawa (JP); Junya Shirai, Kanagawa (JP); Tsuneo Oda, Kanagawa (JP); Mitsunori Kono, Kanagawa (JP); Atsuko Ochida, Kanagawa (JP); Takashi Imada, Kanagawa (JP); Hidekazu Tokuhara, Kanagawa (JP); Yoshihide Tomata, Kanagawa (JP); Naoki Ishii, Kanagawa (JP); Michiko Tawada, Kanagawa (JP); Yoshiyuki Fukase, New York, NY (US); Tomoya Yukawa, Kanagawa (JP); Shoji Fukumoto, Hyogo (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/055,108

(22) Filed: Feb. 26, 2016

(65) Prior Publication Data

US 2016/0176872 A1 Jun. 23, 2016

Related U.S. Application Data

(63) Continuation of application No. 14/755,439, filed on Jun. 30, 2015, now Pat. No. 9,365,520.

(30) Foreign Application Priority Data

| Jul. 1, 2014 | (JP) | 2014-136359 |
| Dec. 25, 2014 | (JP) | 2014-262775 |

(51) Int. Cl.
| C07D 471/04 | (2006.01) |
| C07D 215/00 | (2006.01) |
| C07D 217/26 | (2006.01) |
| C07F 7/08 | (2006.01) |
| C07D 491/048 | (2006.01) |
| C07D 491/056 | (2006.01) |
| A61K 31/4375 | (2006.01) |
| A61K 31/472 | (2006.01) |
| A61K 31/4741 | (2006.01) |
| C07D 217/14 | (2006.01) |
| C07D 491/14 | (2006.01) |

(52) U.S. Cl.
CPC ........ *C07D 217/26* (2013.01); *A61K 31/4375* (2013.01); *A61K 31/472* (2013.01); *A61K 31/4741* (2013.01); *C07D 217/14* (2013.01); *C07D 471/04* (2013.01); *C07D 491/048* (2013.01); *C07D 491/056* (2013.01); *C07D 491/14* (2013.01); *C07F 7/0812* (2013.01)

(58) Field of Classification Search
CPC .......................... C07D 471/04; C07D 215/00
USPC .................................................. 546/112, 152
See application file for complete search history.

(56) References Cited

U.S. PATENT DOCUMENTS

| 9,365,520 | B2 * | 6/2016 | Yamamoto | ........... C07D 217/26 |
| 2004/0266761 | A1 | 12/2004 | Qiao et al. | |
| 2014/0163001 | A1 | 6/2014 | Yamamoto et al. | |
| 2014/0228409 | A1 | 8/2014 | Yamamoto et al. | |
| 2014/0275061 | A1 | 9/2014 | Orwat et al. | |

FOREIGN PATENT DOCUMENTS

| EP | 2 738 170 | 6/2014 |
| EP | 2 759 533 | 7/2014 |
| EP | 2 975 031 | 1/2016 |
| WO | 2004/108892 | 12/2004 |
| WO | 2008/121602 | 10/2008 |
| WO | 2013/018695 | 2/2013 |
| WO | 2013/042782 | 3/2013 |
| WO | 2013/055984 | 4/2013 |
| WO | 2013/056034 | 4/2013 |
| WO | 2013/100027 | 7/2013 |
| WO | 2014/142255 | 9/2014 |
| WO | 2015/002230 | 1/2015 |
| WO | 2015/002231 | 1/2015 |

OTHER PUBLICATIONS

International Search Report issued in International Application No. PCT/JP2015/069370, Sep. 24, 2015, 5 pages.

* cited by examiner

*Primary Examiner* — Niloofar Rahmani
(74) *Attorney, Agent, or Firm* — Hamre, Schumann, Mueller & Larson, P.C.

(57) ABSTRACT

The present invention provides a heterocyclic compound having a RORγt inhibitory action.
The present invention relates to a compound represented by the formula (I):

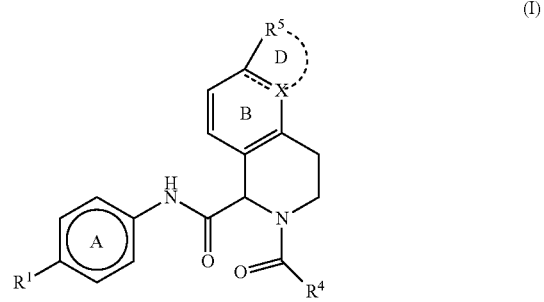

wherein each symbol is as defined in the specification. or a salt thereof.

2 Claims, No Drawings

HETEROCYCLIC COMPOUND

TECHNICAL FIELD

The present invention relates to a heterocyclic compound having an RORγt inhibitory action, a medicament containing the compound, and the like.

BACKGROUND OF THE INVENTION

Th17 cell and inflammatory cytokine (IL-17A, IL-17F, etc.) produced thereby has been drawing attention, since they cause a decrease in QOL as a severe etiology cell and factor accompanying enhancement of a systemic new immune response, in various autoimmune disease such as inflammatory bowel disease (IBD), rheumatoid arthritis, multiple sclerosis or psoriasis. However, the existing therapeutic drugs show only limited effects, and therefore, the earliest possible development of a novel therapeutic drug has been desired.

Moreover, it has been recently clarified that a Retinoid-related Orphan Receptor (ROR) γt, which is one of the orphan nuclear receptors, plays an important role in the differentiation of Th17 cells and production of IL-17A/IL-17F. That is, it has been reported that RORγt is mainly expressed in Th17 cells and functions as a transcription factor of IL-17A and IL-17F, as well as a master regulator of Th17 cell differentiation.

Therefore, a medicament that inhibits the action of RORγt is expected to show a treatment effect on various immune disease by suppressing differentiation and activation of Th17 cells.

Patent Document 1 reports the following compound represented by the general formula:

P-M-M$_1$ wherein
M is a 3- to 8-membered linear chain consisting of carbon atoms, 0-3 carbonyl groups, 0-1 thiocarbonyl group, and 0-4 heteroatoms selected from O, N and S(O)$_p$,
one of P and M$_1$ is -G, and the other is -A-B;
G is a group represented by the formula (IIa) or formula (IIb):

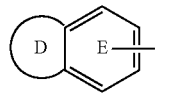

IIa

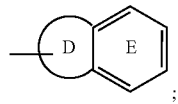

IIb
;

Ring D, including the two atoms of Ring E to which it is attached, is a 5- or 6-membered ring consisting of carbon atoms and 0-3 heteroatoms selected from N, O and S(O)$_p$;
Ring D is substituted with 0-2 R or 0-2 carbonyl, and there are 0-3 ring double bonds;
Ring E is selected from phenyl, pyridyl, pyrimidyl, pyrazinyl and pyridazinyl, which is substituted with 1-3 R;
A is selected from a C$_{3-10}$ carbocycle substituted with 0-2 R$^4$, and a 5- to 12-membered heterocycle consisting of carbon atoms and 1-4 heteroatoms selected from N, O and S(O)$_p$, and substituted with 0-2 R$^4$;
B is X—Y—R$^{4a}$ or the like;
X is absent, —(CR$^2$R$^{2a}$)$_{1-4}$— or the like;
Y is selected from a C$_{3-10}$ carboncycle and a 3- to 10-membered heterocycle; and
R$^{4a}$ is a C$_{1-6}$ alkyl substituted with 0-2 R$^{4c}$, or the like, which has a Xa factor inhibitory action, and is useful for the treatment of thromboembolism.

Patent Document 2 discloses, as a fused heterocyclic compound, a compound represented by the formula:

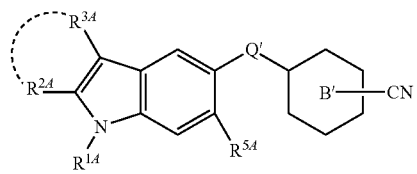

wherein
R$^{1A}$ is an optionally substituted hydrocarbon group or an optionally substituted hydrocarbon-oxy group,
R$^{2A}$ and R$^3$ are each independently a hydrogen atom, an optionally substituted hydrocarbon group or the like, or
R$^{2A}$ and R$^{3A}$ in combination optionally form, together with the carbon atoms which they are bonded to, an optionally substituted hydrocarbon ring,
R$^{5A}$ is a hydrogen atom or a halogen atom,
Q' is

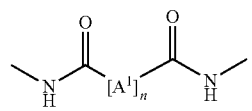

wherein
[A$^1$] are the same or different and each is a methylene group optionally substituted by C$_{1-6}$ alkyl group(s) optionally substituted by hydroxy group(s) and the like, wherein the two substituents bonded to the single carbon atom are optionally combined to each other to form a hydrocarbon ring, and
n is an integer of 1 to 5, or the like, and
Ring B' is a benzene ring optionally further having substituent(s), or the like,
which has a RORγt inhibitory action, and is useful for the treatment of inflammatory bowel disease (IBD) and the like.

Patent Document 3 discloses, as a heterocyclic compound, a compound represented by the formula:

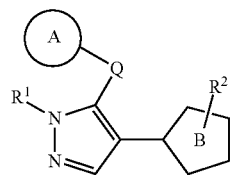

wherein
Ring A is an optionally substituted cyclic group,
Q is a bond, an optionally substituted C$_{1-10}$ alkylene, an optionally substituted C$_{2-10}$ alkenylene or an optionally substituted C$_{2-10}$ alkynylene,
R$^1$ is a substituent, Ring B is a thiazole ring, an isothiazole ring or a dihydrothiazole ring, each optionally further substituted in addition to $R^2$, and $R^2$ is an optionally substituted cyclyl-carbonyl-$C_{1-6}$ alkyl group, an optionally substituted aminocarbonyl-$C_{1-6}$ alkyl group, an optionally substituted cyclyl-$C_{1-6}$ alkyl group, an optionally substituted cyclyl-$C_{1-6}$ alkylamino-carbonyl group, an optionally substituted aminocarbonyl-$C_{2-6}$ alkenyl group, an optionally substituted $C_{1-6}$ alkylcarbonylamino-$C_{1-6}$ alkyl group, an optionally substituted cyclyl-aminocarbonyl group, an optionally substituted cyclyl-carbonyl group or an optionally substituted non-aromatic heterocyclic group, which has a RORγt inhibitory action, and is useful for the treatment of inflammatory disease, autoimmune disease and the like.

Patent Document 4 discloses, as a heterocyclic compound, a compound represented by the formula:

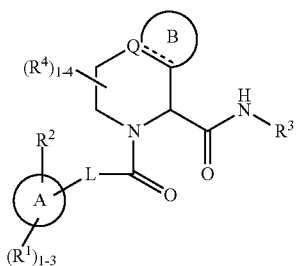

wherein

Ring A is a $C_{3-10}$ carbocycle;

L is a group selected from a bond, —CHR$^{10}$CHR$^{10}$—, —CR$^{10}$=CR$^{10}$— and —C≡C—;

$R^{10}$ is H, halo, OH or $C_{1-4}$ alkyl;

Q is selected from C, CH and N;

---- is an optional bond; provided that when Q is N, then the optional bond is absent;

Ring B is a 5- to 6-membered heterocycle containing heteroatoms selected from N, NR$^6$, O and S(O)$_p$, and substituted by 0-3 $R^5$;

optionally, Ring B is further fused with phenyl substituted with 0-2 $R^5$ or a 5- to 6-membered aromatic heterocycle containing 1 to 2 heteroatoms selected from N, NR$^6$, O and S(O)$_p$, and substituted with 0-2 $R^5$;

$R^1$ are each independently H, halo, $C_{1-2}$ alkyl, —O($C_{1-4}$ alkyl), CN, —CH$_2$NH$_2$ or —C(=NH)NH$_2$;

$R^2$ is H, halo, CN, OH, $C_{1-6}$ alkyl, $C_{1-4}$ alkoxy, $C_{1-6}$ haloalkyl, $C_{1-6}$ haloalkoxy, CO($C_{1-4}$ alkyl), CONH$_2$, CO$_2$H, and a 5- to 7-membered heterocycle containing 1 to 4 heteroatoms selected from N, NH, N($C_{1-4}$ alkyl), O and S(O)$_p$, and substituted with 1-2 $R^{2a}$; and $R^3$ is a $C_{1-6}$ alkyl group substituted with 1-3 $R^{3a}$, a $C_{3-10}$ carboncycle substituted with 1-3 $R^3$, or a 5- to 10-membered heterocycle containing 1 to 4 heteroatoms selected from N, NR$^7$, O and S(O)$_p$, and substituted with 1-3 $R^{3a}$, which is a Factor XIIa, and is useful for the treatment of thromboembolism, inflammatory disease and the like.

Patent Document 5 discloses, as a heterocyclic compound, a compound represented by the formula:

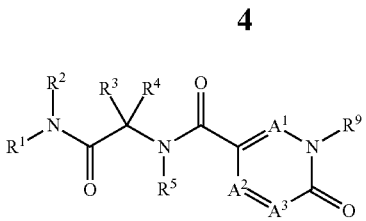

wherein $A^1$ is CR$^{A1}$ wherein R$^{A1}$ is a hydrogen atom or a substituent, or a nitrogen atom, $A^2$ is CR$^{A2}$ wherein R$^{A2}$ is a hydrogen atom or a substituent, or a nitrogen atom, $A^3$ is CR$^{A3}$ wherein R$^{A3}$ is a hydrogen atom or a substituent, or a nitrogen atom, or, provided that when $A^2$ is CR$^{A2}$ wherein R$^{A2}$ is a substituent, and $A^3$ is CR$^{A3}$ wherein R$^{A3}$ is a substituent, then R$^{A2}$ and R$^{A3}$ in combination optionally form, together with the carbon atoms which they are bonded to, a carbocycle or a heterocycle, $R^1$ is 1) an optionally substituted carbocyclic group, 2) an optionally substituted monocyclic heterocyclic group (excluding an optionally substituted 2-oxo-3-azetidyl group), 3) an optionally substituted fused heterocyclic group (excluding an optionally substituted 7-oxo-4-thia-1-azabicyclo[3.2.0]hept-6-yl group, an optionally substituted 8-oxo-1-azabicyclo[4.2.0]oct-2-en-7-yl group and an optionally substituted 8-oxo-5-thia-1-azabicyclo[4.2.0]oct-2-en-7-yl group), or 4) an optionally substituted spiro ring group, $R^2$ is a hydrogen atom or a substituent, one of $R^3$ or $R^4$ is an optionally substituted carbocyclic group, an optionally substituted aromatic nitrogen-containing heterocyclic group or an optionally substituted fused non-aromatic heterocyclic group, and the other is a hydrogen atom or a substituent, $R^5$ is a hydrogen atom or a substituent, and $R^9$ is a hydrogen atom or a hydroxy group, provided that when $R^9$ is a hydroxy group, then $A^1$, $A^2$ and $A^3$ are CR$^{A1}$, CR$^{A2}$ and CR$^{A3}$, respectively.

which has a RORγt inhibitory action, and is useful for the treatment of inflammatory bowel disease (IBD), ulcerative colitis (UC), Crohn's disease (CD), rheumatoid arthritis, multiple sclerosis, psoriasis and the like.

Patent Document 6 discloses, as a heterocyclic compound, a compound represented by the formula:

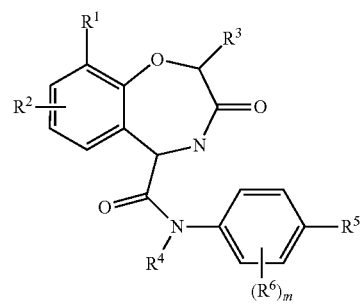

wherein $R^1$ is $C_{1-2}$ alkyl, halogen or CF$_3$;

$R^2$ is H, Cl, F or methyl;

$R^3$ is H, methyl;

$R^4$ is H, $C_{1-6}$ alkyl or benzyl optionally substituted by CF$_3$;

$R^5$ is methyl, nitro, halogen, CN, CF$_3$ or —C(O)OCH$_2$CH$_3$;

$R^6$ is Cl, F or $CF_3$; and
m is 0 or 1,
which is an androgen receptor modulator.

DOCUMENT LIST

Patent Document

[Patent Document 1] WO 2004/108892
[Patent Document 2] WO 2013/042782
[Patent Document 3] WO 2013/018695
[Patent Document 4] WO 2013/055984
[Patent Document 5] WO 2013/100027
[Patent Document 6] WO 2008/121602

SUMMARY OF THE INVENTION

Problems to be Solved by the Invention

The present invention aims to provide a compound having a superior RORγt inhibitory action, and useful as an agent for the prophylaxis or treatment of psoriasis, inflammatory bowel disease (IBD), ulcerative colitis (UC), Crohn's disease (CD), rheumatoid arthritis, multiple sclerosis, uveitis, asthma, ankylopoietic spondylarthritis, systemic lupus erythematosus (SLE) and the like.

Means of Solving the Problems

The present inventors have found that a compound represented by the following formula (I) or a salt thereof has a superior RORγt inhibitory action based on the specific chemical structure thereof and affords superior efficacy as an agent for the prophylaxis or treatment of psoriasis, inflammatory bowel disease (IBD), ulcerative colitis (UC), Crohn's disease (CD), rheumatoid arthritis, multiple sclerosis, uveitis, asthma, ankylopoietic spondylarthritis, systemic lupus erythematosus (SLE) and the like. The present inventors have conducted intensive studies based on the finding and completed the present invention.

Accordingly, the present invention relates to the followings.

[1] A compound represented by the following formula (I):

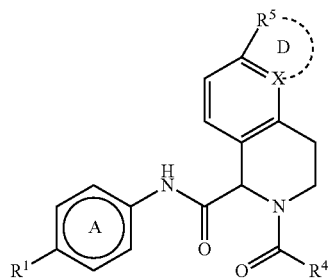

wherein
Ring A is an optionally further substituted 6-membered aromatic ring;
$R^1$ is
(1) a group represented by the formula: —C($R^{1a}$)($CH_3$)($CH_3$) wherein $R^{1a}$ is an optionally substituted $C_{1-6}$ alkoxy-$C_{1-2}$ alkyl group, or $R^{1a}$ is bonded to one substituent on Ring A to form an optionally substituted 5-membered hydrocarbon ring, wherein the one substituent on Ring A is bonded to the position adjacent to the bonding position of $R^1$ on Ring A, or
(2) a trimethylsilyl group;
$R^4$ is an optionally substituted $C_{3-6}$ cycloalkyl group;
X is $CR^6$ or N;
$R^5$ is an optionally substituted $C_{1-6}$ alkyl group or an optionally substituted $C_{1-6}$ alkoxy group;
$R^6$ is a hydrogen atom or a substituent; and
when X is $CR^6$, $R^5$ and $R^6$ in combination optionally form Ring D, wherein Ring D is an optionally substituted 5- or 6-membered oxygen-containing heterocycle containing 1 to 2 oxygen atoms as heteroatoms in addition to carbon atoms, or a salt thereof (hereinafter sometimes to be referred to as compound (I)).

[1'] The compound or salt of the above-mentioned [1], wherein $R^1$ is
(1) a group represented by the formula: —C($R^{1a}$)($CH_3$)($CH_3$) wherein $R^{1a}$ is an optionally substituted $C_{1-6}$ alkoxy-$C_{1-2}$ alkyl group, or
(2) a trimethylsilyl group, or
the group represented by the formula:

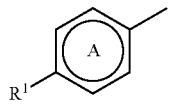

is a group represented by the formula:

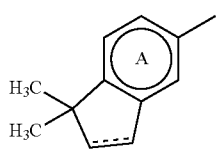

wherein is a single bond or a double bond.

[2] The compound or salt of the above-mentioned [1], wherein
Ring A is a benzene ring optionally further substituted by 1 to 3 halogen atoms;
$R^1$ is
(1) a group represented by the formula: —C($R^{1a}$)($CH_3$)($CH_3$) wherein $R^{1a}$ is a $C_{1-6}$ alkoxy-$C_{1-2}$ alkyl group, or $R^{1a}$ is bonded to one substituent on Ring A to form a 5-membered hydrocarbon ring, wherein the one substituent on Ring A is bonded to the position adjacent to the bonding position of $R^1$ on Ring A, or
(2) a trimethylsilyl group;
$R^4$ is a $C_{3-6}$ cycloalkyl group optionally substituted by 1 to 3 substituents selected from
(1) a carboxy group,
(2) a $C_{1-6}$ alkyl group optionally substituted by 1 to 3 substituents selected from
(i) a carboxy group,
(ii) a $C_{1-6}$ alkoxy-carbonyl group optionally substituted by 3- to 14-membered non-aromatic heterocyclic group(s) optionally substituted by 1 to 3 substituents selected from a $C_{1-6}$ alkyl group and an oxo group, and
(iii) a $C_{7-16}$ aralkyloxy-carbonyl group, (3) a $C_{1-6}$ alkoxy-carbonyl group optionally substituted by 3- to 14-membered non-aromatic heterocyclic group(s) optionally substituted by 1 to 3 substituents selected from a $C_{1-6}$ alkyl group and an oxo group, and (4) a $C_{7-16}$ aralkyloxy-carbonyl group;

X is $CR^6$ or N;

$R^5$ is (1) a $C_{1-6}$ alkyl group optionally substituted by 1 to 3 $C_{1-6}$ alkoxy groups, or (2) a $C_{1-6}$ alkoxy group;

$R^6$ is a hydrogen atom; and when X is $CR^6$, $R^5$ and $R^6$ in combination optionally form Ring D, wherein Ring D is a dihydrofuran ring or a dihydrodioxin ring.

[3] The compound or salt of the above-mentioned [1], wherein

Ring A is a benzene ring optionally further substituted by 1 to 3 halogen atoms;

$R^1$ is (1) a group represented by the formula: —$C(R^{1a})(CH_3)(CH_3)$ wherein $R^{1a}$ is a $C_{1-6}$ alkoxy-$C_{1-2}$ alkyl group, or $R^{1a}$ is bonded to one substituent on Ring A to form a 5-membered hydrocarbon ring, wherein the one substituent on Ring A is bonded to the position adjacent to the bonding position of $R^1$ on Ring A, or (2) a trimethylsilyl group;

$R^4$ is a $C_{3-6}$ cycloalkyl group optionally substituted by 1 to 3 substituents selected from (1) a carboxy group, (2) a $C_{1-6}$ alkyl group optionally substituted by 1 to 3 substituents selected from (i) a carboxy group, (ii) a $C_{1-6}$ alkoxy-carbonyl group optionally substituted by 3- to 14-membered non-aromatic heterocyclic group(s) optionally substituted by 1 to 3 substituents selected from a $C_{1-6}$ alkyl group and an oxo-group, and (iii) a $C_{7-16}$ aralkyloxy-carbonyl group, (3) a $C_{1-6}$ alkoxy-carbonyl group optionally substituted by 3- to 14-membered non-aromatic heterocyclic group(s) optionally substituted by 1 to 3 substituents selected from a $C_{1-6}$ alkyl group and an oxo group, and (4) a $C_{7-16}$ aralkyloxy-carbonyl group;

X is $CR^6$ or N;

$R^5$ is (1) a $C_{1-6}$ alkyl group optionally substituted by 1 to 3 $C_{1-6}$ alkoxy groups, or (2) a $C_{1-6}$ alkoxy group;

$R^6$ is a hydrogen atom; and

Ring D is not formed.

[4] The compound or salt of the above-mentioned [1], wherein $R^1$ is a group represented by the formula: —$C(R^{1a})(CH_3)(CH_3)$ wherein $R^{1a}$ is bonded to one substituent on Ring A to form an optionally substituted 5-membered hydrocarbon ring, wherein the one substituent on Ring A is bonded to the position adjacent to the bonding position of $R^1$ on Ring A.

[4'] The compound or salt of the above-mentioned [4], wherein the group represented by the formula:

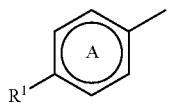

is a group represented by the formula:

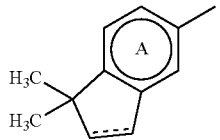

wherein

═════ is a single bond or a double bond.

[5] The compound or salt of the above-mentioned [1], wherein $R^4$ is cyclopropyl or cyclobutyl, each optionally substituted.

[6] The compound or salt of the above-mentioned [1], wherein $R^1$ is a group represented by the formula: —$C(R^{1a})(CH_3)(CH_3)$ wherein $R^{1a}$ is bonded to one substituent on Ring A to form an optionally substituted 5-membered hydrocarbon ring, wherein the one substituent on Ring A is bonded to the position adjacent to the bonding position of $R^1$ on Ring A;

$R^4$ is cyclopropyl or cyclobutyl, each optionally substituted; and

Ring D is not formed.

[7]((1R,2S)-2-(((5R)-5-((7-Fluoro-1,1-dimethyl-2,3-dihydro-1H-inden-5-yl)carbamoyl)-2-methoxy-7,8-dihydro-1,6-naphthyridin-6(5H)-yl)carbonyl)cyclopropyl)acetic acid or a salt thereof.

[8] cis-3-(((5R)-5-((7-Fluoro-1,1-dimethyl-2,3-dihydro-1H-inden-5-yl)carbamoyl)-2-methoxy-7,8-dihydro-1,6-naphthyridin-6(5H)-yl)carbonyl)cyclobutanecarboxylic acid or a salt thereof.

[9](cis-3-(((5R)-5-((7-Fluoro-1,1-dimethyl-2,3-dihydro-1H-inden-5-yl)carbamoyl)-2-methoxy-7,8-dihydro-1,6-naphthyridin-6(5H)-yl)carbonyl)cyclobutyl)acetic acid or a salt thereof.

[10](cis-3-(((1R)-1-((7-Fluoro-1,1-dimethyl-2,3-dihydro-1H-inden-5-yl)carbamoyl)-6-(methoxymethyl)-3,4-dihydroisoquinolin-2(1H)-yl)carbonyl)cyclobutyl)acetic acid or a salt thereof.

[11] A medicament comprising the compound or salt of any of the above-mentioned [1] to [10].

[12] The medicament of the above-mentioned [11], which is a RORγt inhibitor.

[13] The medicament of the above-mentioned [11], which is an agent for the prophylaxis or treatment of psoriasis, inflammatory bowel disease (IBD), ulcerative colitis (UC), Crohn's disease (CD), rheumatoid arthritis, multiple sclerosis, uveitis, asthma, ankylopoietic spondylarthritis or systemic lupus erythematosus (SLE).

[14] A method of inhibiting RORγt in a mammal, which comprises administering an effective amount of the compound or salt of any of the above-mentioned [1] to [10] to the mammal.

[15] A method for the prophylaxis or treatment of psoriasis, inflammatory bowel disease (IBD), ulcerative colitis (UC), Crohn's disease (CD), rheumatoid arthritis, multiple sclerosis, uveitis, asthma, ankylopoietic spondylarthritis or systemic lupus erythematosus (SLE) in a mammal, which comprises administering an effective amount of the compound or salt of any of the above-mentioned [1] to [10] to the mammal.

[16] Use of the compound or salt of any of the above-mentioned [1] to [10] for the production of an agent for the prophylaxis or treatment of psoriasis, inflammatory bowel disease (IBD), ulcerative colitis (UC), Crohn's disease (CD), rheumatoid arthritis, multiple sclerosis, uveitis, asthma, ankylopoietic spondylarthritis or systemic lupus erythematosus (SLE).

[17] The compound or salt of any of the above-mentioned [1] to [10] for use in the prophylaxis or treatment of psoriasis, inflammatory bowel disease (IBD), ulcerative colitis (UC), Crohn's disease (CD), rheumatoid arthritis, multiple sclerosis, uveitis, asthma, ankylopoietic spondylarthritis or systemic lupus erythematosus (SLE).

Effect of the Invention

The compound of the present invention has a superior RORγt inhibitory action, and useful as an agent for the prophylaxis or treatment of psoriasis, inflammatory bowel disease (IBD), ulcerative colitis (UC), Crohn's disease (CD), rheumatoid arthritis, multiple sclerosis, uveitis, asthma, ankylopoietic spondylarthritis, systemic lupus erythematosus (SLE) and the like.

DETAILED DESCRIPTION OF THE INVENTION

The present invention is explained in detail in the following.

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl so group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, a halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, a halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, a halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, a halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, a halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, a halogen atoms. Specific examples thereof include methylsulfonyl, difluoromethylsulfonyl, so trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following Substituent group A.

[Substituent Group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl)($C_{1-6}$ alkyl-carbonyl) an amino group (e.g., N-acetyl-N-methylamino),
(52) a $C_{6-14}$ aryl-carbonylamino group (e.g., phenylcarbonylamino, naphthylcarbonylamino),

(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group, and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 heteroatoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 heteroatoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 heteroatoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the above-mentioned Substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkyl-phosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent group A".

Preferable examples of the optionally substituted amino group include an amino group, a mono- or di- (optionally halogenated $C_{1-6}$ alkyl) an amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di- (optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) an amino group (e.g., methylcarbamoylamino), a (mono- or di-$C_{7-16}$ aralkyl-carbamoyl) an amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl) an amino group (e.g., N-acetyl-N-methylamino) and a ($C_{1-6}$ alkyl) ($C_{6-14}$ aryl-carbonyl) an amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{1-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{1-6}$ aralkyl-carbamoyl group, a $C_{1-6}$ alkylsulfonyl group and a $C_{6-14}$ arylsulfonyl group, each of which optionally has 1 to 3 substituents selected from Substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from Substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from Substituent group A".

Preferable examples of the optionally substituted silyl group include a tri-$C_{1-6}$ alkylsilyl group (e.g., trimethylsilyl, tert-butyl(dimethyl)silyl).

In the present specification, examples of the "$C_{1-6}$ alkylene group" include —$CH_2$—, —$(CH_2)_2$—, —$(CH_2)_3$—, —$(CH_2)_4$—, —$(CH_2)_5$—, —$(CH_2)_6$—, —$CH(CH_3)$—, —$C(CH_3)_2$—, —$CH(C_2H_5)$—, —$CH(C_3H_7)$—, —$CH(CH(CH_3)_2)$—, —$(CH(CH_3))_2$—, —$CH_2$—$CH(CH_3)$—, —$CH(CH_3)$—$CH_2$—, —$CH_2$—$CH_2$—$C(CH_3)_2$—, —$C(CH_3)_2$—$CH_2$—$CH_2$—, —$CH_2$—$CH_2$—$CH_2$—$C(CH_3)_2$— and —$C(CH_3)_2$—$CH_2$—$CH_2$—$CH_2$—.

In the present specification, examples of the "$C_{2-6}$ alkenylene group" include —CH=CH—, —$CH_2$—CH=CH—, —CH=CH—$CH_2$—, —$C(CH_3)_2$—CH=CH—, —CH=CH—$C(CH_3)_2$—, —$CH_2$—CH=CH—$CH_2$—, —$CH_2$—$CH_2$—CH=CH—, —CH=CH—$CH_2$—$CH_2$—, —CH=CH—CH=CH—, —CH=CH—$CH_2$—$CH_2$—$CH_2$— and —$CH_2$—$CH_2$—$CH_2$—CH=CH—.

In the present specification, examples of the "$C_{2-6}$ alkynylene group" include —C≡C—, —$CH_2$—C≡C—, —C≡C—$CH_2$—, —$C(CH_3)_2$—C≡C—, —C≡C—$C(CH_3)_2$—, —$CH_2$—C≡C—$CH_2$—, —$CH_2$—$CH_2$—C≡C—, —C≡C—$CH_2$—$CH_2$—, —C≡C—C≡C—, —C≡C—$CH_2$—$CH_2$—$CH_2$— and —$CH_2$—$CH_2$—$CH_2$—C≡C—.

As shown in the formula:

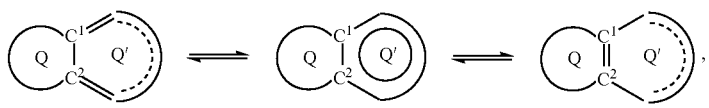

in the present specification, when the non-aromatic Ring Q, which is fused with the aromatic Ring Q', is present, then the non-aromatic Ring Q is expressed as a ring wherein the bond $C^1C^2$ is a double bond.

For example, when the above-mentioned fused Ring QQ' is an indane ring, then the non-aromatic Ring Q is expressed as a cyclopentene ring, and the aromatic Ring Q' is expressed as a benzene ring.

The definition of each symbol in the formula (I) is explained in detail in the following.

Ring A is an optionally further substituted 6-membered aromatic ring.

Examples of the "6-membered aromatic ring" of the "optionally further substituted 6-membered aromatic ring" for Ring A include a benzene ring, a pyridine ring, a pyridazine ring, a pyrimidine ring, a pyrazine ring and a triazine ring.

The "6-membered aromatic ring" of the "optionally further substituted 6-membered aromatic ring" for Ring A is optionally further substituted, for example, by substituent(s) selected from the above-mentioned Substituent Group A. The number of the substituents is, for example, 1 to 3. When the number of the substituents is 2 or more, the respective substituents may be the same or different.

Ring A is preferably a benzene ring optionally further substituted by 1 to 3 halogen atoms (e.g., a fluorine atom).

$R^1$ is
(1) a group represented by the formula: —$C(R^{1a})(CH_3)(CH_3)$ wherein $R^{1a}$ is an optionally substituted $C_{1-6}$ alkoxy-$C_{1-2}$alkyl group, or $R^{1a}$ is bonded to one substituent on Ring A to form an optionally substituted 5-membered hydrocarbon ring, wherein the one substituent on Ring A is bonded to the position adjacent to the bonding position of $R^1$ on Ring A, or
(2) a trimethylsilyl group.

Examples of the "$C_{1-6}$ alkoxy-$C_{1-2}$ alkyl group" of the "optionally substituted $C_{1-6}$ alkoxy-$C_{1-2}$alkyl group" for $R^{1a}$ include methoxymethyl, ethoxymethyl, propoxymethyl, isopropoxymethyl, butoxymethyl, isobutoxymethyl, sec-butoxymethyl, tert-butoxymethyl, pentyloxymethyl, hexyloxymethyl, 1-methoxyethyl, 1-ethoxyethyl, 1-propoxyethyl, 1-isopropoxyethyl, 1-butoxyethyl, 1-isobutoxyethyl, 1-sec-butoxyethyl, 1-tert-butoxyethyl, 1-pentyloxyethyl, 1-hexyloxyethyl, 2-methoxyethyl, 2-ethoxyethyl, 2-propoxyethyl, 2-isopropoxyethyl, 2-butoxyethyl, 2-isobutoxyethyl, 2-sec-butoxyethyl, 2-tert-butoxyethyl, 2-pentyloxyethyl and 2-hexyloxyethyl.

The "$C_{1-6}$ alkoxy-$C_{1-2}$ alkyl group" of the "optionally substituted $C_{1-6}$ alkoxy-$C_{1-2}$ alkyl group" for $R^{1a}$ is optionally substituted, for example, by substituent(s) selected from the above-mentioned Substituent Group A. The number of the substituents is, for example, 1 to 3. When the number of the substituents is 2 or more, the respective substituents may be the same or different.

When $R^{1a}$ is bonded to one substituent on Ring A to form an "optionally substituted 5-membered hydrocarbon ring", wherein the one substituent on Ring A is bonded to the position adjacent to the bonding position of $R^1$ on Ring A, then the group represented by the formula:

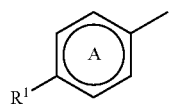

is, for example, a group represented by the formula:

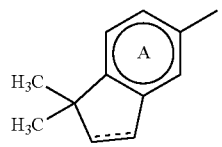

wherein
===
is a single bond or a double bond.

Examples of the "5-membered hydrocarbon ring" of the "optionally substituted 5-membered hydrocarbon ring" formed by $R^{1a}$ and the one substituent on Ring A, wherein the one substituent on Ring A is bonded to the position adjacent to the bonding position of $R^1$ on Ring A, include cyclopentene and cyclopentadiene.

The "5-membered hydrocarbon ring" of the "optionally substituted 5-membered hydrocarbon ring" formed by $R^{1a}$ and the one substituent on Ring A, wherein the one substituent on Ring A is bonded to the position adjacent to the bonding position of $R^1$ on Ring A is optionally substituted, for example, by substituent(s) selected from the above-mentioned Substituent Group A. The number of the substituents is, for example, 1 or 2. When the number of the substituents is 2 or more, the respective substituents may be the same or different.

$R^1$ is preferably
(1) a group represented by the formula: —$C(R^{1a})(CH_3)(CH_3)$ wherein $R^{1a}$ is a $C_{1-6}$ alkoxy-$C_{1-2}$ alkyl group (e.g., methoxymethyl, ethoxymethyl), or $R^{1a}$ is bonded to one substituent on Ring A to form a 5-membered hydrocarbon ring (e.g., cyclopentene), wherein the one substituent on Ring A is bonded to the position adjacent to the bonding position of $R^1$ on Ring A, or
(2) a trimethylsilyl group.

$R^1$ is more preferably
(1) a group represented by the formula: —$C(R^{1a})(CH_3)(CH_3)$ wherein $R^{1a}$ is bonded to one substituent on Ring A to form a 5-membered hydrocarbon ring (e.g., cyclopentene), wherein the one substituent on Ring A is bonded to the position adjacent to the bonding position of $R^1$ on Ring A.

In another embodiment, $R^1$ is preferably a group represented by the formula: —$C(R^{1a})(CH_3)(CH_3)$ wherein $R^{1a}$ is bonded to one substituent on Ring A to form an optionally substituted 5-membered hydrocarbon ring (e.g., cyclopentene), wherein the one substituent on Ring A is bonded to the position adjacent to the bonding position of $R^1$ on Ring A.

$R^4$ is an optionally substituted $C_{3-6}$ cycloalkyl group.

The "$C_{3-6}$ cycloalkyl group" of the "optionally substituted $C_{3-6}$ cycloalkyl group" for $R^4$ is optionally substituted, for example, by substituent(s) selected from the above-mentioned Substituent Group A. The number of the substituents is, for example, 1 to 3. When the number of the substituents is 2 or more, the respective substituents may be the same or different.

$R^4$ is preferably a $C_{3-6}$ cycloalkyl group (e.g., cyclopropyl, cyclobutyl) optionally substituted by 1 to 3 (preferably 1) substituents selected from
(1) a carboxy group, and
(2) a $C_{1-6}$ alkyl group (e.g., methyl) optionally substituted by 1 to 3 (preferably 1) carboxy groups.

In another embodiment, $R^4$ is preferably a $C_{3-6}$ cycloalkyl group (e.g., cyclopropyl, cyclobutyl) optionally substituted by 1 to 3 (preferably 1) substituents selected from (1) a carboxy group,
(2) a $C_{1-6}$ alkyl group (e.g., methyl) optionally substituted by 1 to 3 (preferably 1) substituents selected from
  (i) a carboxy group,
  (ii) a $C_{1-6}$ alkoxy-carbonyl group (e.g., methoxycarbonyl, ethoxycarbonyl, tert-butoxycarbonyl) optionally substituted by 3- to 14-membered non-aromatic heterocyclic group(s) (preferably 3- to 8-membered monocyclic non-aromatic heterocyclic group(s) (e.g., dioxolyl (preferably 1,3-dioxolyl))) optionally substituted by 1 to 3 substituents selected from a $C_{1-6}$ alkyl group (e.g., methyl) and an oxo group, and
  (iii) a $C_{7-16}$ aralkyloxy-carbonyl group (e.g., benzyloxycarbonyl),
(3) a $C_{1-6}$ alkoxy-carbonyl group (e.g., methoxycarbonyl) optionally substituted by 3- to 14-membered non-aromatic heterocyclic group(s) (preferably 3- to 8-membered monocyclic non-aromatic heterocyclic group(s) (e.g., dioxolyl (preferably 1,3-dioxolyl))) optionally substituted by 1 to 3 substituents selected from a $C_{1-6}$ alkyl group (e.g., methyl) and an oxo group, and
(4) a $C_{7-16}$ aralkyloxy-carbonyl group (e.g., benzyloxycarbonyl).

In this embodiment, $R^4$ is more preferably a $C_{3-6}$ cycloalkyl group (e.g., cyclopropyl, cyclobutyl) optionally substituted by 1 to 3 (preferably 1) substituents selected from
(1) a carboxy group,
(2) a $C_{1-6}$ alkyl group (e.g., methyl) optionally substituted by 1 to 3 (preferably 1) substituents selected from
  (i) a carboxy group,
  (ii) a $C_{1-6}$ alkoxy-carbonyl group (e.g., methoxycarbonyl, ethoxycarbonyl) optionally substituted by 3- to 14-membered non-aromatic heterocyclic group(s) (preferably 3- to 8-membered monocyclic non-aromatic heterocyclic group(s) (e.g., dioxolyl (preferably 1,3-dioxolyl))) optionally substituted by 1 to 3 substituents selected from a $C_{1-6}$ alkyl group (e.g., methyl) and an oxo group, and
  (iii) a $C_{7-16}$ aralkyloxy-carbonyl group (e.g., benzyloxycarbonyl),
(3) a $C_{1-6}$ alkoxy-carbonyl group (e.g., methoxycarbonyl) optionally substituted by 3- to 14-membered non-aromatic heterocyclic group(s) (preferably 3- to 8-membered monocyclic non-aromatic heterocyclic group(s) (e.g., dioxolyl (preferably 1,3-dioxolyl))) optionally substituted by 1 to 3 substituents selected from a $C_{1-6}$ alkyl group (e.g., methyl) and an oxo group, and
(4) a $C_{7-16}$ aralkyloxy-carbonyl group (e.g., benzyloxycarbonyl).

In this embodiment, $R^4$ is particularly preferably a $C_{3-6}$ cycloalkyl group (e.g., cyclopropyl, cyclobutyl) optionally substituted by 1 to 3 (preferably 1) substituents selected from
(1) a carboxy group, and
(2) a $C_{1-6}$ alkyl group (e.g., methyl) optionally substituted by 1 to 3 (preferably 1) carboxy groups.

In another embodiment, $R^4$ is preferably cyclopropyl or cyclobutyl, each optionally substituted.

X is $CR^6$ or N.

$R^6$ is a hydrogen atom or a substituent.

$R^6$ is preferably a hydrogen atom.

$R^5$ is an optionally substituted $C_{1-6}$ alkyl group or an optionally substituted $C_{1-6}$ alkoxy group.

The "$C_{1-6}$ alkyl group" of the "optionally substituted $C_{1-6}$ alkyl group" for $R^5$ is optionally substituted, for example, by substituent(s) selected from the above-mentioned Substituent Group A. The number of the substituents is, for example, 1 to 5, preferably 1 to 3, When the number of the substituents is 2 or more, the respective substituents may be the same or different.

The "$C_{1-6}$ alkoxy group" of the "optionally substituted $C_{1-6}$ alkoxy group" for $R^5$ is optionally substituted, for example, by substituent(s) selected from the above-mentioned Substituent Group A. The number of the substituents is, for example, 1 to 5, preferably 1 to 3. When the number of the substituents is 2 or more, the respective substituents may be the same or different.

$R^5$ is preferably
(1) a $C_{1-6}$ alkyl group (e.g., methyl) optionally substituted by 1 to 3 $C_{1-6}$ alkoxy groups (e.g., methoxy), or
(2) a $C_{1-6}$ alkoxy group (e.g., methoxy, ethoxy).

$R^5$ is more preferably
(1) a $C_{1-6}$ alkyl group (e.g., methyl) optionally substituted by 1 to 3 $C_{1-6}$ alkoxy groups (e.g., methoxy), or
(2) a $C_{1-6}$ alkoxy group (e.g., methoxy).

When X is $CR^6$, $R^5$ and $R^6$ in combination optionally form Ring D, wherein Ring D is an optionally substituted 5- or 6-membered oxygen-containing heterocycle containing 1 to 2 oxygen atoms as heteroatoms in addition to carbon atoms.

Examples of the "5- or 6-membered oxygen-containing heterocycle containing 1 to 2 oxygen atoms as heteroatoms in addition to carbon atoms" of the "optionally substituted 5- or 6-membered oxygen-containing heterocycle containing 1 to 2 oxygen atoms as heteroatoms in addition to carbon atoms" formed by $R^5$ and $R^6$ in combination include furan, dihydrofuran, dioxole (e.g., 1,2-dioxole, 1,3-dioxole), dioxin (e.g., 1,2-dioxin, 1,3-dioxin, 1,4-dioxin), dihydrodioxin (e.g., dihydro-1,2-dioxin, dihydro-1,3-dioxin, dihydro-1,4-dioxin) and the like.

The "5- or 6-membered oxygen-containing heterocycle containing 1 to 2 oxygen atoms as heteroatoms in addition to carbon atoms" of the "optionally substituted 5- or 6-membered oxygen-containing heterocycle containing 1 to 2 oxygen atoms as heteroatoms in addition to carbon atoms" formed by $R^5$ and $R^6$ in combination is optionally substituted, for example, by substituent(s) selected from the above-mentioned Substituent Group A. The number of the substituents is, for example, 1 to 3. When the number of the substituents is 2 or more, the respective substituents may be the same or different.

When X is $CR^6$, examples of Ring D formed by $R^5$ and $R^6$ in combination include a dihydrofuran ring and a dihydrodioxin ring (e.g., dihydro-1,4-dioxin).

The partial structure represented by the formula:

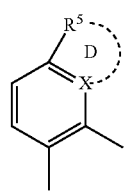

is preferably a partial structure represented by the formula:

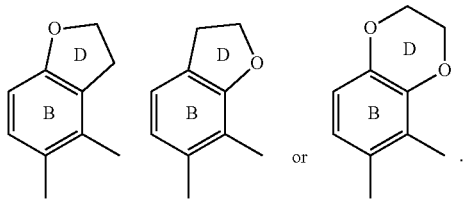

More preferably, Ring D is not formed.

Preferable examples of the ring, group, substituent and the like explained in the present specification are more preferably used in combination.

Preferable examples of compound (I) include the following compounds.

[Compound A-1]
Compound (I) wherein
Ring A is a benzene ring optionally further substituted by 1 to 3 halogen atoms (e.g., a fluorine atom);
$R^1$ is
(1) a group represented by the formula: $-C(R^{1a})(CH_3)(CH_3)$ wherein $R^{1a}$ is a $C_{1-6}$ alkoxy-$C_{1-2}$ alkyl group (e.g., methoxymethyl, ethoxymethyl), or $R^{1a}$ is bonded to one substituent on Ring A to form a 5-membered hydrocarbon ring (e.g., cyclopentene), wherein the one substituent on Ring A is bonded to the position adjacent to the bonding position of $R^1$ on Ring A, or
(2) a trimethylsilyl group;
$R^4$ is a $C_{3-6}$ cycloalkyl group (e.g., cyclopropyl, cyclobutyl) optionally substituted by 1 to 3 (preferably 1) substituents selected from
(1) a carboxy group, and
(2) a $C_{1-6}$ alkyl group (e.g., methyl) optionally substituted by 1 to 3 (preferably 1) carboxy groups;
X is $CR^6$ or N;
$R^5$ is
(1) a $C_{1-6}$ alkyl group (e.g., methyl) optionally substituted by 1 to 3 $C_{1-6}$ alkoxy groups (e.g., methoxy), or
(2) a $C_{1-6}$ alkoxy group (e.g., methoxy, ethoxy);
$R^6$ is a hydrogen atom; and
when X is $CR^6$, $R^5$ and $R^6$ in combination optionally form Ring D, wherein Ring D is a dihydrofuran ring or a dihydrodioxin ring (e.g., dihydro-1,4-dioxin).

[Compound B-1]
Compound (I) wherein
Ring A is a benzene ring optionally further substituted by 1 to 3 halogen atoms (e.g., a fluorine atom);
$R^1$ is a group represented by the formula: $-C(R^{1a})(CH_3)(CH_3)$ wherein $R^{1a}$ is bonded to one substituent on Ring A to form a 5-membered hydrocarbon ring (e.g., cyclopentene), wherein the one substituent on Ring A is bonded to the position adjacent to the bonding position of $R^1$ on Ring A;
$R^4$ is a $C_{3-6}$ cycloalkyl group (e.g., cyclopropyl, cyclobutyl) optionally substituted by 1 to 3 (preferably 1) substituents selected from
(1) a carboxy group, and
(2) a $C_{1-6}$ alkyl group (e.g., methyl) optionally substituted by 1 to 3 (preferably 1) carboxy groups;
X is $CR^6$ or N;
$R^5$ is
(1) a $C_{1-6}$ alkyl group (e.g., methyl) optionally substituted by 1 to 3 $C_{1-6}$ alkoxy groups (e.g., methoxy), or
(2) a $C_{1-6}$ alkoxy group (e.g., methoxy);
$R^6$ is a hydrogen atom; and
Ring D is not formed.

[Compound A-2]
Compound (I) wherein
Ring A is a benzene ring optionally further substituted by 1 to 3 halogen atoms (e.g., a fluorine atom);
$R^1$ is
(1) a group represented by the formula: $-C(R^{1a})(CH_3)(CH_3)$ wherein $R^{1a}$ is a $C_{1-6}$ alkoxy-$C_{1-2}$ alkyl group (e.g., methoxymethyl, ethoxymethyl), or $R^{1a}$ is bonded to one substituent on Ring A to form a 5-membered hydrocarbon ring (e.g., cyclopentene), wherein the one substituent on Ring A is bonded to the position adjacent to the bonding position of $R^1$ on Ring A, or
(2) a trimethylsilyl group;
$R^4$ is a $C_{3-6}$ cycloalkyl group (e.g., cyclopropyl, cyclobutyl) optionally substituted by 1 to 3 (preferably 1) substituents selected from
(1) a carboxy group,
(2) a $C_{1-6}$ alkyl group (e.g., methyl) optionally substituted by 1 to 3 (preferably 1) substituents selected from
(i) a carboxy group,
(ii) a $C_{1-6}$ alkoxy-carbonyl group (e.g., methoxycarbonyl, ethoxycarbonyl, tert-butoxycarbonyl) optionally substituted by 3- to 14-membered non-aromatic heterocyclic group(s) (preferably 3- to 8-membered monocyclic non-aromatic heterocyclic group(s) (e.g., dioxolyl (preferably 1,3-dioxolyl))) optionally substituted by 1 to 3 substituents selected from a $C_{1-6}$ alkyl group (e.g., methyl) and an oxo group, and
(iii) a $C_{7-16}$ aralkyloxy-carbonyl group (e.g., benzyloxycarbonyl),
(3) a $C_{1-6}$ alkoxy-carbonyl group (e.g., methoxycarbonyl) optionally substituted by 3- to 14-membered non-aromatic heterocyclic group(s) (preferably 3- to 8-membered monocyclic non-aromatic heterocyclic group(s) (e.g., dioxolyl (preferably 1,3-dioxolyl))) optionally substituted by 1 to 3 substituents selected from a $C_{1-6}$ alkyl group (e.g., methyl) and an oxo group, and
(4) a $C_{7-16}$ aralkyloxy-carbonyl group (e.g., benzyloxycarbonyl);
X is $CR^6$ or N;
$R^5$ is
(1) a $C_{1-6}$ alkyl group (e.g., methyl) optionally substituted by 1 to 3 $C_{1-6}$ alkoxy groups (e.g., methoxy), or
(2) a $C_{1-6}$ alkoxy group (e.g., methoxy, ethoxy);
$R^6$ is a hydrogen atom; and
when X is $CR^6$, $R^5$ and $R^6$ in combination optionally form Ring D, wherein Ring D is a dihydrofuran ring or a dihydrodioxin ring (e.g., dihydro-1,4-dioxin).

[Compound B-2]
Compound (I) wherein
Ring A is a benzene ring optionally further substituted by 1 to 3 halogen atoms (e.g., a fluorine atom);
$R^1$ is
(1) a group represented by the formula: $-C(R^{1a})(CH_3)(CH_3)$ wherein $R^{1a}$ is a $C_{1-6}$ alkoxy-$C_{1-2}$ alkyl group (e.g., methoxymethyl, ethoxymethyl), or $R^{1a}$ is bonded to one substituent on Ring A to form a 5-membered hydrocarbon ring (e.g., cyclopentene), wherein the one substituent on Ring A is bonded to the position adjacent to the bonding position of $R^1$ on Ring A, or
(2) a trimethylsilyl group;
$R^4$ is a $C_{3-6}$ cycloalkyl group (e.g., cyclopropyl, cyclobutyl) optionally substituted by 1 to 3 (preferably 1) substituents selected from
(1) a carboxy group,
(2) a $C_{1-6}$ alkyl group (e.g., methyl) optionally substituted by 1 to 3 (preferably 1) substituents selected from
(i) a carboxy group, (ii) a $C_{1-6}$ alkoxy-carbonyl group (e.g., methoxycarbonyl, ethoxycarbonyl) optionally substituted by 3- to 14-membered non-aromatic heterocyclic group(s) (preferably 3- to 8-membered monocyclic non-aromatic heterocyclic group(s) (e.g., dioxolyl (preferably 1,3-dioxolyl))) optionally substituted by 1 to 3 substituents selected from a $C_{1-6}$ alkyl group (e.g., methyl) and an oxo group, and (iii) a $C_{7-16}$ aralkyloxy-carbonyl group (e.g., benzyloxycarbonyl), (3) a $C_{1-6}$ alkoxy-carbonyl group (e.g., methoxycarbonyl) optionally substituted by 3- to 14-membered non-aromatic heterocyclic group(s) (preferably 3- to 8-membered monocyclic non-aromatic heterocyclic group(s) (e.g., dioxolyl (preferably 1,3-dioxolyl))) optionally substituted by 1 to 3 substituents selected from a $C_{1-6}$ alkyl group (e.g., methyl) and an oxo group, and (4) a $C_{7-16}$ aralkyloxy-carbonyl group (e.g., benzyloxycarbonyl);

X is $CR^6$ or N;

$R^5$ is (1) a $C_{1-6}$ alkyl group (e.g., methyl) optionally substituted by 1 to 3 $C_{1-6}$ alkoxy groups (e.g., methoxy), or (2) a $C_{1-6}$ alkoxy group (e.g., methoxy, ethoxy);

$R^6$ is a hydrogen atom; and

Ring D is not formed.

[Compound C-2]

Compound (I) wherein

Ring A is a benzene ring optionally further substituted by 1 to 3 halogen atoms (e.g., a fluorine atom);

$R^1$ is a group represented by the formula: —$C(R^{1a})(CH_3)(CH_3)$ wherein $R^{1a}$ is bonded to one substituent on Ring A to form a 5-membered hydrocarbon ring (e.g., cyclopentene), wherein the one substituent on Ring A is bonded to the position adjacent to the bonding position of $R^1$ on Ring A;

$R^4$ is a $C_{3-6}$ cycloalkyl group (e.g., cyclopropyl, cyclobutyl) optionally substituted by 1 to 3 (preferably 1) substituents selected from (1) a carboxy group, and (2) a $C_{1-6}$ alkyl group (e.g., methyl) optionally substituted by 1 to 3 (preferably 1) carboxy groups;

X is $CR^6$ or N;

$R^5$ is (1) a $C_{1-6}$ alkyl group (e.g., methyl) optionally substituted by 1 to 3 $C_{1-6}$ alkoxy groups (e.g., methoxy), or (2) a $C_{1-6}$ alkoxy group (e.g., methoxy);

$R^6$ is a hydrogen atom; and

Ring D is not formed.

Specific examples of compound (I) include the compounds of Examples 1 to 48.

Examples of salts of compound (I) include metal salts, ammonium salts, salts with organic base, salts with inorganic acid, salts with organic acid, salts with basic or acidic amino acids, and the like. Preferable examples of the metal salt include alkaline metal salts such as sodium salt, potassium salt and the like; alkaline earth metal salts such as calcium salt, magnesium salt, barium salt and the like; aluminum salts, and the like. Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include salts with hydrochloric acid, hydrobromic acid, nitric acid, sulfuric acid, phosphoric acid and the like. Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include salts with arginine, lysine, ornithine and the like. Preferable examples of the salt with acidic amino acid include salt with aspartic acid, glutamic acid and the like.

Among them, pharmaceutically acceptable salts are preferable. For example, if the compound has an acidic functional group therein, examples of the salt include inorganic salts such as alkaline metal salts (e.g., sodium salt, potassium salt and the like), alkaline earth metal salts (e.g., calcium salt, magnesium salt, barium salt and the like) and the like; ammonium salt, and the like. If the compound has a basic functional group therein, examples of the salt thereof include salts with inorganic acids such as hydrochloric acid, hydrobromic acid, nitric acid, sulfuric acid, phosphoric acid and the like, and salts with organic acids such as acetic acid, phthalic acid, fumaric acid, oxalic acid, tartaric acid, maleic acid, citric acid, succinic acid, methanesulfonic acid, p-toluenesulfonic acid and the like.

The production method of compound (I) of the present invention is explained below.

The intermediates produced in the following production methods may be isolated and purified according to methods such as column chromatography, recrystallization, distillation and the like, or may be directly used without isolation for the next step. The intermediate may be in the form of a salt. Examples of the salt include those exemplified as the salt of compound (I).

Ring A represented by the formula:

in the following production methods is used for the same meaning as Ring A represented by the formula:

which is defined in compound (I) of the present invention.

Compound (I) of the present invention can be produced according to the following Method A.

[Method A]

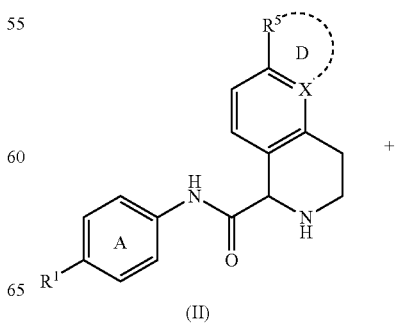

(II)

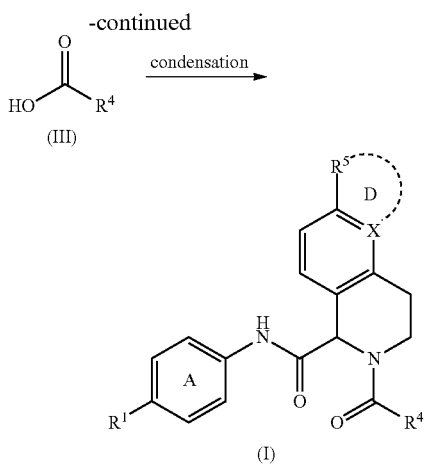

wherein each symbol is as defined above.

This step is a step of subjecting compound (II) or a salt thereof to an acylation reaction to convert compound (II) or a salt thereof to compound (I).

In the acylation reaction, compound (I) can be produced by reacting compound (II) or a salt thereof with compound (III) or a salt thereof.

Compound (III) or a salt thereof may be a commercially available product, or can also be produced according to a method known per se or a method analogous thereto.

The acylation reaction can be carried out according to a method known per se, for example, the method described in Jikken Kagaku Kouza, 4th Edition, 1991, vol. 22, organic synthesis IV (the Chemical Society of Japan ed.) and the like, or a method analogous thereto. Examples of the method include a method using a condensing agent, a method via a reactive derivative, and the like.

Examples of the condensing agent to be used for the "method using a condensing agent" include (dimethylamino)-N,N-dimethyl(3H-[1,2,3]triazolo[4,5-b]pyridin-3-yloxy)methaneiminium hexafluorophosphorate (HATU), 1-[(1-(cyano-2-ethoxy-2-oxoethylideneaminooxy)-dimethylamino-morpholino)]carbenium hexafluorophosphorate (COMU), 2,4,6-tripropyl-1,3,5,2,4,6-trioxatriphosphorinane-2,4,6-trioxide (T3P), dicyclohexylcarbodiimide (DCC), diisopropylcarbodiimide (DIC), N-ethyl-N'-3-dimethylaminopropylcarbodiimide and a hydrochloride thereof (WSC, WSC HCl, EDCI), benzotriazol-1-yl-tris(dimethylamino)phosphonium hexafluorophosphorate (BOP), diphenylphosphorylazide (DPPA), diethyl (4-oxobenzo[d][1,2,3]triazin-3(4H)-yl) phosphate (DETBT), (3-hydroxy-3H-1,2,3-triazolo[4,5-b]pyridinato-O)tri-1-pyrrolidinyl-phosphorus hexafluorophosphorate (PyAOP), N,N,N',N'-tetramethyl-O-(3,4-dihydro-4-oxo-1,2,3-benzotriazin-3-yl)uronium tetrafluoroborate (TDBTU), 4-(4,6-dimethoxy-1,3,5-triazin-2-yl)-4-methylmorpholinium chloride (DMT-MM) and a hydrate thereof and the like. They can be used alone or in combination with an additive (e.g., N-hydroxysuccinimide, 1-hydroxybenzotriazole or 3-hydroxy-4-oxo-3,4-dihydro-1,2,3-benzotriazine, etc.). The amount of the condensing agent to be used is about 1 to 10 mol equivalent, preferably about 1 to 2 mol equivalent, per 1 mol of compound (II). The amount of the additive to be used is about 1 to 10 mol equivalent, preferably about 1 to 2 mol equivalent, per 1 mol of compound (II).

The above-mentioned reaction is generally carried out in a solvent that does not adversely influence the reaction, and a base may be added for the progress of the reaction. Examples of the solvent include hydrocarbons (benzene, toluene, etc.), ethers (diethyl ether, dioxane, tetrahydrofuran, etc.), esters (ethyl acetate, etc.), halogenated hydrocarbons (chloroform, dichloromethane, etc.), amides (N,N-dimethylformamide, etc.), aromatic amines (pyridine, etc.), water and the like, and they may be mixed as appropriate. Examples of the base include alkali metal hydroxides (sodium hydroxide, potassium hydroxide, etc.), hydrogencarbonates (sodium hydrogencarbonate, potassium hydrogencarbonate, etc.), carbonates (sodium carbonate, potassium carbonate, etc.), acetates (sodium acetate, etc.), tertiary amines (trimethylamine, triethylamine, N-methylmorpholine, diisopropylamine, etc.), aromatic amines (pyridine, picoline, N,N-dimethylaniline, 4-dimethylaminopyridine, etc.) and the like. The amount of the base to be used is generally about 1 to 100 mol equivalent, preferably about 1 to 5 mol equivalent, per 1 mol of compound (II).

The reaction temperature is generally about −80 to 150° C., preferably about 0 to 50° C., and the reaction time is generally about 0.5 to 48 hr, preferably 0.5 to 16 hr.

Examples of the reactive derivative in the "method via a reactive derivative" include a compound represented by the formula:

wherein LG is a leaving group, and the other symbols are as defined above (hereinafter to be referred to as compound (IIIa)) or a salt thereof (e.g., acid halides, anhydrides, mixed anhydrides, activated esters, etc.) and the like.

Examples of the leaving group for LG include halogen atoms (a chlorine atom, a bromine atom, a iodine atom, etc.), substituted sulfonyloxy groups ($C_{1-6}$ alkylsulfonyloxy groups such as methanesulfonyloxy, ethanesulfonyloxy and the like; $C_{6-14}$ arylsulfonyloxy groups such as benzenesulfonyloxy, p-toluenesulfonyloxy and the like; $C_{7-16}$ aralkylsulfonyloxy groups such as benzylsulfonyloxy group and the like, etc.), acyloxy groups (acetoxy, benzoyloxy, etc.), oxy groups substituted by a heterocyclic group or an aryl group (2,5-dioxo-1-pyrrolidinyl, benzotriazolyl, quinolyl, 4-nitrophenyl, etc.), heterocyclic groups (imidazolyl, etc.) and the like. In addition, LG is optionally bonded to $R^4$ to form a ring, and compound (IIIa) may be, for example, anhydrides (3-oxabicyclo[3.1.1]heptane-2,4-dione, 3-oxabicyclo[3.1.0]hexane-2,4-dione, 3-oxabicyclo[4.1.0]heptane-2,4-dione, 3-oxabicyclo[4.2.1]nonane-2,4-dione, etc.).

The conversion of compound (III) to the reactive derivative (compound (IIIa)) can be carried out according to a method known per se. For example, the conversion of compound (III) to the acid halide can be carried out by employing a method using an acid halide (e.g., thionyl chloride, oxalyl chloride, etc.), a method using a halide of phosphorus and phosphoric acid (e.g., phosphorus trichloride, phosphorus pentachloride, etc.), and the like. The method via a reactive derivative is generally carried out in a solvent that does not adversely influence the reaction, which varies depending on the kind of compound (IIIa), and a base may be added for the progress of the reaction. The kinds and amounts of the solvent and base to be used for the reaction, the reaction temperature and the reaction time are the same as in the above-mentioned "method using a condensing agent".

The raw material compound used in Method A can be produced according to the following Methods B-L.

[Method B]
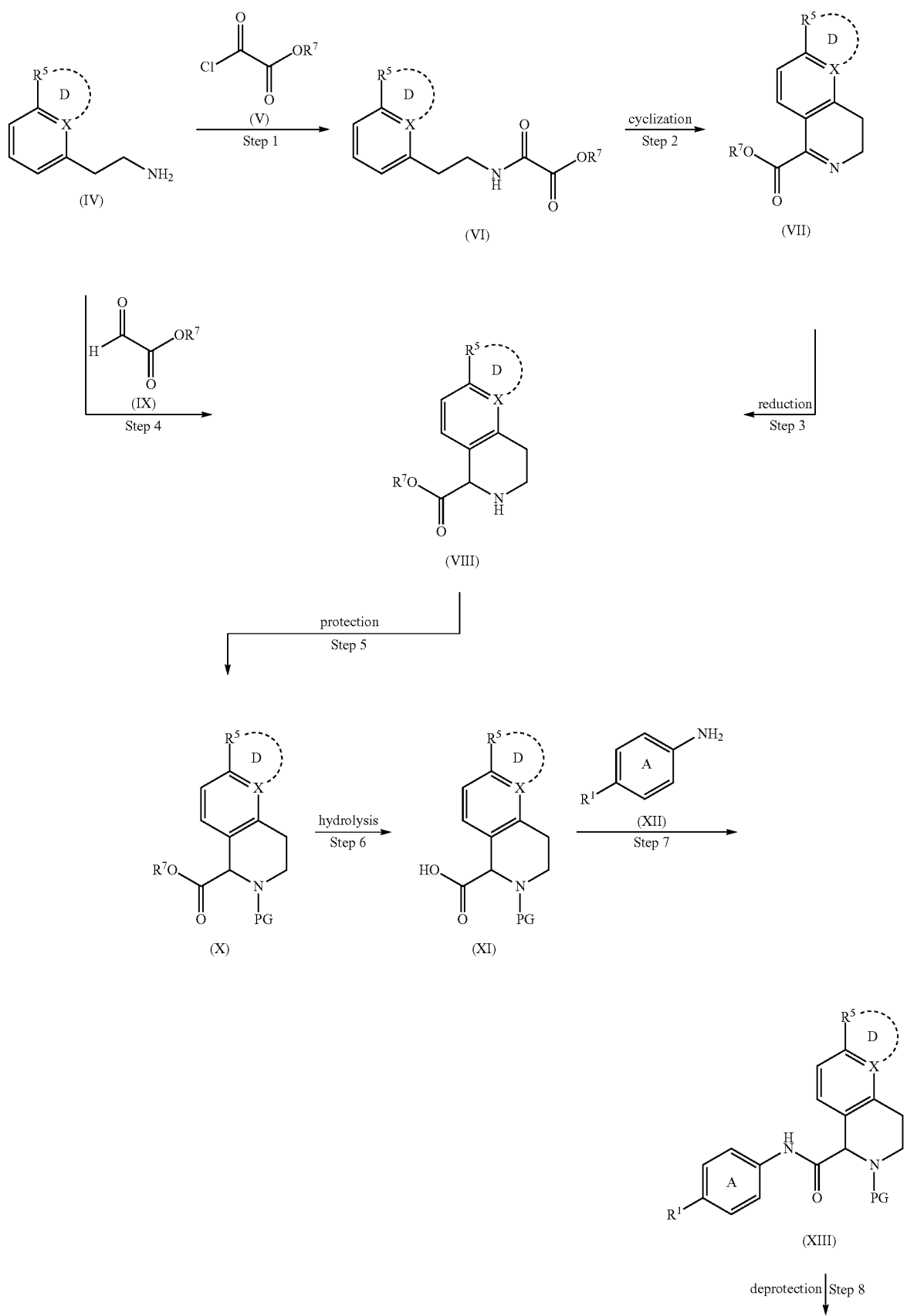

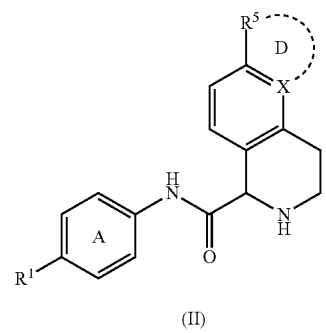

(II)

wherein R⁷ is an optionally substituted hydrocarbon group, PG is an amino-protecting group, and the other symbols are as defined above.

Examples of the amino-protecting group for PG include a tert-butoxycarbonyl (Boc) group, a benzyloxycarbonyl (Cbz or Z) group, a benzyl (Bn) group, a 4-methoxybenzyl (PMB) group, a trifluoroacetyl (CF₃CO) group and the like.

(Step 1)

This step is a step of reacting compound (IV) or a salt thereof with compound (V) or a salt thereof in the presence of a base to produce compound (VI) or a salt thereof.

Compound (IV) or a salt thereof and compound (V) or a salt thereof may be a commercially available product, or can also be produced according to a method known per se or a method analogous thereto.

The amount of compound (V) to be used is generally about 1 to 10 mol equivalent, preferably about 1 to 2 mol equivalent, per 1 mol of compound (IV).

The above-mentioned reaction is generally carried out in a solvent that does not adversely influence the reaction, and a base may be added for the progress of the reaction. Examples of the solvent include hydrocarbons (benzene, toluene, etc.), ethers (diethyl ether, dioxane, tetrahydrofuran, etc.), esters (ethyl acetate, etc.), halogenated hydrocarbons (chloroform, dichloromethane, etc.), amides (N,N-dimethylformamide, etc.), aromatic amines (pyridine, etc.), water and the like, and they may be mixed as appropriate. Examples of the base include alkali metal hydroxides (sodium hydroxide, potassium hydroxide, etc.), hydrogencarbonates (sodium hydrogencarbonate, potassium hydrogencarbonate, etc.), carbonates (sodium carbonate, potassium carbonate, etc.), acetates (sodium acetate, etc.), tertiary amines (trimethylamine, triethylamine, N-methylmorpholine, diisopropylamine, etc.), aromatic amines (pyridine, picoline, N,N-dimethylaniline, 4-dimethylaminopyridine, etc.) and the like. The amount of the base to be used is generally about 1 to 100 mol equivalent, preferably about 1 to 5 mol equivalent, per 1 mol of compound (IV).

The reaction temperature is generally about −80 to 150° C., preferably about 0 to 50° C., and the reaction time is generally about 0.5 to 48 hr, preferably 0.5 to 16 hr.

(Step 2)

This step is a step of treating compound (VI) or a salt thereof with phosphorus oxychloride and zinc(II) chloride to produce compound (VII) or a salt thereof.

The amount of the phosphorus oxychloride to be used is generally about 1 to 10 mol equivalent, preferably about 1 to 5 mol equivalent, per 1 mol of compound (VI).

The amount of the zinc(II) chloride to be used is generally about 0.1 to 2 mol equivalent, preferably about 0.1 to 1 mol equivalent, per 1 mol of compound (VI).

The reaction is generally carried out in a solvent that does not adversely influence the reaction. Examples of the solvent include hydrocarbons (benzene, toluene, etc.), ethers (diethyl ether, dioxane, tetrahydrofuran, etc.), nitriles (acetonitrile, etc.), halogenated hydrocarbons (chloroform, dichloromethane, etc.) and the like, and they may be mixed as appropriate.

The reaction temperature is generally about −80 to 150° C., preferably about 0 to 10° C., and the reaction time is generally about 0.5 to 100 hr, preferably 0.5 to 10 hr.

(Step 3)

This step is a step of subjecting compound (VII) or a salt thereof to a reduction reaction to produce compound (VIII) or a salt thereof.

This reaction can be carried out in a solvent inert to the reaction by employing various reduction reactions. The reduction reaction can be carried out according to a method known per se. Examples thereof include a method using a metal hydride, a method employing a catalytic hydrogenation reaction.

Examples of the metal hydride include sodium borohydride, lithium borohydride, zinc borohydride, sodium cyanoborohydride, sodium triacetoxyborohydride, lithium cyanoborohydride, dibutylaluminium hydride, aluminium hydride, lithium aluminium hydride, borane complexes (borane-THF complex, catecholborane, etc.) and the like. Among them, sodium borohydride, sodium cyanoborohydride, sodium triacetoxyborohydride and the like are preferable. The amount of the metal hydride to be used is, for example, about 1 to about 50 mol equivalent, preferably about 1 to about 10 mol equivalent, per 1 mol of compound (VII).

The reduction reaction using a metal hydride is generally carried out in a solvent inert to the reaction. Examples of the solvent include aromatic hydrocarbons (toluene, xylene, etc.), aliphatic hydrocarbons (heptane, hexane, etc.), halogenated hydrocarbons (chloroform, dichloromethane, etc.), ethers (diethyl ether, tetrahydrofuran, dioxane, etc.), alcohols (methanol, ethanol, 2-propanol, butanol, benzyl alcohol, etc.), nitriles (acetonitrile, etc.), N,N-dimethylformamide, dimethyl sulfoxide and the like. These solvents may be used in a mixture of two or more kinds thereof in an appropriate ratio.

The reaction temperature is generally about −80° C. to about 80° C., preferably about −40° C. to about 40° C., and the reaction time is generally about 5 min to about 48 hr, preferably about 1 hr to about 24 hr.

The catalytic hydrogenation reaction can be carried out in the presence of a catalyst under hydrogen atmosphere. Examples of the catalyst include palladiums such as palladium on carbon, palladium hydroxide carbon, palladium oxide and the like; nickels such as Raney-nickel catalyst and the like; platinums such as platinum oxide, platinum on carbon and the like; rhodiums such as rhodium on carbon and the like, and the like. The amount thereof to be used is generally about 0.001 to about 1 mol equivalent, preferably about 0.01 to about 0.5 mol equivalent, per 1 mol of compound (VII).

The catalytic hydrogenation reaction is generally carried out in a solvent inert to the reaction. Examples of the solvent include alcohols (methanol, ethanol, propanol, butanol, etc.), hydrocarbons (benzene, toluene, xylene, etc.), halogenated hydrocarbons (dichloromethane, chloroform, etc.), ethers (diethyl ether, dioxane, tetrahydrofuran, etc.), esters (ethyl acetate, etc.), amides (N,N-dimethylformamide, etc.), carboxylic acids (acetic acid, etc.), water and mixtures thereof.

The hydrogen pressure for the reaction is generally about 1 to about 50 atm, preferably about 1 to about 10 atm. The reaction temperature is generally about 0° C. to about 150° C., preferably about 20° C. to about 100° C., and the reaction time is generally about 5 min to about 72 hr, preferably about 0.5 hr to about 40 hr.

(Step 4)

This step is a step of subjecting compound (IV) or a salt thereof to a cyclization reaction with compound (IX) or a salt thereof to produce compound (VIII) or a salt thereof.

Compound (IV) or a salt thereof and compound (IX) or a salt thereof used for this reaction may be a commercially available product, or can also be produced according to a method known per se or a method analogous thereto.

The amount of compound (IX) to be used is generally about 1 to 10 mol equivalent, preferably about 1 to 2 mol equivalent, per 1 mol of compound (IV).

The reaction is generally carried out in a solvent that does not adversely influence the reaction, and an acid may be added for the progress of the reaction. Examples of the solvent that does not adversely influence the reaction include alcohols (methanol, ethanol, propanol, 2-propanol, butanol, isobutanol, t-butanol, etc.), aromatic hydrocarbons (benzene, toluene, xylene, etc.), aliphatic hydrocarbons (hexane, heptane, etc.), halogenated hydrocarbons (dichloromethane, chloroform, etc.), ethers (diethyl ether, diisopropyl ether, t-butyl methyl ether, tetrahydrofuran, dioxane, dimethoxyethane, etc.), nitriles (acetonitrile, etc.), esters (ethyl acetate, etc.) and the like.

The reaction temperature is, for example, within about 0 to 200° C., preferably about 25 to 120° C. While the reaction time varies depending on the kind of compound (IV) or a salt thereof, the reaction temperature and the like, it is, for example, about 0.5 to 100 hr, preferably about 0.5 to 24 hr.

Examples of the acid to be used for the progress of the reaction include mineral acids (hydrochloric acid, hydrobromic acid, sulfuric acid, etc.), Lewis acids (aluminium chloride, tin chloride, zinc bromide, etc.) and the like. Among them, hydrochloric acid, hydrobromic acid and aluminium chloride are preferable. While the amount of the acid to be used varies depending on the kind of solvent and the other reaction condition, it is generally about 1 mol equivalent or more, per 1 mol of compound (IV).

(Step 5)

This step is a step of subjecting compound (VIII) or a salt thereof to an amino-protection reaction to produce compound (X) or a salt thereof.

When the amino group is protected by a Boc group, the reaction is carried out by reacting compound (VIII) or a salt thereof with di-tert-butyl dicarbonate ($Boc_2O$) in the presence of a base, in a solvent that does not adversely influence the reaction.

Examples of the base to be used in this step include inorganic bases (alkali metal hydrides such as sodium hydride, lithium hydride and the like, alkali metal hydroxides such as lithium hydroxide, sodium hydroxide, potassium hydroxide and the like, alkali metal hydrogencarbonates such as sodium hydrogencarbonate, potassium hydrogencarbonate and the like, alkali metal carbonates such as lithium carbonate, sodium carbonate, potassium carbonate, cesium carbonate and the like, alkali metal alkoxides such as sodium methoxide, sodium ethoxide and the like, etc.), organic bases (amines such as trimethylamine, triethylamine, diisopropylethylamine and the like, cyclic amines such as pyridine, 4-dimethylaminopyridine and the like, etc.) and the like. Among them, sodium hydride and triethylamine are preferable. While the amount of the base to be used varies depending on the kind of solvent and the other reaction condition, it is generally about 1 to 10 mol equivalent, preferably about 1 to 5 mol equivalent, per 1 mol of compound (VIII).

Examples of the solvent that does not adversely influence the reaction include aromatic hydrocarbons (benzene, toluene, xylene, etc.), aliphatic hydrocarbons (hexane, heptane, etc.), halogenated hydrocarbons (dichloromethane, chloroform, etc.), ethers (diethyl ether, diisopropyl ether, t-butyl methyl ether, tetrahydrofuran, dioxane, dimethoxyethane, etc.), nitriles (acetonitrile, etc.), esters (ethyl acetate, etc.), amides (dimethylformamide, etc.), sulfoxides (dimethyl sulfoxide, etc.), and water and the like. These solvents may be used in a mixture of two or more kinds thereof in an appropriate ratio.

The amount of the $Boc_2O$ used in this step is about 1 to 10 mol equivalent, preferably about 1 to 2 mol equivalent, per 1 mol of compound (VIII).

The reaction temperature is, for example, within about −10 to 100° C. While the reaction time varies depending on the kind of compound (VIII) or a salt thereof, the reaction temperature and the like, it is, for example, about 0.5 to 100 hr, preferably about 0.5 to 24 hr.

When the amino group is protected by a Cbz (Z) group, the reaction is carried out by reacting compound (VIII) or a salt thereof with benzyl chloroformate in a solvent that does not adversely influence the reaction. The kinds and amounts of the base, solvent and reagent to be used in this step, the reaction temperature and the reaction time are the same as in the above-mentioned protection of the amino group by a Boc group.

When the amino group is protected by a Bn group, the reaction is carried out by reacting compound (VIII) or a salt thereof with benzaldehyde in a solvent that does not adversely influence the reaction, and then treating the resulting compound with a reducing agent, or by reacting compound (VIII) or a salt thereof with benzyl bromide in the presence of a base, in a solvent that does not adversely influence the reaction.

When compound (VIII) or a salt thereof is reacted with benzaldehyde, examples of the solvent that does not adversely influence the reaction include hydrocarbons (heptane, hexane, toluene, xylene, etc.), halogenated hydrocarbons (chloroform, dichloromethane, 1,2-dichloroethane, etc.), ethers (diethyl ether, tetrahydrofuran, dioxane, etc.), esters (ethyl acetate, t-butyl acetate, etc.), alcohols (methanol, ethanol, 2-propanol, etc.), nitriles (acetonitrile, butyronitrile, etc.), amides (dimethylformamide, dimethylacetamide, etc.), sulfoxides (dimethyl sulfoxide, etc.), and mixed solvents thereof.

Examples of the reducing agent to be used for this reaction include metal hydrides (e.g., sodium borohydride, lithium borohydride, zinc borohydride, sodium cyanoborohydride, sodium triacetoxyborohydride, lithium cyanoborohydride, diisobutylaluminium hydride, aluminium hydride, lithium aluminium hydride), borane complexs (borane-THF complex, catecholborane, etc.) and the like. The amount of the metal hydride to be used is about 1 to about 50 mol equivalent, per 1 mol of compound (VIII).

In this reaction, a catalyst may be added for the progress of the reaction, if necessary. Examples of the catalyst include mineral acids (hydrochloric acid, hydrobromic acid, sulfuric acid, etc.), carboxylic acids (formic acid, acetic acid, propionic acid, trifluoroacetic acid, etc.), sulfonic acids (methanesulfonic acid, p-toluenesulfonic acid, etc.), Lewis acids (aluminium chloride, zinc chloride, zinc bromide, boron trifluoride, titanium chloride, etc.), acetates (sodium acetate, potassium acetate, etc.), molecular sieves (molecular sieves 3A, 4A, 5A, etc.), dehydrating agents (magnesium sulfate, etc.) and the like. The amount of the catalyst to be used is generally about 0.01 to 50 mol equivalent, preferably about 0.1 to 10 mol equivalent, per 1 mol of compound (VIII).

The amount of the benzaldehyde to be used is generally about 1 to 10 mol equivalent, preferably about 1 to 2 mol equivalent, per 1 mol of compound (VIII).

The reaction temperature is generally about 0° C. to 200° C., preferably about 20° C. to 150° C., and the reaction time is generally about 0.5 hr to 48 hr, preferably about 0.5 hr to 24 hr.

When compound (VIII) or a salt thereof is reacted with benzyl bromide, examples of the base to be used for this reaction include inorganic bases (alkali metal hydrides such as sodium hydride, lithium hydride and the like, alkali metal hydroxides such as lithium hydroxide, sodium hydroxide, potassium hydroxide and the like, alkali metal hydrogencarbonates such as sodium hydrogencarbonate, potassium hydrogencarbonate and the like, alkali metal carbonates such as lithium carbonate, sodium carbonate, potassium carbonate, cesium carbonate and the like, alkali metal alkoxides such as sodium methoxide, sodium ethoxide and the like, etc.), organic bases (amines such as trimethylamine, triethylamine, diisopropylethylamine and the like, cyclic amines such as pyridine, 4-dimethylaminopyridine and the like, etc.) and the like. Among them, potassium carbonate is preferable. While the amount of the base to be used varies depending on the kind of solvent and the other reaction condition, it is generally about 1 to 10 mol equivalent, preferably about 1 to 5 mol equivalent, per 1 mol of compound (VIII).

The amount of the benzyl bromide to be used is generally about 1 to 10 mol equivalent, preferably about 1 to 2 mol equivalent, per 1 mol of compound (VIII).

Examples of the solvent that does not adversely influence the reaction include aromatic hydrocarbons (benzene, toluene, xylene, etc.), aliphatic hydrocarbons (hexane, heptane, etc.), halogenated hydrocarbons (dichloromethane, chloroform, etc.), ethers (diethyl ether, diisopropyl ether, t-butyl methyl ether, tetrahydrofuran, dioxane, dimethoxyethane, etc.), nitriles (acetonitrile, etc.), esters (ethyl acetate, etc.), amides (dimethylformamide, etc.), sulfoxides (dimethyl sulfoxide, etc.) and the like. Among them, acetonitrile is preferable. These solvents may be used in a mixture of two or more kinds thereof in an appropriate ratio.

The reaction temperature is, for example, within about 0 to 200° C., preferably about 25 to 100° C. While the reaction time varies depending on the kind of compound (VIII) or a salt thereof, the reaction temperature and the like, it is, for example, about 0.5 to 100 hr, preferably about 0.5 to 24 hr.

When the amino group is protected by a PMB group, the reaction is carried out by reacting compound (VIII) or a salt thereof with 4-methoxybenzaldehyde in a solvent that does not adversely influence the reaction, and then treating the resulting compound with a reducing agent.

The kinds and amounts of the solvent, reducing agent, reagent and additive to be used in this step, the reaction temperature and the reaction time are the same as in the above-mentioned protection of the amino group by a Bn group.

When the amino group is protected by a $CF_3CO$ group, the reaction is carried out by reacting compound (VIII) or a salt thereof with trifluoroacetic anhydride in the presence of a base, in a solvent that does not adversely influence the reaction. The kinds and amounts of the base, solvent and reagent to be used in this step, the reaction temperature and the reaction time are the same as in the above-mentioned protection of the amino group by a Boc group.

(Step 6)

This step is a step of subjecting compound (X) or a salt thereof to hydrolysis to convert compound (X) or a salt thereof to compound (XI) or a salt thereof. This reaction can be carried out according to a method known per se, generally in the presence of an acid or a base, in a solvent that does not adversely influence the reaction, if necessary.

Examples of the acid include mineral acids (hydrochloric acid, hydrobromic acid, sulfuric acid, etc.), carboxylic acids (acetic acid, trifluoroacetic acid, trichloroacetic acid, etc.), sulfonic acids (methanesulfonic acid, p-toluenesulfonic acid, etc.), Lewis acids (aluminium chloride, tin chloride, zinc bromide, etc.) and the like, and they may be used in a mixture of two or more kinds thereof. While the amount of the acid to be used varies depending on the kind of solvent and the other reaction condition, it is generally about 0.1 mol equivalent or more, per 1 mol of compound (X). They may be used as a solvent.

Examples of the base include inorganic bases (alkali metal hydroxides such as lithium hydroxide, sodium hydroxide, potassium hydroxide and the like, alkali metal hydrogencarbonates such as sodium hydrogencarbonate, potassium hydrogencarbonate and the like, alkali metal carbonates such as sodium carbonate, potassium carbonate and the like, alkoxides such as sodium methoxide, sodium ethoxide and the like, etc.), organic bases (amines such as trimethylamine, triethylamine, diisopropylethylamine and the like, cyclic amines such as pyridine, 4-dimethylaminopyridine and the likes, etc.) and the like. Among them, sodium hydroxide is preferable. While the amount of the base to be used varies depending on the kind of solvent and the other reaction condition, it is generally about 0.1 to 10 mol equivalent, preferably about 1 to 5 mol equivalent, per 1 mol of compound (X).

Examples of the solvent that does not adversely influence the reaction include alcohols (methanol, ethanol, propanol, 2-propanol, butanol, isobutanol, t-butanol, etc.), hydrocarbons (benzene, toluene, xylene, hexane, heptane, etc.), halogenated hydrocarbons (dichloromethane, chloroform, etc.), ethers (diethyl ether, diisopropyl ether, t-butyl methyl ether, tetrahydrofuran, dioxane, dimethoxyethane, etc.), nitriles (acetonitrile, etc.), carboxylic acids (acetic acid, etc.), amides (dimethylformamide, dimethylacetamide, etc.), sulfoxides (dimethyl sulfoxide, etc.), water and the like. Among them, ethanol, tetrahydrofuran and water are preferable. These solvents may be used in a mixture of two or more kinds thereof in an appropriate ratio.

The reaction temperature is, for example, within about −50 to 200° C., preferably about 0 to 100° C. While the reaction time varies depending on the kind of compound (X) or a salt thereof, the reaction temperature and the like, it is, for example, about 0.5 to 100 hr, preferably about 0.5 to 24 hr.

(Step 7)

This step is a step of reacting compound (XI) or a salt thereof with compound (XII) or a salt thereof in the presence of a condensing agent to produce compound (XIII) or a salt thereof.

This step can be carried out in the same manner as in the "method using a condensing agent" in Method A.

(Step 8)

This step is a step of subjecting compound (XIII) or a salt thereof to a deprotection reaction to produce compound (II) or a salt thereof.

The deprotection reaction can be carried out according to a method known per se (e.g., the method described in "Protective Groups in Organic Synthesis, 3rd Ed", Wiley-Interscience, Inc. (1999) (Theodora W. Greene, Peter G. M. Wuts)).

When PG is a Boc group, the deprotection reaction can be carried out in the presence of an acid, in a solvent that does not adversely influence the reaction.

Examples of the acid include mineral acids (hydrochloric acid, hydrobromic acid, sulfuric acid, etc.), carboxylic acids (acetic acid, trifluoroacetic acid, trichloroacetic acid, etc.), sulfonic acids (methanesulfonic acid, p-toluenesulfonic acid, etc.), Lewis acids (aluminium chloride, tin chloride, zinc bromide, etc.) and the like, and they may be used in a mixture of two or more kinds thereof. While the amount of the acid to be used varies depending on the kind of solvent and the other reaction condition, it is generally about 0.1 mol equivalent or more, per 1 mol of compound (XIII). They may be used as a solvent.

Examples of the solvent that does not adversely influence the reaction include alcohols (methanol, ethanol, propanol, 2-propanol, butanol, isobutanol, t-butanol, etc.), aromatic hydrocarbons (benzene, toluene, xylene, etc.), aliphatic hydrocarbons (hexane, heptane, etc.), halogenated hydrocarbons (dichloromethane, chloroform, etc.), ethers (diethyl ether, diisopropyl ether, t-butyl methyl ether, tetrahydrofuran, dioxane, dimethoxyethane, etc.), nitriles (acetonitrile, etc.), esters (ethyl acetate, etc.), carboxylic acids (acetic acid, etc.), amides (N,N-dimethylformamide, etc.), sulfoxides (dimethyl sulfoxide, etc.), water, and mixed solvents thereof.

The reaction temperature is, for example, within about −50 to 200° C., preferably about 0 to 100° C. While the reaction time varies depending on the kind of compound (XIII) or a salt thereof, the reaction temperature and the like, it is, for example, about 0.5 to 100 hr, preferably about 0.5 to 24 hr.

When PG is a Bn group, a Cbz (Z) group or a PMB group, the deprotection reaction can be carried out by a catalytic hydrogenation reaction, an oxidation reaction or an acid hydrolysis.

The catalytic hydrogenation reaction can be carried out in the presence of a catalyst under hydrogen atmosphere. Examples of the catalyst include palladiums such as palladium on carbon, palladium hydroxide carbon, palladium oxide and the like; nickels such as Raney-nickel catalyst and the like; platinums such as platinum oxide, platinum on carbon and the like; rhodiums such as rhodium on carbon and the like, and the like. The amount thereof to be used is generally about 0.001 to 1 mol equivalent, preferably about 0.01 to 0.5 mol equivalent, per 1 mol of compound (XIII).

The catalytic hydrogenation reaction is generally carried out in a solvent inert to the reaction. Examples of the solvent include alcohols such as methanol, ethanol, propanol, butanol and the like; hydrocarbons such as benzene, toluene, xylene and the like; halogenated hydrocarbons such as dichloromethane, chloroform and the like; ethers such as diethyl ether, dioxane, tetrahydrofuran and the like; esters such as ethyl acetate and the like; amides such as N,N-dimethylformamide and the like; carboxylic acids such as acetic acid and the like; water and mixtures thereof.

The hydrogen pressure for the reaction is generally about 1 to 50 atm, preferably about 1 to 10 atm. The reaction temperature is generally about 0° C. to 150° C., preferably about 20° C. to 100° C., and the reaction time is generally about 5 min to 72 hr, preferably about 0.5 hr to 40 hr.

Examples of the oxidizing agent to be used for the oxidation reaction include ammonium cerium(IV) nitrate. The amount thereof to be used is about 1 to about 50 mol equivalent, per 1 mol of compound (XIII).

The oxidation reaction is carried out in a solvent that does not adversely influence the reaction. Examples of the solvent include nitriles (e.g., acetonitrile), hydrocarbons (e.g., benzene, toluene, xylene), halogenated hydrocarbons (e.g., dichloromethane, chloroform), ethers (e.g., diethyl ether, dioxane, tetrahydrofuran), amides (e.g., N,N-dimethylformamide), water and mixtures thereof.

The reaction temperature is generally about 0° C. to 150° C., preferably about 20° C. to 100° C., and the reaction time is generally about 5 min to 72 hr, preferably about 0.5 hr to 40 hr.

Examples of the acid to be used for the acid hydrolysis include trifluoroacetic acid. The acid may be used as a solvent. The reaction temperature is generally about 0° C. to 150° C., preferably about 0° C. to 30° C., and the reaction time is generally about 5 min to 72 hr, preferably about 0.5 hr to 40 hr.

When PG is a $CF_3CO$ group, the deprotection reaction can be carried out in the presence of a base, in a solvent that does not adversely influence the reaction.

Examples of the base include inorganic bases (alkali metal hydroxides such as lithium hydroxide, sodium hydroxide, potassium hydroxide and the like, alkali metal hydrogencarbonates such as sodium hydrogencarbonate, potassium hydrogencarbonate and the like, alkali metal carbonates such as sodium carbonate, potassium carbonate and the like, alkoxides such as sodium methoxide, sodium ethoxide and the like, etc.) and the like. The amount of the base to be used is about 1 to 100 mol equivalent, preferably about 1 to 20 mol equivalent, per 1 mol of compound (XIII).

Examples of the solvent that does not adversely influence as the reaction include hydrocarbons (benzene, toluene, xylene, hexane, heptane, etc.), halogenated hydrocarbons (dichloromethane, chloroform, etc.), ethers (diethyl ether, diisopropyl ether, t-butyl methyl ether, tetrahydrofuran, dioxane, dimethoxyethane, etc.), nitriles (acetonitrile, etc.), amides (N,N-dimethylformamide, N,N-dimethylacetamide, etc.), sulfoxides (dimethyl sulfoxide, etc.), water and the like. These solvents may be used in a mixture of two or more kinds thereof in an appropriate ratio.

The reaction temperature is, for example, within about −50 to 200° C., preferably about 0 to 100° C. While the reaction time varies depending on the kind of compound (XIII) or a salt thereof, the reaction temperature and the like, it is, for example, about 0.5 to 24 hr, preferably about 0.5 to 2 hr.

[Method C]

When compound (XI) is a compound represented by the formula:

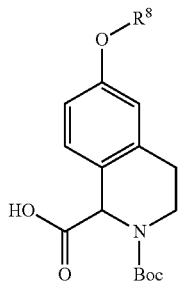

(XIa)

wherein $R^8$ is an optionally substituted $C_{1-6}$ alkyl group, and the other symbols are as defined above (hereinafter to be referred to as compound (XIa)) or a salt thereof, this compound can be produced according to Method C.

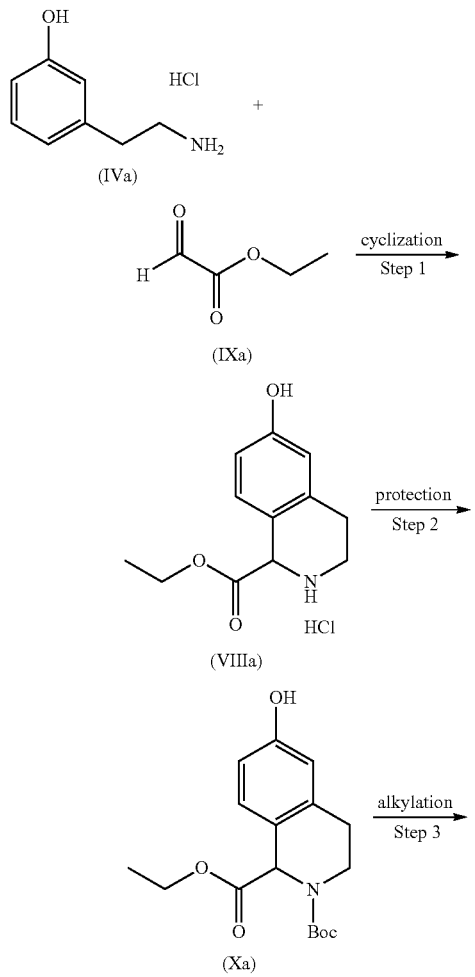

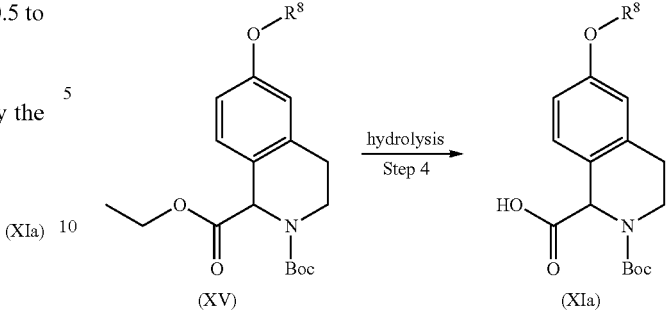

wherein Boc is a tert-butoxycarbonyl group, and the other symbols are as defined above.

(Step 1)

This step is a step of subjecting compound (IVa) to a cyclization reaction with compound (IXa) to produce compound (VIIIa).

Compound (IVa) and compound (IXa) used for this reaction may be a commercially available product, or can also be produced according to a method known per se or a method analogous thereto.

The amount of compound (IXa) to be used is generally about 1 to 10 mol equivalent, preferably about 1 to 2 mol equivalent, per 1 mol of compound (IVa).

This step is carried out in a solvent that does not adversely influence the reaction. Examples of the solvent that does not adversely influence the reaction include alcohols (methanol, ethanol, propanol, 2-propanol, butanol, isobutanol, t-butanol, etc.), aromatic hydrocarbons (benzene, toluene, xylene, etc.), aliphatic hydrocarbons (hexane, heptane, etc.), halogenated hydrocarbons (dichloromethane, chloroform, etc.), ethers (diethyl ether, diisopropyl ether, t-butyl methyl ether, tetrahydrofuran, dioxane, dimethoxyethane, etc.), nitriles (acetonitrile, etc.), esters (ethyl acetate, etc.) and the like.

The reaction temperature is, for example, within about 0 to 200° C., preferably about 25 to 100° C. While the reaction time varies depending on the reaction temperature and the like, it is, for example, about 0.5 to 100 hr, preferably about 0.5 to 24 hr.

(Step 2)

This step is a step of subjecting compound (VIIIa) to a protection reaction by a Boc group to produce compound (Xa).

This reaction is carried out by reacting compound (VIIIa) with di-tert-butyl dicarbonate (Boc$_2$O) in the presence of a base, in a solvent that does not adversely influence the reaction.

Examples of the base to be used in this step include inorganic bases (alkali metal hydrides such as sodium hydride, lithium hydride and the like, alkali metal hydroxides such as lithium hydroxide, sodium hydroxide, potassium hydroxide and the like, alkali metal hydrogencarbonates such as sodium hydrogencarbonate, potassium hydrogencarbonate and the like, alkali metal carbonates such as lithium carbonate, sodium carbonate, potassium carbonate, cesium carbonate and the like, alkali metal alkoxides such as sodium methoxide, sodium ethoxide and the like, etc.), organic bases (amines such as trimethylamine, triethylamine, diisopropylethylamine and the like, cyclic amines such as pyridine, 4-dimethylaminopyridine and the like, etc.) and the like. Among them, sodium hydride and triethylamine are preferable. While the amount of the base to be used varies depending on the kind of solvent and the other reaction condition, it is generally about 1 to 10 mol equivalent, preferably about 1 to 5 mol equivalent, per 1 mol of compound (VIIIa).

Examples of the solvent that does not adversely influence the reaction include aromatic hydrocarbons (benzene, toluene, xylene, etc.), aliphatic hydrocarbons (hexane, heptane, etc.), halogenated hydrocarbons (dichloromethane, chloroform, etc.), ethers (diethyl ether, diisopropyl ether, t-butyl methyl ether, tetrahydrofuran, dioxane, dimethoxyethane, etc.), nitriles (acetonitrile, etc.), esters (ethyl acetate, etc.), amides (dimethylformamide, etc.), sulfoxides (dimethyl sulfoxide, etc.), and water and the like. These solvents may be used in a mixture of two or more kinds thereof in an appropriate ratio.

The amount of the $Boc_2O$ used in this step is about 1 to 10 mol equivalent, preferably about 1 to 2 mol equivalent, per 1 mol of compound (VIIIa).

The reaction temperature is, for example, within about −10 to 100° C. While the reaction time varies depending on the kind of compound (VIIIa) or a salt thereof, the reaction temperature and the like, it is, for example, about 0.5 to 100 hr, preferably about 0.5 to 24 hr.

(Step 3)

This step is a step of subjecting compound (Xa) to an alkylation reaction with a compound represented by the formula:

wherein each symbol is as defined above (hereinafter to be referred to as compound (XIV)) or a salt thereof, in the presence of a base, to produce compound (XV) or a salt thereof.

Compound (XIV) may be a commercially available product, or can also be produced according to a method known per se or a method analogous thereto.

Examples of the base used for this reaction include inorganic bases (alkali metal hydrides such as sodium hydride, lithium hydride and the like, alkali metal hydroxides such as lithium hydroxide, sodium hydroxide, potassium hydroxide and the like, alkali metal hydrogencarbonates such as sodium hydrogencarbonate, potassium hydrogencarbonate and the like, alkali metal carbonates such as lithium carbonate, sodium carbonate, potassium carbonate, cesium carbonate and the like) and the like. While the amount of the base to be used varies depending on the kind of solvent and the other reaction condition, it is generally about 1 to 10 mol equivalent, preferably about 1 to 5 mol equivalent, per 1 mol of compound (Xa).

The amount of compound (XIV) to be used is generally about 1 to 10 mol equivalent, preferably about 1 to 3 mol equivalent, per 1 mol of compound (Xa).

This step is carried out in a solvent that does not adversely influence the reaction. Examples of the solvent that does not adversely influence the reaction include aromatic hydrocarbons (benzene, toluene, xylene, etc.), aliphatic hydrocarbons (hexane, heptane, etc.), halogenated hydrocarbons (dichloromethane, chloroform, etc.), ethers (diethyl ether, diisopropyl ether, t-butyl methyl ether, tetrahydrofuran, dioxane, dimethoxyethane, etc.), nitriles (acetonitrile, etc.), esters (ethyl acetate, etc.), amides (dimethylformamide, etc.), sulfoxides (dimethyl sulfoxide, etc.) and the like. These solvents may be used in a mixture of two or more kinds thereof in an appropriate ratio.

The reaction temperature is, for example, within about −75 to 200° C., preferably about −10 to 30° C. While the reaction time varies depending on the kind of compound (Xa), the reaction temperature and the like, it is, for example, about 0.5 to 100 hr, preferably about 0.5 to 24 hr.

(Step 4)

This step is a step of subjecting compound (XV) or a salt thereof to hydrolysis to convert compound (XV) or a salt thereof to compound (XIa) or a salt thereof.

This step can be carried out in the same manner as in the method described in Step 6 of Method B

[Method D]

When compound (XI) is a compound represented by the formula:

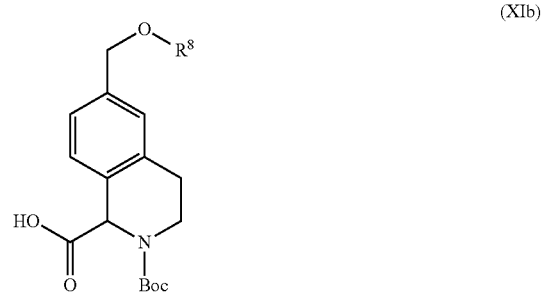

wherein $R^8$ is an optionally halogenated $C_{1-6}$ alkyl group, and the other symbols are as defined above (hereinafter to be referred to as compound (XIb)) or a salt thereof, this compound can be produced according to Method D.

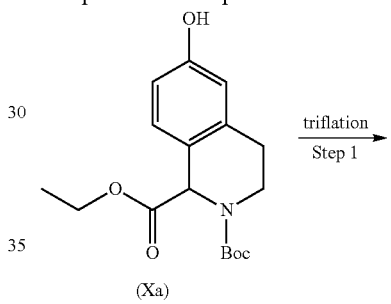

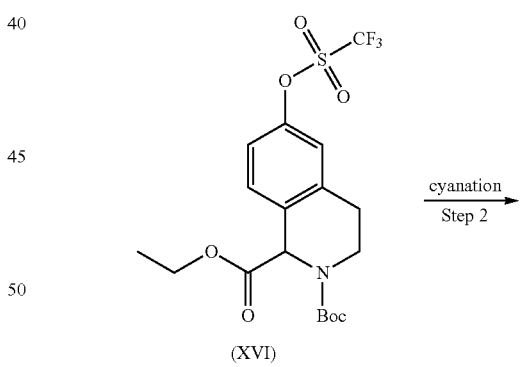

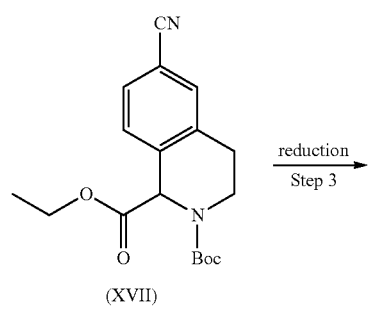

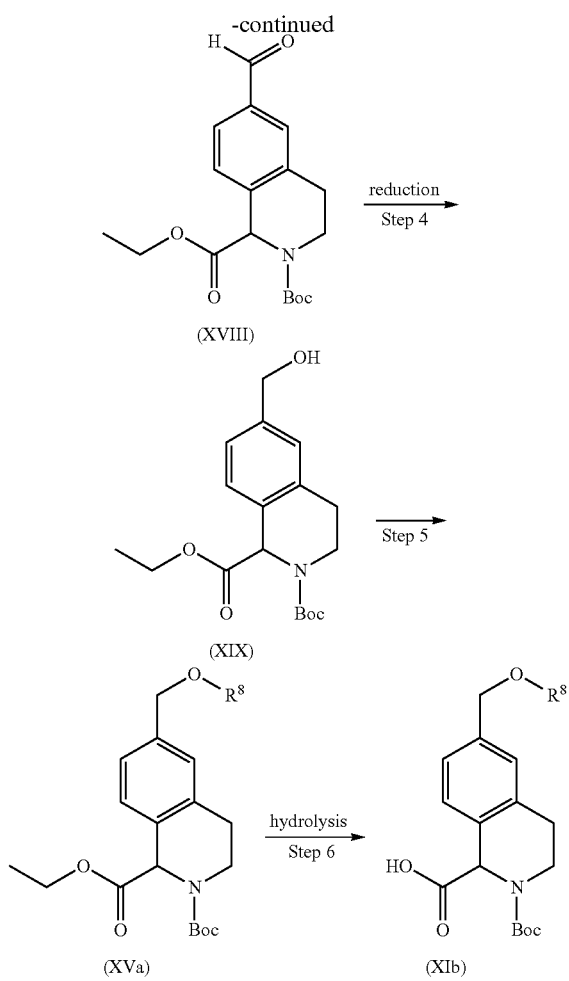

wherein each symbol is as defined above.
(Step 1)

This step is a step of subjecting compound (Xa) to a triflation reaction to produce compound (XVI).

This reaction can be carried out in the presence of a base and a triflating agent.

Examples of the base used for this reaction include inorganic bases (alkali metal hydrides such as sodium hydride, lithium hydride and the like, alkali metal hydroxides such as lithium hydroxide, sodium hydroxide, potassium hydroxide and the like, alkali metal hydrogencarbonates such as sodium hydrogencarbonate, potassium hydrogencarbonate and the like, alkali metal carbonates such as lithium carbonate, sodium carbonate, potassium carbonate, cesium carbonate and the like, etc.), organic bases (amines such as trimethylamine, triethylamine, diisopropylethylamine, 1,8-diazabicyclo[5,4,0]undec-7-ene and the like, cyclic amines such as pyridine, 4-dimethylaminopyridine and the like, etc.) and the like. While the amount of the base to be used varies depending on the kind of solvent and the other reaction condition, it is generally about 1 to 10 mol equivalent, preferably about 1 to 5 mol equivalent, per 1 mol of compound (Xa).

Examples of the triflating agent used for this reaction include trifluoromethanesulfonyl chloride, trifluoromethanesulfonic anhydride, N-phenylbis(trifluoromethanesulfonimide), N-(5-chloro-2-pyridyl)triflimide and the like. While the amount of the triflating agent to be used varies depending on the kind of solvent and the other reaction condition, it is generally about 1 to 10 mol equivalent, preferably about 1 to 5 mol equivalent, per 1 mol of compound (Xa).

This step is carried out in a solvent that does not adversely influence the reaction. Examples of the solvent that does not adversely influence the reaction include aromatic hydrocarbons (benzene, toluene, xylene, etc.), aliphatic hydrocarbons (hexane, heptane, etc.), halogenated hydrocarbons (dichloromethane, chloroform, etc.), ethers (diethyl ether, diisopropyl ether, t-butyl methyl ether, tetrahydrofuran, dioxane, dimethoxyethane, etc.), nitriles (acetonitrile, etc.), esters (ethyl acetate, etc.), amides (dimethylformamide, etc.), sulfoxides (dimethyl sulfoxide, etc.) and the like. These solvents may be used in a mixture of two or more kinds thereof in an appropriate ratio.

The reaction temperature is, for example, within about −10 to 100° C. While the reaction time varies depending on the kind of compound (Xa), the reaction temperature and the like, it is, for example, about 0.5 to 100 hr, preferably about 0.5 to 24 hr.
(Step 2)

This step is a step of subjecting compound (XVI) to a cyanation reaction to produce compound (XVII).

This reaction can be carried out using a cyanating agent in the presence of a transition metal catalyst, in a solvent that does not adversely influence the reaction.

Examples of the transition metal catalyst used for this reaction include palladium catalysts (palladium acetate, palladium chloride, tetrakis(triphenylphosphine)palladium, etc.), nickel catalysts (nickel chloride, etc.) and the like. Where necessary, a ligand (triphenylphosphine, tri-tert-butylphosphine, S-Phos, BINAP, etc.) can be used. While the amount of the transition metal catalyst to be used varies depending on the kind of solvent and the other reaction condition, it is generally about 0.001 to 1 mol equivalent, preferably about 0.1 to 0.5 mol equivalent, per 1 mol of compound (XVI). The amount of the ligand to be used is about 0.001 to 1 mol equivalent, per 1 mol of compound (XVI).

Examples of the cyanating agent used for this reaction include zinc cyanide, copper cyanide and the like. While the amount of the cyanating agent to be used varies depending on the kind of solvent and the other reaction condition, it is generally about 0.5 to 10 mol equivalent, preferably about 0.5 to 2 mol equivalent, per 1 mol of compound (XVI).

Examples of the solvent that does not adversely influence the reaction include aromatic hydrocarbons (benzene, toluene, xylene, etc.), aliphatic hydrocarbons (hexane, heptane, etc.), halogenated hydrocarbons (dichloromethane, chloroform, etc.), ethers (diethyl ether, diisopropyl ether, t-butyl methyl ether, tetrahydrofuran, dioxane, dimethoxyethane, etc.), nitriles (acetonitrile, etc.), esters (ethyl acetate, etc.), amides (dimethylformamide, etc.), sulfoxides (dimethyl sulfoxide, etc.) and the like. These solvents may be used in a mixture of two or more kinds thereof in an appropriate ratio.

The reaction temperature is, for example, within about −10 to 200° C. While the reaction time varies depending on the kind of compound (XVI), the reaction temperature and the like, it is, for example, about 0.5 to 100 hr, preferably about 0.5 to 24 hr. Where necessary, the reaction may be carried out under microwave irradiation.
(Step 3)

This step is a step of subjecting compound (XVII) to a reduction reaction to produce compound (XVIII).

The reduction reaction can be carried out in the presence of Raney-nickel catalyst, under hydrogen atmosphere or using a hydrogen donor.

The amount of the Raney-nickel catalyst to be used is generally about 0.001 to 10 mol equivalent, preferably about 0.01 to 2 mol equivalent, per 1 mol of compound (XVII).

The hydrogen pressure for the reaction is generally about 1 to 50 atm, preferably about 1 to 10 atm.

Examples of the hydrogen donor include sodium hypophosphite. The amount thereof to be used is generally about 1 to 100 mol equivalent, preferably about 1 to 20 mol equivalent, per 1 mol of compound (XVII).

This reaction is carried out in a solvent inert to the reaction. Examples of the solvent include alcohols such as methanol, ethanol, propanol, butanol and the like; hydrocarbons such as benzene, toluene, xylene and the like; halogenated hydrocarbons such as dichloromethane, chloroform and the like; ethers such as diethyl ether, dioxane, tetrahydrofuran and the like; esters such as ethyl acetate and the like; amides such as N,N-dimethylformamide and the like; carboxylic acids such as acetic acid and the like; bases such as pyridine, triethylamine and the like; water and mixtures thereof.

The reaction temperature is generally about 0° C. to 150° C., preferably about 20° C. to 100° C., and the reaction time is generally about 5 min to 72 hr, preferably about 0.5 hr to 40 hr.

(Step 4)

This step is a step of treating compound (XVIII) with a reducing agent to produce compound (XIX).

Examples of the reducing agent to be used for this reaction include metal hydrides (e.g., sodium borohydride, lithium borohydride, zinc borohydride, sodium cyanoborohydride, sodium triacetoxyborohydride, lithium cyanoborohydride) and the like. The amount of the metal hydride to be used is about 1 to 50 mol equivalent, per 1 mol of compound (XVIII).

This reaction is carried out in a solvent that does not adversely influence the reaction. Examples of the solvent include alcohols such as methanol, ethanol, propanol, butanol and the like; hydrocarbons such as benzene, toluene, xylene and the like; halogenated hydrocarbons such as dichloromethane, chloroform and the like; ethers such as diethyl ether, dioxane, tetrahydrofuran and the like; esters such as ethyl acetate and the like; amides such as N,N-dimethylformamide and the like; carboxylic acids such as acetic acid and the like; water and mixtures thereof.

The reaction temperature is, for example, within about −50 to 200° C., preferably about 0 to 50° C. While the reaction time varies depending on the kind of compound (XVIII), the reaction temperature and the like, it is, for example, about 0.1 to 100 hr, preferably about 0.1 to 6 hr.

(Step 5)

This step is a step of subjecting compound (XIX) to a mesylation reaction to convert compound (XIX) into a compound represented by the formula:

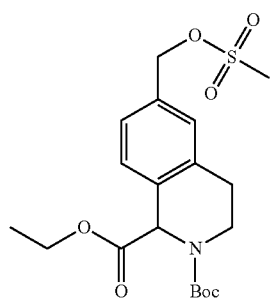

(XIXa)

wherein each symbol is as defined above (hereinafter to be referred to as compound (XIXa)), and then reacting compound (XIXa) with a compound represented by the formula:

$R^8$—OH     (XIVa)

wherein each symbol is as defined above (hereinafter to be referred to as compound (XIVa)) or a salt thereof in the presence of a base to produce compound (XVa) or a salt thereof.

The mesylation reaction can be carried out in the presence of a base and a mesylating agent.

Compound (XIVa) or a salt thereof may be a commercially available product, or can also be produced according to a method known per se or a method analogous thereto.

The kind and amount of the base for the mesylation reaction are the same as in Step 1 of Method D.

Examples of the mesylating agent include methanesulfonyl chloride and the like. While the amount of the mesylating agent to be used varies depending on the kind of solvent and the other reaction condition, it is generally about 1 to 10 mol equivalent, preferably about 1 to 5 mol equivalent, per 1 mol of compound (XIX).

Examples of the base for the reaction of compound (XIXa) with compound (XIVa) or a salt thereof in the presence of a base include organic amines (trimethylamine, triethylamine, diisopropylamine, N-methylmorpholine, 1,8-diazabicyclo[5,4,0]undec-7-ene, pyridine, N,N-dimethylaniline, etc.), alkali metal salts (sodium hydrogencarbonate, potassium hydrogencarbonate, sodium carbonate, potassium carbonate, cesium carbonate, sodium phosphate, potassium phosphate, sodium hydroxide, potassium hydroxide, lithium acetate, etc.), metal hydrides (potassium hydride, sodium hydride, etc.) and the like. The amount of the base to be used is about 1 to 10 mol equivalent, per 1 mol of compound (XIXa).

This step is carried out in a solvent that does not adversely influence the reaction. Examples of the solvent that does not adversely influence the reaction include hydrocarbons (benzene, toluene, xylene, etc.), halogenated hydrocarbons (chloroform, 1,2-dichloroethane, etc.), nitriles (acetonitrile, etc.), ethers (dimethoxyethane, tetrahydrofuran), aprotic polar solvents (dimethylformamide, dimethyl sulfoxide, hexamethylphosphoroamide, etc.) and mixtures thereof. Compound (XIVa) may be used as a solvent.

The reaction temperature is generally about −100 to 200° C., preferably about −20 to 100° C., and the reaction time is generally about 0.5 to 48 hr, preferably about 0.5 to 24 hr.

(Step 6)

This step is a step of subjecting compound (XVa) or a salt thereof to hydrolysis to convert compound (XVa) or a salt thereof to compound (XIb) or a salt thereof.

This step can be carried out in the same manner as in the method described in Step 6 of Method B.

[Method E]

When compound (XI) is a compound represented by the formula:

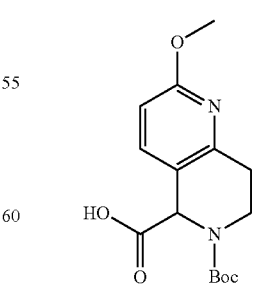

(XIc)

wherein each symbol is as defined above (hereinafter to be referred to as compound (XIc)) or a salt thereof, this compound can be produced according to Method E.

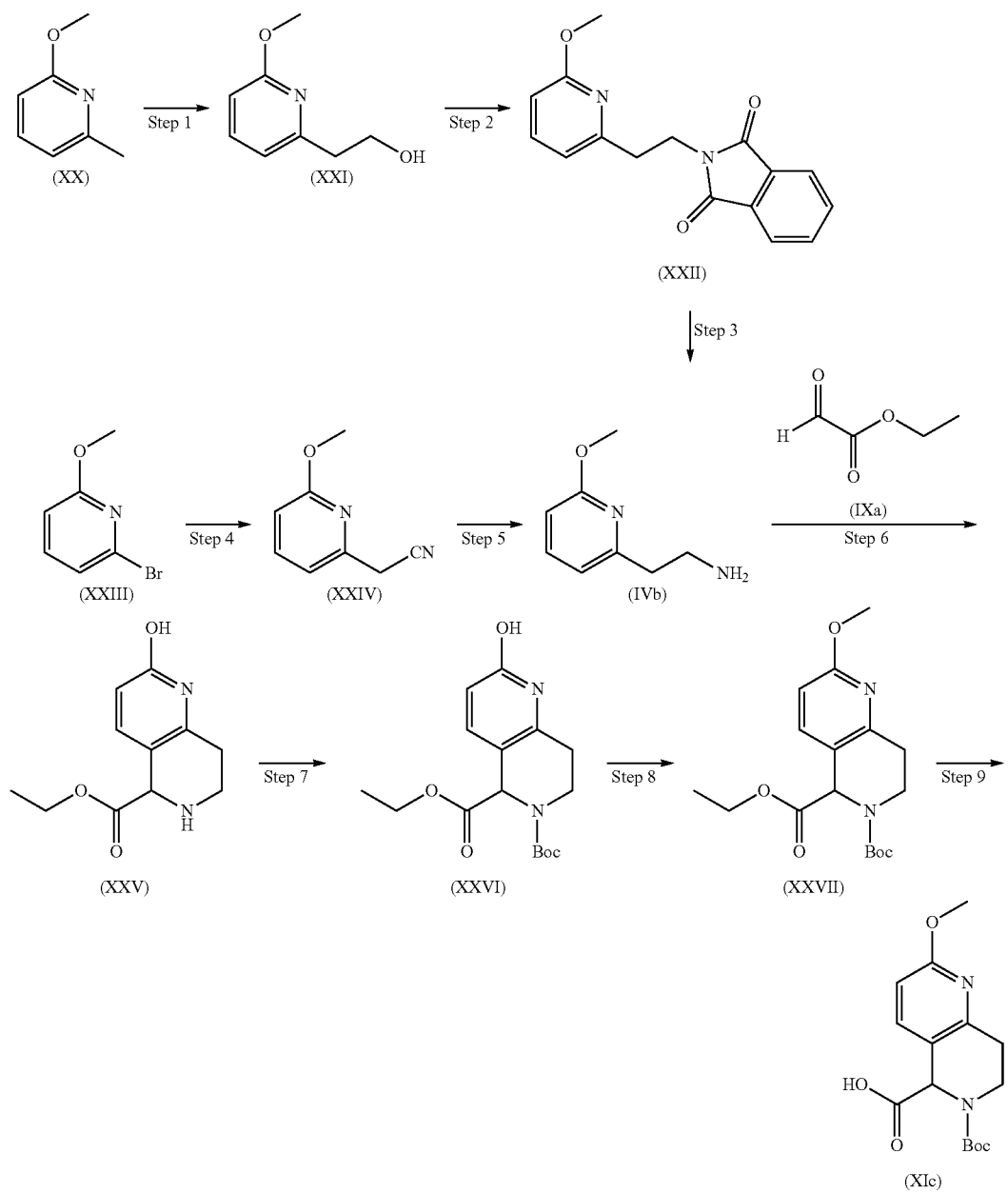

wherein each symbol is as defined above.

(Step 1)

This step is a step of subjecting compound (XX) or a salt thereof to a hydroxymethylation reaction to convert compound (XX) or a salt thereof to compound (XXI) or a salt thereof.

Compound (XX) or a salt thereof may be a commercially available product, or can also be produced according to a method known per se or a method analogous thereto.

In this reaction, compound (XXI) or a salt thereof can be produced by reacting compound (XX) or a salt thereof with paraformaldehyde in the presence of a base.

Examples of the base used for this reaction include organic lithium reagents (e.g., n-butyllithium, phenyllithium, lithiumdiisopropylamide), alkali metal hydrides (e.g., sodium hydride, lithium hydride) and the like. While the amount of the base to be used varies depending on the kind of solvent and the other reaction condition, it is generally about 1 to 10 mol equivalent, preferably about 1 to 2 mol equivalent, per 1 mol of compound (XX).

The amount of the paraformaldehyde used for this reaction to be used is about 1 to 10 mol equivalent, preferably about 1 to 5 mol equivalent, per 1 mol of compound (XX).

This step is carried-out in a solvent that does not adversely influence the reaction. Examples of the solvent that does not adversely influence the reaction include aromatic hydrocarbons (benzene, toluene, xylene, etc.), aliphatic hydrocarbons (hexane, heptane, etc.), halogenated hydrocarbons (dichloromethane, chloroform, etc.), ethers (diethyl ether, diisopropyl ether, t-butyl methyl ether, tetrahydrofuran, dioxane, dimethoxyethane, etc.) and the like. These solvents may be used in a mixture of two or more kinds thereof in an appropriate ratio.

The reaction temperature is, for example, within about −100 to 50° C., preferably about −78 to 25° C., and the reaction time is, for example, about 0.5 to 100 hr, preferably about 0.5 to 24 hr.

(Step 2)

This step is a step of subjecting compound (XXI) or a salt thereof to phthalimidation reaction to convert compound (XXI) or a salt thereof to compound (XXII) or a salt thereof.

In this reaction, compound (XXII) or a salt thereof can be produced by reacting compound (XXI) or a salt thereof with phthalimide in the presence of an azodicarboxylate reagent and triphenylphosphine.

Examples of the azodicarboxylate reagent used for this reaction include diethyl azodicarboxylate (DEAD) and diisopropyl azodicarboxylate (DIAD). While the amount of the azodicarboxylate reagent to be used varies depending on the kind of solvent and the other reaction condition, it is generally about 1 to 5 mol equivalent, preferably about 1 to 2 mol equivalent, per 1 mol of compound (XXI).

The amount of the triphenylphosphine used for this reaction to be used is about 1 to 5 mol equivalent, preferably about 1 to 2 mol equivalent, per 1 mol of compound (XXI).

The amount of the phthalimide used for this reaction to be used is about 1 to 5 mol equivalent, preferably about 1 to 2 mol equivalent, per 1 mol of compound (XXI).

This step is carried out in a solvent that does not adversely influence the reaction. Examples of the solvent that does not adversely influence the reaction include aromatic hydrocarbons (benzene, toluene, xylene, etc.), aliphatic hydrocarbons (hexane, heptane, etc.), halogenated hydrocarbons (dichloromethane, chloroform, etc.), ethers (diethyl ether, diisopropyl ether, t-butyl methyl ether, tetrahydrofuran, dioxane, dimethoxyethane, etc.) and the like. These solvents may be used in a mixture of two or more kinds thereof in an appropriate ratio.

The reaction temperature is, for example, within about −50 to 50° C., preferably about 0 to 25° C., and the reaction time is, for example, about 0.5 to 100 hr, preferably about 0.5 to 24 hr.

(Step 3)

This step is a step of reacting compound (XXII) or a salt thereof with hydrazine to convert compound (XXII) or a salt thereof to compound (IVb) or a salt thereof.

The amount of the hydrazine used for this reaction to be used is about 1 to 20 mol equivalent, preferably about 3 to 7 mol equivalent, per 1 mol of compound (XXII).

This step is carried out in a solvent that does not adversely influence the reaction. Examples of the solvent that does not adversely influence the reaction include alcohols (methanol, ethanol, propanol, 2-propanol, butanol, isobutanol, t-butanol, etc.), water, nitriles (acetonitrile, etc.), amides (dimethylformamide, dimethylacetamide, etc.), sulfoxides (dimethyl sulfoxide, etc.), ethers (diethyl ether, diisopropyl ether, t-butyl methyl ether, tetrahydrofuran, dioxane, dimethoxyethane, etc.) and the like. These solvents may be used in a mixture of two or more kinds thereof in an appropriate ratio.

The reaction temperature is, for example, within about 0 to 200° C., preferably about 0 to 100° C., and the reaction time is, for example, about 0.5 to 100 hr, preferably about 0.5 to 24 hr.

(Step 4)

This step is a step of subjecting compound (XXIII) or a salt thereof to a cyanomethylation reaction to convert compound (XXIII) or a salt thereof to compound (XXIV) or a salt thereof.

Compound (XXIII) or a salt thereof may be a commercially available product, or can also be produced according to a method known per se or a method analogous thereto.

In this step, compound (XXIV) or a salt thereof is produced by treating acetonitrile in the presence of n-butyllithium to produce lithioacetonitrile, and then reacting the lithioacetonitrile with compound (XXIII) or a salt thereof.

The amounts of the n-butyllithium and acetonitrile used in the production of the lithioacetonitrile to be used are about 1 to 10 mol equivalent, preferably about 1 to 5 mol equivalent, per 1 mol of compound (XXIII), respectively.

This step is carried out in a solvent that does not adversely influence the reaction. Examples of the solvent that does not adversely influence the reaction include aromatic hydrocarbons (benzene, toluene, xylene, etc.), aliphatic hydrocarbons (hexane, heptane, etc.), halogenated hydrocarbons (dichloromethane, chloroform, etc.), ethers (diethyl ether, diisopropyl-ether, t-butyl methyl ether, tetrahydrofuran, dioxane, dimethoxyethane, etc.) and the like. These solvents may be used in a mixture of two or more kinds thereof in an appropriate ratio.

The reaction temperature is, for example, within about −100 to 50° C., preferably about −78 to 25° C., and the reaction time is, for example, about 0.5 to 100 hr, preferably about 0.5 to 8 hr.

(Step 5)

This step is a step of subjecting compound (XXIV) or a salt thereof to a catalytic hydrogenation reaction using a transition metal catalyst to produce compound (IVb) or a salt thereof.

Examples of the transition metal catalyst used for this reaction include palladiums (palladium on carbon, palladium hydroxide, palladium oxide, etc.), nickels (Raney-nickel, etc.), platinums (platinum oxide, platinum on carbon, etc.), rhodiums (rhodium acetate, rhodium on carbon, etc.) and the like. The amount thereof to be used is, for example, about 0.001 to 1 equivalent, preferably about 0.01 to 0.5 equivalent, per 1 mol of compound (XXIV).

The catalytic hydrogenation reaction is generally carried out in a solvent inert to the reaction. Examples of the solvent include alcohols (methanol, ethanol, propanol, butanol, etc.), hydrocarbons (benzene, toluene, xylene, etc.), halogenated hydrocarbons (dichloromethane, chloroform, etc.), ethers (diethyl ether, dioxane, tetrahydrofuran, etc.), esters (ethyl acetate, etc.), amides (N,N-dimethylformamide, etc.), carboxylic acids (acetic acid, etc.), water and mixtures thereof. The hydrogen pressure for the reaction is generally about 1 to 50 atm, preferably about 1 to 10 atm.

The reaction temperature is generally about 0 to 150° C., preferably about 20 to 100° C., and the reaction time is generally about 5 min to 72 hr, preferably about 0.5 to 40 hr.

(Step 6)

This step is a step of subjecting compound (IVb) or a salt thereof to a cyclization reaction with compound (IXa) to produce compound (XXV) or a salt thereof.

This step can be carried out in the same manner as in the method described in Step 1 of Method C.

(Step 7)

This step is a step of subjecting compound (XXV) or a salt thereof to an amino-protection reaction with a t-butoxycarbonyl (Boc) group to produce compound (XXVI) or a salt thereof.

This step can be carried out in the same manner as in the method described in Step 5 of Method B.

(Step 8)

This step is a step of subjecting compound (XXVI) or a salt thereof to an O-methylation reaction to produce compound (XXVII) or a salt thereof.

In this reaction, compound (XXVII) or a salt thereof can be produced by reacting compound (XXVI) or a salt thereof with methyl iodide in the presence of a base.

Examples of the base used for this reaction include silver salts (e.g., silver carbonate, silver nitrate, silver sulfate, silver acetate, silver chloride).

The amount of the silver salt used for this reaction to be used is about 1 to 5 mol equivalent, preferably about 1 to 2 mol equivalent, per 1 mol of compound (XXVI).

This step can be carried out in the same manner as in the method described in Step 3 of Method C.

(Step 9)

This step is a step of subjecting compound (XXVII) or a salt thereof to hydrolysis to convert compound (XXVII) or a salt thereof to compound (XIc) or a salt thereof.

This step can be carried out in the same manner as in the method described in Step 6 of Method B.

[Method F]

When compound (XII) is a compound represented by the formula:

(XIIa)

(hereinafter to be referred to as compound (XIIa)) or a salt thereof, this compound can be produced according to Method F.

(XXVIII) →Step 1→ (XXIX) →Step 2→ (XIIa)

(Step 1)

This step is a step of reacting compound (XXVIII) with a silylating agent in the presence of a transition metal catalyst or in the non-presence of a transition metal catalyst to produce compound (XXIX).

Compound (XXVIII) may be a commercially available product.

Examples of the transition metal catalyst used for this reaction include palladium catalysts (palladium acetate, palladium chloride, tetrakis(triphenylphosphine)palladium, etc.), nickel catalysts (nickel chloride, etc.) and the like. Where necessary, a ligand (triphenylphosphine, tri-t-butyl-phosphine, S-Phos, BINAP, etc.) or a base (e.g., organic amines (trimethylamine, triethylamine, diisopropylamine, N-methylmorpholine, 1,8-diazabicyclo[5,4,0]undec-7-ene, pyridine, N,N-dimethylaniline, etc.), alkali metal salts (sodium hydrogencarbonate, potassium hydrogencarbonate, sodium carbonate, potassium carbonate, cesium carbonate, sodium phosphate, potassium phosphate, sodium hydroxide, potassium hydroxide, etc.), metal hydrides (potassium hydride, sodium hydride, etc.), alkali metal alkoxides (sodium methoxide, sodium ethoxide, sodium t-butoxide, potassium t-butoxide, etc.), alkali disilazides (lithium disilazide, sodium disilazide, potassium disilazide, etc.)) may be added. A metal oxide (copper oxide, silver oxide, etc.) and the like may be used as a co-catalyst. The amount of the catalyst to be used is about 0.0001 to 1 mol equivalent, preferably about 0.01 to 0.5 mol equivalent, per 1 mol of compound (XXVIII). The amount of the ligand to be used is about 0.0001 to 4 mol equivalent, preferably about 0.01 to 2 mol equivalent, per 1 mol of compound (XXVIII). The amount of the base to be used is about 1 to 10 mol equivalent, preferably about 1 to 2 mol equivalent, per 1 mol of compound (XXVIII). The amount of the co-catalyst to be used is about 0.0001 to 4 mol equivalent, preferably about 0.01 to 2 mol equivalent, per 1 mol of compound (XXVIII).

Examples of the silylating agent include 1,1,1,2,2,2-hexamethyldisilane and chlorotrimethylsilane. The amount of the silylating agent to be used is about 1 to 10 mol equivalent, preferably about 1 to 4 mol equivalent, per 1 mol of compound (XXVIII).

The solvent is not limited as long as it does not adversely influence the reaction, and examples thereof include hydrocarbons (benzene, toluene, xylene, etc.), halogenated hydrocarbons (chloroform, 1,2-dichloroethane, etc.), nitriles (acetonitrile, etc.), ethers (dimethoxyethane, tetrahydrofuran), alcohols (methanol, ethanol, etc.), aprotic polar solvents (dimethylformamide, dimethyl sulfoxide, hexamethylphosphoroamide, etc.), water and mixtures thereof.

The reaction temperature is generally about −100 to 200° C., preferably about −80 to 150° C., and the reaction time is generally about 0.5 to 48 hr, preferably about 0.5 to 24 hr. Where necessary, the reaction may be carried out under microwave irradiation.

(Step 2)

This step is a step of subjecting compound (XXIX) to a catalytic hydrogenation reaction using a transition metal catalyst to produce compound (XIIa) or a salt thereof.

Examples of the transition metal catalyst used for this reaction include palladiums (palladium on carbon, palladium hydroxide, palladium oxide, etc.), nickels (Raney-nickel, etc.), platinums (platinum oxide, platinum on carbon, etc.), rhodiums (rhodium acetate, rhodium on carbon, etc.) and the like. The amount thereof to be used is, for example, about 0.001 to 1 equivalent, preferably about 0.01 to 0.5 equivalent, per 1 mol of compound (XXIX). The catalytic hydrogenation reaction is generally carried out in a solvent inert to the reaction. Examples of the solvent include alcohols (methanol, ethanol, propanol, butanol, etc.), hydrocarbons (benzene, toluene, xylene, etc.), halogenated hydrocarbons (dichloromethane, chloroform, etc.), ethers (diethyl ether, dioxane, tetrahydrofuran, etc.), esters (ethyl acetate, etc.), amides (N,N-dimethylformamide, etc.), carboxylic acids (acetic acid, etc.), water and mixtures thereof. The hydrogen pressure for the reaction is generally about 1 to 50 atm, preferably about 1 to 10 atm.

The reaction temperature is generally about 0 to 150° C., preferably about 20 to 100° C., and the reaction time is generally about 5 min to 72 hr, preferably about 0.5 to 40 hr.

[Method G]

When compound (XII) is a compound represented by the formula:

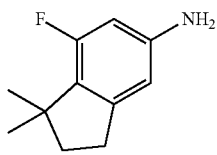

(XIIb)

(hereinafter to be referred to as compound (XIIb)) or a salt thereof, this compound can be produced according to Method G1 or Method G2.

[Method G1]

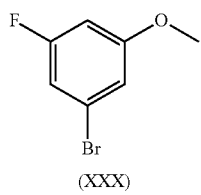

(XXX)

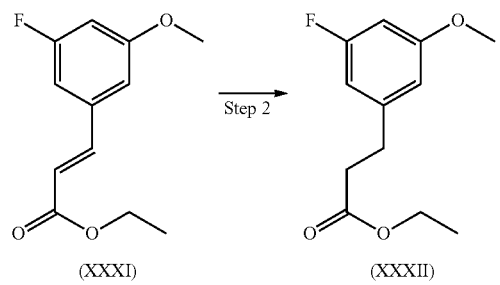

(XXXI)    (XXXII)

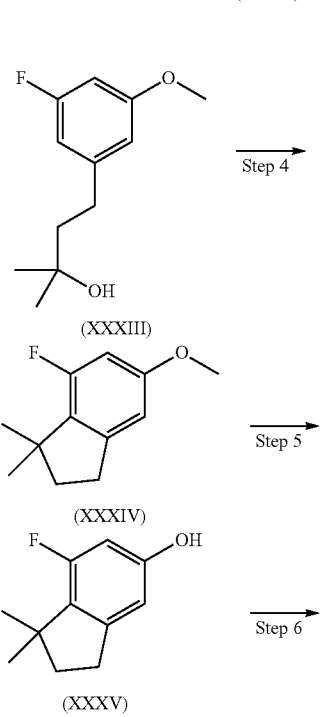

(XXXIII)

(XXXIV)

(XXXV)

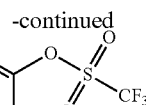

(XXXVI)

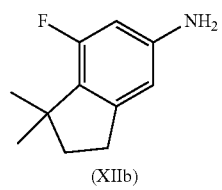

(XIIb)

(Step 1)

This step is a step of subjecting compound (XXX) to a carbon-carbon bond-forming reaction with ethyl acrylate in the presence of a transition metal catalyst to produce compound (XXXI).

Compound (XXX) may be a commercially available product, or can also be produced according to a method known per se or a method analogous thereto.

Examples of the transition metal catalyst used for this reaction include palladium catalysts (palladium acetate, palladium chloride, tetrakis(triphenylphosphine)palladium, etc.), nickel catalysts (nickel chloride, etc.) and the like. Where necessary, a ligand (tris(2-methylphenyl)phosphane, triphenylphosphine, tri-t-butylphosphine, S-Phos, BINAP, etc.) or a base (e.g., organic amines (trimethylamine, triethylamine, diisopropylamine, N-methylmorpholine, 1,8-diazabicyclo[5,4,0]undec-7-ene, pyridine, N, N-dimethylaniline, etc.), alkali metal salts (sodium hydrogencarbonate, potassium hydrogencarbonate, sodium carbonate, potassium carbonate, cesium carbonate, sodium phosphate, potassium phosphate, sodium hydroxide, potassium hydroxide, etc.), metal hydrides (potassium hydride, sodium hydride, etc.), alkali metal alkoxides (sodium methoxide, sodium ethoxide, sodium t-butoxide, potassium t-butoxide, etc.), alkali disilazides (lithium disilazide, sodium disilazide, potassium disilazide, etc.)) may be added. A metal oxide (copper oxide, silver oxide, etc.) and the like may be used as a co-catalyst. The amount of the catalyst to be used is about 0.0001 to 1 mol equivalent, preferably about 0.01 to 0.5 mol equivalent, per 1 mol of compound (XXX). The amount of the ligand to be used is about 0.0001 to 4 mol equivalent, preferably about 0.01 to 2 mol equivalent, per 1 mol of compound (XXX). The amount of the base to be used is about 1 to 10 mol equivalent, per 1 mol of compound (XXX). Base may be used as a solvent. The amount of the co-catalyst to be used is about 0.0001 to 4 mol equivalent, preferably about 0.01 to 2 mol equivalent, per 1 mol of compound (XXX).

The solvent is not limited as long as it does not adversely influence the reaction, and examples thereof include hydrocarbons (benzene, toluene, xylene, etc.), halogenated hydrocarbons (chloroform, 1,2-dichloroethane, etc.), nitriles (acetonitrile, etc.), ethers (dimethoxyethane, tetrahydrofuran), alcohols (methanol, ethanol, etc.), aprotic polar solvents (dimethylformamide, dimethyl sulfoxide, hexamethylphosphoroamide, etc.), amines (triethylamine, etc.), water and mixtures thereof.

The reaction temperature is generally about −100 to 200° C., preferably about −80 to 150° C., and the reaction time is generally about 0.5 to 72 hr, preferably about 0.5 to 48 hr.

Where necessary, the reaction may be carried out under microwave irradiation.

(Step 2)

This step is a step of subjecting compound (XXXI) to a reduction reaction to produce compound (XXXII) or a salt thereof.

This step can be carried out in the same manner as in the method described in the "method employing a catalytic hydrogenation reaction" in Step 3 of Method B.

(Step 3)

This step is a step of reacting compound (XXXII) with methylmagnesium bromide to produce compound (XXXIII).

The amount of the methylmagnesium bromide used for this reaction to be used is about 2 to 10 mol equivalent, preferably about 2 to 5 mol equivalent, per 1 mol of compound (XXXII).

This step is carried out in a solvent that does not adversely influence the reaction. Examples of the solvent that does not adversely influence the reaction include ethers (diethyl ether, diisopropyl ether, t-butyl methyl ether, tetrahydrofuran, dioxane, dimethoxyethane, etc.) and the like.

These solvents may be used in a mixture of two or more kinds thereof in an appropriate ratio.

The reaction temperature is, for example, within about 0 to 100° C., preferably about 0 to 30° C., and the reaction time is, for example, about 0.5 to 24 hr, preferably about 0.5 to 2 hr.

(Step 4)

This step is a step of subjecting compound (XXXIII) to a cyclization reaction using an acid to produce compound (XXXIV).

Examples of the acid used for this reaction include mineral acids (hydrochloric acid, hydrobromic acid, sulfuric acid, etc.), organic acids (polyphosphoric acid, methanesulfonic acid, etc.), Lewis acids (aluminium chloride, tin chloride, zinc bromide, etc.) and the like. Among them, polyphosphoric acid is preferable. While the amount of the acid to be used varies depending on the kind of solvent and the other reaction condition, it is generally about 1 mol equivalent or more, per 1 mol of compound (XXXIII).

This step is carried out in a solvent that does not adversely influence the reaction. Examples of the solvent that does not adversely influence the reaction include aromatic hydrocarbons (benzene, toluene, xylene, etc.), aliphatic hydrocarbons (hexane, heptane, etc.), halogenated hydrocarbons (dichloromethane, chloroform, etc.), ethers (diethyl ether, diisopropyl ether, t-butyl methyl ether, tetrahydrofuran, dioxane, dimethoxyethane, etc.) and the like. An acid may be used as a solvent.

The reaction temperature is, for example, within about 0 to 150° C., preferably about 10 to 190° C., and the reaction time is, for example, about 0.5 to 24 hr, preferably about 0.5 to 2 hr.

(Step 5)

This step is a step of subjecting compound (XXXIV) to a de-methylation reaction to produce compound (XXXV).

The de-methylation reaction can be carried out according a method known per se (e.g., the method described in "Protective Groups in Organic Synthesis, 3rd Ed", Wiley-Interscience, Inc. (1999) (Theodora W. Greene, Peter G. M. Wuts)). For example, compound (XXXV) can be obtained by treating compound (XXXIV) with aluminium chloride in the presence of 1-dodecanethiol.

The amount of the 1-dodecanethiol to be used is about 1 to 10 mol equivalent, per 1 mol of compound (XXXIV). The amount of the aluminium chloride to be used is about 1 to 10 mol equivalent, per 1 mol of compound (XXXIV).

This reaction is carried out in a solvent that does not adversely influence the reaction. Examples of the solvent include hydrocarbons such as benzene, toluene, xylene and the like; halogenated hydrocarbons such as dichloromethane, chloroform and the like; ethers such as diethyl ether, dioxane, tetrahydrofuran and the like; and the like.

The reaction temperature is, for example, within about −50 to 100° C., preferably about −10 to 50° C. While the reaction time varies depending on the reaction temperature and the like, it is, for example, about 0.1 to 100 hr, preferably about 0.1 to 6 hr.

(Step 6)

This step is a step of subjecting compound (XXXV) to a triflation reaction to produce compound (XXXVI).

This step can be carried out in the same manner as in the method described in Step 1 of Method D.

(Step 7)

This step is a step of reacting compound (XXXVI) with an aminating agent in the presence of a transition metal catalyst, and then treating the resulting compound with an acid or hydroxyamine hydrochloride and sodium acetate to produce compound (XIIb) or a salt thereof.

Examples of the transition metal catalyst used for this reaction include palladium catalysts (palladium acetate, palladium chloride, tetrakis(triphenylphosphine)palladium, tris(dibenzylideneacetone)dipalladium(0), etc.), nickel catalysts (nickel chloride, etc.) and the like. Where necessary, a ligand (triphenylphosphine, tri-t-butylphosphine, S-Phos, BINAP, 2'-(di-tert-butylphosphino)-N,N-dimethyl-[1,1'-biphenyl]-2-amine, XANTPHOS, etc.) or a base (e.g., organic amines (trimethylamine, triethylamine, diisopropylamine, N-methylmorpholine, 1,8-diazabicyclo[5,4,0]undec-7-ene, pyridine, N,N-dimethylaniline, etc.), alkali metal salts (sodium hydrogencarbonate, potassium hydrogencarbonate, sodium carbonate, potassium carbonate, cesium carbonate, sodium phosphate, potassium phosphate, sodium hydroxide, potassium hydroxide, lithium acetate, etc.), metal hydrides (potassium hydride, sodium hydride, etc.), alkali metal alkoxides (sodium methoxide, sodium ethoxide, sodium t-butoxide, potassium t-butoxide, etc.), alkali disilazides (lithium disilazide, sodium disilazide, potassium disilazide, etc.)) may be added. A metal oxide (copper oxide, silver oxide, etc.) and the like may be used as a co-catalyst. The amount of the catalyst to be used is about 0.0001 to 1 mol equivalent, preferably about 0.01 to 0.5 mol equivalent, per 1 mol of compound (XXXVI). The amount of the ligand to be used is about 0.0001 to 4 mol equivalent, preferably about 0.01 to 2 mol equivalent, per 1 mol of compound (XXXVI). The amount of the base to be used is about 1 to 10 mol equivalent, preferably about 1 to 2 mol equivalent, per 1 mol of compound (XXXVI). The amount of the co-catalyst to be used is about 0.0001 to 4 mol equivalent, preferably about 0.01 to 2 mol equivalent, per 1 mol of compound (XXXVI).

This step is carried out in a solvent that does not adversely influence the reaction. Examples of the solvent that does not adversely influence the reaction include hydrocarbons (benzene, toluene, xylene, etc.), halogenated hydrocarbons (chloroform, 1,2-dichloroethane, etc.), nitriles (acetonitrile, etc.), ethers (dimethoxyethane, tetrahydrofuran), alcohols (methanol, ethanol, etc.), aprotic polar solvents (dimethylformamide, dimethyl sulfoxide, hexamethylphosphoroamide, etc.), water and mixtures thereof.

The reaction temperature is generally about −100 to 200° C., preferably about −80 to 150° C., and the reaction time is generally about 0.5 to 48 hr, preferably about 0.5 to 24 hr.

The aminating agent is preferably diphenylmethanimine. The amount of the aminating agent to be used is about 1 to 5 mol equivalent, preferably about 1 to 2 mol equivalent, per 1 mol of compound (XXXVI).

Examples of the acid include mineral acids (hydrochloric acid, hydrobromic acid, sulfuric acid, etc.). While the amount of the acid to be used varies depending on the kind of solvent and the other reaction condition, it is generally about 0.1 mol equivalent or more, per 1 mol of compound (XXXVI). The solvent is THF or water. The reaction temperature is about −20 to 100° C., preferably about 0 to 30° C., and the reaction time is generally about 0.1 to 100 hr, preferably about 0.1 to 24 hr.

The amounts of the hydroxyamine hydrochloride and sodium acetate to be used are about 1 to 5 mol equivalent, preferably about 1 to 2 mol equivalent, per 1 mol of compound (XXXVI), respectively.

The solvent used for the treatment with hydroxyamine hydrochloride and sodium acetate is methanol. The reaction temperature is about −20 to 100° C., preferably about 0 to 30° C., and the reaction time is generally about 1 to 100 hr, preferably about 1 to 72 hr.

[Method G2]

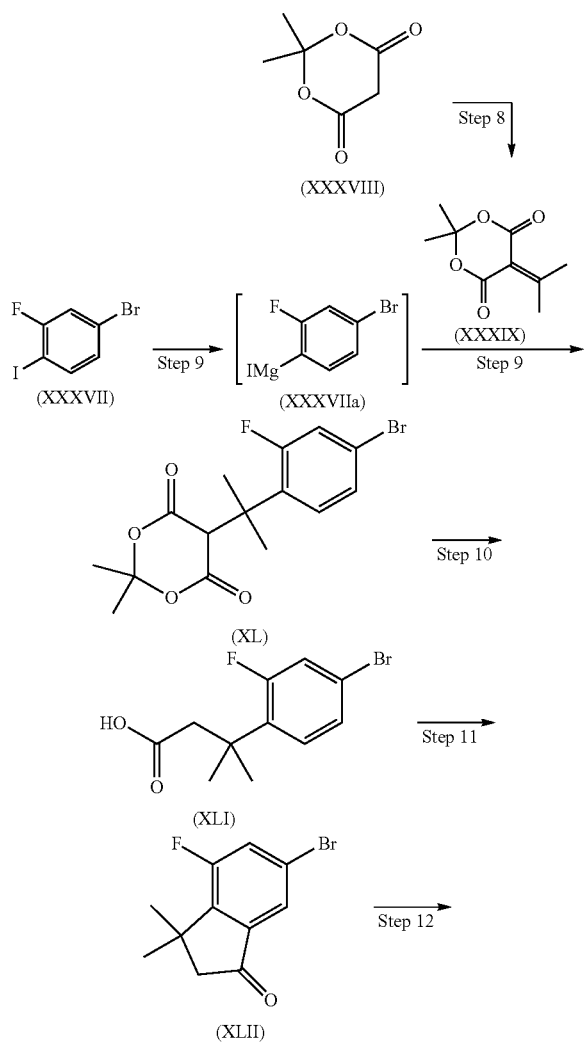

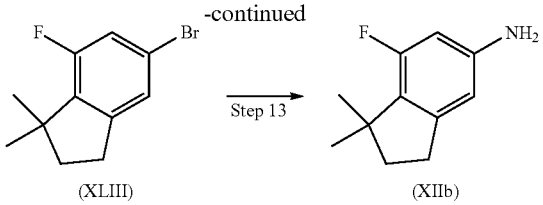

(Step 8)

This step is a step of subjecting compound (XXXVIII) (2,2-dimethyl-1,3-dioxane-4,6-dione) to a dehydration condensation with acetone in the presence of a morpholine and acetic acid to produce compound (XXXIX).

Compound (XXXVIII) may be a commercially available product.

The amounts of the morpholine and acetic acid to be used are about 0.01 to 1 mol equivalent, preferably about 0.01 to 0.05 mol equivalent, per 1 mol of compound (XXXVIII), respectively.

The amount of the acetone to be used is about 1 to 100 mol equivalent, per 1 mol of compound (XXXVIII). Acetone may be used as a solvent.

The reaction temperature is generally about 0 to 80° C., preferably about 0 to 50° C., and the reaction time is generally about 0.5 to 48 hr, preferably 1 to 24 hr.

(Step 9)

This step is a step of converting compound (XXXVII) to Grignard reagent (XXXVIIa), and then coupling Grignard reagent (XXXVIIa) with compound (XXXIX) to produce compound (XL).

Compound (XXXVII) may be a commercially available product.

The step of the conversion of compound (XXXVII) to Grignard reagent (XXXVIIa) can be carried out by reacting compound (XXXVII) with isopropylmagnesium chloride.

Isopropylmagnesium chloride may be a commercially available product. The amount thereof to be used is about 1 to 2 mol equivalent, preferably about 1 to 1.2 mol equivalent, per 1 mol of compound (XXXVII).

This reaction is generally carried out in a solvent that does not adversely influence the reaction. Examples of the solvent include hydrocarbons (benzene, toluene, etc.), ethers (diethyl ether, dioxane, tetrahydrofuran, etc.) and the like, and they may be mixed as appropriate.

The reaction temperature is generally about −80 to 30° C., preferably about −50 to 0° C., and the reaction time is generally about 0.5 to 4 hr, preferably 0.5 to 2 hr.

The coupling reaction with compound (XXXIX) can be carried out without isolation of Grignard reagent (XXXVIIa).

In the coupling reaction with compound (XXXIX), the amount of the compound (XXXIX) to be used is about 1 to 2 mol equivalent, preferably about 1 to 1.2 mol equivalent, per 1 mol of Grignard reagent (XXXVIIa).

This reaction is generally carried out in a solvent that does not adversely influence the reaction. Examples of the solvent include those similar to the solvent used in the conversion of compound (XXXVII) to Grignard reagent (XXXVIIa).

The reaction temperature is generally about −80 to 30° C., preferably about −50 to 0° C., and the reaction time is generally about 0.5 to 8 hr, preferably 0.5 to 5 hr.

(Step 10)

This step is a step of treating compound (XL) with hydrochloric acid to produce compound (XLI) or a salt thereof.

The amount of the hydrochloric acid to be used is about 1 to 50 mol equivalent, preferably about 1 to 5 mol equivalent, per 1 mol of compound (XL).

This reaction is generally carried out in a solvent that does not adversely influence the reaction. Examples of the solvent include ethers (diethyl ether, tetrahydrofuran, dioxane, etc.), alcohols (methanol, ethanol, 2-propanol, etc.), nitriles (acetonitrile, butyronitrile, etc.), amides (dimethylformamide, dimethylacetamide, etc.), sulfoxides (dimethyl sulfoxide, etc.), water and the like, and they may be mixed as appropriate.

The reaction temperature is generally about 0 to 150° C., preferably about 20 to 120° C., and the reaction time is generally about 0.5 to 48 hr, preferably 1 to 36 hr.
(Step 11)

This step is a step of treating compound (XLI) or a salt thereof with polyphosphoric acid to produce compound (XLII).

The amount of the polyphosphoric acid to be used is about 1 to 50-fold weight, preferably about 1 to 10-fold weight, relative to compound (XLI).

The reaction temperature is generally about 20 to 150° C., preferably about 50 to 120° C., and the reaction time is generally about 0.5 to 24 hr, preferably 0.5 to 10 hr.
(Step 12)

This step is a step of treating compound (XLII) with triethylsilane in trifluoroacetic acid to produce compound (XLIII).

The amount of the triethylsilane to be used is about 1 to 10 mol equivalent, preferably about 1 to 5 mol equivalent, per 1 mol of compound (XLII).

The reaction temperature is generally about −20 to 100° C., preferably about 0 to 50° C., and the reaction time is generally about 0.5 to 100 hr, preferably 1 to 50 hr.
(Step 13)

This step is a step of subjecting compound (XLIII) to an amination reaction to produce compound (XIIb) or a salt thereof.

This step can be carried out in the same manner as in the method described in Step 7 of Method G1.

[Method H]
When compound (XII) is a compound represented by the formula:

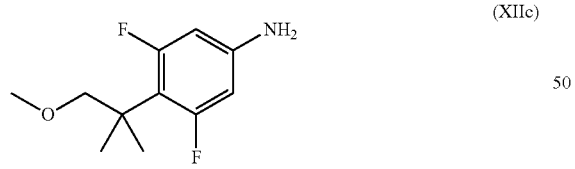

(XIIc)

(hereinafter to be referred to as compound (XIIc)) or a salt thereof, this compound can be produced according to Method H.

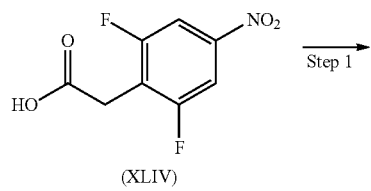

(XLIV)

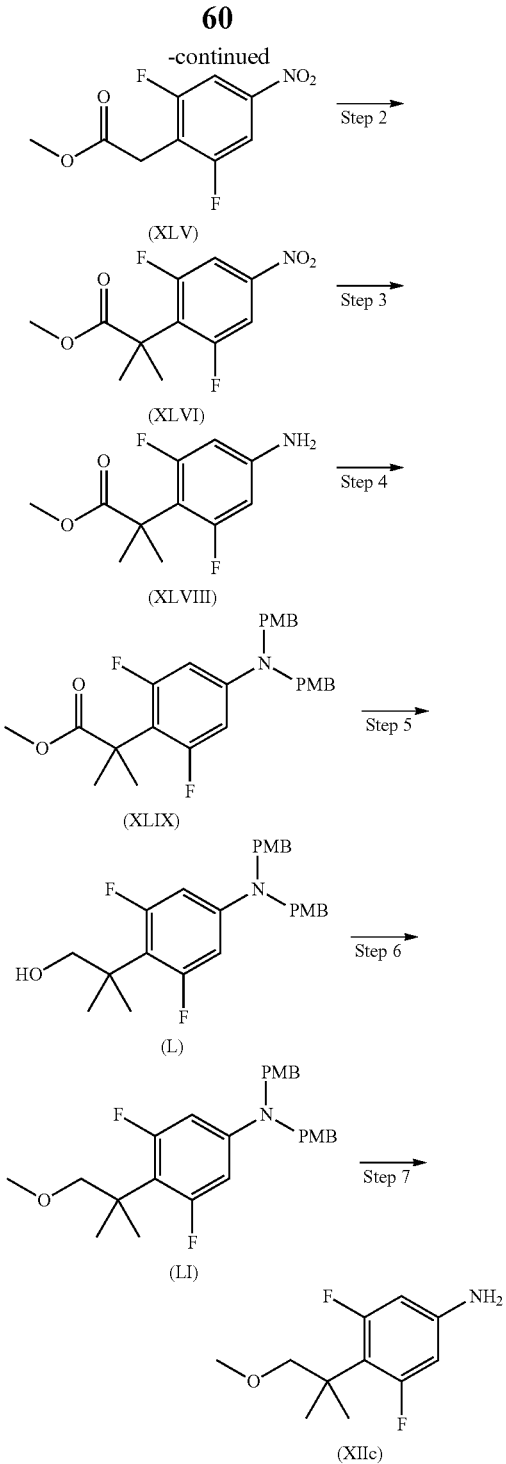

wherein PMB is a 4-methoxybenzyl group.
(Step 1)

This step is a step of subjecting compound (XLIV) or a salt thereof to a methyl esterification to produce compound (XLV).

Compound (XLIV) or a salt thereof may be a commercially available product, or can also be produced according to a method known per se or a method analogous thereto.

This reaction can be carried out according to a method known per se (e.g., the method described in "Protective Groups in Organic Synthesis, 3rd Ed", Wiley-Interscience, Inc. (1999) (Theodora W. Greene, Peter G. M. Wuts)). For example, compound (XLV) can be carried out by heating compound (XLIV) or a salt thereof in methanol in the presence of an acid catalyst.

Examples of the acid catalyst used for this reaction include mineral acids (hydrochloric acid, sulfuric acid, etc.), organic sulfonic acids (methanesulfonic acid, p-toluenesulfonic acid, etc.), Lewis acids (boron fluoride etherate, etc.), thionyl chloride and the like. While the amount of the acid to be used varies depending on the kind of solvent and the other reaction condition, it is generally about 0.0001 to 10 mol equivalent, preferably about 0.01 to 0.1 mol equivalent, per 1 mol of compound (XLIV).

In this reaction, methanol can be used as a solvent. The reaction temperature is, for example, within about 0 to 120° C., preferably about 25 to 80° C., and the reaction time is, for example, about 0.5 to 100 hr, preferably about 0.5 to 24 hr.

(Step 2)

This step is a step of subjecting compound (XLV) to a methylation to produce compound (XLVI).

In this reaction, compound (XLVI) can be obtained by treating compound (XLV) with iodomethane in the presence of a base.

Examples of the base used for this reaction include alkali metal hydrides (e.g., sodium hydride, lithium hydride). While the amount of the base to be used varies depending on the kind of solvent and the other reaction condition, it is generally about 2 to 10 mol equivalent, preferably about 2 to 5 mol equivalent, per 1 mol of compound (XLV).

The amount of the iodomethane to be used is generally about 2 to 10 mol equivalent, preferably about 2 to 3 mol equivalent, per 1 mol of compound (XLV).

This step is carried out in a solvent that does not adversely influence the reaction. Examples of the solvent that does not adversely influence the reaction include aromatic hydrocarbons (benzene, toluene, xylene, etc.), aliphatic hydrocarbons (hexane, heptane, etc.), halogenated hydrocarbons (dichloromethane, chloroform, etc.), ethers (diethyl ether, diisopropyl ether, t-butyl methyl ether, tetrahydrofuran, dioxane, dimethoxyethane, etc.), nitriles (acetonitrile, etc.), esters (ethyl acetate, etc.), amides (dimethylformamide, etc.), sulfoxides (dimethyl sulfoxide, etc.) and the like. These solvents may be used in a mixture of two or more kinds thereof in an appropriate ratio.

The reaction temperature is, for example, within about −75 to 100° C., preferably about −10 to 30° C. While the reaction time varies depending on the reaction temperature and the like, it is, for example, about 0.5 to 100 hr, preferably about 0.5 to 24 hr.

(Step 3)

This step is a step of subjecting compound (XLVI) to a catalytic hydrogenation reaction using a transition metal catalyst to produce compound (XLVIII) or a salt thereof.

This step can be carried out in the same manner as in the method described in Step 2 of Method F.

(Step 4)

This step is a step of reacting compound (XLVIII) or a salt thereof with α-chloro-4-methoxytoluene in the presence of a base to produce compound (XLIX).

Examples of the base used for this reaction include inorganic bases (alkali metal hydrides such as sodium hydride, lithium hydride and the like, alkali metal hydroxides such as lithium hydroxide, sodium hydroxide, potassium hydroxide and the like, alkali metal hydrogencarbonates such as sodium hydrogencarbonate, potassium hydrogencarbonate and the like, alkali metal carbonates such as lithium carbonate, sodium carbonate, potassium carbonate, cesium carbonate and the like, alkali metal alkoxides such as sodium methoxide, sodium ethoxide and the like, etc.), organic bases (amines such as trimethylamine, triethylamine, diisopropylethylamine and the like, cyclic amines such as pyridine, 4-dimethylaminopyridine and the like, etc.) and the like. While the amount of the base to be used varies depending on the kind of solvent and the other reaction condition, it is generally about 2 to 10 mol equivalent, preferably about 2 to 5 mol equivalent, per 1 mol of compound (XLVIII).

The amount of the α-chloro-4-methoxytoluene to be used is about 2 to 10 mol equivalent, preferably about 2 to 5 mol equivalent, per 1 mol of compound (XLVIII).

This step is carried out in a solvent that does not adversely influence the reaction. Examples of the solvent that does not adversely influence the reaction include aromatic hydrocarbons (benzene, toluene, xylene, etc.), aliphatic hydrocarbons (hexane, heptane, etc.), halogenated hydrocarbons (dichloromethane, chloroform, etc.), ethers (diethyl ether, diisopropyl ether, t-butyl methyl ether, tetrahydrofuran, dioxane, dimethoxyethane, etc.), amides (N,N-dimethylformamide, etc.) and the like. These solvents may be used in a mixture of two or more kinds thereof in an appropriate ratio.

The reaction temperature is, for example, within about −100 to 150° C., preferably about −78 to 50° C., and the reaction time is, for example, about 0.5 to 100 hr, preferably about 0.5 to 24 hr.

This reaction can also be carried out under the condition described in the "when the amino group is protected by a PMB group" in Step 5 of Method B.

(Step 5)

This step is a step of treating compound (XLIX) with a reducing agent to produce compound (L).

Examples of the reducing agent to be used for this reaction include metal hydrides (e.g., lithium borohydride, diisobutylaluminium hydride, aluminium hydride, lithium aluminium hydride). The amount of the metal hydride to be used is about 0.5 to 50 mol equivalent, per 1 mol of compound (XLIX).

This step is carried out in a solvent that does not adversely influence the reaction. Examples of the solvent that does not adversely influence the reaction include aromatic hydrocarbons (benzene, toluene, xylene, etc.), aliphatic hydrocarbons (hexane, heptane, etc.), halogenated hydrocarbons (dichloromethane, chloroform, etc.), ethers (diethyl ether, diisopropyl ether, t-butyl methyl ether, tetrahydrofuran, dioxane, dimethoxyethane, etc.) and the like. These solvents may be used in a mixture of two or more kinds thereof in an appropriate ratio.

The reaction temperature is generally about −20 to 100° C., preferably about 0 to 30° C., and the reaction time is generally about 1 to 100 hr, preferably about 1 to 72 hr.

(Step 6)

This step is a step of subjecting compound (L) to a methylation reaction to produce compound (LI).

This step can be carried out in the same manner as in the method described in Step 8 of Method E.

(Step 7)

This step is a step of subjecting compound (LI) to a deprotection reaction to produce compound (XIIc) or a salt thereof.

This step can be carried out in the same manner as in the method described in Step 8 of Method B.

[Method I]

When compound (III) is a compound represented by the formula:

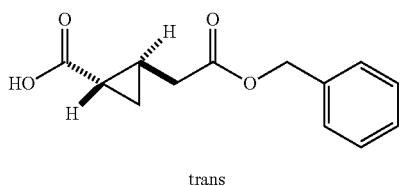

(hereinafter to be referred to as compound (IIIb)) or a salt thereof, this compound can be produced according to Method I.

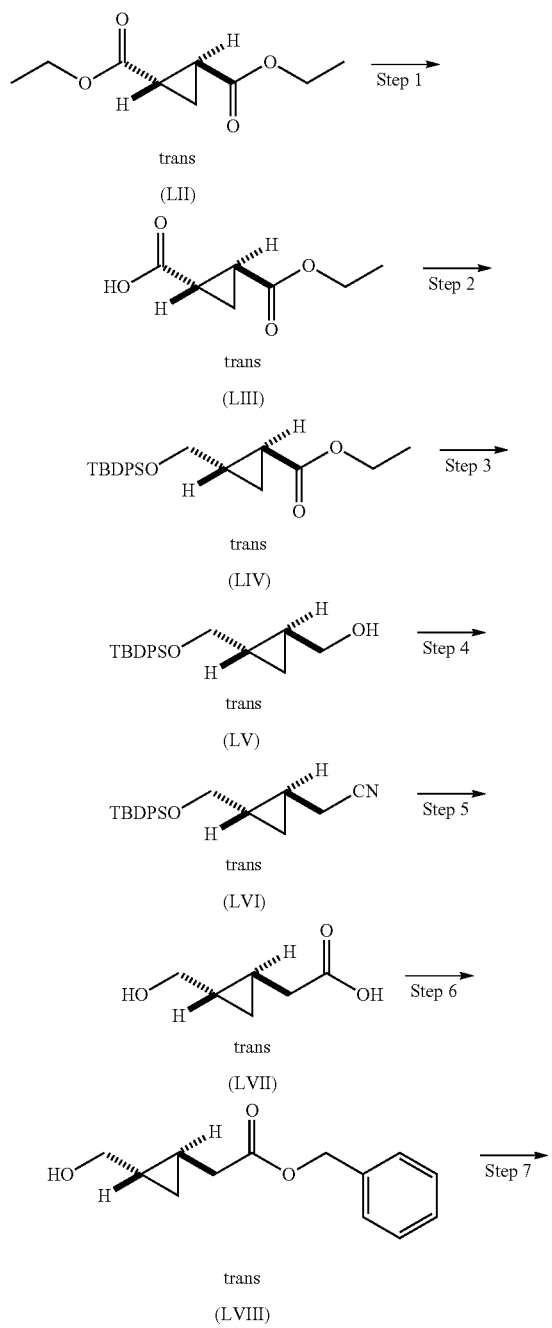

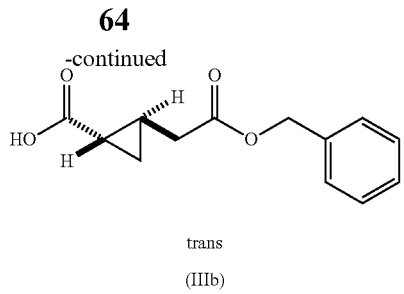

wherein TBDPSO is a tert-butyldiphenylsilyloxy group.

(Step 1)

This step is a step of subjecting compound (LII) to hydrolysis using a base to convert compound (LII) to compound (LIII) or a salt thereof.

Compound (LII) may be a commercially available product, is or can also be produced according to a method known per se or a method analogous thereto.

Examples of the base used for this reaction include inorganic bases (alkali metal hydroxides such as lithium hydroxide, sodium hydroxide, potassium hydroxide and the like, alkoxides such as sodium methoxide, sodium ethoxide and the like, etc.) and the like. Among them, sodium hydroxide is preferable. While the amount of the base to be used varies depending on the kind of solvent and the other reaction condition, it is generally about 1 to 3 mol equivalent, preferably about 1 to 1.5 mol equivalent, per 1 mol of compound (LII).

Examples of the solvent that does not adversely influence the reaction include alcohols (methanol, ethanol, propanol, 2-propanol, butanol, isobutanol, t-butanol, etc.), hydrocarbons (benzene, toluene, xylene, hexane, heptane, etc.), halogenated hydrocarbons (dichloromethane, chloroform, etc.), ethers (diethyl ether, diisopropyl ether, t-butyl methyl ether, tetrahydrofuran, dioxane, dimethoxyethane, etc.), nitriles (acetonitrile, etc.) or water and the like. Among them, ethanol and water are preferable. These solvents may be used in a mixture of two or more kinds thereof in an appropriate ratio.

The reaction temperature is, for example, within about −50 to 100° C., preferably about 0 to 30° C. While the reaction time varies depending on the kind of compound (LII) or a salt thereof, the reaction temperature and the like, it is, for example, about 0.5 to 24 hr, preferably about 0.5 to 4 hr.

(Step 2)

This step is a step of subjecting compound (LIII) or a salt thereof to a reduction reaction, and then protecting the resulting compound by a TBDMS (tert-butyldimethylsilyl) group to convert compound (LIII) or a salt thereof to compound (LIV).

The reduction reaction can be carried out in the same manner as in the method described in Step 3 of Method B.

The protection reaction of the product obtained in the so reduction reaction by a TBDMS group can be carried out by reacting compound (LIII) or a salt thereof with tert-butylchlorodiphenylsilane in the presence of imidazole in a solvent that does not adversely influence the reaction.

The amounts of the imidazole and tert-butylchlorodiphenylsilane used for this reaction to be used are about 1 to 5 mol equivalent, per 1 mol of compound (LIII), respectively.

Examples of the solvent that does not adversely influence the reaction include hydrocarbons (benzene, toluene, etc.), ethers (diethyl ether, dioxane, tetrahydrofuran, etc.), nitriles (acetonitrile, etc.), halogenated hydrocarbons (chloroform, dichloromethane, etc.), aprotic polar solvents (dimethylformamide, dimethylsulfoxide, etc.) and the like, and they may be mixed as appropriate.

The reaction temperature is generally about −30 to 100° C., preferably about 0 to 30° C., and the reaction time is generally about 0.5 to 24 hr, preferably 0.5 to 10 hr.

(Step 3)

This step is a step of subjecting compound (LIV) to a reduction reaction to produce compound (LV).

The reduction reaction can be carried out in the same manner as in the method described in Step 3 of Method B.

(Step 4)

This step is a step of subjecting compound (LV) to a mesylation reaction to convert compound (LV) to a compound represented by the formula:

(LVa)

TBDPSO⟋⟍⟋OMs
trans wherein MsO is a methylsulfonyloxy group (hereinafter to be referred to as compound (LVa)), and then reacting compound (LVa) with metal cyanide to produce compound (LVI).

The mesylation reaction can be carried out in the same manner as in the method described in Step 5 of Method D.

Examples of the metal cyanide used for the reaction of compound (LVa) with metal cyanide include sodium cyanide, potassium cyanide and the like. The amount thereof to be used is about 1 to 5 mol equivalent, per 1 mol of compound (LVa).

This reaction is carried out in a solvent inert to the reaction. Examples of the solvent include hydrocarbons such as benzene, toluene, xylene and the like; halogenated hydrocarbons such as dichloromethane, chloroform and the like; ethers such as diethyl ether, dioxane, tetrahydrofuran and the like; esters such as ethyl acetate and the like; amides such as N,N-dimethylformamide and the like, and mixtures thereof.

The reaction temperature is generally about 0° C. to 150° C., preferably about 20° C. to 100° C., and the reaction time is generally about 5 min to 72 hr, preferably about 0.5 hr to 40 hr.

(Step 5)

This step is a step of subjecting compound (LVI) to hydrolysis to convert compound (LVI) to compound (LVII) or a salt thereof.

This step can be carried out in the same manner as in the method described in Step 6 of Method B.

(Step 6)

This step is a step of reacting compound (LVII) or a salt thereof with benzyl bromide in the presence of potassium carbonate to produce compound (LVIII).

The amounts of the potassium carbonate and benzyl bromide to be used are about 1 to 10 mol equivalent, preferably about 1 to 5 mol equivalent, per 1 mol of compound (LVII), respectively.

This reaction is carried out in a solvent inert to the reaction. Examples of the solvent include hydrocarbons such as benzene, toluene, xylene and the like; halogenated hydrocarbons such as dichloromethane, chloroform and the like; ethers such as diethyl ether, dioxane, tetrahydrofuran and the like; esters such as ethyl acetate and the like; amides such as N,N-dimethylformamide and the like, and mixtures thereof.

The reaction temperature is generally about 0° C. to 100° C., preferably about 0° C. to 30° C., and the reaction time is generally about 0.5 hr to 24 hr, preferably about 0.5 hr to 14 hr.

(Step 7)

This step is a step of subjecting compound (LVIII) to an oxidation reaction to produce compound (IIIb) or a salt thereof.

Examples of the oxidizing agent to be used for the oxidation reaction include a mixture of sodium metaperiodate and ruthenium(IV) oxide. The amount of the sodium metaperiodate to be used is about 1 to about 10 mol equivalent, per 1 mol of compound (LVIII). The amount of the ruthenium(IV) oxide to be used is about 0.01 to about 0.5 mol equivalent, per 1 mol of compound (LVIII).

The oxidation reaction is carried out in a solvent that does not adversely influence the reaction. Examples of the solvent include nitriles (e.g., acetonitrile), hydrocarbons (e.g., benzene, toluene, xylene), halogenated hydrocarbons (e.g., dichloromethane, chloroform), ethers (e.g., diethyl ether, dioxane, tetrahydrofuran), ketones (e.g., acetone), water and mixtures thereof.

The reaction temperature is generally about −20° C. to 50° C., preferably about 0° C. to 30° C., and the reaction time is generally about 0.5 hr to 24 hr, preferably about 0.5 hr to 4 hr.

[Method J]

When compound (III) is a compound represented by the formula:

(IIIc)

(hereinafter to be referred to as compound (IIIc)) or a salt thereof, this compound can be produced according to Method J.

(LIX) → Step 1 → (LX) → Step 2 →

(LXI) → Step 3 →

(LXII) → Step 4 →

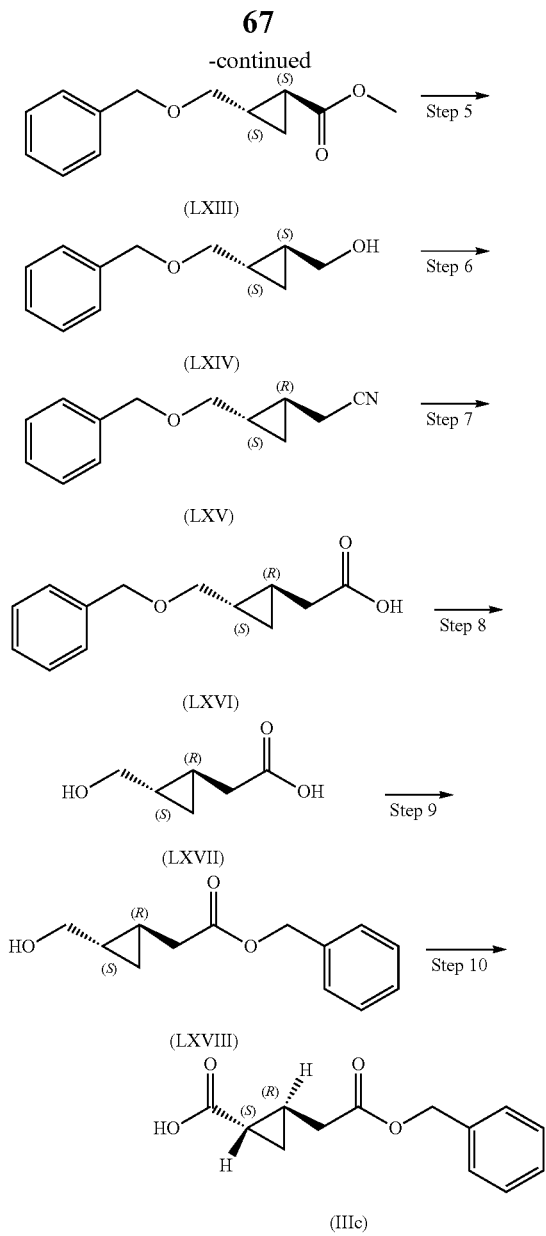

wherein TsO is a p-toluenesulfonyloxy group.
(Step 1)
This step is a step of subjecting compound (LIX) to a tosylation reaction to produce compound (LX).

Compound (LIX) may be a commercially available product, or can also be produced according to a method known per se or a method analogous thereto.

The tosylation reaction can be carried out in the presence of a base and a tosylating agent.

The kinds and amounts of the base and solvent used for the tosylation reaction, the reaction temperature and the reaction time are the same as in Step 1 of Method D.

Examples of the tosylating agent include p-toluenesulfonyl chloride and the like. While the amount of the tosylating agent to be used varies depending on the kind of solvent and the other reaction condition, it is generally 1 about 1 to 10 mol equivalent, preferably about 1 to 5 mol equivalent, per 1 mol of compound (LIX).
(Step 2)
This step is a step of treating compound (LX) with a base to produce compound (LXI).

Examples of the base to be used in this step include inorganic bases (alkali metal hydrides such as sodium hydride, lithium hydride and the like, alkali metal hydroxides such as lithium hydroxide, sodium hydroxide, potassium hydroxide and the like, alkali metal hydrogencarbonates such as sodium hydrogencarbonate, potassium hydrogencarbonate and the like, alkali metal carbonates such as lithium carbonate, sodium carbonate, potassium carbonate, cesium carbonate and the like, alkali metal alkoxides such as sodium methoxide, sodium ethoxide and the like, etc.) and the like. Among them, sodium methoxide is preferable. While the amount of the base to be used varies depending on the kind of solvent and the other reaction condition, it is generally about 1 to 10 mol equivalent, preferably about 1 to 5 mol equivalent, per 1 mol of compound (LX).

Examples of the solvent that does not adversely influence the reaction include aromatic hydrocarbons (benzene, toluene, xylene, etc.), alcohols (methanol, ethanol, etc.), aliphatic hydrocarbons (hexane, heptane, etc.), halogenated hydrocarbons (dichloromethane, chloroform, etc.), ethers (diethyl ether, diisopropyl ether, t-butyl methyl ether, tetrahydrofuran, dioxane, dimethoxyethane, etc.), nitriles (acetonitrile, etc.), esters (ethyl acetate, etc.), amides (dimethylformamide, etc.), sulfoxides (dimethyl sulfoxide, etc.) and the like. These solvents may be used in a mixture of two or more kinds thereof in an appropriate ratio.

The reaction temperature is, for example, within about −10 to 100° C. While the reaction time varies depending on the kind of compound (LX), the reaction temperature and the like, it is, for example, about 0.5 to 24 hr, preferably about 0.5 to 4 hr.
(Step 3)
This step is a step of treating compound (LXI) with lithiumdiisopropylamide (LDA) to produce compound (LXII).

The amount of the LDA is about 1 to 5 mol equivalent, preferably about 1 to 2 mol equivalent, per 1 mol of compound (LXI).

This reaction is carried out in a solvent that does not adversely influence the reaction. Examples of the solvent include hydrocarbons (benzene, toluene, etc.), ethers (diethyl ether, dioxane, tetrahydrofuran, etc.), halogenated hydrocarbons (chloroform, dichloromethane, etc.), amides (N,N-dimethylformamide, etc.) and the like, and they may be mixed as appropriate.

The reaction temperature is generally about −80 to 30° C., preferably about −80 to 10° C., and the reaction time is generally about 0.5 to 24 hr, preferably 0.5 to 4 hr.
(Step 4)
This step is a step of subjecting compound (LXII) to a protection by a benzyl group to produce compound (LXIII).

This reaction can be carried out in the same manner as in the method described in the "when the amino group is protected by a Bn group" in Step 5 of Method B In addition, tetra-n-butylammonium iodide may be used as an additive for the progress of the reaction. The amount thereof to be used is about 0.01 to 1 mol equivalent, preferably about 0.05 to 0.5 mol equivalent, per 1 mol of compound (LXII).
(Step 5)
This step is a step of subjecting compound (LXIII) to a reduction reaction to convert compound (LXIII) to compound (LXIV).

The reduction reaction can be carried out in the same manner as in the method described in Step 3 of Method B.

(Step 6)

This step is a step of subjecting compound (LXIV) to a mesylation reaction to convert compound (LXIV) to a compound represented by the formula:

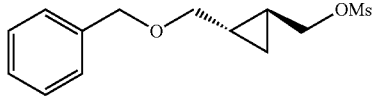

(LXIVa)

wherein MsO is a methylsulfonyloxy group (hereinafter to be referred to as compound (LXIVa)), and then reacting compound (LXIVa) with metal cyanide to produce compound (LXV).

This step can be carried out in the same manner as in the method described in Step 4 of Method I.

(Step 7)

This step is a step of subjecting compound (LXV) to hydrolysis to convert compound (LXV) to compound (LXVI) or a salt thereof.

This step can be carried out in the same manner as in the method described in Step 6 of Method B.

(Step 8)

This step is a step of subjecting compound (LXVI) or a salt thereof to a deprotection reaction to produce compound (LXVII) or a salt thereof.

This step can be carried out in the same manner as in the method described in the "deprotection reaction employing catalytic hydrogenation reaction" in Step 8 of Method B.

(Step 9)

This step is a step of reacting compound (LXVII) or a salt thereof with benzyl bromide in the presence of potassium carbonate to produce compound (LXVIII).

This step can be carried out in the same manner as in the method described in Step 6 of Method I.

(Step 10)

This step is a step of subjecting compound (LXVIII) to an oxidation reaction to produce compound (IIIc) or a salt thereof.

This step can be carried out in the same manner as in the method described in Step 7 of Method I.

[Method K]

When compound (III) is a compound represented by the formula:

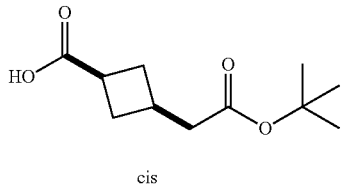

(IIId)

(hereinafter to be referred to as compound (IIId)) or a salt thereof, this compound can be produced according to Method K.

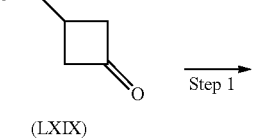

(LXIX)

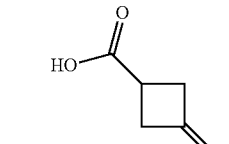

(LXX)

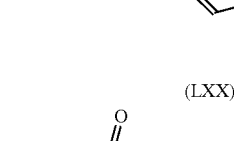

cis/trans
(LXXI)

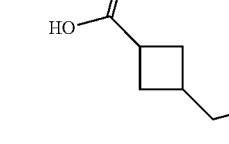

cis
(LXXII)

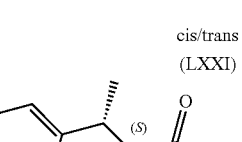

cis
(IIId)

(Step 1)

This step is a step of reacting compound (LXIX) or a salt thereof with tert-butyl triphenylphosphoranylideneacetate to produce compound (LXX) or a salt thereof.

Compound (LXIX) or a salt thereof and tert-butyl triphenylphosphoranylideneacetate may be a commercially available product, or can also be produced according to a method-known per se or a method analogous thereto.

The amount of the tert-butyl triphenylphosphoranylidenacetate to be used is about 1 to about 5 mol equivalent, per 1 mol of compound (LXIX).

This reaction is carried out in a solvent that does not adversely influence the reaction. Examples of the solvent include nitriles (e.g., acetonitrile), hydrocarbons (e.g., benzene, toluene, xylene), halogenated hydrocarbons (e.g., dichloromethane, chloroform), ethers (e.g., diethyl ether, dioxane, tetrahydrofuran) and mixtures thereof.

The reaction temperature is generally about −20° C. to 150° C., preferably about 10° C. to 100° C., and the reaction time is generally about 0.5 hr to 24 hr, preferably about 0.5 hr to 14 hr.
(Step 2)

This step is a step of subjecting compound (LXX) or a salt thereof to a reduction reaction to produce compound (LXXI) or a salt thereof.

This step can be carried out in the same manner as in the method described in the "method employing a catalytic hydrogenation reaction" in Step 3 of Method B.
(Step 3)

This step is a step of reacting compound (LXXI) or a salt thereof with (R)-1-phenylethanol in the presence of DEAD and triphenylphosphine to produce compound (LXXII).

In this step, two stereoisomers are produced, and subjected to chiral column chromatography to give compound (LXXII).

The amounts of the DEAD, triphenylphosphine and (R)-1-phenylethanol used for this reaction to be used are about 1 to 5 mol equivalent, preferably about 1 to 2 mol equivalent, per 1 mol of compound (LXXI), respectively.

This reaction is carried out in a solvent that does not adversely influence the reaction. Examples of the solvent include nitriles (e.g., acetonitrile), hydrocarbons (e.g., benzene, toluene, xylene), halogenated hydrocarbons (e.g., dichloromethane, chloroform), ethers (e.g., diethyl ether, dioxane, tetrahydrofuran) and mixtures thereof.

The reaction temperature is generally about −20° C. to 150° C., preferably about 10° C. to 100° C., and the reaction time is generally about 0.5 hr to 24 hr, preferably about 0.5 hr to 14 hr.
(Step 4)

This step is a step of subjecting compound (LXXII) to a deprotection reaction to produce compound (IIId) or a salt thereof.

This step can be carried out in the same manner as in the method described in the "deprotection reaction employing catalytic hydrogenation reaction" in Step 8 of Method B.

[Method L]

When compound (III) is a compound represented by the formula:

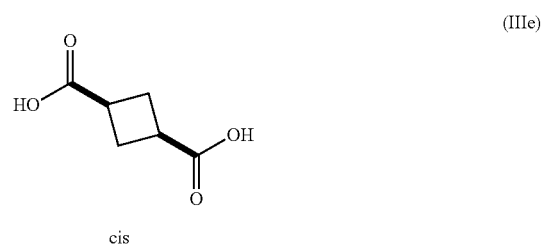

(hereinafter to be referred to as compound (IIIe)) or a salt thereof, or a compound represented by the

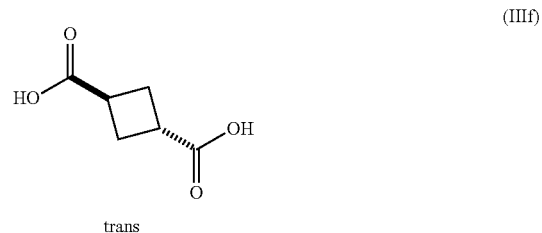

(hereinafter to be referred to as compound (IIIf)) or a salt thereof, this compound can be produced according to Method L.

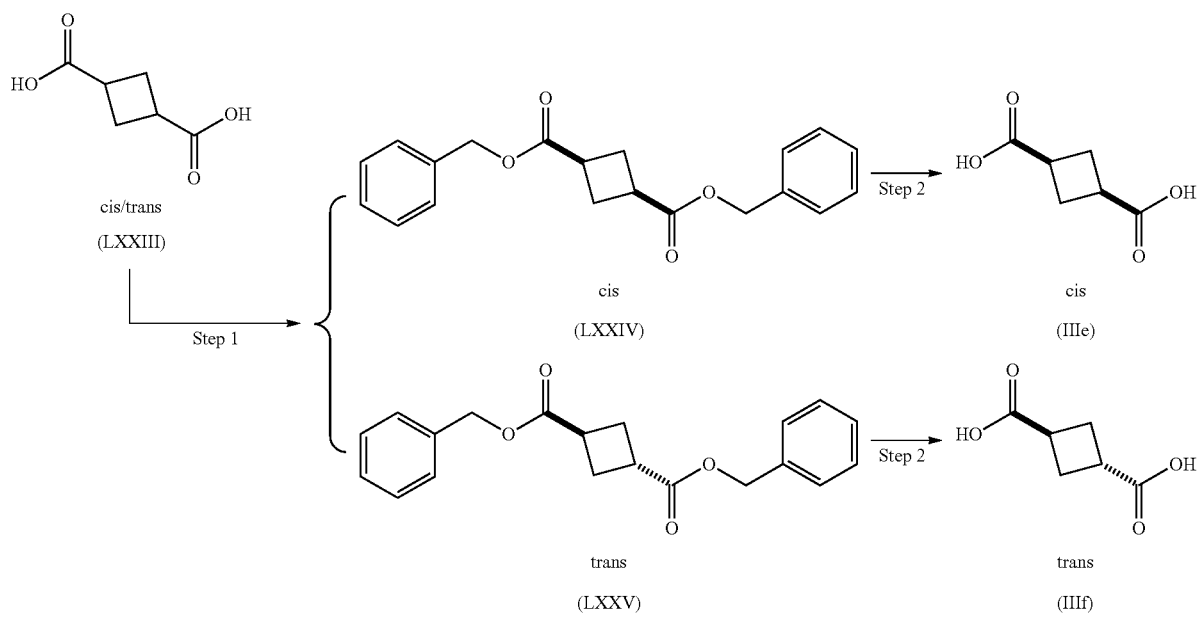

(Step 1)

This step is a step of reacting compound (LXXIII) or a salt thereof with benzyl bromide in the presence of potassium carbonate to produce compound (LXXIV) and compound (LXXV).

Compound (LXXIII) or a salt thereof may be a commercially available product, or can also be produced according to a method known per se or a method analogous thereto.

This step can be carried out in the same manner as in the method described in Step 6 of Method I.

Compound (LXXIV) and compound (LXXV) can be each isolated by separation and purification using silica gel chromatography.

(Step 2)

This step is a step of subjecting compound (LXXIV) or compound (LXXV) to a deprotection reaction to produce compound (IIIe) or a salt thereof, or compound (IIIf) or a salt thereof, respectively.

This step can be carried out in the same manner as in the method described in the "deprotection reaction employing catalytic hydrogenation reaction" in Step 8 of Method B.

In each reaction for the production of the objective compound and the raw material compound, when the raw material compound has an amino group, a carboxyl group or a hydroxy group, these groups may be protected by a protecting group generally used in peptide chemistry and the like. By removing the protecting group as necessary after the reaction, the objective compound can be obtained.

Examples of the protecting group include those described in "Protective Groups in Organic Synthesis, 3rd Ed", Wiley-Interscience, Inc. (1999) (Theodora W. Greene, Peter G. M. Wuts)

Examples of the amino-protecting group include a formyl group, $C_{1-6}$ alkyl-carbonyl groups (e.g., acetyl, propionyl groups, etc.), a phenylcarbonyl group, $C_{1-6}$ alkyl-oxycarbonyl groups (e.g., methoxycarbonyl, ethoxycarbonyl groups, etc.), aryloxycarbonyl groups (e.g., a phenyloxycarbonyl group, etc.), $C_{7-10}$ aralkyl-carbonyl groups (e.g., a benzyloxycarbonyl group, etc.), a benzyl group, a benzhydryl group, a trityl group, a phthaloyl group and the like. These protecting groups optionally have substituent(s). Examples of the substituent include halogen atoms (e.g., fluorine, chlorine, bromine, iodine atoms), $C_{1-6}$ alkyl-carbonyl groups (e.g., acetyl, propionyl, butylcarbonyl groups, etc.), a nitro group and the like. The number of the substituent is 1 to 3.

Examples of the carboxyl-protecting group include $C_{1-6}$ alkyl groups (e.g., methyl, ethyl, n-propyl, i-propyl, n-butyl, tert-butyl groups, etc.), a phenyl group, a trityl group, a silyl group and the like. These protecting groups optionally have substituent(s). Examples of the substituent include halogen atoms (fluorine, chlorine, bromine, iodine atoms), a formyl group, $C_{1-6}$ alkyl-carbonyl groups (e.g., acetyl, propionyl, butylcarbonyl groups, etc.), a nitro group and the like. The number of the substituent is 1 to 3.

Examples of the hydroxyl-protecting group include $C_{1-6}$ alkyl groups (e.g., methyl, ethyl, n-propyl, i-propyl, n-butyl, tert-butyl groups, etc.), a phenyl group, $C_{7-10}$ aralkyl groups (e.g., a benzyl group, etc.), a formyl group, $C_{1-6}$ alkyl-carbonyl groups (e.g., acetyl, propionyl groups, etc.), aryloxycarbonyl groups (e.g., a phenyloxycarbonyl group, etc.), $C_{7-10}$ aralkyl-carbonyl groups (e.g., a benzyloxycarbonyl group, etc.), a pyranyl group, a furanyl group, a silyl group and the like. These protecting groups optionally have substituent(s). Examples of the substituent include halogen atoms (fluorine, chlorine, bromine, iodine atoms), $C_{1-6}$ alkyl groups, a phenyl group, $C_{7-10}$ aralkyl groups, a nitro group and the like. The number of the substituent is 1 to 4.

The removal of the protecting group can be carried out according to a method known per se, for example, the method described in "Protective Groups in Organic Synthesis, 3rd Ed", Wiley-Interscience, Inc. (1999) (Theodora W. Greene, Peter G. M. Wuts) and the like, or a method analogous thereto. For example, a method treating with an acid, a base, reduction, ultraviolet radiation, hydrazine, phenylhydrazine, sodium N-methyldithiocarbamate, tetrabutylammonium fluoride, palladium acetate and the like can be employed.

When the object product is obtained in a free form by the above-mentioned reaction, it may be converted to a salt by a conventional method. When it is obtained as a salt, it can also be converted to a free form or other salt by a conventional method. The thus-obtained compound (I) can be isolated and purified from the reaction solution by a known means, for example, phase transfer, concentration, solvent extraction, fractionation, crystallization, recrystallization, chromatography and the like.

When compound (I) contains an isomer such as a tautomer, an optical isomer, a stereoisomer, a regioisomer, a rotamer and the like, any isomer and a mixture thereof are also encompassed in the compound of the present invention. Furthermore, when compound (I) contains an optical isomer, an optical isomer resolved from racemate compound is also encompassed in compound (I).

The optical isomer can be produced according to a method known per se. Specifically, the optical isomer is obtained using an optically active synthetic intermediate or by subjecting the racemic final product to an optical resolution according to a known method.

The method of optical resolution may be a method known per se, such as a fractional recrystallization method, a chiral column method, a diastereomer method etc.

1) Fractional Recrystallization Method

A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine etc.) is formed, which is separated by a fractional recrystallization method, and if desired, a neutralization step to give a free optical isomer.

2) Chiral Column Method

A method wherein a racemate or a salt thereof is applied to a column (a chiral column) for separation of an optical isomer to allow separation. In the case of a liquid chromatography, for example, a mixture of the optical isomers is applied to a chiral column such as ENANTIO-OVM (manufactured by Tosoh Corporation), CHIRAL series (manufactured by Daicel Chemical Industries, Ltd.) and the like, and developed with water, various buffers (e.g., phosphate buffer, etc.) and organic solvents (e.g., ethanol, methanol, isopropanol, acetonitrile, trifluoroacetic acid, diethylamine, etc.) as an eluent, solely or in admixture to separate the optical isomer. In the case of a gas chromatography, for example, a chiral column such as CP-Chirasil-DeX CB (manufactured by GL Sciences Inc.) and the like is used to allow separation.

3) Diastereomer Method

A method wherein a racemic mixture is prepared into a diastereomeric mixture by chemical reaction with an optically active reagent, which is made into a single substance by a typical separation means (e.g., a fractional recrystallization method, a chromatography method etc.) and the like, and is subjected to a chemical treatment such as hydrolysis and the like to separate an optically active reagent moiety, whereby an optical isomer is obtained. For example, when compound (I) contains hydroxy or primary or secondary amino in a molecule, the compound and an optically active organic acid (e.g., MTPA [α-methoxy-α-(trifluoromethyl) phenylacetic acid], (−)-menthoxyacetic acid etc.) and the like are subjected to condensation reaction to give diastereomers of the ester compound or the amide compound, respectively. When compound (I) has a carboxyl group, the compound and an optically active amine or an optically active alcohol reagent are subjected to condensation reaction to give diastereomers of the amide compound or the ester compound, respectively. The separated diastereomer is converted to an optical isomer of the original compound by acid hydrolysis or base hydrolysis.

Compound (I) may be a crystal. Even if compound (I) is in a single crystal form or mixed crystal form, it is encompassed in compound (I).

Compound (I) may be a pharmaceutically acceptable cocrystal or a salt thereof. The cocrystal or a salt thereof means a crystalline substance constituted with two or more special solids at room temperature, each having different physical properties (e.g., structure, melting point, melting heat, hygroscopicity, solubility and stability etc.). The cocrystal or a salt thereof can be produced according to a cocrystallization method known per se.

The crystal of compound (I) can be produced according to a crystallization method known per se.

Examples of the crystallization method include crystallization method from a solution, crystallization method from vapor, crystallization method from a melt, and the like.

The "crystallization method from a solution" is typically a method of shifting a non-saturated state to supersaturated state by varying factors involved in solubility of compounds (solvent composition, pH, temperature, ionic strength, redox state, etc.) or the amount of solvent. Specific examples thereof include a concentration method, a slow cooling method, a reaction method (a diffusion method, an electrolysis method), a hydrothermal growth method, a flux method and the like. Examples of the solvent to be used include aromatic hydrocarbons (e.g., benzene, toluene, xylene, etc.), halogenated hydrocarbons (e.g., dichloromethane, chloroform, etc.), saturated hydrocarbons (e.g., hexane, heptane, cyclohexane, etc.), ethers (e.g., diethyl ether, diisopropyl ether, tetrahydrofuran, dioxane, etc.), nitriles (e.g., acetonitrile, etc.), ketones (e.g., acetone, etc.), sulfoxides (e.g., dimethyl sulfoxide, etc.), acid amides (e.g., N,N-dimethylformamide, etc.), esters (e.g., ethyl acetate, etc.), alcohols (e.g., methanol, ethanol, isopropanol, etc.), water and the like. These solvents are used alone or in a combination of two or more at a suitable ratio (e.g., 1:1 to 1:100 (a volume ratio)). Where necessary, a seed crystal can be used.

The "crystallization method from vapor" is, for example, a vaporization method (a sealed tube method, a gas stream method), a gas phase reaction method, a chemical transportation method and the like.

The "crystallization method from a melt" is, for example, a normal freezing method (a pulling method, a temperature gradient method, a Bridgman method), a zone melting method (a zone leveling method, a floating zone method), a special growth method (a VLS method, a liquid phase epitaxy method) and the like.

Preferable examples of the crystallization method include a method comprising dissolving compound (I) in a suitable solvent (e.g., alcohols such as methanol, ethanol etc.) at 20° C. to 120° C., and cooling the obtained solution to a temperature (e.g., 0-50° C., preferably 0-20° C.) not higher than the dissolution temperature, and the like.

The thus-obtained crystals of the present invention can be isolated, for example, by filtration and the like.

An analysis method of the obtained crystal is generally a method of crystal analysis by powder X-ray diffraction.

As a method of determining crystal orientation, a mechanical method or an optical method and the like can also be used.

In the present specification, the peak by powder X-RAY diffraction means the peak measured, for example, by RINT2100 (Rigaku Corporation) and the like using Cu-Kα1-ray (tube voltage: 40 KV; tube current: 50 mA) as a source.

Generally, the peaks by melting point and powder X-RAY diffraction may vary depending on measurement equipment, measurement condition and the like. The crystal in the present specification may show peaks different from those by melting point or powder X-RAY diffraction described in the present specification as long as they are within general error range.

The crystal of compound (I) obtained by the above-mentioned production method (hereinafter to be referred to as "the crystal of the present invention") has high purity, high quality, and low hygroscopicity, is not denatured even after a long-term preservation under general conditions, and is extremely superior in the stability. In addition, it is also superior in the biological properties (e.g., pharmacokinetics (absorption, distribution, metabolism, excretion), efficacy expression etc.) and is extremely useful as a medicament.

In the present specification, the specific optical rotation ($[\alpha]_D$) means a specific optical rotation measured, for example, by polarimeter (JASCO), P-1030 polarimeter (No. AP-2)) and the like.

In the present specification, the melting point means a melting point measured, for example, by micro melting point apparatus (Yanako, MP-500D), DSC (differential scanning calorimetry analysis) apparatus (SEIKO, EXSTAR6000) and the like.

Compound (I) may be a solvate (e.g., a hydrate (e.g., hemihydrate, monohydrate, dihydrate etc.)) or a non-solvate (e.g., non-hydrate, etc.), and they are also encompassed in compound (I).

Compound (I) may be labeled or substituted with an isotope (e.g., $^2$H, $^3$H, $^{11}$C, $^{14}$C, $^{18}$F, $^{35}$S, or $^{125}$I), and they are also encompassed in compound (I). Compound (I) labeled or substituted with an isotope can be used, for example, as a tracer (PET tracer) used for positron emission tomography (PET), and is useful in the field such as medical diagnosis and the like.

The prodrug of compound (I) means a compound which can be converted into compound (I) by reaction with an enzyme, gastric acid, or the like under physiological conditions in the living body. In other words, it means a compound which can be converted into compound (I) by enzymatic oxidation, reduction, hydrolysis or the like, or a compound which can be converted into compound (I) by hydrolysis with gastric acid or the like. Examples of the prodrug of compound (I) include a compound in which amino of compound (I) is acylated, alkylated or phosphorylated (e.g., the amino of compound (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated or tert-butylated); a compound in which hydroxyl of compound (I) is acylated, alkylated, phosphorylated or borated (e.g., hydroxyl of compound (I) is acetylated, palmitoylated, propanoylated, pivaloylated, succinylated, fumarylated, alanylated or dimethylaminomethylcarbonylated); a compound in which carboxy of compound (I) is esterified or amidated (e.g., a compound in which carboxy of compound (I) is ethyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl)methyl esterified, cyclohexyloxycarbonylethyl esterified or methylamidated). These compounds can be produced from compound (I) by a method known per se. The prodrug of compound (I) may be a compound that converts to compound (I) under physiological conditions as described in Development of Pharmaceutical Products, vol. 7, Molecule Design, 163-198, Hirokawa Shoten (1990).

Since compound (I) and a prodrug thereof [hereinafter sometimes to be abbreviated as the compound of the present invention] show superior RORγt inhibitory activity, they are useful as safe medicaments based on such action.

For example, the medicament of the present invention containing the compound of the present invention can be used for a mammal (e.g., mouse, rat, hamster, rabbit, cat, dog, bovine, sheep, monkey, human etc.) as a prophylactic or therapeutic agent for RORγt associated diseases, Th17 cell associated diseases and IL-17A or IL-17F associated diseases, more specifically, the diseases described in (1)-(4) below.

(1) inflammatory diseases (e.g., rheumatoid arthritis, acute pancreatitis, chronic pancreatitis, asthma, bronchial asthma, adult respiratory distress syndrome, chronic obstructive pulmonary disease (COPD), inflammatory bone disease, inflammatory pulmonary disease, inflammatory bowel disease, celiac disease, Behcet's disease, hepatitis, alcoholic liver fibrosis, alcoholic hepatitis, alcoholic cirrhosis, hepatitis B viral liver disorder, primary biliary cirrhosis (PBC), primary sclerosing cholangitis (PSC), transient ischemic attack (TIA), systemic inflammatory response syndrome (SIRS), dry eye, glaucoma, uveitis, orbital cellulitis, sudden orbital inflammation, age-related macular degeneration, postoperative or posttraumatic inflammation, liver disorder, pneumonia, nephritis, meningitis, cystitis, pharyngolaryngitis, gastric mucosal injury, spondylitis, arthritis, dermatitis, chronic pneumonia, bronchitis, pulmonary infarction, silicosis, pulmonary sarcoidosis, autoimmune anemia, Goodpasture's syndrome, Graves' disease, Hashimoto's thyroiditis, vasculitis, Basedow disease, sinusitis, allergic rhinitis, chronic hypertrophic rhinitis etc.), (2) autoimmune diseases (e.g., rheumatoid arthritis, ankylosing spondylitis, psoriasis, multiple sclerosis (MS), polymyositis, neuromyelitis optica (NMO), chronic inflammatory demyelinating polyneuropathy (CIDP), dermatomyositis (DM), polyarteritis nodosa (PN), mixed connective tissue disease (MCTD), amyotrophic lateral sclerosis (ALS), Guillain-Barre syndrome, myasthenia gravis, Parkinson's disease, spinal muscular atrophy, spinal cerebellar atrophy, progressive supranuclea palsy, Fisher syndrome, central nervous lupus, acute disseminated encephalomyelitis, multiple system atrophy, Huntington's disease, Alzheimer's disease, cerebrovascular dementia, diffuse Lewy body disease, cerebrovascular disorder, cerebral infarction, transient ischemic attack, intracerebral hemorrhage, vascular disease of spinal cord, spinal cord infarction, polyneuropathy, Lambert-Eaton syndrome, muscular dystrophy, metabolic myopathy, inflammatory myopathy, inclusion body myositis, encephalitis, meningitis, Sjogren's syndrome, systemic lupus erythematosus, scleroderma, pemphigus, profundus lupus erythematosus, chronic thyroiditis, Graves' disease, autoimmune gastritis, type I and type II diabetes, autoimmune hemolytic anemia, autoimmune neutropenia, thrombocytopenia, atopic dermatitis, chronic active hepatitis, myasthenia gravis, inflammatory bowel disease (IBD), ulcerative colitis (UC), Crohn's disease, graft versus host disease, Addison's disease, abnormal immunoresponse, arthritis, dermatitis, radiodermatitis, sarcoidosis, type I diabetes etc.), (3) bone or joint degenerative diseases (e.g., rheumatoid arthritis, osteoporosis, osteoarthritis etc.), (4) neoplastic diseases [e.g., malignant tumor, angiogenesis glaucoma, infantile hemangioma, multiple myeloma, acute myeloblastic leukemia, chronic sarcoma, multiple myeloma, chronic myelogenous leukemia, metastasis melanoma, Kaposi's sacroma, vascular proliferation, cachexia, metastasis of the breast cancer, cancer (e.g., colorectal cancer (e.g., familial colorectal cancer, hereditary nonpolyposis colorectal cancer, gastrointestinal stromal tumor and the like), lung cancer (e.g., non-small cell lung cancer, small cell lung cancer, malignant mesothelioma and the like), mesothelioma, pancreatic cancer (e.g., pancreatic duct cancer and the like), gastric cancer (e.g., papillary adenocarcinoma, mucinous adenocarcinoma, adenosquamous carcinoma and the like), breast cancer (e.g., invasive ductal carcinoma, ductal carcinoma in situ, inflammatory breast cancer and the like), ovarian cancer (e.g., ovarian epithelial carcinoma, extragonadal germ cell tumor, ovarian germ cell tumor, ovarian low malignant potential tumor and the like), prostate cancer (e.g., hormone-dependent prostate cancer, non-hormone dependent prostate cancer and the like), liver cancer (e.g., primary liver cancer, extrahepatic bile duct cancer and the like), thyroid cancer (e.g., medullary thyroid carcinoma and the like), kidney cancer (e.g., renal cell carcinoma, transitional cell carcinoma in kidney and urinary duct and the like), uterine cancer, endometrial cancer, brain tumor (e.g., pineal astrocytoma, pilocytic astrocytoma, diffuse astrocytoma, anaplastic astrocytoma and the like), melanoma (melanoma), sarcoma, urinary bladder cancer, hematologic cancer and the like including multiple myeloma, hypophyseal adenoma, glioma, acoustic neurinoma, retinoblastoma, head and neck cancer, pharyngeal cancer, laryngeal cancer, cancer of the tongue, thymoma, esophagus cancer, duodenal cancer, colorectal cancer, rectal cancer, hepatoma, pancreatic endocrine tumor, cancer of the bile duct, gallbladder cancer, penile cancer, urinary duct cancer, testis tumor, vulvar cancer, cervix cancer, endometrial cancer, uterus sarcoma, cholionic disease, vaginal cancer, skin cancer, fungoid mycosis, basal cell tumor, soft tissue sarcoma, malignant lymphoma, Hodgkin's disease, myelodysplastic syndrome, acute lymphocytic leukemia, chronic lymphocytic leukemia, adult T cell leukemia, chronic bone marrow proliferative disease, pancreatic endocrine tumor, fibrous histiocytoma, leiomyosarcoma, rhabdomyosarcoma, cancer of unknown primary].

The medicament of the present invention can be preferably used as an agent for the prophylaxis or treatment of psoriasis, inflammatory bowel disease (IBD), ulcerative colitis (UC), Crohn's disease (CD), rheumatoid arthritis, multiple sclerosis, uveitis, asthma, ankylopoietic spondylarthritis, systemic lupus erythematosus (SLE) and the like.

In another embodiment, the medicament of the present invention can be preferably used as an agent for the prophylaxis or treatment of autoimmune disease, inflammatory disease, bone or articular disease, or neoplastic disease, particularly preferably psoriasis, inflammatory bowel disease (IBD), ulcerative colitis (UC), Crohn's disease (CD), rheumatoid arthritis, multiple sclerosis, uveitis, asthma, ankylopoietic spondylarthritis, systemic lupus erythematosus (SLE), chronic obstructive pulmonary diseases, ovarian cancer, non small cell lung cancer, breast cancer, stomach cancer, head and neck cancer, prostate cancer or endometrial cancer.

Here, the above-mentioned "prophylaxis" of a disease means, for example, administration of a medicament containing the compound of the present invention to patients who are expected to have a high risk of the onset due to some factor relating to the disease but have not developed the disease or patients who have developed the disease but do not have a subjective symptom, or administration of a medicament containing the compound of the present invention to patients who are feared to show recurrence of the disease after treatment of the disease.

The medicament of the present invention shows superior pharmacokinetics (e.g., a half-life of the drug in plasma), low toxicity (e.g., HERG inhibition, CYP inhibition, CYP induction), and decreased drug interaction. The compound of the present invention can be directly used as a medicament, or as the medicament of the present invention by producing a pharmaceutical composition by mixing with a pharmaceutically acceptable carrier by a means known per se and generally used in a production method of pharmaceutical preparations. The medicament of the present invention can be orally or parenterally administered safely to mammals (e.g., humans, monkeys, cows, horses, pigs, mice, rats, hamsters, rabbits, cats, dogs, sheep and goats).

A medicament containing the compound of the present invention can be safely administered solely or by mixing with a pharmacologically acceptable carrier according to a method known per se (e.g., the method described in the Japanese Pharmacopoeia etc.) as the production method of a pharmaceutical preparation, and in the form of, for example, tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal and intratumor administrations, administration to the vicinity of tumor, and direct administration to the lesion).

The content of the compound of the present invention in the medicament of the present invention is about 0.01 to 100% by weight of the entire medicament. While the dose varies depending on the subject of administration, administration route, disease and the like, for example, for oral administration to an adult inflammatory bowel disease (IBD) patient (body weight about 60 kg), it is about 0.1 mg/kg body weight to 30 mg/kg body weight, preferably about 1 mg/kg body weight to 20 mg/kg body weight as an active ingredient (compound (I)) for one day, which is administered once to several times, preferably once or two to three times.

The pharmaceutically acceptable carrier, which may be used for the production of the medicament of the present invention, may be exemplified by various organic or inorganic carrier materials that are conventionally used as preparation materials, for example, excipient, lubricant, binding agent and disintegrant for solid preparations; or solvent, solubilizing agent, suspending agent, isotonic agent, buffering agent, soothing agent and the like for liquid preparations. Furthermore, when necessary, ordinary additives such as preservative, antioxidant, colorant, sweetening agent, adsorbing agent, wetting agent and the like can be also used as appropriate in an appropriate amount.

Examples of the excipient include lactose, white sugar, D-mannitol, starch, corn starch, crystalline cellulose, light anhydrous silicic acid and the like.

Examples of the lubricant include magnesium stearate, calcium stearate, talc, colloidal silica and the like.

Examples of the binding agent include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, carboxymethylstarch sodium, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffering agent include buffer solutions such as phosphates, acetates, carbonates, citrates and the like.

Examples of the soothing agent include benzyl alcohol and the like.

Examples of the preservative include parahydroxybenzoates, chlorobutanol, benzyl alcohol, phenylethyl alcohol, dehydroacetic acid, sorbic acid and the like.

Examples of the antioxidant include sulfites, ascorbic acid, α-tocopherol and the like.

For the prophylaxis or treatment of various diseases, the compound of the present invention can also be used together with other medicaments. In the following, a medicament to be used when the compound of the present invention is used together with other drug is referred to as "the combination agent of the present invention".

For example, when the compound of the present invention is used as an RORγt inhibitor, Th17 cell inhibitor, IL-17A or IL-17F inhibitor, it can be used in combination with the following drugs.
(1) non-steroidal anti-inflammatory drug (NSAIDs)
(i) Classical NSAIDs
  alcofenac, aceclofenac, sulindac, tolmetin, etodolac, fenoprofen, thiaprofenic acid, meclofenamic acid, meloxicam, tenoxicam, lornoxicam, nabumeton, acetaminophen, phenacetin, ethenzamide, sulpyrine, antipyrine, migrenin, aspirin, mefenamic acid, flufenamic acid, diclofenac sodium, loxoprofen sodium, phenylbutazone, indomethacin, ibuprofen, ketoprofen, naproxen, oxaprozin, flurbiprofen, fenbufen, pranoprofen, floctafenine, piroxicam, epirizole, tiaramide hydrochloride, zaltoprofen, gabexate mesylate, camostat mesylate, ulinastatin, colchicine, probenecid, sulfinpyrazone, benzbromarone, allopurinol, sodium aurothiomalate, hyaluronate sodium, sodium salicylate, morphine hydrochloride, salicylic acid, atropine, scopolamine, morphine, pethidine, levorphanol, oxymorphone or a salt thereof and the like.
(ii) cyclooxygenase inhibitor (COX-1 selective inhibitor, COX-2 selective inhibitor and the like)
  salicylic acid derivatives (e.g., celecoxib, aspirin), etoricoxib, valdecoxib, diclofenac, indomethacin, loxoprofen and the like.
(iii) nitric oxide-releasing NSAIDs
(2) disease-modifying anti-rheumatic drugs (DMARDs)
(i) Gold preparation
  auranofin and the like.
(ii) penicillamine
  D-penicillamine.
(iii) aminosalicylic acid preparation
  sulfasalazine, mesalazine, olsalazine, balsalazide, salazosulfapyridine.
(iv) antimalarial drug
  chloroquine and the like.
(v) pyrimidine synthesis inhibitor
  leflunomide and the like.
(vi) tacrolimus
(3) anti-cytokine drug
(I) protein drug
(i) TNF inhibitor
  etanercept, infliximab, adalimumab, certolizumab pegol, golimumab, PASSTNF-α, soluble TNF-α receptor, TNF-α binding protein, anti-TNF-α antibody and the like.
(ii) interleukin-1 inhibitor
  anakinra (interleukin-1 receptor antagonist), canakinumab, rilonacept, soluble interleukin-1 receptor and the like.
(iii) interleukin-6 inhibitor
  tocilizumab (anti-interleukin-6 receptor antibody), anti-interleukin-6 antibody and the like.
(iv) interleukin-10 drug
  interleukin-10 and the like.
(v) interleukin-12/23 inhibitor
  ustekinumab, briakinumab (anti-interleukin-12/23 antibody) and the like.
(vi) B cell activation inhibitor
  rituxan, benrista, ocrelizumab and the like.
(vii) co-stimulatory molecules related protein drug abatacept and the like.
(II) non-protein drug
(i) MAPK inhibitor
  BMS-582949 and the like.
(ii) gene modulator
  inhibitor of molecule involved in signal transduction, such as NF-κ, NF-κB, IKK-1, IKK-2, AP-1 and the like, and the like.
(iii) cytokine production inhibitor
  iguratimod, tetomilast and the like.
(iv) TNF-α converting enzyme inhibitor
(v) interleukin-1β converting enzyme inhibitor
  belnacasan and the like.
(vi) interleukin-6 antagonist
  HMPL-004 and the like.
(vii) interleukin-8 inhibitor
  IL-8 antagonist, CXCR1 & CXCR2 antagonist, reparixin and the like.
(viii) chemokine antagonist
  CCR9 antagonist (vercirnon (vercirnon sodium), CCX025, N-{4-chloro-2-[(1-oxidepyridin-4-yl)carbonyl]phenyl}-4-(propan-2-yloxy)benzenesulfonamide), MCP-1 antagonist and the like.
(ix) interleukin-2 receptor antagonist
  denileukin, diftitox and the like.
(x) therapeutic vaccines
  TNF-α vaccine and the like.
(xi) gene therapy drug
  gene therapy drugs aiming at promoting the expression of gene having an anti-inflammatory action such as interleukin-4, interleukin-10, soluble interleukin-1 receptor, soluble TNF-α receptor and the like.
(xii) antisense compound
  ISIS 104838, SMAD7 antisense oligonucleotide and the like.
(xiii) other antibody, biological preparation
  Abciximab, basiliximab, cetuximab, brentuximab, daclizumab, palivizumab, trastuzumab, omalizumab, Efalizumab, bevacizumab, basiliximab, ranibizumab, eculizumab, mogamulizumab, ofatumumab, denosumab, ipilimumab, alefacept, romiplostim, belatacept, aflibercept and the like.
(4) integrin inhibitor
  natalizumab, vedolizumab, AJM300, TRK-170, E-6007 and the like.
(5) immunomodulator (immunosuppressant)
  methotrexate, mizoribine, cyclophosphamide, MX-68, atiprimod dihydrochloride, abatacept, CKD-461, rimexolone, cyclosporine, tacrolimus, gusperimus, azathiopurine, antilymphocyte serum, freeze-dried sulfonated normal immunoglobulin, erythropoietin, colony stimulating factor, interleukin, interferon, cyclophosphamide, mycophenolate mofetil, immunoglobulin preparation for injection, fingolimod, S1P1 receptor agonist, dimethyl fumarate, copaxone, interferon β preparation, laquinimod, teriflunomide, and the like.
(6) proteasome inhibitor
  velcade and the like.
(7) JAK inhibitor
  tofacitinib and the like.
(8) steroid
  dexamethasone, hexestrol, methimazole, betamethasone, triamcinolone, triamcinolone acetonide, fluocinonide, fluocinolone acetonide, predonisolone, methylpredonisolone, cortisone acetate, hydrocortisone, fluorometholone, beclomethasone dipropionate, estriol and the like.
(9) angiotensin converting enzyme inhibitor
  enalapril, captopril, ramipril, lisinopril, cilazapril, perindopril and the like.
(10) angiotensin II receptor antagonist
  candesartan cilexetil, valsartan, irbesartan, olmesartan, eprosartan and the like.
(11) diuretic drug
  hydrochlorothiazide, spironolactone, furosemide, indapamide, bendrofluazide, cyclopenthiazide and the like.
(12) cardiotonic drug
  digoxin, dobutamine and the like.
(13) β receptor antagonist
  carvedilol, metoprolol, atenolol and the like.
(14) Ca sensitizer
  caldaret hydrate and the like.
(15) Ca channel antagonist
  nifedipine, diltiazem, verapamil and the like.
(16) anti-platelet drug, anticoagulator
  heparin, aspirin, warfarin and the like.
(17) HMG-CoA reductase inhibitor
  atorvastatin, simvastatin and the like.

(18) contraceptive
(i) sex hormone or derivatives thereof
gestagen or a derivative thereof (progesterone, 17α-hydroxy progesterone, medroxyprogesterone, medroxyprogesterone acetate, norethisterone, norethisterone enanthate, norethindrone, norethindrone acetate, norethynodrel, levonorgestrel, norgestrel, ethynodiol diacetate, desogestrel, norgestimate, gestodene, progestin, etonogestrel, drospirenone, dienogest, trimegestone, nestorone, chlormadinone acetate, mifepristone, nomegestrol acetate, tosagestin, TX-525, ethinylestradiol/TX525) or a combination agent of a gestagen or a derivative thereof and an estrogen or a derivative thereof (estradiol, estradiol benzoate, estradiol cypionate, estradiol dipropionate, estradiol enanthate, estradiol hexahydrobenzoate, estradiol phenylpropionate, estradiol undecanoate, estradiol valerate, estrone, ethinylestradiol, mestranol) and the like.
(ii) antiestrogen
ormeloxifene, mifepristone, Org-33628 and the like.
(iii) spermatocide
ushercell and the like.
(19) others
(i) T cell inhibitors
(ii) inosine monophosphate dehydrogenase (IMPDH) inhibitor
mycophenolate mofetil and the like.
(iii) adhesion molecule inhibitor
alicaforsen sodium, selectin inhibitor, ELAM-1 inhibitor, VCAM-1 inhibitor, ICAM-1 inhibitor and the like.
(iv) thalidomide
(v) cathepsin inhibitor
(vi) matrix metalloprotease (MMPs) inhibitor
V-85546 and the like.
(vii) glucose-6-phosphate dehydrogenase inhibitor
(viii) Dihydroorotate dehydrogenase (DHODH) inhibitor
(ix) phosphodiesterase IV (PDE IV) inhibitor
roflumilast, apremilast, CG-1088 and the like.
(x) phospholipase $A_2$ inhibitor
(xi) iNOS inhibitor
VAS-203 and the like.
(xii) microtubule stimulating drug
paclitaxel and the like.
(xiii) microtuble inhibitor
reumacon and the like.
(xiv) MHC class II antagonist
(xv) prostacyclin agonist
iloprost and the like.
(xvi) CD4 antagonist
zanolimumab and the like.
(xvii) CD23 antagonist
(xviii) LTB4 receptor antagonist
DW-1350 and the like.
(xix) 5-lipoxygenase inhibitor
zileuton and the like.
(xx) cholinesterase inhibitor
galanthamine and the like.
(xxi) tyrosine kinase inhibitor
Tyk2 inhibitor (WO2010/142752) and the like.
(xxii) cathepsin B inhibitor
(xxiii) adenosine deaminase inhibitor
pentostatin and the like.
(xxiv) osteogenesis stimulator
(xxv) dipeptidylpeptidase inhibitor
(xxvi) collagen agonist
(xxvii) capsaicin cream
(xxviii) hyaluronic acid derivative
synvisc (hylan G-F 20), orthovisc and the like.
(xxix) glucosamine sulfate
(xxx) amiprilose
(xxxi) CD-20 inhibitor
rituximab, ibritumomab, tositumomab, ofatumumab and the like.
(xxxii) BAFF inhibitor
belimumab, tabalumab, atacicept, blisibimod and the like.
(xxxiii) CD52 inhibitor
alemtuzumab and the like.

Other concomitant drugs besides the above-mentioned drug include, for example, antibacterial agent, antifungal agent, antiprotozoal agent, antibiotic, antitussive and expectorant drug, sedative, anesthetic, antiulcer drug, antiarrhythmic agent, hypotensive diuretic drug, anticoagulant, tranquilizer, antipsychotic, antitumor drug, hypolipidemic drug, muscle relaxant, antiepileptic drug, antidepressant, antiallergic drug, cardiac stimulants, therapeutic drug for arrhythmia, vasodilator, vasoconstrictor, therapeutic drug for diabetes, antinarcotic, vitamin, vitamin derivative, antiasthmatic, therapeutic agent for pollakisuria/anischuria, therapeutic agent for atopic dermatitis, therapeutic agent for allergic rhinitis, hypertensor, endotoxin-antagonist or -antibody, signal transduction inhibitor, inhibitor of inflammatory mediator activity, antibody to inhibit inflammatory mediator activity, inhibitor of anti-inflammatory mediator activity, antibody to inhibit anti-inflammatory mediator activity and the like. Specific examples thereof include the following.

(1) Antibacterial agent
(i) sulfa drug
sulfamethizole, sulfisoxazole, sulfamonomethoxine, salazosulfapyridine, silver sulfadiazine and the like.
(ii) quinolone antibacterial agent
nalidixic acid, pipemidic acid trihydrate, enoxacin, norfloxacin, ofloxacin, tosufloxacin tosylate, ciprofloxacin hydrochloride, lomefloxacin hydrochloride, sparfloxacin, fleroxacin and the like.
(iii) antiphthisic
isoniazid, ethambutol (ethambutol hydrochloride), p-aminosalicylic acid (calcium p-aminosalicylate), pyrazinamide, ethionamide, protionamide, rifampicin, streptomycin sulfate, kanamycin sulfate, cycloserine and the like.
(iv) antiacidfast bacterium drug
diaphenylsulfone, rifampicin and the like.
(v) antiviral drug
idoxuridine, acyclovir, vidarabine, gancyclovir and the like.
(vi) anti-HIV agent
zidovudine, didanosine, zalcitabine, indinavir sulfate ethanolate, ritonavir and the like.
(vii) antispirochetele
(viii) antibiotic
tetracycline hydrochloride, ampicillin, piperacillin, gentamicin, dibekacin, kanendomycin, lividomycin, tobramycin, amikacin, fradiomycin, sisomicin, tetracycline, oxytetracycline, rolitetracycline, doxycycline, ampicillin, piperacillin, ticarcillin, cephalothin, cephapirin, cephaloridine, cefaclor, cephalexin, cefroxadine, cefadroxil, cefamandole, cefotoam, cefuroxime, cefotiam, cefotiam hexetil, cefuroxime axetil, cefdinir, cefditoren pivoxil, ceftazidime, cefpiramide, cefsulodin, cefmenoxime, cefpodoxime proxetil, cefpirome, cefozopran, cefepime, cefsulodin, cefmenoxime, cefmetazole, cefminox, cefoxitin, cefbuperazone, latamoxef, flomoxef, cefazolin, cefotaxime, cefoperazone, ceftizoxime, moxalactam, thienamycin, sulfazecin, aztreonam or a salt thereof, griseofulvin, lankacidin-group [Journal of Antibiotics (J. Antibiotics), 38, 877-885(1985)], azole compound [2-[(1R,2R)-2-(2,4-difluorophenyl)-2-hydroxy-1-methyl-3-(1H-1,2,4-triazol-1-yl)propyl]-4-[4-(2,2,3,3-tetrafluoropropoxy)phenyl]-3(2H,4H)-1,2,4-triazolone, fluconazole, itraconazole and the like] and the like.

(2) antifungal agent
(i) polyethylene antibiotic (e.g., amphotericin B, nystatin, trichomycin)
(ii) griseofulvin, pyrrolnitrin and the like
(iii) cytosine metabolism antagonist (e.g., flucytosine)
(iv) imidazole derivative (e.g., econazole, clotrimazole, miconazole nitrate, bifonazole, croconazole)
(v) triazole derivative (e.g., fluconazole, itraconazole)
(vi) thiocarbamic acid derivative (e.g., trinaphthol) and the like.

(3) antiprotozoal agent
metronidazole, tinidazole, diethylcarbamazine citrate, quinine hydrochloride, quinine sulfate and the like.

(4) antitussive and expectorant drug
ephedrine hydrochloride, noscapine hydrochloride, codeine phosphate, dihydrocodeine phosphate, isoproterenol hydrochloride, ephedrine hydrochloride, methylephedrine hydrochloride, noscapine hydrochloride, alloclamide, chlophedianol, picoperidamine, cloperastine, protokylol, isoproterenol, salbutamol, terbutaline oxymetebanol, morphine hydrochloride, dextromethorfan hydrobromide, oxycodone hydrochloride, dimemorphan phosphate, tipepidine hibenzate, pentoxyverine citrate, clofedanol hydrochloride, benzonatate, guaifenesin, bromhexine hydrochloride, ambroxol hydrochloride, acetylcysteine, ethyl cysteine hydrochloride, carbocysteine and the like.

(5) sedative
chlorpromazine hydrochloride, atropine sulfate, phenobarbital, barbital, amobarbital, pentobarbital, thiopental sodium, thiamylal sodium, nitrazepam, estazolam, flurazepam, haloxazolam, triazolam, flunitrazepam, bromovalerylurea, chloral hydrate, triclofos sodium and the like.

(6) anesthetic
(6-1) local anesthetic
cocaine hydrochloride, procaine hydrochloride, lidocaine, dibucaine hydrochloride, tetracaine hydrochloride, mepivacaine hydrochloride, bupivacaine hydrochloride, oxybuprocaine hydrochloride, ethyl aminobenzoate, oxethazaine and the like.

(6-2) general anesthetic
(i) inhalation anesthetic (e.g., ether, halothane, nitrous oxide, isoflurane, enflurane),
(ii) intravenous anesthetic (e.g., ketamine hydrochloride, droperidol, thiopental sodium, thiamylal sodium, pentobarbital) and the like.

(7) antiulcer drug
histidine hydrochloride, lansoprazole, metoclopramide, pirenzepine, cimetidine, ranitidine, famotidine, urogastrone, oxethazaine, proglumide, omeprazole, sucralfate, sulpiride, cetraxate, gefarnate, aldioxa, teprenone, vonoprazan, prostaglandin and the like.

(8) antiarrhythmic agent
(i) sodium channel blocker (e.g., quinidine, procainamide, disopyramide, ajmaline, lidocaine, mexiletine, phenytoin),
(ii) β-blocker (e.g., propranolol, alprenolol, bufetolol hydrochloride, oxprenolol, atenolol, acebutolol, metoprolol, bisoprolol, pindolol, carteolol, arotinolol hydrochloride),
(iii) potassium channel blocker (e.g., amiodarone),
(iv) calcium channel blocker (e.g., verapamil, diltiazem) and the like.

(9) hypotensive diuretic drug
hexamethonium bromide, clonidine hydrochloride, hydrochlorothiazide, trichlormethiazide, furosemide, ethacrynic acid, bumetanide, mefruside, azosemide, spironolactone, potassium canrenoate, triamterene, amiloride, acetazolamide, D-mannitol, isosorbide, aminophylline and the like.

(10) anticoagulant
heparin sodium, sodium citrate, activated protein C, tissue factor pathway inhibitor, antithrombin III, dalteparin sodium, warfarin potassium, argatroban, gabexate, sodium citrate, ozagrel sodium, ethyl icosapentate, beraprost sodium, alprostadil, ticlopidine hydrochloride, pentoxifylline, dipyridamole, tisokinase, urokinase, streptokinase and the like.

(11) tranquilizer
diazepam, lorazepam, oxazepam, chlordiazepoxide, medazepam, oxazolam, cloxazolam, clotiazepam, bromazepam, etizolam, fludiazepam, hydroxyzine and the like.

(12) antipsychotic
chlorpromazine hydrochloride, prochlorperazine, trifluoperazine, thioridazine hydrochloride, perphenazine maleate, fluphenazine enanthate, prochlorperazine maleate, levomepromazine maleate, promethazine hydrochloride, haloperidol, bromperidol, spiperone, reserpine, clocapramine hydrochloride, sulpiride, zotepine and the like.

(13) antitumor drug
6-O—(N-chloroacetylcarbamoyl)fumagillol, bleomycin, methotrexate, actinomycin D, mitomycin C, daunorubicin, adriamycin, neocarzinostatin, cytosine arabinoside, fluorouracil, tetrahydrofuryl-5-fluorouracil, picibanil, lentinan, levamisole, bestatin, azimexon, glycyrrhizin, doxorubicin hydrochloride, aclarubicin hydrochloride, bleomycin hydrochloride, peplomycin sulfate, vincristine sulfate, vinblastine sulfate, irinotecan hydrochloride, cyclophosphamide, melphalan, busulfan, thiotepa, procarbazine hydrochloride, cisplatin, azathioprine, mercaptopurine, tegafur, carmofur, cytarabine, methyltestosterone, testosterone propionate, testosterone enanthate, mepitiostane, fosfestrol, chlormadinone acetate, leuprorelin acetate, buserelin acetate and the like.

(14) hypolipidemic drug
clofibrate, ethyl 2-chloro-3-[4-(2-methyl-2-phenylpropoxy)phenyl]propionate [Chemical and Pharmaceutical Bulletin (Chem. Pharm. Bull), 38, 2792-2796 (1990)], pravastatin, simvastatin, probucol, bezafibrate, clinofibrate, nicomol, cholestyramine, dextran sulfate sodium and the like.

(15) muscle relaxant
pridinol, tubocurarine, pancuronium, tolperisone hydrochloride, chlorphenesin carbamate, baclofen, chlormezanone, mephenesin, chlorzoxazone, eperisone, tizanidine and the like.

(16) antiepileptic drug
phenytoin, ethosuximide, acetazolamide, chlordiazepoxide, trimethadione, carbamazepine, phenobarbital, primidone, sulthiame, sodium valproate, clonazepam, diazepam, nitrazepam and the like.

(17) antidepressant
imipramine, clomipramine, noxiptiline, phenelzine, amitriptyline hydrochloride, nortriptyline hydrochloride, amoxapine, mianserin hydrochloride, maprotiline hydrochloride, sulpiride, fluvoxamine maleate, trazodone hydrochloride and the like.

(18) antiallergic drug
diphenhydramine, chlorpheniramine, tripelennamine, metodilamine, clemizole, diphenylpyraline, methoxyphenamine, sodium cromoglicate, tranilast, repirinast, amlexanox, ibudilast, ketotifen, terfenadine, mequitazine, azelastine hydrochloride, epinastine, ozagrel hydrochloride, pranlukast hydrate, seratrodast and the like.

(19) cardiac stimulants trans-n-oxocamphor, terephyllol, aminophylline, etilefrine, dopamine, dobutamine, denopamine, aminophylline, vesnarinone, amrinone, pimobendan, ubidecarenone, digitoxin, digoxin, methyldigoxin, lanatoside C, G-strophanthin and the like.

(20) vasodilator oxyfedrine, diltiazem, tolazoline, hexobendine, bamethan, clonidine, methyldopa, guanabenz and the like.

(21) vasoconstrictor dopamine, dobutamine denopamine and the like.

(22) hypotensive diuretic hexamethonium bromide, pentolinium, mecamylamine, ecarazine, clonidine, diltiazem, nifedipine and the like.

(23) therapeutic drug for diabetes tolbutamide, chlorpropamide, acetohexamide, glibenclamide, tolazamide, acarbose, epalrestat, troglitazone, glucagon, glymidine, glipizide, phenformin, buformin, metformin, DPP4 inhibitor, insulin preparation and the like.

(24) antinarcotic levallorphan, nalorphine, naloxone or a salt thereof and the like.

(25) liposoluble vitamins (i) vitamin A: vitamin $A_1$, vitamin $A_2$ and retinol palmitate
(ii) vitamin D: vitamin $D_1$, $D_2$, $D_3$, $D_4$ and $D_5$
(iii) vitamin E: α-tocopherol, α-tocopherol, γ-tocopherol, δ-tocopherol, dl-α-tocopherol nicotinate
(iv) vitamin K: vitamin $K_1$, $K_2$, $K_3$ and $K_4$
(v) folic acid (vitamin M) and the like.

(26) vitamin derivative various derivatives of vitamins, for example, vitamin $D_3$ derivatives such as 5,6-trans-cholecalciferol, 2,5-hydroxycholecalciferol, 1-α-hydroxycholecalciferol, calcipotriol and the like, vitamin $D_2$ derivatives such as 5,6-trans-ergocalciferol and the like, and the like.

(27) antiasthmatic isoprenaline hydrochloride, salbutamol sulfate, procaterol hydrochloride, terbutaline sulfate, trimetoquinol hydrochloride, tulobuterol hydrochloride, orciprenaline sulfate, fenoterol hydrobromide, ephedrine hydrochloride, ipratropium bromide, oxitropium bromide, flutropium bromide, theophylline, aminophylline, sodium cromoglicate, tranilast, repirinast, amlexanox, ibudilast, ketotifen, terfenadine, mequitazine, azelastine, epinastine, ozagrel hydrochloride, pranlkast hydrate, seratrodast, dexamethasone, prednisolone, hydrocortisone, hydrocortisone sodium succinate, beclometasone dipropionate, ciclesonide and the like.

(28) therapeutic agent for pollakisuria/anischuria flavoxate hydrochloride and the like.

(29) therapeutic agent for atopic dermatitis sodium cromoglicate and the like.

(30) therapeutic agent for allergic rhinitis sodium cromoglicate, chlorpheniramine maleate, alimemazine tartrate, clemastine fumarate, homochlorcyclizine hydrochloride, fexofenadine, mequitazine, ketotifen fumarate, cetirizine hydrochloride, oxatomide, azelastine, ebastine, epinastine hydrochloride, loratadine and the like.

(31) hypertensor dopamine, dobutamine, denopamine, digitoxin, digoxin, methyldigoxin, lanatoside C, G-strophanthin and the like.

(32) therapeutic agent for dry eye artificial tears, therapeutic agent for corneal and conjunctive epithelium disorder, diquafosol sodium and the like.

(32) others hydroxycam, diacerein, megestrol acetate, nicergoline, prostaglandins, lamivudine, adefovir, entecavir, tenofovir, peginterferon α, ribavirin, telaprevir, simeprevir, vaniprevir, daclatasvir, asunaprevir, sofosbuvir, glycyrrhetinic acid, ursodeoxycholic acid and the like.

For combined use, the administration time of the compound of the present invention and the concomitant drug is not restricted, and the compound of the present invention or the concomitant drug can be administered to an administration subject simultaneously, or may be administered at different times. The dosage of the concomitant drug may be determined according to the dose clinically used, and can be appropriately selected depending on an administration subject, administration route, disease, combination and the like.

The administration form of the combined use is not particularly limited, and the compound of the present invention and a concomitant drug only need to be combined on administration. Examples of such administration mode include the following:

(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The mixing ratio of the compound of the present invention and a concomitant drug in the combination agent of the present invention can be appropriately selected based on the subject of administration, administration route, disease and the like.

For example, while the content of the compound of the present invention in the combination agent of the present invention varies depending on the preparation form, it is generally about 0.01-100 wt %, preferably about 0.1-50 wt %, more preferably about 0.5-20 wt %, of the whole preparation.

The content of the concomitant drug in the combination agent of the present invention varies depending on the preparation form, and generally about 0.01 to 100% by weight, preferably about 0.1 to 50% by weight, further preferably about 0.5 to 20% by weight, of the entire preparation.

While the content of the additive such as a carrier and the like in the combination agent of the present invention varies depending on the form of a preparation, it is generally about 1 to 99.99% by weight, preferably about 10 to 90% by weight, based on the preparation.

When the compound of the present invention and the concomitant drug are separately prepared, the same content may be adopted.

The dose varies depending on the kind of the compound of the present invention, administration route, symptom, age of patients and the like. For example, for oral administration to patients (body weight about 60 kg) with inflammatory bowel disease (IBD), about 0.1 mg/kg body weight-about 30 mg/kg body weight, preferably about 1 mg/kg body weight-20 mg/kg body weight, of compound (I) can be administered once to several portions per day.

The dose of the medicament of the present invention as a sustained-release preparation varies depending on the kind and content of compound (I), dosage form, period of sustained drug release, subject animal of administration (e.g., mammals such as mouse, rat, hamster, guinea pig, rabbit, cat, dog, bovine, horse, swine, sheep, monkey, human and the like), and administration object. For example, for application by parenteral administration, about 0.1 to about 100 mg of compound (I) needs to be released from the administered preparation per 1 week.

Any amount of the concomitant drug can be adopted as long as the side effects do not cause a problem. The daily dosage in terms of the concomitant drug varies depending on the severity, age, sex, body weight, sensitivity difference of the subject, administration period, interval, and nature, pharmacology, kind of the pharmaceutical preparation, kind of effective ingredient, and the like, and not particularly restricted, and the amount of a drug is, in the case of oral administration for example, generally about 0.001 to 2000 mg, preferably about 0.01 to 500 mg, further preferably about 0.1 to 100 mg, per 1 kg of a mammal and this is generally administered once to 4-times divided in a day.

When the combination agent of the present invention is administered, the compound of the present invention and the concomitant drug can be administered simultaneously, or may be administered in a staggered manner. When administered at a time interval, the interval varies depending on the effective ingredient, dosage form and administration method, and, for example, when the concomitant drug is administered first, a method in which the compound of the present invention is administered within time range of from 1 minute to 3 days, preferably from 10 minutes to 1 day, more preferably from 15 minutes to 1 hour, after administration of the concomitant drug is an example. When the compound of the present invention is administered first, a method in which the concomitant drug is administered within time range of from 1 minute to 1 day, preferably from 10 minutes to 6 hours, more preferably from 15 minutes to 1 hour after administration of the compound of the present invention is an example.

EXAMPLES

The present invention is explained in more detail in the following by referring to Examples, Formulation Examples and Experimental Examples, which are not to be construed as limitative and may be modified without departing from the scope of the invention.

Unless particularly specified, the elution in column chromatography in the Examples was performed under observation by TLC (Thin Layer Chromatography). For TLC observation, 60F254 manufactured by Merck was used as a TLC plate, and the solvent used as an elution solvent for column chromatography was used as a developing solvent. For detection, a UV detector was adopted. In silica gel column chromatography, NH means use of aminopropylsilane-bonded silica gel, and Diol means use of 3-(2,3-dihydroxypropoxy)propylsilane-bonded silica gel. In preparative HPLC (high performance liquid chromatography), C18 means use of octadecyl-bonded silica gel. The ratios of elution solvents are volume mixing ratios, unless otherwise specified. The room temperature generally means a temperature about 10° C. to 35° C. For drying extracts, sodium sulfate or magnesium sulfate was used.

The peak by powder X-RAY diffraction in Example means the peak measured using Cu Kα-ray as a source by Ultima IV (Rigaku Corporation, Japan) at room temperature. The measurement conditions are as follows.
Electric pressure/Electric current: 40 kV/50 mA
Scan speed: 6 degree/min
Scan range of 2 Theta: 2-35 degree
The crystallinity by powder X-RAY diffraction in Example was calculated by Hermans method.

In the chemical structure formulas described in Examples, the wavy line bonded to the asymmetric carbon

∿∿∿ means one stereochemical structure which is not determined, and the solid line

— means a mixture of two stereochemical structure.

The abbreviations in the present specification or the Examples mean as follows.
LC: liquid chromatography
MS: mass analysis spectrum
API: atmospheric pressure ionization method
M: molecular weight of the compound
NMR: nuclear magnetic resonance spectrum
Hz: hertz
J: coupling constant
m: multiplet
q: quartet
t: triplet
d: doublet
dd: double doublet
ddd: double double doublet
s: singlet
dt: double triplet
sxt: sextet
brs: broad singlet
quin: quintet
quant.: quantitative
ADDP: 1,1'-(azodicarbonyl)dipiperidine
AIBN: 2,2'-azobis(isobutyronitrile)
BINAP: 2,2'-bis(diphenylphosphino)-1,1'-binaphthyl
Boc: tert-butyloxycarbonyl group
Boc$_2$O: di-tert-butyl dicarbonate
CDI: carbonyldiimidazole
COMU: 1-[(1-(cyano-2-ethoxy-2-oxoethylideneaminooxy)-dimethylamino-morpholino)]carbenium hexafluorophosphate
CPME: cyclopentyl methyl ether
DBU: 1,8-diazabicyclo[5.4.0]undec-7-ene
DEAD: diethyl azodicarboxylate/40% toluene solution
DIAD: diisopropyl azodicarboxylate
DIBAL-H: diisobutylaluminium hydride
DIEA: diisopropylethylamine
DMA: dimethylacetamide
DMAP: 4-dimethylaminopyridine
DME: dimethoxyethane
DMF: N,N-dimethylformnamide
DMSO: dimethyl sulfoxide
DPPA: diphenylphosphoryl azide
Et$_2$O: diethyl ether
EtOH: ethanol
HATU: 2-(1H-7-azabenzotriazol-1-yl)-1,1,3,3-tetramethyl-uronium hexafluorophosphorate
HMDS: 1,1,1,2,2,2-hexamethyldisilane
HOBt: 1H-benzo[d][1,2,3]triazol-1-ol hydrate
IPE: diisopropyl ether MeOH: methanol
M: mol concentration
MEK: methyl ethyl ketone
N: normal concentration
NaHMDS: sodium bis(trimethylsilyl)amide
NBS: N-bromosuccinimide
n-BuLi: 1.6M n-butyllithium/hexane solution
NMP: N-methyl-2-pyrrolidone
Pd(PPh$_3$)$_4$: tetrakis(triphenylphosphine) palladium(0)
Pd$_2$(dba)$_3$: tris(dibenzylideneacetone)dipalladium(0)
PdCl$_2$(dppf): 1,1'-bis(diphenylphosphino)ferrocene-palladium(II)dichloride-dichloromethane complex
PPA: polyphosphoric acid
PPh$_3$: triphenylphosphine
t-: tert-
T3P: 1.6M 2,4,6-tripropyl-1,3,5,2,4,6-trioxatriphosphorinane-2,4,6-trioxide/ethyl acetate solution or DMF solution
TEA: triethylamine
TFA: trifluoroacetic acid
THF: tetrahydrofuran
TMSCl: trimethylsilyl chloride, trimethylsilane chloride
WSC: N$^1$-((ethylimino)methylene)-N$^3$,N$^3$-dimethylpropane-1,3-diamine
WSC.HCl: N$^1$-((ethylimino)methylene)-N$^3$,N$^3$-dimethylpropane-1,3-diamine hydrochloride
XANTPHOS: 4,5-bis(diphenylphosphino)-9,9-dimethylxanthene
LAH: lithium aluminium hydride Example 1 trans-2-(((1R)-1-((3,5-difluoro-4-(trimethylsilyl)phenyl)carbamoyl)-6-methoxy-3,4-dihydroisoquinolin-2(1H)-yl)carbonyl)cyclopropanecarboxylic acid (a mixture of two diastereomers)

(Step 1)
To a solution of 1,3-difluoro-5-nitrobenzene (3 g, 18.86 mmol) in THF (60 mL) was added trimethylsilyl chloride (7.23 mL, 56.57 mmol) at −78° C. under nitrogen atmosphere. To the reaction solution was added sodium hexamethyldisilazide (19.85 mL, 37.71 mmol), and the mixture was kept at −75° C. or lower. The reaction solution was stirred for 1 hr, and water and ethyl acetate were added thereto. The organic layer was separated, and the aqueous layer was extracted with ethyl acetate. The organic layer was dried over magnesium sulfate, and the solvent was evaporated under reduced pressure. The obtained residue was purified by silica gel column chromatography (solvent; hexane) to give (2,6-difluoro-4-nitrophenyl)trimethylsilane (3.51 g, 15.18 mmol, 80%) as a colorless oil.
$^1$H NMR (300 MHz, CDCl$_3$): δ0.42 (9H, s), 7.61-7.71 (2H, m).

A mixture of (2,6-difluoro-4-nitrophenyl)trimethylsilane (3.5 g, 15.13 mmol) and 10% palladium-carbon (350 mg, 0.16 mmol, 50% wet) in MeOH (70 mL) was stirred at room temperature for 5 hr under hydrogen atmosphere (1 atm). The catalyst was removed by filtration, and the filtrate was concentrated under reduced pressure. The obtained residue was purified by silica gel column chromatography (solvent; ethyl acetate/hexane) to give 3,5-difluoro-4-(trimethylsilyl)aniline (2.50 g, 12.42 mmol, 82%) as a pale-yellow oil.
$^1$H NMR (300 MHz, CDCl$_3$): δ0.30 (9H, s), 3.88 (2H, brs), 5.99-6.16 (2H, m).

(Step 2)
A solution of 3-(2-aminoethyl)phenol hydrochloride (4.60 g, 26.49 mmol) and 47% ethyl glyoxylate/toluene solution (polymer form) (6.15 mL, 29.14 mmol) in a mixed solvent of toluene/EtOH (50 mL) was heated under reflux for 18 hr. The reaction mixture was concentrated under reduced pressure. The precipitate was collected by filtration, and washed with ethyl acetate/diethyl ether to give ethyl 6-hydroxy-1,2,3,4-tetrahydroisoquinoline-1-carboxylate hydrochloride (6.15 g, 23.86 mmol, 90%) as a white powder.
$^1$H NMR (300 MHz, DMSO-d$_6$): δ1.25 (3H, t, J=7.0 Hz), 2.94 (2H, t, J=6.2 Hz), 3.35 (1H, brs), 3.38-3.52 (2H, m), 4.26 (2H, q, J=7.1 Hz), 5.27 (1H, s), 6.64 (1H, d, J=2.3 Hz), 6.73 (1H, dd, J=8.7, 2.6 Hz), 7.21 (1H, d, J=8.7 Hz), 9.77 (1H, s), 9.99 (1H, br s)

(Step 3)
Boc$_2$O (5.47 g, 25.06 mmol) was added to a solution of ethyl 6-hydroxy-1,2,3,4-tetrahydroisoquinoline-1-carboxylate hydrochloride (6.15 g, 23.86 mmol) and TEA (3.33 mL, 23.86 mmol) in a mixed solvent of THF (65 mL) and water (25 mL) at room temperature, and the mixture was vigorously stirred for 2 hr. The reaction mixture was poured into water (250 mL), and the mixture was extracted with ethyl acetate (×3). The organic layer was washed with water and brine, and dried over magnesium sulfate, and the solvent was evaporated under reduced pressure. The obtained residue was purified by silica gel column chromatography (solvent gradient; 5→30% ethyl acetate/hexane) to give 1-ethyl 2-tert-butyl 6-hydroxy-3,4-dihydroisoquinoline-1,2(1H)-dicarboxylate (7.85 g, 24.43 mmol, quant.) as a colorless oil.
$^1$H NMR (300 MHz, CDCl$_3$): δ1.19-1.29 (3H, m), 1.45-1.52 (9H, m), 2.72-2.96 (2H, m), 3.65-3.83 (2H, m), 4.08-4.19 (2H, m), 5.16-5.50 (2H, m), 6.63 (1H, s), 6.67-6.73 (1H, m), 7.31-7.37 (1H, m).

(Step 4)
Iodomethane (3.04 mL, 48.85 mmol) was added to a solution of 1-ethyl 2-tert-butyl 6-hydroxy-3,4-dihydroisoquinoline-1,2(1H)-dicarboxylate (7.85 g, 24.43 mmol) and cesium carbonate (10.35 g, 31.75 mmol) in DMF (50 mL) at room temperature, and the mixture was stirred for 2.5 hr. To the reaction mixture was added water, and the mixture was extracted with ethyl acetate (×3). The organic layer was washed with 0.1% aqueous sodium thiosulfate solution and brine, and dried over magnesium sulfate, and the solvent was evaporated under reduced pressure to give 1-ethyl 2-tert-butyl 6-methoxy-3,4-dihydroisoquinoline-1,2(1H)-dicarboxylate (8.23 g, 24.54 mmol, 100%) as a colorless oil.
$^1$H NMR (300 MHz, CDCl$_3$): δ1.20-1.29 (3H, m), 1.46-1.51 (9H, m), 2.75-2.99 (2H, m), 3.69-3.81 (5H, m), 4.08-4.19 (2H, m), 5.33-5.51 (1H, m), 6.68 (1H, s), 6.77 (1H, dd, J=8.3, 2.6 Hz), 7.36-7.43 (1H, m).

(Step 5)
2N Aqueous lithium hydroxide solution (73.6 mL, 147.23 mmol) was added to a solution of 1-ethyl 2-tert-butyl 6-methoxy-3,4-dihydroisoquinoline-1,2(1H)-dicarboxylate (8.23 g, 24.54 mmol) in a mixed solvent of EtOH (35 mL) and THF (35 mL) at room temperature, and the mixture was stirred for 2 hr. To the reaction mixture was added water, the pH of the mixture was adjusted to 3 with 2N hydrochloric acid, and the mixture was extracted with ethyl acetate (×3). The organic layer was washed with brine, and dried over magnesium sulfate, and the solvent was evaporated under reduced pressure to give 2-(tert-butoxycarbonyl)-6-methoxy-1,2,3,4-tetrahydroisoquinoline-1-carboxylic acid (7.59 g, 24.70 mmol, quant.) as a colorless oil.
$^1$H NMR (300 MHz, CDCl$_3$): δ1.41-1.52 (9H, m), 2.72-3.00 (2H, m), 3.56-3.67 (1H, m), 3.71-3.87 (4H, m), 5.33-

5.53 (1H, m), 6.68 (1H, d, J=2.3 Hz), 6.77 (1H, dd, J=8.7, 2.3 Hz), 7.37 (1H, d, J=8.7 Hz) (The exchangeable 1H was not observed).
(Step 6)

To a solution of 3,5-difluoro-4-(trimethylsilyl)aniline (700 mg, 3.48 mmol), 2-(tert-butoxycarbonyl)-6-methoxy-1,2,3,4-tetrahydroisoquinoline-1-carboxylic acid (1176 mg, 3.83 mmol), DMAP (467 mg, 3.83 mmol) and DIEA (3.04 mL, 17.39 mmol) in ethyl acetate (6.0 mL) was added T3P (6.14 mL, 10.43 mmol) at room temperature, and the mixture was stirred at 80° C. for 2 hr. To the reaction mixture was added water, and the mixture was extracted with ethyl acetate. The organic layer was washed with brine, and dried over magnesium sulfate, and the solvent was evaporated under reduced pressure. The precipitate was washed with diethyl ether/hexane to give tert-butyl 1-((3,5-difluoro-4-(trimethylsilyl)phenyl)carbamoyl)-6-methoxy-3,4-dihydroisoquinoline-2(1H)-carboxylate (994.1 mg, 2.026 mmol, 58.3%) as white crystals.

$^1$H NMR (300 MHz, CDCl$_3$): δ0.32 (9H, s), 1.52 (9H, s), 2.76-2.98 (2H, m), 3.51-3.75 (2H, m), 3.80 (3H, s), 5.58 (1H, brs), 6.73 (1H, d, J=2.3 Hz), 6.81 (1H, dd, J=8.3, 2.3 Hz), 6.97-7.07 (2H, m), 7.19 (1H, brs), 9.11 (1H, brs).
(Step 7)

tert-Butyl 1-((3,5-difluoro-4-(trimethylsilyl)phenyl)carbamoyl)-6-methoxy-3,4-dihydroisoquinoline-2(1H)-carboxylate (900 mg) was subjected so to optical resolution by chiral column chromatography. The fraction having a shorter retention time was concentrated to give tert-butyl (R)-1-((3,5-difluoro-4-(trimethylsilyl)phenyl)carbamoyl)-6-methoxy-3,4-dihydroisoquinoline-2(1H)-carboxylate (410 mg, >99.6% ee) as a white solid.
purification condition by chiral column chromatography
  column: CHIRALPAK AD(NF001) 50 mmID×500 mmL
  solvent: hexane/EtOH=850/150
  flow rate: 80 mL/min
  temperature: 30° C.
  detection method: UV 220 nm
(Step 8)

Cooled TFA (4.5 mL) was added to tert-butyl (R)-1-((3,5-difluoro-4-(trimethylsilyl)phenyl)carbamoyl)-6-methoxy-3,4-dihydroisoquinoline-2(1H)-carboxylate (439 mg, 0.89 mmol) at room temperature, and the mixture was stirred at room temperature for 2 min. The reaction mixture was poured into ice and aqueous sodium hydrogencarbonate solution, the pH of mixture was adjusted to 8 with potassium carbonate, and the mixture was extracted with ethyl acetate (×3). The organic layer was washed with brine, and dried over magnesium sulfate, and the solvent was evaporated under reduced pressure. The precipitate was washed with IPE/hexane to give (R)—N-(3,5-difluoro-4-(trimethylsilyl)phenyl)-6-methoxy-1,2,3,4-tetrahydroisoquinoline-1-carboxamide (246 mg, 0.630 mmol, 70.4%) as white crystals.

$^1$H NMR (300 MHz, CDCl$_3$): δ0.27 (9H, d, J=1.1 Hz), 2.23 (1H, brs), 2.69-2.80 (1H, m), 2.84-2.94 (1H, m), 3.14 (2H, t, J=5.9 Hz), 3.78 (3H, s), 4.63 (1H, s), 6.64 (1H, d, J=2.6 Hz), 6.78 (1H, dd, J=8.7, 2.6 Hz), 7.17 (1H, dd), 7.24-7.30 (1H, m), 7.45 (1H, dd, J=10.6, 1.9 Hz), 7.53 (1H, d, J=8.7 Hz), 9.45 (1H, s).
(Step 9)

HATU (161 mg, 0.42 mmol) was added to a solution of (R)—N-(3,5-difluoro-4-(trimethylsilyl)phenyl)-6-methoxy-1,2,3,4-tetrahydroisoquinoline-1-carboxamide (150 mg, 0.38 mmol), trans-cyclopropane-1,2-dicarboxylic acid (100 mg, 0.77 mmol) and DIEA (0.134 mL, 0.77 mmol) in DMF (2 mL), and the mixture was stirred at room temperature for 2 hr. To the reaction mixture was added water, and the mixture was extracted with ethyl acetate. The organic layer was washed with water, and dried over magnesium sulfate, and the solvent was evaporated under reduced pressure. The obtained residue was purified by silica gel column chromatography (solvent gradient; 30→100% ethyl acetate/hexane) to give the title compound.

$^1$H NMR (300 MHz, DMSO-d$_6$): δ0.21-0.39 (9H, m), 1.11-1.41 (2H, m), 1.64-1.87 (1H, m), 1.90-2.07 (1H, m), 2.88 (1H, d, J=16.2 Hz), 3.10-3.26 (1H, m), 3.58-3.83 (4H, m), 4.10-4.35 (1H, m), 5.50-5.69 (1H, m), 6.72-6.91 (2H, m), 7.02-7.28 (2H, m), 7.33-7.56 (1H, m), 10.76 (1H, s), 12.57 (1H, brs).

Example 2 trans-2-(((1R)-1-((3,5-difluoro-4-(trimethylsilyl)phenyl)carbamoyl)-6-methoxy-3, 4-dihydroisoquinolin-2(1H)-yl)carbonyl)cyclopropanecarboxylic acid (single stereoisomer, shorter retention time)

Example 3 trans-2-(((1R)-1-((3,5-difluoro-4-(trimethylsilyl)phenyl)carbamoyl)-6-methoxy-3, 4-dihydroisoquinolin-2(1H)-yl)carbonyl)cyclopropanecarboxylic acid (single stereoisomer, longer retention time)

HATU (193 mg, 0.51 mmol) was added to a solution of (R)—N-(3,5-difluoro-4-(trimethylsilyl)phenyl)-6-methoxy-1,2,3,4-tetrahydroisoquinoline-1-carboxamide (180 mg, 0.46 mmol), trans-cyclopropane-1,2-dicarboxylic acid (90 mg, 0.69 mmol) and DIEA (0.161 mL, 0.92 mmol) in DMF (2 mL), and the mixture was stirred at room temperature for 2 hr. To the reaction mixture was added water to give blue-white precipitates. The precipitate was purified by silica gel column chromatography (solvent gradient; 40→100% ethyl acetate/hexane), and then preparative HPLC (C18, mobile phase: water/acetonitrile (containing 0.1% TFA)). The fraction having a shorter retention time was concentrated to give the compound of Example 2 (36 mg, 0.072 mmol, 16%), and the fraction having a longer retention time was concentrated to give the compound of Example 3 (20 mg, 0.040 mmol, 9%), respectively.
NMR spectrum of the compound of Example 2

$^1$H NMR (300 MHz, DMSO-d$_6$): δ0.22-0.36 (9H, m), 1.21-1.39 (2H, m), 1.72-1.88 (1H, m), 2.43-2.51 (1H, m), 2.80-2.96 (1H, m, J=15.9 Hz), 3.08-3.25 (1H, m), 3.63-3.82 (4H, m), 4.10-4.30 (1H, m), 5.58 (1H, s), 6.77-6.91 (2H, m), 7.10-7.25 (2H, m), 7.47 (1H, d, J=8.3 Hz), 10.76 (1H, s), 12.58 (1H, brs).
NMR spectrum of the compound of Example 3

$^1$H NMR (300 MHz, DMSO-ds): δ0.23-0.38 (9H, m), 1.21-1.39 (2H, m), 1.75-1.86 (1H, m), 2.80-2.94 (1H, m, J=15.5 Hz), 2.86-2.87 (1H, m), 3.19 (1H, ddd, J=15.3, 9.6, 5.3 Hz), 3.59-3.80 (4H, m), 4.10-4.33 (1H, m), 5.47-5.96 (1H, m), 6.76-6.90 (2H, m), 7.09-7.27 (2H, m), 7.40-7.57 (1H, m), 10.63-10.96 (1H, m), 12.58 (1H, brs).
specific optical rotation of the compound of Example 3
  $[\alpha]_D^{25}$+68.4 (c 0.2000, MeOH)

Example 4

(3-(((1R)-1-((3,5-difluoro-4-(trimethylsilyl)phenyl)carbamoyl)-6-methoxy-3,4-dihydroisoquinolin-2 (1H)-yl)carbonyl)cyclobutyl)acetic acid (Step 1)

A mixture of 3-oxocyclobutanecarboxylic acid (0.303 g, 2.66 mmol), tert-butyl triphenylphosphoranylidenacetate (1 g, 2.66 mmol) and toluene (5 mL) was stirred overnight at 90° C. The reaction solution was concentrated under reduced pressure, and the obtained residue was purified by silica gel column chromatography (solvent gradient; 70→100% ethyl acetate/hexane) to give 3-(2-(tert-butoxy)-2-oxoethylidene)cyclobutanecarboxylic acid (0.500 g, 2.356 mmol, 89%) as pale-yellow crystals.

$^1$H NMR (300 MHz, CDCl$_3$): δ1.47 (9H, s), 2.99-3.55 (5H, m), 5.58 (1H, quin, J=2.3 Hz) (The peak derived from CO$_2$H was not observed).
(Step 2)

HATU (148 mg, 0.39 mmol) was added to a solution of (R)—N-(3,5-difluoro-4-(trimethylsilyl)phenyl)-6-methoxy-1,2,3,4-tetrahydroisoquinoline-1-carboxamide (138 mg, 0.35 mmol), DIEA (0.068 mL, 0.39 mmol) and 3-(2-(tert-butoxy)-2-oxoethylidene)cyclobutanecarboxylic acid (83 mg, 0.39 mmol) in DMF (4 mL), and the mixture was stirred at room temperature for 2.5 hr. To the reaction mixture was added water to give pale-yellow precipitates. The precipitate was collected by filtration to give tert-butyl 2-(3-((R)-1-((3,5-difluoro-4-(trimethylsilyl)phenyl)carbamoyl)-6-methoxy-1,2,3,4-tetrahydroisoquinoline-2-carbonyl)cyclobutylidene)acetate (138 mg, 0.236 mmol, 67%).

MS(API): Calculated 584.7. Found 583.4 (M-H).
(Step 3)

A mixture of tert-butyl 2-(3-((R)-1-((3,5-difluoro-4-(trimethylsilyl)phenyl)carbamoyl)-6-methoxy-1,2,3,4-tetrahydroisoquinoline-2-carbonyl)cyclobutylidene)acetate (138 mg, 0.24 mmol) and 10% palladium-carbon (25.1 mg, 0.24 mmol, 50%, wet) in MeOH (20 mL) was stirred overnight at room temperature under hydrogen atmosphere (1 atm). The catalyst was removed by filtration, and the filtrate was concentrated under reduced pressure. The obtained residue was purified by silica gel column chromatography (solvent gradient; 5→50% ethyl acetate/hexane) to give tert-butyl (R)-2-(3-(1-((3,5-difluoro-4-(trimethylsilyl)phenyl)carbamoyl)-6-methoxy-1,2,3,4-tetrahydroisoquinoline-2-carbonyl)cyclobutyl)acetate (118 mg, 0.201 mmol, 85%) as a colorless oil.

MS(API): Calculated 586.7. Found 585.4 (M-H).
(Step 4)

Cooled TFA (4 mL) was added to tert-butyl (R)-2-(3-(1-((3,5-difluoro-4-(trimethylsilyl)phenyl)carbamoyl)-6-methoxy-1,2,3,4-tetrahydroisoquinoline-2-carbonyl)cyclobutyl)acetate (118 mg, 0.20 mmol) at 0° C., and the mixture was stirred at 0° C. for 1 hr. The reaction mixture was poured into ice and aqueous sodium hydrogencarbonate solution (pH 6), and the mixture was extracted with ethyl acetate. The organic layer was dried over magnesium sulfate, and the solvent was evaporated under reduced pressure. The obtained residue was purified by silica gel column chromatography (solvent gradient; 10→100% ethyl acetate/hexane) to give the title compound (70.0 mg, 0.132 mmol, 65.6%) as a white solid.

$^1$H NMR (300 MHz, DMSO-d$_6$): δ0.30 (9H, s), 1.71-1.96 (2H, m), 2.21-2.42 (4H, m), 2.42-2.62 (1H, m), 2.77 (1H, dt, J=15.4, 5.0 Hz), 2.95-3.14 (1H, m), 3.15-3.56 (2H, m), 3.72 (3H, s), 3.83-4.06 (1H, m), 5.44-5.70 (1H, m), 6.70-6.94 (2H, m), 7.05-7.35 (2H, m), 7.38-7.56 (1H, m), 10.66-10.95 (1H, m), 12.06 (1H, brs).

Example 5 cis-3-(((1R)-1-((3,5-difluoro-4-(trimethylsilyl)phenyl)carbamoyl)-6-methoxy-3,4-dihydroisoquinolin-2(1H)-yl)carbonyl)cyclobutanecarboxylic acid HATU (82 mg, 0.22 mmol) was added to a solution of (R)—N-(3,5-difluoro-4-(trimethylsilyl)phenyl)-6-methoxy-1,2,3,4-tetrahydroisoquinoline-1-carboxamide (70 mg, 0.18 mmol), DIEA (0.061 mL, 0.36 mmol) and cis-cyclobutane-1,3-dicarboxylic acid (78 mg, 0.54 mmol) in DMF (2.0 mL) at room temperature, and the mixture was stirred overnight at room temperature. To the reaction mixture was added water, and the mixture was is extracted with ethyl acetate. The organic layer was washed with brine, and dried over magnesium sulfate, and the solvent was evaporated under reduced pressure. The obtained residue was purified by silica gel column chromatography (solvent gradient; 20→90% ethyl acetate/hexane), and then preparative HPLC (C18, mobile phase: water/acetonitrile (containing 0.1% TFA)) to give the title compound (29.7 mg, 0.057 mmol, 32.1%) as a white solid.

$^1$H NMR (300 MHz, DMSO-d$_6$): δ0.30 (9H, s), 2.17-2.44 (4H, m), 2.68-2.87 (1H, m), 2.88-3.17 (2H, m), 3.36-3.53 (2H, m), 3.72 (3H, s), 3.82-4.02 (1H, m), 5.58 (1H, s), 6.72-6.91 (2H, m), 7.20 (2H, m, J=9.8 Hz), 7.37-7.51 (1H, m), 10.81 (1H, s), 11.85-12.49 (1H, m)

Example 6

((1R,2S)-2-(((5R)-5-((7-fluoro-1,1-dimethyl-2,3-dihydro-1H-inden-5-yl)carbamoyl)-2-methoxy-7,8-dihydro-1,6-naphthyridin-6(5H)-yl)carbonyl)cyclopropyl)acetic acid (Step 1)

To a solution of 1-bromo-3-fluoro-5-methoxybenzene (15 g, 73.16 mmol), tris(2-methylphenyl)phosphane (1.781 g, 5.85 mmol) and ethyl acrylate (11.90 mL, 109.74 mmol) in TEA (135 mL) was added palladium(II)acetate (0.329 g, 1.46 mmol) at room temperature under nitrogen atmosphere, and the mixture was stirred at 90° C. for 2 days. The solvent was evaporated under reduced pressure, the residue was diluted with water, and the mixture was extracted with ethyl acetate. The organic layer was washed with water and brine, and dried over magnesium sulfate, and the solvent was evaporated under reduced pressure. The obtained residue was purified by silica gel column chromatography to give ethyl (E)-3-(3-fluoro-5-methoxyphenyl)acrylate (14.2 g, 63.3 mmol, 87%) as a colorless oil.
(Step 2)

A mixture of ethyl (E)-3-(3-fluoro-5-methoxyphenyl)acrylate (14.2 g, 63.33 mmol) and 10% palladium-carbon (1.4 g, 0.66 mmol, 50%, wet) in EtOH (300 mL) was is stirred at room temperature for 5 hr under hydrogen atmosphere (1 atm). The catalyst was removed by filtration through Celite, and the filtrate was concentrated under reduced pressure to give ethyl 3-(3-fluoro-5-methoxyphenyl)propanoate (13.9 g, 61.4 mmol, 97%) as a colorless oil.
(Step 3)

To a solution of ethyl 3-(3-fluoro-5-methoxyphenyl)propanoate (13.9 g, 61.44 mmol) in anhydrous THF (200 mL) was added dropwise 3M methylmagnesium bromide/diethyl ether solution (61.4 mL, 184.31 mmol) at 0° C., and the mixture was stirred at room temperature for 1 hr under nitrogen atmosphere. To the reaction mixture were added water and ethyl acetate, and the organic layer was separated. The organic layer was dried over magnesium sulfate, and the solvent was evaporated under reduced pressure to give 4-(3-fluoro-5-methoxyphenyl)-2-methylbutan-2-ol (12.1 g, 57.01 mmol, 93%). This compound was used for the next step without purification.
(Step 4)

A mixture of 4-(3-fluoro-5-methoxyphenyl)-2-methylbutan-2-ol (12.1 g, 57.01 mmol) and PPA (100 g, 57.01 mmol)

was stirred at 90° C. for 1 hr. The reaction mixture was poured into ice water, and the mixture was extracted with ethyl acetate. The organic layer was dried over magnesium sulfate, and the solvent was evaporated under reduced pressure. The obtained residue was purified by silica gel column chromatography (solvent; ethyl acetate/hexane) to give 7-fluoro-5-methoxy-1,1-dimethyl-2,3-dihydro-1H-indene (4.76 g, 24.51 mmol, 43%) as a colorless oil.
(Step 5)

To a solution of 7-fluoro-5-methoxy-1,1-dimethyl-2,3-dihydro-1H-indene (4.76 g, 24.51 mmol) and 1-dodecanethiol (17.71 mL, 73.52 mmol) in toluene (50 mL) was added aluminium chloride (9.80 g, 73.52 mmol) at 0° C., and the mixture was stirred at room temperature for 2 hr. To the reaction mixture was added 1N hydrochloric acid, and the mixture was extracted with ethyl acetate. The organic layer was dried over magnesium sulfate, and the solvent was evaporated under reduced pressure. The obtained residue was purified by silica gel column chromatography (solvent; ethyl acetate/hexane) to give 7-fluoro-1,1-dimethyl-2,3-dihydro-1H-inden-5-ol (4.17 g, 23.14 mmol, 94%) as an off-white solid.
(Step 6)

To a solution of 7-fluoro-1,1-dimethyl-2,3-dihydro-1H-inden-5-ol (4.17 g, 23.14 mmol) in THF (80 mL) was added sodium hydride (60%, oil, 1.111 g, 27.77 mmol) at 0° C., and the mixture was stirred at room temperature 15 min. Then, 1,1,1-trifluoro-N-phenyl-N-((trifluoromethyl)sulfonyl)methanesulfonamide (9.09 g, 25.45 mmol) was added thereto at 0° C., and the mixture was stirred at room temperature for 2 hr. The reaction mixture was poured into ice water, and the mixture was extracted with ethyl acetate. The organic layer was dried over magnesium sulfate, and the solvent was evaporated under reduced pressure. The obtained residue was purified by silica gel column chromatography (solvent; ethyl acetate/hexane) to give 7-fluoro-1,1-dimethyl-2,3-dihydro-1H-inden-5-yl trifluoromethanesulfonate (6.21 g, 19.89 mmol, 86%) as a colorless oil.
(Step 7)

A mixture of 7-fluoro-1, 1-dimethyl-2,3-dihydro-1H-inden-5-yl trifluoromethanesulfonate (5.18 g, 16.59 mmol), diphenylmethanimine (3.61 g, 19.91 mmol), $Pd_2(dba)_3$ (0.759 g, 0.83 mmol), BINAP (1.033 g, 1.66 mmol), sodium tert-butoxide (2.391 g, 24.88 mmol) and toluene (75 mL) was stirred at 80° C. for 2 hr. The reaction mixture was poured into water, and the mixture was extracted with ethyl acetate. The organic layer was dried over magnesium sulfate, and the solvent was evaporated under reduced pressure. The obtained residue was dissolved in THF (200 mL), 1N hydrochloric acid (83 mL, 82.94 mmol) was added thereto, and the mixture was stirred at room temperature for 30 min, and basified with 1N aqueous sodium hydroxide solution. The mixture was extracted with ethyl acetate. The organic layer was washed with brine, and dried over magnesium sulfate, and the solvent was evaporated under reduced pressure. The obtained residue was purified by silica gel column chromatography (solvent gradient; 0→10% ethyl acetate/hexane) to give 7-fluoro-1,1-dimethyl-2,3-dihydro-1H-inden-5-amine (1.92 g, 10.71 mmol, 65%) as an orange oil.

$^1$H NMR (300 MHz, $CDCl_3$): δ1.34 (6H, s), 1.89 (2H, t, J=7.4 Hz), 2.82 (2H, t, J=7.2 Hz), 3.61 (2H, brs), 6.13-6.21 (1H, m), 6.28-6.33 (H, m).
(Step 8)

Morpholine (261 mg, 261 μL, 2.99 mmol) and acetic acid (200 mg, 191 μL, 3.32 mmol) were added to a solution of 2,2-dimethyl-1,3-dioxane-4,6-dione (24.0 g, 166.17 mmol) in acetone (120 g) at room temperature under argon atmosphere, and the mixture was stirred at room temperature for 18 hr. The reaction mixture was concentrated under reduced pressure. To the obtained residue was added saturated aqueous sodium hydrogencarbonate solution (200 mL), and the mixture was extracted with toluene (200 mL). The organic layer was washed with 10% brine (200 mL), and the solvent was evaporated under reduced pressure to give 5-isopropylidene-2,2-dimethyl-1,3-dioxane-4,6-dione as a white solid. The obtained white solid was subjected to azeotropy with toluene (100 mL) (×2).

$^1$H NMR (500 MHz, $CDCl_3$): δ1.72 (6H, s), 2.52 (6H, s).

A solution (183 mL, 182.79 mmol) of 1M isopropylmagnesium chloride in THF was added dropwise to a solution of 4-bromo-2-fluoro-1-iodobenzene (50.0 g, 166.17 mmol) in anhydrous THF (96 mL) over 20 min at −20° C. under argon atmosphere. The reaction mixture was stirred at −20° C. for 30 min, and added dropwise to a solution of 5-isopropylidene-2,2-dimethyl-1,3-dioxane-4,6-dione in anhydrous toluene (84 mL) over 20 min at −20° C., and then the used container was washed with THF (24 mL). The reaction mixture was stirred at 0° C. for 3 hr, 10% aqueous citric acid solution (200 mL) was added thereto at 0° C., and the mixture was extracted with toluene (200 mL). The organic layer was concentrated under reduced pressure to give 5-(2-(4-bromo-2-fluorophenyl)propan-2-yl)-2,2-dimethyl-1,3-dioxane-4,6-dione as a pale-yellow oil.

4M Hydrochloric acid (96 mL) was added to a solution of 5-(2-(4-bromo-2-fluorophenyl)propan-2-yl)-2,2-dimethyl-1,3-dioxane-4,6-dione in DMF (60 mL), and the mixture was stirred at 100° C. for 24 hr. The reaction mixture was concentrated under reduced pressure at 75° C., and the pH of the obtained residue were adjusted to 9.0 with DMF (40 mL), water (100 mL), 8M aqueous sodium hydroxide solution (50 mL), 6M hydrochloric acid (about 10 mL) and 8M aqueous sodium hydroxide solution (10 mL). The mixture was stirred at 0° C. for 10 min, and filtered, and the filtrate was washed with water (100 mL). The pH of the filtrate was adjusted to 4.0 with 6M hydrochloric acid (20 mL) at 0° C., and mixture was stirred at 0° C. for 1 hr. The precipitate was collected by filtration, washed with ice water, and dried at 50° C. to give 3-(4-bromo-2-fluorophenyl)-3-methylbutanoic acid (23.52 g, 85.49 mmol, 51%) as white crystals.

$^1$H NMR (500 MHz, $CDCl_3$): δ1.46 (6H, s), 2.80 (2H, s), 7.13-7.22 (3H, m) (The peak derived from COOH was not observed).
(Step 9)

A mixture of 3-(4-bromo-2-fluorophenyl)-3-methylbutanoic acid (20.0 g, 72.70 mmol) and PPA (200 g) was stirred at 100° C. for 4 hr. To the reaction mixture was added ice water (200 mL) at 0° C., and the mixture was extracted with ethyl acetate (200 mL) (×2). To the organic layer was added saturated aqueous sodium hydrogencarbonate solution (200 mL), and the pH of the aqueous layer was adjusted to 7.0 with 8M aqueous sodium hydroxide solution (35 mL). The organic layer was washed with 10% brine (200 mL), and concentrated under reduced pressure. The obtained residue was subjected to azeotropy with ethanol (600 mL). To a mixture of the obtained residue in DMF (140 mL) and EtOH (140 mL) was added water (240 mL) at room temperature, and the mixture was stirred at 0° C. for 2 hr. The precipitate was collected by filtration, washed with water (100 mL), and dried at 50° C. to give 6-bromo-4-fluoro-3,3-dimethylindan-1-one (17.0 g, 66.12 mmol, 91%) as pale-orange crystals.

$^1$H NMR (500 MHz, $CDCl_3$): δ1.52 (6H, s), 2.63 (2H, s), 7.41 (1H, dd, J=9.0, 1.7 Hz), 7.65 (1H, d, J=0.6 Hz).

(Step 10)

Triethylsilane (1.59 g, 2.17 mL, 13.63 mmol) was added to a solution of 6-bromo-4-fluoro-3,3-dimethylindan-1-one (1.5 g, 5.83 mmol) in TFA (30 mL) at room temperature and the mixture was stirred at room temperature for 40 hr. To the reaction mixture was added ice water at 0° C., and the mixture was extracted with ethyl acetate (×2). The organic layer was washed with aqueous sodium hydroxide solution (the pH of the aqueous layer was adjusted to 7.0) and 10% brine, dried over sodium sulfate, and concentrated under reduced pressure to give crude 5-bromo-7-fluoro-1,1-dimethylindane as an orange oil.

$^1$H NMR (500 MHz, CDCl$_3$): δ1.35 (6H, s), 1.93 (2H, t, J=7.3 Hz), 2.90 (2H, t, J=7.4 Hz), 6.98 (1H, dt, J=9.5, 0.8 Hz), 7.06-7.13 (1H, m).

Pd$_2$(dba)$_3$ (267 mg, 0.29 mmol), BINAP (363 mg, 0.58 mmol), sodium tert-butoxide (841 mg, 8.75 mmol) and benzophenone imine (1.05 g, 0.98 mL, 5.83 mmol) were added to a solution of the crude 5-bromo-7-fluoro-1,1-dimethylindane in anhydrous toluene (30 mL) at room temperature, and the mixture was stirred at 80° C. for 1 hr under argon atmosphere. To the reaction mixture was added ice water, and the mixture was extracted with ethyl acetate (×2). The organic layer was concentrated under reduced pressure to give crude N-(7-fluoro-1,1-dimethyl-2,3-dihydro-1H-inden-5-yl)-1,1-diphenylmethanimine as an orange oil.

To a solution of the crude N-(7-fluoro-1,1-dimethyl-2,3-dihydro-1H-inden-5-yl)-1,1-diphenylmethanimine in THF (30 mL) was added LM hydrochloric acid (29 mL, 29.17 mmol) at room temperature, and the mixture was stirred at room temperature for 30 min. The pH of the reaction mixture was adjusted to >7 with sodium hydroxide, and the mixture was extracted with ethyl acetate (×2). The organic layer was washed with 10% brine, dried over sodium sulfate, and concentrated under is reduced pressure to give the crude 7-fluoro-1,1-dimethyl-2,3-dihydro-1H-inden-5-amine as an orange oil.

$^1$H NMR (500 MHz, CDCl$_3$): δ1.32 (6H, s), 1.88 (2H, t, J=7.4 Hz), 2.81 (2H, t, J=7.4 Hz), 3.59 (2H, s), 6.15-6.17 (1H, m), 6.28-6.29 (1H, m).

A solution of (+)-camphorsulfonic acid (1.49 g, 6.42 mmol) in ethyl acetate (37.5 mL) was added to a solution of the crude 7-fluoro-1,1-dimethyl-2,3-dihydro-1H-inden-5-amine in ethyl acetate (15 mL) at room temperature, and the used container was washed with ethyl acetate (7.5 mL). The mixture was stirred at 0° C. for 1 hr, and filtered, and the used filter was washed with ethyl acetate. The filtrate was concentrated under reduced pressure, ethyl acetate (60 mL) was added to the residue, and the mixture was stirred at 0° C. for 2 hr. The precipitate was collected by filtration, washed with ethyl acetate, and dried over at 40° C. to give 7-fluoro-1,1-dimethyl-2,3-dihydro-1H-inden-5-amine (+)-camphorsulfonate (1.38 g, 3.36 mmol, 58%) as pale-yellow crystals.

$^1$H NMR (500 MHz, CDCl$_3$): δ0.74 (3H, s), 0.93 (3H, s), 1.22-1.30 (1H, m), 1.34 (6H, s), 1.52-1.60 (1H, m), 1.77-1.90 (2H, m), 1.93 (2H, t, J=7.4 Hz), 1.96-2.00 (1H, m), 2.23-2.30 (1H, m), 2.35-2.44 (1H, m), 2.74 (1H, d, J=14.8 Hz), 2.91 (2H, t, J=7.4 Hz), 3.31 (1H, d, J=14.5 Hz), 7.05-7.10 (1H, m), 7.15-7.20 (1H, m), 8.58-10.43 (2H, br) (The exchangeable 1H was not observed).

(Step 11)

1.6M n-Butyllithium/hexane solution (282 mL, 451.96 mmol) was added dropwise to a solution of 2-methoxy-6-methylpyridine (50.60 g, 410.87 mmol) in THF (625 mL) over 1 hr at −78° C. under argon atmosphere. The reaction mixture was stirred at −78° C. for 45 min, paraformaldehyde (49.3 g, 1643.49 mmol) was added thereto at −78° C., and the mixture was stirred vigorously at room temperature for 3.5 hr. The reaction mixture was poured into ice water (1000 mL), and NaCl was added thereto to give a saturated solution. The saturated solution was extracted with a mixed solvent of ethyl acetate/THF (3:1) (×3). The organic layer was washed with water and brine, and dried over magnesium sulfate, and the solvent was evaporated under reduced pressure. The obtained residue was purified by silica gel column chromatography (solvent gradient; 8→50% ethyl acetate/hexane) to give 2-(6-methoxypyridin-2-yl)ethanol (23.22 g, 152 mmol, 37%) as a colorless oil.

$^1$H NMR (300 MHz, CDCl$_3$): δ2.94 (2H, t, J=5.5 Hz), 3.91 (3H, s), 4.00 (2H, q, J=4.5 Hz), 4.30 (H, t, J=5.9 Hz), 6.62 (1H, d, J=8.3 Hz), 6.73 (1H, d, J=7.2 Hz), 7.51 (1H, dd, J=8.3, 7.2 Hz).

(Step 12)

ADDP (49.0 g, 194.09 mmol) was added to a mixture of 2-(6-methoxypyridin-2-yl)ethanol (22.87 g, 149.30 mmol), phthalimide (24.16 g, 164.23 mmol), tributylphosphine (48.5 mL, 194.09 mmol) and THF (340 mL) at 0° C. under argon atmosphere to give a solution. The solution was stirred at room temperature for 16 hr, to the reaction mixture was added ethyl acetate (about 500 mL), and the mixture was stirred at 0° C. for 20 min. The insoluble substance was removed by filtration with ethyl acetate, and washed with ethyl acetate. The filtrate was poured into water (1000 mL), and the mixture was extracted with ethyl acetate (×3). The organic layer was washed with water and brine, and dried over magnesium sulfate, and the solvent was evaporated under reduced pressure. The obtained residue was purified by silica gel column chromatography (solvent gradient; 5→20% ethyl acetate/hexane), and the precipitate was collected by filtration with hexane to give 2-(2-(6-methoxypyridin-2-yl)ethyl) isoindoline-1,3-dione (29.03 g, 103 mmol, 69%) as an off-white powder.

$^1$H NMR (300 MHz, CDCl$_3$): δ3.08 (2H, t, J=7.2 Hz), 3.78 (3H, s), 4.11 (2H, t, J=7.2 Hz), 6.54 (1H, d, J=7.9 Hz), 6.72 (1H, d, J=7.2 Hz), 7.43 (1H, dd, J=8.3, 7.2 Hz), 7.70 (0.2H, dd, J=5.5, 3.2 Hz), 7.82 (2H, dd, J=6.3, 3.0 Hz).

(Step 13)

Hydrazine monohydrate (24.94 mL, 514.18 mmol) was added to a solution of 2-(2-(6-methoxypyridin-2-yl)ethyl) isoindoline-1,3-dione (29.03 g, 102.84 mmol) in EtOH (300 mL) at room temperature. The mixture was heated under reflux for 1 hr, and allowed to be cooled to room temperature. The insoluble substance was removed by filtration, and washed with a mixed solvent of diethyl ether/IPE (1:1). The filtrate was concentrated under reduced pressure, and to the obtained residue was added toluene (about 250 mL), and the mixture was concentrated again under reduced pressure. The obtained residue was purified by silica gel column chromatography (NH, solvent gradient; 10→100% ethyl acetate/hexane) to give 2-(6-methoxypyridin-2-yl)ethanamine (14.43 g, 95 mmol, 92%) as a colorless oil.

$^1$H NMR (300 MHz, CDCl$_3$): δ1.31 (2H, brs), 2.82 (2H, t, J=7.5 Hz), 3.11 (2H, t, J=6.0 Hz), 3.92 (3H, s), 6.57 (1H, d, J=7.9 Hz), 6.73 (1H, d, J=7.2 Hz), 7.48 (1H, dd, J=8.1, 7.4 Hz).

(Step 14)

1.6M n-Butyllithium/hexane solution (300 mL, 479.43 mmol) was added to a solution of acetonitrile (21.87 g, 532.70 mmol) in THF (630 mL) at −78° C. under argon atmosphere, and the mixture was stirred at −78° C. for 30 min. 2-Bromo-6-methoxypyridine (25.04 g, 133.18 mmol) was added dropwise thereto over 15 min at −78° C., and the reaction mixture was stirred at room temperature for 4 hr.

The reaction mixture was poured into ice water (900 mL), and the mixture was extracted with ethyl acetate (×3). The organic layer was washed with water and brine, and dried over magnesium sulfate, and the solvent was evaporated under reduced pressure. The obtained residue was purified by silica gel column chromatography (solvent gradient; 2→20% ethyl acetate/hexane) to give 2-(6-methoxypyridin-2-yl)acetonitrile (11.37 g, 77 mmol, 58%) as a colorless oil.

$^1$H NMR (300 MHz, CDCl$_3$): δ3.81 (2H, s), 3.93 (3H, s), 6.69 (1H, d, J=8.3 Hz), 6.93-6.98 (1H, m), 7.58 (1H, dd, J=8.3, 7.6 Hz).

(Step 15)

A solution of 2-(6-methoxypyridin-2-yl)acetonitrile (5.00 g, 33.75 mmol) in 2M ammonia/MeOH (84 mL, 168.73 mmol) was stirred in the presence of Raney-nickel (8 g, 136.30 mmol) [obtained by washing Kawaken NDHT-90 with 4N aqueous sodium hydroxide solution (40 mL), water (×5) and MeOH (×3)] at room temperature for 22 hr under hydrogen atmosphere (0.5 MPa). The catalyst was removed by decantation, and the reaction solution was concentrated under reduced pressure. To the obtained residue was added toluene (about 80 mL), and the mixture was concentrated again under reduced pressure. The obtained residue was purified by silica gel column chromatography (NH, solvent gradient; 10→100% ethyl acetate/hexane) to give 2-(6-methoxypyridin-2-yl)ethanamine (4.30 g, 28.3 mmol, 84%) as a yellow oil.

(Step 16)

A solution of 2-(6-methoxypyridin-2-yl)ethanamine (14.43 g, 94.81 mmol), 4N hydrogen chloride/CPME (26.1 mL, 104.29 mmol) and 47% ethyl glyoxylate/toluene solution (polymer form) (30.0 mL, 142.22 mmol) in EtOH (175 mL) was heated under reflux for 8 hr. To the reaction mixture were added 4N hydrogen chloride/CPME (26.1 mL, 104.29 mmol) and 47% ethyl glyoxylate/toluene solution (polymer form) (30.0 mL, 142.22 mmol), and the mixture was heated again under reflux for 16 hr. The reaction mixture was concentrated under reduced pressure to half volume, and to the residue was added diethyl ether (ca. 150 mL). The precipitate was collected by filtration, and washed with EtOH/diethyl ether to give crude ethyl 2-hydroxy-5,6,7,8-tetrahydro-1,6-naphthyridine-5-carboxylate hydrochloride (20.01 g, 77 mmol, 82%) as an off-white powder.

$^1$H NMR (300 MHz, DMSO-d$_6$): δ1.25 (3H, t, J=7.0 Hz), 2.71-2.93 (2H, m), 3.37-3.51 (2H, m), 4.19-4.31 (2H, m), 5.23 (1H, s), 6.30 (1H, d, J=9.4 Hz), 7.43 (1H, d, J=9.4 Hz), 8.12 (1H, brs), 9.65 (1H, brs), 10.56 (1H, brs).

(Step 17)

Boc$_2$O (17.72 g, 81.22 mmol) was added to a mixture of ethyl 2-hydroxy-5,6,7,8-tetrahydro-1,6-naphthyridine-5-carboxylate hydrochloride (20.01 g, 77.35 mmol), TEA (11.32 mL, 81.22 mmol), THF (205 mL) and water (75 mL) at room temperature, and the mixture was stirred vigorously at room temperature for 5.5 hr. The reaction mixture was poured into water (500 mL), and the mixture was saturated with NaCl, and extracted with a mixed solvent of ethyl acetate/THF (3:1) (×3). The organic layer was washed with water and brine, and dried over magnesium sulfate, and the solvent was evaporated under reduced pressure. The precipitate was collected by filtration, and washed with IPE/hexane to give 5-ethyl 6-tert-butyl 2-hydroxy-7,8-dihydro-1,6-naphthyridine-5,6(5H)-dicarboxylate (16.57 g, 51.4 mmol, 66%) as a white powder.

$^1$H NMR (300 MHz, CDCl$_3$): δ1.24-1.32 (3H, m), 1.45-1.50 (9H, m), 2.66-2.92 (2H, m), 3.37-3.55 (1H, m), 4.10-4.29 (3H, m), 5.18-5.43 (1H, m), 6.46 (1H, d, J=9.4 Hz), 7.58-7.66 (1H, m), 12.94 (1H, brs).

(Step 18)

Iodomethane (8.69 mL, 139.60 mmol) was added to a mixture of 5-ethyl 6-tert-butyl 2-hydroxy-7,8-dihydro-1,6-naphthyridine-5,6(5H)-dicarboxylate (7.50 g, 23.27 mmol), silver(I) carbonate (8.34 g, 30.25 mmol) and THF (150 mL) at room temperature (the reaction vessel was protected from light). The mixture was stirred at room temperature for 15 hr, and then at 50° C. for 5 hr. The insoluble substance was removed by filtration through Celite, and washed with ethyl acetate. The filtrate was concentrated under reduced pressure, and the obtained residue was purified by silica gel column chromatography (solvent gradient; 5→30% ethyl acetate/hexane) to give 5-ethyl 6-tert-butyl 2-methoxy-7,8-dihydro-1,6-naphthyridine-5,6(5H)-dicarboxylate (6.93 g, 20.60 mmol, 89%) as a pale-yellow oil.

$^1$H NMR (300 MHz, CDCl$_3$): δ1.21-1.30 (3H, m), 1.44-1.53 (9H, m), 2.84-2.96 (2H, m), 3.55-3.70 (1H, m), 3.91 (3H, s), 4.01-4.22 (3H, m), 5.33-5.54 (1H, m), 6.60 (1H, d, J=8.7 Hz), 7.69 (1H, t, J=7.5 Hz).

(Step 19)

Trimethyloxonium tetrafluoroborate (1.775 g, 12.00 mmol) was added to a mixture of 5-ethyl 6-tert-butyl 2-hydroxy-7,8-dihydro-1,6-naphthyridine-5,6(5H)-dicarboxylate (1.289 g, 4.00 mmol) and acetonitrile (18 mL) at 0° C. The mixture was stirred at 0° C. for 2 hr, and the reaction mixture was poured into ice-cooled saturated aqueous sodium hydrogencarbonate solution (100 mL), and the mixture was extracted with ethyl acetate (×3). The organic layer was washed with water and brine, and dried over magnesium sulfate, and the solvent was evaporated under reduced pressure. The obtained residue was purified by silica gel column chromatography (solvent gradient; 2→19% ethyl acetate/hexane) to give 5-ethyl 6-tert-butyl 2-methoxy-7,8-dihydro-1,6-naphthyridine-5,6(5H)-dicarboxylate (372 mg, 1.106 mmol, 28%) as a colorless oil.

(Step 20)

2N Aqueous lithium hydroxide solution (61.8 mL, 123.61 mmol) was added to a solution of 5-ethyl 6-tert-butyl 2-methoxy-7,8-dihydro-1,6-naphthyridine-5,6(5H)-dicarboxylate (6.93 g, 20.60 mmol) in a mixed solvent of EtOH (30 mL) and THF (30 mL) at room temperature, and the mixture was stirred at room temperature for 1.5 hr. The reaction mixture was poured into ice-cooled water, and the pH of the mixture was adjusted to 4 with 6N hydrochloric acid. Then, the mixture was extracted with a mixed solvent of mixed ethyl acetate/THF (3:1) (×3). The organic layer was washed with water and brine, and dried over magnesium sulfate, and the solvent was evaporated under reduced pressure to give 6-(tert-butoxycarbonyl)-2-methoxy-5,6,7,8-tetrahydro-1,6-naphthyridine-5-carboxylic acid (6.37 g, 20.66 mmol, 100%) as a colorless amorphous solid.

$^1$H NMR (300 MHz, CDCl$_3$): δ1.44-1.52 (9H, m), 2.85-2.95 (2H, m), 3.57-3.68 (1H, m), 3.90 (3H, s), 3.97-4.07 (1H, m), 5.36-5.57 (1H, m), 6.61 (1H, d, J=8.3 Hz), 7.68 (1H, d, J=8.7 Hz) (The exchangeable 1H was not observed).

(Step 21)

T3P (4.89 mL, 8.22 mmol) was added to a solution of 6-(tert-butoxycarbonyl)-2-methoxy-5,6,7,8-tetrahydro-1,6-naphthyridine-5-carboxylic acid (1.69 g, 5.48 mmol), 7-fluoro-1,1-dimethyl-2,3-dihydro-1H-inden-5-amine (0.982 g, 5.48 mmol), DIEA (4.77 mL, 27.41 mmol) and DMAP (0.737 g, 6.03 mmol) in ethyl acetate (40 mL) at room temperature. The mixture was stirred at 65° C. for 15 hr, the reaction mixture was poured into water (150 mL), and the mixture was extracted with ethyl acetate (×3). The organic layer was washed with 10% aqueous citric acid solution, aqueous sodium hydrogencarbonate solution, water and brine, and dried over magnesium sulfate, and the solvent was evaporated under reduced pressure. The obtained precipitate was washed with hexane to give tert-butyl 5-((7-fluoro-1,1-dimethyl-2,3-dihydro-1H-inden-5-yl) carbamoyl)-2-methoxy-7,8-dihydro-1,6-naphthyridine-6 (5H)-carboxylate (2.09 g, 4.45 mmol, 81%) as an off-white powder.

$^1$H NMR (300 MHz, CDCl$_3$): δ1.34 (6H, s), 1.53 (9H, s), 1.91 (2H, t, J=7.4 Hz), 2.83-3.01 (4H, m), 3.45 (1H, brs), 3.91 (3H, s), 4.06 (1H, dt, J=13.2, 4.9 Hz), 5.56 (1H, brs), 6.64 (1H, d, J=8.3 Hz), 7.05-7.12 (2H, m), 7.48 (1H, brs), 8.70 (1H, brs).

(Step 22)

tert-Butyl 5-((7-fluoro-1,1-dimethyl-2,3-dihydro-1H-inden-5-yl)carbamoyl)-2-methoxy-7,8-dihydro-1,6-naphthyridine-6(5H)-carboxylate (2.09 g) was subjected to optical resolution by chiral column chromatography. The fraction having a shorter retention time was concentrated to give tert-butyl (R)-5-((7-fluoro-1,1-dimethyl-2,3-dihydro-1H-inden-5-yl)carbamoyl)-2-methoxy-7,8-dihydro-1,6-naphthyridine-6(5H)-carboxylate (960 mg, >99% ee), and the fraction having a longer retention time was concentrated to give tert-butyl (S)-5-((7-fluoro-1,1-dimethyl-2,3-dihydro-1H-inden-5-yl)carbamoyl)-2-methoxy-7,8-dihydro-1,6-naphthyridine-6(5H)-carboxylate (920 mg, >99% ee), as an off-white amorphous solid, respectively.

purification condition by chiral column chromatography
    column: CHIRALPAK IA(QK001) 50 mmID×500 mm
    solvent: hexane/EtOH=900/100
    flow rate: 80 mL/min
    temperature: 30° C.
    detection method: UV 220 nm (Step 23)

TFA (13 mL) was added to tert-butyl (R)-5-((7-fluoro-1,1-dimethyl-2,3-dihydro-1H-inden-5-yl)carbamoyl)-2-methoxy-7,8-dihydro-1,6-naphthyridine-6(5H)-carboxylate (957 mg, 2.04 mmol) at room temperature, and the mixture was stirred at room temperature for 20 min. The reaction mixture was poured into ice-cooled saturated aqueous sodium hydrogencarbonate solution (110 mL), and the pH of the mixture was adjusted to 8 with potassium carbonate. Then, the mixture was extracted with ethyl acetate (×3). The organic layer was washed with water and brine, and dried over magnesium sulfate, and the solvent was evaporated under reduced pressure to give (R)—N-(7-fluoro-1,1-dimethyl-2,3-dihydro-1H-inden-5-yl)-2-methoxy-5,6,7,8-tetrahydro-1,6-naphthyridine-5-carboxamide (732 mg, 1.981 mmol, 97%) as an off-white amorphous solid.

$^1$H NMR (300 MHz, CDCl$_3$): δ1.34 (6H, s), 1.69 (1H, brs), 1.91 (2H, t, J=7.4 Hz), 2.73-2.98 (4H, m), 3.12-3.28 (2H, m), 3.90 (3H, s), 4.57 (1H, s), 6.60 (1H, d, J=8.7 Hz), 7.11-7.17 (2H, m), 7.84 (1H, d, J=8.7 Hz), 9.41 (1H, s).

(Step 24)

To a solution of (S)-5-(hydroxymethyl)dihydrofuran-2 (3H)-one (25.97 g, 223.66 mmol) in THF (125 mL) were added p-toluenesulfonyl chloride (44.8 g, 234.84 mmol), pyridine (45.2 mL, 559.14 mmol) and DMAP (30.1 g, 246.02 mmol) at 0° C., and the mixture was stirred at room temperature for 4 hr. The reaction mixture was poured into ice water (400 mL), and the pH of the mixture was adjusted to 3 with 6N hydrochloric acid. Then, the mixture was extracted with ethyl acetate (×3). The organic layer was washed with water and brine, and dried over magnesium sulfate, and the solvent was evaporated under reduced pressure. The crystals were collected by filtration, and washed with IPE/hexane to give (S)-(5-oxotetrahydrofuran-2-yl)methyl 4-methylbenzenesulfonate (51.81 g, 192 mmol, 86%) as a white powder.

$^1$H NMR (300 MHz, CDCl$_3$): δ2.06-2.20 (1H, m), 2.28-2.42 (1H, m), 2.46 (3H, s), 2.49-2.67 (2H, m), 4.10-4.22 (2H, m), 4.64-4.73 (1H, m), 7.37 (2H, d, J=7.9 Hz), 7.79 (2H, d, J=8.3 Hz).

(Step 25)

28% Sodium methoxide/MeOH solution (74.0 g, 383.35 mmol) was added to a mixture of (S)-(5-oxotetrahydrofuran-2-yl)methyl 4-methylbenzenesulfonate (51.81 g, 191.67 mmol) and dehydrated MeOH (280 mL) at room temperature, and the mixture was stirred at room temperature for 1.5 hr. The reaction mixture was cooled under ice-cooling, and the mixture was neutralized with acetic acid (about 15 mL). The reaction mixture was concentrated to about half-volume under reduced pressure, and ice water (350 mL) was added thereto. Then, the mixture was extracted with a mixed solvent of ethyl acetate/diethyl ether (3:1) (×3). The organic layer was washed successively with aqueous sodium hydrogencarbonate solution, water and brine, and dried over magnesium sulfate, and the solvent was evaporated under reduced pressure to give crude methyl (S)-3-(oxiran-2-yl) propanoate (13.12 g, 101 mmol, 53%) as a colorless oil.

$^1$H NMR (300 MHz, CDCl$_3$): δ1.78 (1H, dq, J=14.0, 7.1 Hz), 1.99 (1H, dtd, J=14.5, 7.4, 4.4 Hz), 2.48 (2H, t, J=7.4 Hz), 2.50-2.53 (1H, m), 2.77 (1H, dd, J=5.0, 4.0 Hz), 2.95-3.03 (1H, m), 3.69 (3H, s).

(Step 26)

1.6M n-Butyllithium/hexane solution (76 mL, 120.98 mmol) was added dropwise to a solution of diisopropylamine (12.24 g, 120.98 mmol) in THF (240 mL) at 0° C. over 12 min under argon atmosphere. The mixture was stirred at 0° C. for 30 min, and the reaction mixture was cooled to −78° C. A solution of methyl (S)-3-(oxiran-2-yl)propanoate (13.12 g, 100.81 mmol) in THF (10 mL) was added dropwise thereto at −78° C. over 12 min. The reaction mixture was stirred at −15° C. for 2 hr, and poured into cooled 0.5N hydrochloric acid (600 mL), and the mixture was extracted with ethyl acetate (×3). The organic layer was washed with water and brine, and dried over magnesium sulfate, and the solvent was evaporated under reduced pressure. The obtained residue was purified by silica gel column chromatography (solvent gradient; 49→70% ethyl acetate/hexane) to give methyl (1S,2S)-2-(hydroxymethyl)cyclopropanecarboxylate (2.27 g, 17.44 mmol, 17%) as a colorless oil.

$^1$H NMR (300 MHz, CDCl$_3$): δ0.88 (1H, ddd, J=8.5, 6.2, 4.2 Hz), 1.19-1.29 (1H, m), 1.49 (1H, t, J=5.7 Hz), 1.55-1.61 (1H, m), 1.74 (1H, dqd, J=8.9, 6.3, 4.2 Hz), 3.48 (H, ddd, J=11.6, 6.5, 5.7 Hz), 3.63 (1H, dd, J=11.5, 6.0 Hz), 3.68 (3H, s).

(Step 27)

Sodium hydride (60%, oil, 0.907 g, 22.68 mmol) was added to a solution of methyl (1S,2S)-2-(hydroxymethyl) cyclopropanecarboxylate (2.27 g, 17.44 mmol) in THF (110 mL) at 0° C. under argon atmosphere. The reaction mixture was stirred at room temperature for 1 hr, and cooled to 0° C. To the reaction mixture were added benzyl bromide (2.70 mL, 22.68 mmol) and tetra-n-butylammonium iodide (0.644 g, 1.74 mmol), and the mixture was stirred at room temperature for 15 hr. The reaction mixture was poured into cooled 0.5N hydrochloric acid (350 mL), and the mixture was extracted with ethyl acetate (×3). The organic layer was washed with water and brine, and dried over magnesium sulfate, and the solvent was evaporated under reduced pressure. The obtained residue was purified by silica gel column chromatography (solvent gradient; 2→25% ethyl acetate/hexane) to give methyl (1S,2S)-2-((benzyloxy)methyl)cyclopropanecarboxylate (1.38 g, 6.27 mmol, 36%) as a colorless oil.

$^1$H NMR (300 MHz, CDCl$_3$): δ0.87 (1H, ddd, J=8.4, 6.4, 4.6 Hz), 1.18-1.29 (1H, m), 1.55-1.61 (1H, m), 1.75 (1H, dqd, J=8.7, 6.3, 4.2 Hz), 3.34 (1H, dd, J=10.4, 6.4H z), 3.46 (1H, dd, J=10.4, 6.4 Hz), 3.67 (3H, s), 4.52 (2H, s), 7.27-7.38 (5H, m).

(Step 28)

Lithium aluminium hydride (0.238 g, 6.27 mmol) was added to a solution of methyl (1S,2S)-2-((benzyloxy)methyl)cyclopropanecarboxylate (1.38 g, 6.27 mmol) in THF (15 mL) at 0° C. The reaction mixture was stirred at room temperature for 15 hr, and ethyl acetate (5 mL) and saturated aqueous potassium sodium tartrate solution (25 mL) were added thereto at 0° C. The mixture was stirred at room temperature for 30 min, water (60 mL) was added thereto, and the mixture was extracted with ethyl acetate (×3). The organic layer was washed with water and brine, and dried over magnesium sulfate, and the solvent was evaporated under reduced pressure. The obtained residue was purified by silica gel column chromatography (solvent gradient; 37→58% ethyl acetate/hexane) to give ((1S,2S)-2-((benzyloxy)methyl)cyclopropyl)methanol (1.01 g, 5.25 mmol, 84%) as a colorless oil.

$^1$H NMR (300 MHz, CDCl$_3$): δ0.50 (2H, dd, J=7.0, 5.9 Hz), 0.97-1.09 (2H, m), 1.55 (1H, t, J=5.7 Hz), 3.30 (1H, dd, J=10.4, 6.5 Hz), 3.37-3.55 (3H, m), 4.53 (2H, s), 7.26-7.36 (5H, m).

(Step 29)

Methanesulfonyl chloride (443 μL, 5.72 mmol) was added to a solution of ((1S,2S)-2-((benzyloxy)methyl)cyclopropyl)methanol (1.00 g, 5.20 mmol) and TEA (797 μL, 5.72 mmol) in THF (15 mL) at 0° C., and the mixture was stirred at room temperature for 3 hr. The reaction mixture was poured into water (80 mL), and the mixture was extracted with ethyl acetate (×3). The organic layer was washed with water and brine, and dried over magnesium sulfate, and the solvent was evaporated under reduced pressure. The obtained residue was dissolved in DMF (15 mL), and potassium cyanide (0.677 g, 10.40 mmol) was added thereto at room temperature. The reaction mixture was stirred at 60° C. for 2 hr, and poured into water (100 mL), and the mixture was extracted with ethyl acetate (×3). The organic layer was washed with water and brine, and dried over magnesium sulfate, and the solvent was evaporated under reduced pressure. The obtained residue was purified by silica gel column chromatography (solvent gradient; 17→38% ethyl acetate/hexane) to give 2-((1R,2S)-2-((benzyloxy)methyl)cyclopropyl)acetonitrile (782 mg, 3.89 mmol, 75%) as a colorless oil.

$^1$H NMR (300 MHz, CDCl$_3$): δ0.56-0.67 (2H, m), 0.93-1.05 (1H, m), 1.12 (1H, dqd, J=8.3, 6.2, 4.2 Hz), 2.35 (1H, dd, J=17.5, 6.5H z), 2.48 (1H, dd, J=17.5, 6.5 Hz), 3.32 (1H, dd, J=10.5, 6.6 Hz), 3.42 (H, dd, J=10.5, 6.6 Hz), 4.52 (2H, s), 7.27-7.38 (5H, m).

(Step 30)

4N Aqueous sodium hydroxide solution (14.48 mL, 57.91 mmol) was added to a solution of 2-((1R,2S)-2-((benzyloxy)methyl)cyclopropyl)acetonitrile (777 mg, 3.86 mmol) in EtOH (14.5 mL) at room temperature, and the mixture was stirred at 80° C. for 15 hr. The reaction mixture was poured into ice water (80 mL), and the pH of the mixture was adjusted to 3 with 6N hydrochloric acid. Then, the mixture was extracted with ethyl acetate (×3). The organic layer was washed with water and brine, and dried over magnesium sulfate, and the solvent was evaporated under reduced pressure to give 2-((1R,2S)-2-((benzyloxy)methyl)cyclopropyl)acetic acid (890 mg, 4.04 mmol, quant.) as a pale-yellow oil.

$^1$H NMR (300 MHz, CDCl$_3$): δ0.46-0.61 (2H, m), 0.90-1.06 (2H, m), 2.33 (2H, d, J=6.8 Hz), 3.33 (1H, dd, J=10.2, 6.8 Hz), 3.40 (1H, dd, J=10.2, 6.4 Hz), 4.54 (2H, s), 7.27-7.38 (5H, m) (The peak derived from COOH was not observed).

(Step 31)

A mixture of 2-((1R,2S)-2-((benzyloxy)methyl)cyclopropyl)acetic acid (884 mg, 4.01 mmol) in MeOH (20 mL) was stirred in the presence of 10% palladium-carbon (310 mg, 50%, wet) at room temperature for 3 hr under hydrogen atmosphere (1 atm). The catalyst was removed by filtration, and the filtrate was concentrated under reduced pressure. To the residue was added toluene (about 20 mL), and the mixture was concentrated to give 2-((1R,2S)-2-(hydroxymethyl)cyclopropyl)acetic acid (542 mg, 4.16 mmol, quant.) as a colorless oil.

$^1$H NMR (300 MHz, CDCl$_3$): δ0.46-0.61 (2H, m), 0.85-1.04 (2H, m), 2.01 (1H, dd, J=17.3, 9.2 Hz), 2.66 (1H, dd, J=17.4, 4.9 Hz), 3.16 (1H, dd, J=11.0, 8.7 Hz), 3.81 (1H, dd, J=11.0, 5.7 Hz), 5.11 (2H, brs).

(Step 32)

Benzyl bromide (539 μL, 4.53 mmol) was added to a mixture of 2-((1R,2S)-2-(hydroxymethyl)cyclopropyl)acetic acid (536 mg, 4.12 mmol), potassium carbonate (626 mg, 4.53 mmol) and DMF (8 mL) at room temperature, and the mixture was stirred at room temperature for 15 hr. The reaction mixture was poured into water (80 mL), and the mixture was extracted with ethyl acetate (×3). The organic layer was washed with water and brine, and dried over magnesium sulfate, and the solvent was evaporated under reduced pressure. The obtained residue was purified by silica gel column chromatography (solvent gradient; 33→53% ethyl acetate/hexane) to give benzyl 2-((1R,2S)-2-(hydroxymethyl)cyclopropyl)acetate (718 mg, 3.26 mmol, 79%) as a colorless oil.

$^1$H NMR (300 MHz, CDCl$_3$): δ0.44-0.59 (2H, m), 0.85-1.01 (2H, m), 2.00-2.10 (2H, m), 2.63 (1H, dd, J=17.0, 5.3 Hz), 3.17 (1H, ddd, J=11.1, 8.1, 3.4 Hz), 3.73 (1H, ddd, J=11.0, 7.5, 5.7H), 5.10-5.19 (2H, m), 7.29-7.41 (5H, m).

(Step 33)

Sodium metaperiodate (1729 mg, 8.08 mmol) and ruthenium(IV) oxide hydrate (48.8 mg, 0.32 mmol) were added to a solution of benzyl 2-((1R,2S)-2-(hydroxymethyl)cyclopropyl)acetate (712 mg, 3.23 mmol) in acetone (11.5 mL) and water (13 mL) at 0° C., and the mixture was stirred at 0° C. for 2.5 hr. The reaction mixture was poured into water (100 mL), and the mixture was extracted with ethyl acetate (×3). The organic layer was washed with water and brine, and dried over magnesium sulfate, and the solvent was evaporated under reduced pressure to give (1S,2R)-2-(2-(benzyloxy)-2-oxoethyl)cyclopropanecarboxylic acid (690 mg, 2.95 mmol, 91%) as a colorless oil.

$^1$H NMR (300 MHz, CDCl$_3$): δ0.90 (1H, ddd, J=8.2, 6.3, 4.7 Hz), 1.33 (1H, dt, J=9.2, 4.6 Hz), 1.51 (1H, dt, J=8.4, 4.3 Hz), 1.74-1.86 (1H, m), 2.39 (2H, d, J=7.2 Hz), 5.14 (2H, s), 7.29-7.40 (5H, m) (The peak derived from COOH was not observed).

(Step 34)

HATU (1450 mg, 3.81 mmol) was added to a solution of (R)—N-(7-fluoro-1,1-dimethyl-2,3-dihydro-1H-inden-5-yl)-2-methoxy-5,6,7,8-tetrahydro-1,6-naphthyridine-5-carboxamide (1083 mg, 2.93 mmol), (1S,2R)-2-(2-(benzyloxy)-2-oxoethyl)cyclopropanecarboxylic acid (687 mg, 2.93 mmol) and DIEA (1.022 mL, 5.87 mmol) in DMF (14.5 mL) at room temperature, and the mixture was stirred at room temperature for 15 hr. The reaction mixture was poured into water (120 mL), and the mixture was extracted with ethyl acetate (×3). The organic layer was washed with water and brine, and dried over magnesium sulfate, and the solvent was evaporated under reduced pressure. The obtained residue was purified by silica gel column chromatography (solvent gradient; 37→58% ethyl acetate/hexane) to give benzyl 2-((1R,2S)-2-((R)-5-((7-fluoro-1, 1-dimethyl-2,3-dihydro-1H-inden-5-yl)carbamoyl)-2-methoxy-5,6,7,8-tetrahydro-1,6-naphthyridine-6-carbonyl)cyclopropyl)acetate (1.60 g, 2.73 mmol, 93%) as a colorless amorphous solid.

$^1$H NMR (300 MHz, CDCl$_3$): δ0.87-0.95 (1H, m), 1.27-1.34 (7H, m), 1.77-1.93 (4H, m), 2.26 (1H, dd, J=16.1, 8.1 Hz), 2.63 (1H, dd, J=15.9, 6.0 Hz), 2.84 (2H, t, J=7.4 Hz), 2.95-3.02 (2H, m), 3.71-3.82 (1H, m), 3.93 (3H, s), 4.08-4.17 (1H, m), 5.12 (2H, s), 5.95 (1H, s), 6.66 (1H, d, J=8.7 Hz), 6.99 (1H, s), 7.08 (1H, d, J=11.7 Hz), 7.25-7.33 (5H, m), 7.41 (1H, d, J=8.3 Hz), 9.17 (1H, s).

(Step 35)

A solution of benzyl 2-((1R,2S)-2-((R)-5-((7-fluoro-1,1-dimethyl-2,3-dihydro-1H-inden-5-yl)carbamoyl)-2-methoxy-5,6,7,8-tetrahydro-1,6-naphthyridine-6-carbonyl)cyclopropyl)acetate (1.59 g, 2.71 mmol) in MeOH (45 mL) was stirred in the presence of 10% palladium-carbon (550 mg, 50%, wet) at room temperature for 1.5 hr under hydrogen atmosphere (1 atm). The catalyst was removed by filtration, and the filtrate was concentrated under reduced pressure. The obtained residue was purified by silica gel column chromatography (Diol, solvent gradient; 30→100% ethyl acetate/hexane) to give the title compound (1.24 g, 2.502 mmol, 92%) as a colorless amorphous solid.

$^1$H NMR (300 MHz, CDCl$_3$): δ0.88-0.95 (1H, m), 1.29-1.37 (7H, m), 1.77-1.90 (4H, m), 2.16 (1H, dd, J=16.4, 8.2 Hz), 2.66 (1H, dd, J=16.1, 5.5 Hz), 2.81 (2H, t, J=7.4 Hz), 2.95-3.17 (2H, m), 3.90 (3H, s), 3.92-4.04 (1H, m), 4.13-4.23 (1H, m), 5.96 (1H, s), 6.62 (1H, d, J=8.3 Hz), 6.95 (1H, s), 7.03 (1H, d, J=12.1 Hz), 7.49 (1H, d, J=8.3 Hz), 9.35 (1H, s) (The peak derived from COOH was not observed).

$[\alpha]_D^{25}$+130.6 (c 0.2510, MeOH)

Example 8 cis-3-(((1R)-1-((3,5-difluoro-4-(trimethylsilyl)phenyl)carbamoyl)-6-ethoxy-3,4-dihydroisoquinolin-2 (1H)-yl)carbonyl)cyclobutanecarboxylic acid HATU (226 mg, 0.59 mmol) was added to a solution of (R)—N-(3,5-difluoro-4-(trimethylsilyl)phenyl)-6-ethoxy-1, 2,3,4-tetrahydroisoquinoline-1-carboxamide (200 mg, 0.49 mmol), DIEA (0.169 mL, 0.99 mmol) and cis-cyclobutane-1,3-dicarboxylic acid (214 mg, 1.48 mmol) in DMF (2.0 mL) at room temperature, and the mixture was stirred at room temperature for 5 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 20→90% ethyl acetate/hexane), and then preparative HPLC (C18, mobile phase: water/acetonitrile (containing 0.1% TFA)) to give the title compound (74.8 mg, 0.141 mmol, 28.5%) as a white solid.

$^1$H NMR (300 MHz, DMSO-d$_6$): δ0.30 (9H, s), 1.29 (3H, t, J=7.0 Hz), 2.19-2.41 (4H, m), 2.70-2.83 (1H, m), 2.84-3.12 (2H, m), 3.26-3.54 (2H, m), 3.86-4.06 (3H, m), 5.58 (1H, s), 6.71-6.86 (2H, m), 7.13-7.27 (2H, m), 7.42 (1H, s), 10.85 (1H, s)

$[\alpha]_D^{25}$+14.1 (c 0.2515, MeOH)

Example 9 trans-3-(((1R)-1-((3,5-difluoro-4-(trimethylsilyl) phenyl)carbamoyl)-6-ethoxy-3,4-dihydroisoquinolin-2(1H)-yl)carbonyl)cyclobutanecarboxylic acid HATU (226 mg, 0.59 mmol) was added to a solution of (R)—N-(3,5-difluoro-4-(trimethylsilyl)phenyl)-6-ethoxy-1, 2, 3,4-tetrahydroisoquinoline-1-carboxamide (200 mg, 0.49 mmol), DIEA (0.169 mL, 0.99 mmol) and trans-cyclobutane-1,3-dicarboxylic acid (214 mg, 1.48 mmol) in DMF (2.0 mL) at room temperature, and the mixture was stirred at room temperature for 5 hr. To the reaction mixture was added aqueous sodium hydrogencarbonate solution, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 20→90% ethyl acetate/hexane, 0→10% MeOH/ethyl acetate), and then preparative HPLC (C18, mobile phase: water/acetonitrile (containing 0.1% TFA)) to give the title compound (53.8 mg, 0.101 mmol, 20.51%) as a white solid.

$^1$H NMR (300 MHz, DMSO-d$_6$): δ0.29 (9H, s), 1.29 (3H, t, J=7.0 Hz), 2.25-2.47 (4H, m), 2.69-2.84 (1H, m), 2.86-3.12 (2H, m), 3.36-3.57 (2H, m), 3.79-3.91 (1H, m), 3.99 (2H, q, J=7.0 Hz), 5.60 (1H, s), 6.74-6.86 (2H, m), 7.14-7.27 (2H, m), 7.38-7.49 (1H, m), 10.82 (1H, s), 12.25 (H, brs)

$[\alpha]_D^{25}$+6.7 (c 0.1275, MeOH)

Example 10 cis-3-(((5R)-5-((7-fluoro-1, 1-dimethyl-2,3-dihydro-1H-inden-5-yl)carbamoyl)-2-methoxy-7,8-dihydro-1,6-naphthyridin-6(5H)-yl)carbonyl)cyclobutanecarboxylic acid (Step 1)

Potassium carbonate (575 mg, 4.16 mmol) and benzyl bromide (0.495 mL, 4.16 mmol) were added to a solution of cyclobutane-1,3-dicarboxylic acid (cis-trans mixture) (200 mg, 1.39 mmol) in DMF (4.0 mL) at room temperature, and the mixture was stirred overnight at room temperature. To the reaction mixture was added water at room temperature, and the mixture was extracted with ethyl acetate. The organic layer was washed with water and brine, and dried over magnesium sulfate, and the solvent was evaporated under reduced pressure. The obtained residue was purified by silica gel column chromatography (solvent gradient; 0→5% ethyl acetate/hexane) to give dibenzyl cis-cyclobutane-1,3-dicarboxylate (106.3 mg, 0.328 mmol, 23.6%) as a less polar compound, and dibenzyl trans-cyclobutane-1,3-dicarboxylate (103.1 mg, 0.318 mmol, 22.9%) as a more polar compound, respectively.

NMR spectrum of dibenzyl cis-cyclobutane-1,3-dicarboxylate $^1$H NMR (300 MHz, CDCl$_3$): δ2.56 (4H, t, J=7.9 Hz), 3.20-3.34 (2H, m), 5.15 (4H, s), 7.29-7.44 (10H, m)

NMR spectrum of dibenzyl trans-cyclobutane-1,3-dicarboxylate $^1$H NMR (300 MHz, CDCl$_3$): δ2.40-2.69 (4H, m), 2.99-3.21 (2H, m), 5.12 (4H, s), 7.29-7.41 (10H, m)

(Step 2)

To a solution of dibenzyl cis-cyclobutane-1,3-dicarboxylate (5.29 g, 16.31 mmol) in MeOH (100 mL) was added 10% palladium-carbon (500 mg, 50%, wet), and the mixture was stirred at room temperature for 5 hr under hydrogen atmosphere (1 atm). The catalyst was removed by filtration through Celite, and the filtrate was concentrated under reduced pressure. The residue was solidified with hexane to give crude cis-cyclobutane-1,3-dicarboxylic acid (2.23 g, 15.47 mmol, 95%) as a white solid.

$^1$H NMR (300 MHz, DMSO-$d_6$): δ2.17-2.38 (4H, m), 2.88-3.06 (2H, m), 12.17 (2H, brs)

(Step 3)

HATU (124 mg, 0.32 mmol) was added to a solution of (R)—N-(7-fluoro-1,1-dimethyl-2,3-dihydro-1H-inden-5-yl)-2-methoxy-5,6,7,8-tetrahydro-1,6-naphthyridine-5-carboxamide (100 mg, 0.27 mmol), DIEA (0.093 mL, 0.54 mmol) and cis-cyclobutane-1,3-dicarboxylic acid (58.5 mg, 0.41 mmol) in DMF (2.0 mL) at room temperature, and the mixture was stirred at room temperature for 5 hr. To the reaction mixture was added water, and the mixture was extracted with ethyl acetate. The organic layer was washed with water and brine, and dried over magnesium sulfate, and the solvent was evaporated under reduced pressure. The obtained residue was purified by silica gel column chromatography (solvent gradient; 20→90% ethyl acetate/hexane), and then preparative HPLC (C18, mobile phase: water/acetonitrile (containing 0.1% TFA)) to give the title compound (44.5 mg, 0.090 mmol, 33%) as a colorless amorphous solid.

$^1$H NMR (300 MHz, DMSO-$d_6$): δ1.29 (6H, s), 1.87 (2H, t, J=7.4 Hz), 2.23-2.45 (4H, m), 2.71-2.91 (3H, m), 2.92-3.09 (2H, m), 3.37-3.51 (1H, m), 3.69-3.80 (1H, m), 3.82 (3H, s), 3.89-4.02 (1H, m), 5.70 (1H, s), 6.72 (1H, d, J=8.3 Hz), 7.11-7.31 (2H, m), 7.78 (1H, d, J=8.7 Hz), 10.53 (1H, s), 12.18 (1H, brs)

$[α]_D^{25}$ +114.7 (c 0.2505, MeOH)

Example 11 trans-3-(((5R)-5-((7-fluoro-1,1-dimethyl-2,3-dihydro-1H-inden-5-yl)carbamoyl)-2-methoxy-7,8-dihydro-1,6-naphthyridin-6(5H)-yl)carbonyl)cyclobutanecarboxylic acid (Step 1)

A mixture of dibenzyl trans-cyclobutane-1,3-dicarboxylate (100 mg, 0.31 mmol) and 10% palladium-carbon (10 mg, 0.09 mmol, 50%, wet) in MeOH (2.0 mL) was stirred at room temperature for 5 hr under hydrogen atmosphere (1 atm). The catalyst was removed by filtration, and the filtrate was concentrated under reduced pressure to give crude trans-cyclobutane-1,3-dicarboxylic acid as a colorless oil.

(Step 2)

HATU (124 mg, 0.32 mmol) was added to a solution of (R)—N-(7-fluoro-1,1-dimethyl-2,3-dihydro-1H-inden-5-yl)-2-methoxy-5,6,7,8-tetrahydro-1,6-naphthyridine-5-carboxamide (100 mg, 0.27 mmol), DIEA (0.093 mL, 0.54 mmol) and the crude trans-cyclobutane-1,3-dicarboxylic acid (58.5 mg, 0.41 mmol) in DMF (2.0 mL) at room temperature, and the mixture was stirred at room temperature for 5 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 20→90% ethyl acetate/hexane), and then preparative HPLC (C18, mobile phase: water/acetonitrile (containing 0.1% TFA)) to give the title compound (24.0 mg, 0.048 mmol, 17.89%) as a white solid.

$^1$H NMR (300 MHz, DMSO-$d_6$): δ1.29 (6H, s), 1.81-1.93 (2H, m), 2.28-2.47 (4H, m), 2.77-3.03 (5H, m), 3.44-3.60 (1H, m), 3.60-3.74 (1H, m), 3.82 (3H, s), 3.86-3.99 (1H, m), 5.72 (1H, s), 6.72 (1H, d, J=8.7 Hz), 7.10-7.29 (2H, m), 7.79 (1H, d, J=8.7 Hz), 10.54 (1H, s), 12.26 (1H, brs)

Example 12 trans-3-(((1R)-1-((3,5-difluoro-4-(trimethylsilyl)phenyl)carbamoyl)-6-methoxy-3,4-dihydroisoquinolin-2(1H)-yl)carbonyl)cyclobutanecarboxylic acid HATU (234 mg, 0.61 mmol) was added to a solution of (R)—N-(3,5-difluoro-4-(trimethylsilyl)phenyl)-6-methoxy-1,2,3,4-tetrahydroisoquinoline-1-carboxamide (200 mg, 0.51 mmol), DIEA (0.175 mL, 1.02 mmol) and trans-cyclobutane-1,3-dicarboxylic acid (111 mg, 0.77 mmol) in DMF (2.0 mL) at room temperature, and the mixture was stirred at room temperature for 5 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 20→90% ethyl acetate/hexane), and then preparative HPLC (C18, mobile phase: water/acetonitrile (containing 0.1% TFA)) to give the title compound (32.1 mg, 0.062 mmol, 12.13%) as a white solid.

$^1$H NMR (300 MHz, DMSO-$d_6$): δ0.24-0.36 (9H, m), 2.23-2.47 (4H, m), 2.68-2.98 (2H, m), 2.98-3.13 (1H, m), 3.35-3.56 (2H, m), 3.67-3.75 (3H, m), 3.77-3.93 (1H, m), 5.61 (1H, s), 6.75-6.87 (2H, m), 7.14-7.27 (2H, m), 7.38-7.53 (1H, m), 10.82 (1H, s), 12.30 (H, brs)

Example 13

((1R,2S)-2-(((5R)-5-((3,5-difluoro-4-(trimethylsilyl)phenyl)carbamoyl)-2-methoxy-7,8-dihydro-1,6-naphthyridin-6(5H)-yl)carbonyl)cyclopropyl)acetic acid (Step 1)

1N Sodium hydroxide (81 mL, 81.36 mmol) was added to a solution of diethyl trans-cyclopropane-1,2-dicarboxylate (15.15 g, 81.36 mmol) in EtOH (100 mL) at 0° C., and the mixture was stirred at 0° C. for 3 hr. The reaction mixture was concentrated under reduced pressure, 2M hydrochloric acid and NaCl were added thereto, and the mixture was extracted with ethyl acetate. The organic layer was dried over magnesium sulfate, and the solvent was evaporated under reduced pressure. The obtained residue was purified by silica gel column chromatography (solvent gradient; 5→100% ethyl acetate/hexane) to give trans-2-(ethoxycarbonyl)cyclopropanecarboxylic acid (11.20 g, 70.8 mmol, 87%) as a colorless oil.

$^1$H NMR (300 MHz, CDCl$_3$): δ1.28 (3H, t, J=7.2 Hz), 1.41-1.55 (2H, m), 2.12-2.28 (2H, m), 4.12-4.20 (2H, m) (The peak derived from COOH was not observed).

(Step 2)

1M Borane-THF complex THF solution (85 mL, 84.98 mmol) was added to a solution of trans-2-(ethoxycarbonyl)cyclopropanecarboxylic acid (11.2 g, 70.82 mmol) in THF (100 mL) at 0° C., and the mixture was stirred overnight at room temperature. MeOH was added thereto, and then the gas was not generated. The reaction mixture was concentrated under reduced pressure. The residue was dissolved in DMF (50 mL), tert-butylchlorodiphenylsilane (20.10 mL, 84.98 mmol) and imidazole (5.79 g, 84.98 mmol) were added thereto, and the mixture was stirred for 5 hr. To the reaction mixture was added water, and the mixture was extracted with ethyl acetate. The organic layer was washed with water and brine, dried over magnesium sulfate, and concentrated under reduced pressure, and the obtained residue was purified by is silica gel column chromatography (solvent gradient; 2→35% ethyl acetate/hexane) to give ethyl trans-2-((tert-butyldiphenylsilyloxy)methyl)cyclopropanecarboxylate (21.40 g, 55.9 mmol, 79%) as a colorless oil.

$^1$H NMR (300 MHz, CDCl$_3$): δ0.81-0.94 (1H, m), 1.04 (9H, s), 1.08-1.18 (1H, m), 1.20-1.32 (3H, m), 1.51-1.59 (1H, m), 1.60-1.71 (1H, m), 3.55-3.62 (1H, m), 3.66-3.75 (1H, m), 4.12 (2H, q, J=7.2 Hz), 7.32-7.45 (6H, m), 7.58-7.72 (4H, m)

(Step 3)

To a suspension of LAH (0.92 g, 24.24 mmol) in THF (100 mL) was added a solution of ethyl trans-2-((tert-butyldiphenylsilyloxy)methyl)cyclopropanecarboxylate (21.4 g, 55.94 mmol) in THF (20 mL) at 0° C., and the mixture was stirred for 2 hr. To the reaction mixture were added successively water (0.92 mL), 15% aqueous sodium hydroxide solution (0.92 mL) and water (2.76 mL). The precipitate was removed by filtration, and the filtrate was concentrated under reduced pressure. The obtained residue was purified by silica gel column chromatography (solvent gradient; 1→30% ethyl acetate/hexane) to give trans-(2-((tert-butyldiphenylsilyloxy)methyl)cyclopropyl)methanol (14.16 g, 41.66 mmol, 74%) as a colorless oil.

$^1$H NMR (300 MHz, CDCl$_3$): δ0.31-0.53 (2H, m), 0.89-1.01 (2H, m), 1.02-1.10 (9H, m), 1.21-1.26 (1H, m), 3.34-3.52 (3H, m), 3.69 (1H, dd, J=10.8, 5.5 Hz), 7.32-7.46 (6H, m), 7.61-7.73 (4H, m)

(Step 4)

TEA (0.450 mL, 3.23 mmol) was added to a mixture of trans-(2-((tert-butyldiphenylsilyloxy)methyl)cyclopropyl)methanol (1 g, 2.94 mmol), methanesulfonyl chloride (0.250 mL, 3.23 mmol) and THF (10 mL) at 0° C., and the mixture was stirred at room temperature for 2 hr. To the reaction mixture was added water, and the mixture was extracted with ethyl acetate. The organic layer was washed with brine, and dried over magnesium sulfate, and the solvent was evaporated under reduced pressure to give trans-(2-(((tert-butyldiphenylsilyl)oxy)methyl)cyclopropyl)methyl methanesulfonate (1.230 g, 2.94 mmol, 100%) as a colorless oil.

$^1$H NMR (300 MHz, CDCl$_3$): δ0.50-0.66 (2H, m), 1.04 (9H, s), 1.06-1.19 (2H, m), 2.99 (3H, s), 3.44-3.57 (1H, m), 3.71 (1H, dd, J=11.0, 4.9 Hz), 4.08 (2H, d, J=7.2 Hz), 7.32-7.48 (6H, m), 7.65 (4H, dd, J=7.0, 0.9 Hz).

(Step 5)

A mixture of trans-(2-(((tert-butyldiphenylsilyl)oxy)methyl)cyclopropyl)methyl methanesulfonate (1.23 g, 2.94 mmol), potassium cyanide (0.383 g, 5.88 mmol) and DMF (10 mL) was stirred overnight at 60° C. To the reaction mixture was added water, and the mixture was extracted with ethyl acetate. The organic layer was washed with water, and dried over magnesium sulfate, and the solvent was evaporated under reduced pressure. The obtained residue was purified by silica gel column chromatography (solvent gradient; 10→60% ethyl acetate/hexane) to give trans-2-(2-(((tert-butyldiphenylsilyl)oxy)methyl)cyclopropyl)acetonitrile (0.970 g, 2.78 mmol, 94%) as a colorless oil.

$^1$H NMR (300 MHz, CDCl$_3$): δ0.41-0.64 (2H, m), 0.83-0.94 (1H, m), 0.96-1.06 (10H, m), 2.21-2.47 (2H, m), 3.48 (1H, dd, J=11.0, 6.0 Hz), 3.71 (1H, dd, J=10.8, 5.1 Hz), 7.33-7.45 (6H, m), 7.61-7.69 (4H, m).

(Step 6)

8M Aqueous sodium hydroxide solution (1 mL) was added to a mixture of trans-2-(2-(((tert-butyldiphenylsilyl)oxy)methyl)cyclopropyl) acetonitrile (100 mg, 0.29 mmol) in EtOH (2 mL) and water (1 mL), and the mixture was stirred at 80° C. for 5 hr. The reaction mixture was allowed to be cooled to room temperature, and washed with toluene. The aqueous layer was acidified with 6M hydrochloric acid, and the mixture was extracted with ethyl acetate. The organic layer was dried over sodium sulfate, and the solvent was evaporated under reduced pressure to give trans-2-(2-(hydroxymethyl)cyclopropyl)acetic acid (50.0 mg, 0.384 mmol, 134%) as a colorless oil.

$^1$H NMR (300 MHz, CDCl$_3$): δ0.41-0.66 (2H, m), 0.81-1.04 (2H, m), 1.93-2.16 (2H, m), 2.67 (1H, dd, J=17.4, 5.3 Hz), 3.18 (1H, dd, J=11.1, 8.5 Hz), 3.79 (1H, dd, J=11.0, 5.3 Hz) (The peak derived from COOH was not observed).

(Step 7)

A mixture of trans-2-(2-(hydroxymethyl)cyclopropyl) acetic acid (50 mg, 0.38 mmol), benzyl bromide (0.050 mL, 0.42 mmol), potassium carbonate (58.4 mg, 0.42 mmol) and DMF (2 mL) was stirred overnight at room temperature. To the reaction mixture was added water, and the mixture was extracted with ethyl acetate. The organic layer was dried over magnesium sulfate, and the solvent was evaporated under reduced pressure. The obtained residue was purified by silica gel column chromatography (solvent gradient; 5→80% ethyl acetate/hexane) to give benzyl trans-2-(2-(hydroxymethyl)cyclopropyl)acetate (44.0 mg, 0.200 mmol, 52%) as a colorless oil.

$^1$H NMR (300 MHz, CDCl$_3$): δ0.41-0.62 (2H, m), 0.83-1.03 (2H, m), 1.98-2.13 (2H, m), 2.64 (1H, dd, J=16.8, 5.1 Hz), 3.17 (1H, ddd, J=11.1, 8.1, 3.4 Hz), 3.74 (1H, ddd, J=10.9, 7.5, 5.5 Hz), 5.07-5.21 (2H, m), 7.30-7.43 (5H, m).

(Step 8)

Sodium metaperiodate (107 mg, 0.50 mmol) and ruthenium(IV) oxide hydrate (3.02 mg, 0.02 mmol) were added to a solution of benzyl trans-2-(2-(hydroxymethyl)cyclopropyl)acetate (44 mg, 0.20 mmol) in acetone (1 mL) and water (1 mL) at 0° C., and the mixture was stirred at 0° C. to room temperature for 1 hr. The reaction mixture was filtered through Celite (while washing with acetone), and the filtrate was concentrated under reduced pressure. The residue was extracted with ethyl acetate. The organic layer was washed with brine, and dried over magnesium sulfate, and the solvent was evaporated under reduced pressure to give trans-2-(2-(benzyloxy)-2-oxoethyl)cyclopropanecarboxylic acid (46.0 mg, 0.196 mmol, 98%) as a colorless oil.

$^1$H NMR (300 MHz, CDCl$_3$): δ0.90 (1H, ddd, J=8.3, 6.4, 4.5 Hz), 1.28-1.38 (1H, m), 1.52 (1H, dt, J=8.5, 4.4 Hz), 1.80 (1H, dqd, J=8.9, 6.9, 4.2 Hz), 2.40 (2H, d, J=7.2 Hz), 5.15 (2H, s), 7.30-7.41 (5H, m) (The peak derived from COOH was not observed).

(Step 9)

T3P (3.84 mL, 6.45 mmol) was added to a solution of 6-(tert-butoxycarbonyl)-2-methoxy-5,6,7,8-tetrahydro-1,6-naphthyridine-5-carboxylic acid (1.326 g, 4.3 mmol), 3,5-difluoro-4-(trimethylsilyl)aniline (0.866 g, 4.30 mmol), DIEA (3.74 mL, 21.50 mmol) and DMAP (0.578 g, 4.73 mmol) in ethyl acetate (31 mL) at room temperature, and the mixture was stirred at 65° C. for 15 hr. To the reaction mixture was added water, and the mixture was extracted with ethyl acetate (×3). The organic layer was washed with 10% aqueous citric acid solution, aqueous sodium hydrogencarbonate solution and brine, and dried over magnesium sulfate, and the solvent was evaporated under reduced pressure. The precipitate was washed with cooled hexane to give tert-butyl 5-((3,5-difluoro-4-(trimethylsilyl)phenyl)carbamoyl)-2-methoxy-7,8-dihydro-1,6-naphthyridine-6(5H)-carboxylate (1.69 g, 3.44 mmol, 80%) as white crystals.

$^1$H NMR (300 MHz, CDCl$_3$): δ0.33 (9H, t, J=1.3 Hz), 1.54 (9H, s), 2.83-3.02 (2H, m), 3.47 (1H, brs), 3.92 (3H, s), 3.98-4.09 (1H, m), 5.58 (1H, brs), 6.64 (1H, d, J=8.3 Hz), 6.98-7.06 (2H, m), 7.46 (1H, brs), 9.06 (1H, brs).

(Step 10)

tert-Butyl 5-((3,5-difluoro-4-(trimethylsilyl)phenyl)carbamoyl)-2-methoxy-7,8-dihydro-1,6-naphthyridine-6(5H)-carboxylate (1.69 g) was subjected to optical resolution by chiral column chromatography. The fraction having a shorter retention time was concentrated to give tert-butyl (R)-5-((3,5-difluoro-4-(trimethylsilyl)phenyl)carbamoyl)-2-methoxy-7,8-dihydro-1,6-naphthyridine-6(5H)-carboxylate (750 mg, >99% ee), and the fraction having a longer retention time was concentrated to give tert-butyl (S)-5-((3,5-difluoro-4-(trimethylsilyl)phenyl)carbamoyl)-2-methoxy-7,8-dihydro-1,6-naphthyridine-6(5H)-carboxylate (750 mg, >99% ee), as a white solid, respectively.

purification condition by chiral column chromatography
    column: CHIRALPAK AD(NF001) 50 mmID×500 mmL
    solvent: hexane/EtOH-900/100
    flow rate: 80 mL/min
    temperature: 30° C.
    detection method: UV 220 nm (Step 11)

Cooled TFA (10.5 mL) was added to tert-butyl (R)-5-((3,5-difluoro-4-(trimethylsilyl)phenyl)carbamoyl)-2-methoxy-7,8-dihydro-1,6-naphthyridine-6(5H)-carboxylate (747 mg, 1.52 mmol) at room temperature, and the mixture was stirred at room temperature for 3 min. The reaction mixture was poured into ice and aqueous sodium hydrogencarbonate solution, and the pH of the mixture was adjusted to 8 with aqueous sodium hydrogencarbonate solution. Then, the mixture was extracted with ethyl acetate (×3). The organic layer was washed with brine, and dried over magnesium sulfate, and the solvent was evaporated under reduced pressure to give (R)—N-(3,5-difluoro-4-(trimethylsilyl)phenyl)-2-methoxy-5,6,7,8-tetrahydro-1,6-naphthyridine-5-carboxamide (567 mg, 1.448 mmol, 95%) as a white solid.

$^1$H NMR (300 MHz, CDCl$_3$): δ0.32 (9H, t, J=1.3 Hz), 1.66 (1H, brs), 2.74-2.97 (2H, m), 3.11-3.29 (2H, m), 3.90 (3H, s), 4.58 (1H, s), 6.61 (1H, d, J=8.3 Hz), 7.05-7.13 (2H, m), 7.80 (1H, d, J=8.3 Hz), 9.60 (1H, s).

(Step 12)

HATU (137 mg, 0.36 mmol) was added to a solution of (R)—N-(3,5-difluoro-4-(trimethylsilyl)phenyl)-2-methoxy-5,6,7,8-tetrahydro-1,6-naphthyridine-5-carboxamide (128 mg, 0.33 mmol), trans-2-(2-(benzyloxy)-2-oxoethyl)cyclopropanecarboxylic acid (84 mg, 0.36 mmol) and DIEA (0.065 mL, 0.36 mmol) in DMF (2 mL) at room temperature, and the mixture was stirred at room temperature for 2 hr. To the reaction mixture was added water, and the mixture was extracted with ethyl acetate. The organic layer was washed with water, and dried over magnesium sulfate, and the solvent was evaporated under reduced pressure. The obtained residue was purified by silica gel column chromatography (solvent gradient; 30→80% ethyl acetate/hexane) to give benzyl 2-((1R,2S)-2-((R)-5-((3,5-difluoro-4-(trimethylsilyl)phenyl)carbamoyl)-2-methoxy-5,6,7,8-tetrahydro-1,6-naphthyridine-6-carbonyl)cyclopropyl)acetate (46 mg, 0.076 mmol, 23%) as a less polar compound, and benzyl 2-((1S,2R)-2-((R)-5-((3,5-difluoro-4-(trimethylsilyl)phenyl)carbamoyl)-2-methoxy-5,6,7,8-tetrahydro-1,6-naphthyridine-6-carbonyl)cyclopropyl)acetate (39 mg, 0.064 mmol, 20%) as a more polar compound, respectively.

MS spectrum of benzyl 2-((1R,2S)-2-((R)-5-((3,5-difluoro-4-(trimethylsilyl)phenyl)carbamoyl)-2-methoxy-5, 6,7,8-tetrahydro-1,6-naphthyridine-6-carbonyl)cyclopropyl)acetate MS(API): Calculated 607.7. Found 606.1 (M-H).

MS spectrum of benzyl 2-((1S,2R)-2-((R)-5-((3,5-difluoro-4-(trimethylsilyl)phenyl)carbamoyl)-2-methoxy-5,6,7,8-tetrahydro-1,6-naphthyridine-6-carbonyl)cyclopropyl)acetate MS(API): Calculated 607.7. Found 606.1 (M-H).

(Step 13)

A mixture of benzyl 2-((1R,2S)-2-((R)-5-((3,5-difluoro-4-(trimethylsilyl)phenyl)carbamoyl)-2-methoxy-5,6,7,8-tetrahydro-1,6-naphthyridine-6-carbonyl)cyclopropyl)acetate (46 mg, 0.08 mmol) and 10% palladium-carbon (8.06 mg, 0.08 mmol, 50%, wet) in MeOH (15 mL) was stirred at room temperature for 1 hr under hydrogen atmosphere (1 atm). The catalyst was removed by filtration, and the filtrate was concentrated under reduced pressure. The obtained residue was purified by silica gel column chromatography (solvent gradient; 30→100% ethyl acetate/hexane) to give the title compound (30.6 mg, 0.059 mmol, 78%) as a white solid.

$^1$H NMR (300 MHz, DMSO-d$_6$): δ0.30 (9H, s), 0.76 (1H, t, J=8.9 Hz), 0.92-1.10 (1H, m), 1.44 (1H, brs), 2.08 (1H, dt, J=8.2, 4.4 Hz), 2.16-2.29 (2H, m), 2.39 (1H, dd, J=16.6, 6.4 Hz), 2.83-3.14 (2H, m), 3.84 (3H, s), 3.98-4.37 (2H, m), 5.76 (1H, s), 6.73 (1H, d, J=8.7 Hz), 7.21 (2H, d, J=9.8 Hz), 7.70-7.85 (1H, m), 10.82 (1H, s), 12.16 (1H, brs).

$[α]_D^{25}$+121.9 (c 0.2520, MeOH)

Example 14

(2-(((5R)-5-((3,5-difluoro-4-(trimethylsilyl)phenyl)carbamoyl)-2-methoxy-7,8-dihydro-1,6-naphthyridin-6(5H)-yl)carbonyl)cyclopropyl)acetic acid A mixture of benzyl 2-((1R,2S)-2-((R)-5-((3,5-difluoro-4-(trimethylsilyl)phenyl)carbamoyl)-2-methoxy-5, 6,7,8-tetrahydro-1,6-naphthyridine-6-carbonyl)cyclopropyl)acetate (46 mg, 0.08 mmol) and 10% palladium-carbon (8.06 mg, 0.08 mmol, 50%, wet) in MeOH (15 mL) was stirred at room temperature for 2 hr under hydrogen atmosphere (1 atm). The catalyst was removed by filtration, and the filtrate was concentrated under reduced pressure. The obtained residue was purified by silica gel column chromatography (solvent gradient; 30→100% ethyl acetate/hexane) to give the title compound (31.2 mg, 0.060 mmol, 80%) as a white solid.

1H NMR (300 MHz, DMSO-d$_6$): δ0.30 (9H, s), 0.61-0.78 (1H, m), 0.95-1.15 (1H, m), 1.29-1.44 (1H, m), 2.05 (1H, dt, J=8.2, 4.4 Hz), 2.27-2.39 (2H, m), 2.82-2.97 (1H, m), 3.02-3.21 (1H, m), 3.67-3.90 (3H, m), 3.95-4.17 (1H, m), 4.18-4.35 (1H, m), 5.55-5.75 (1H, m), 6.73 (1H, d, J=8.7 Hz), 7.07-7.35 (2H, m), 7.64-7.88 (1H, m), 10.67-10.94 (1H, m), 12.17 (1H, brs).

Example 15

(cis-3-(((5R)-5-((7-fluoro-1, 1-dimethyl-2,3-dihydro-1H-inden-5-yl)carbamoyl)-2-methoxy-7,8-dihydro-1,6-naphthyridin-6(5H)-yl)carbonyl)cyclobutyl)acetic acid (Step 1)

A mixture of 3-(2-(tert-butoxy)-2-oxoethylidene)cyclobutanecarboxylic acid (3.4 g, 16.02 mmol) and 10% palladium-carbon (100 mg, 0.94 mmol, 50%, wet) in MeOH (30 mL) was stirred at room temperature for 5 hr under hydrogen atmosphere (1 atm). The catalyst was removed by filtration, and the filtrate was concentrated under reduced pressure. The obtained residue was purified by silica gel column chromatography (solvent gradient; 30→100% ethyl acetate/hexane) to give 3-(2-(tert-butoxy)-2-oxoethyl)cyclobutanecarboxylic acid (3.40 g, 15.87 mmol, 99%) as a colorless oil.

$^1$H NMR (300 MHz, CDCl$_3$): δ1.35-1.46 (9H, m), 1.90-2.10 (2H, m), 2.27-2.87 (5H, m), 2.96-3.21 (1H, m) (The peak derived from COOH was not observed).
(Step 2)

DEAD (7.23 mL, 15.87 mmol) was added to a solution of 3-(2-(tert-butoxy)-2-oxoethyl)cyclobutanecarboxylic acid (3.4 g, 15.87 mmol), PPh$_3$ (4.16 g, 15.87 mmol) and (R)-1-phenylethanol (1.904 mL, 15.87 mmol) in THF (20 mL) at 0° C., and the mixture was stirred overnight at room temperature. The reaction mixture was concentrated under reduced pressure, and the obtained residue was purified by silica gel column chromatography (solvent gradient; 5→65% ethyl acetate/hexane), and then again silica gel column chromatography (solvent gradient; 10→70% ethyl acetate/hexane) to give a mixture (2.7 g) of two diastereomeric isomers as an oil.

$^1$H NMR (300 MHz, CDCl$_3$): δ1.38-1.45 (9H, m), 1.49-1.55 (3H, m), 1.85-2.07 (2H, m), 2.22-2.84 (5H, m), 2.90-3.22 (1H, m), 5.77-5.96 (1H, m), 7.27-7.39 (5H, m).

The obtained oil (2.7 g) was subjected to chiral column chromatography to resolve the mixture of the diastereomeric isomers. The fraction having a shorter retention time was concentrated to give (S)-1-phenylethyl cis-3-(2-(tert-butoxy)-2-oxoethyl)cyclobutanecarboxylate (1.8 g, 5.65 mmol, 67%), and the fraction having a longer retention time was concentrated to give (S)-1-phenylethyl trans-3-(2-(tert-butoxy)-2-oxoethyl)cyclobutanecarboxylate (0.4 g, 1.256 mmol, 15%), respectively.

NMR spectrum of (S)-1-phenylethyl cis-3-(2-(tert-butoxy)-2-oxoethyl)cyclobutanecarboxylate $^1$H NMR (300 MHz, CDCl$_3$): δ1.42 (9H, s), 1.52 (3H, d, J=6.8 Hz), 1.83-2.05 (2H, m), 2.24-2.46 (4H, m), 2.48-2.68 (1H, m), 2.89-3.11 (1H, m), 5.86 (1H, q, J=6.8 Hz), 7.28-7.40 (5H, m).

NMR spectrum of (S)-1-phenylethyl trans-3-(2-(tert-butoxy)-2-oxoethyl)cyclobutanecarboxylate $^1$H NMR (300 MHz, CDCl$_3$): δ1.42 (9H, s), 1.53 (3H, d, J=6.4 Hz), 1.89-2.08 (2H, m), 2.30-2.54 (4H, m), 2.61-2.85 (1H, m), 3.13 (1H, ttd, J=9.4, 5.9, 1.1 Hz), 5.90 (1H, q, J=6.4 Hz), 7.27-7.38 (5H, m).

purification condition by chiral column chromatography
column: CHIRALPAK AD(AF003) 50 mmID×500 mmL
solvent: hexane/EtOH=980/20
flow rate: 80 mL/min
temperature: 30° C.
detection method: UV 220 nm
(Step 3)

A mixture of (S)-1-phenylethyl cis-3-(2-(tert-butoxy)-2-oxoethyl)cyclobutanecarboxylate (1.8 g, 5.65 mmol) and 10% palladium-carbon (0.602 g, 5.65 mmol, 50% wet) in MeOH (20 mL) was stirred at room temperature for 2 hr under hydrogen atmosphere (1 atm). The catalyst was removed by filtration, and the filtrate was concentrated under reduced pressure to give cis-3-(2-(tert-butoxy)-2-oxoethyl)cyclobutanecarboxylic acid (1.200 g, 5.60 mmol, 99%) as a colorless oil.

$^1$H NMR (300 MHz, CDCl$_3$): δ1.43 (9H, s), 1.92-2.10 (2H, m), 2.29-2.48 (4H, m), 2.48-2.78 (1H, m), 2.93-3.16 (1H, m) (The peak derived from COOH was not observed).
(Step 4)

A solution of HATU (125 mg, 0.33 mmol), (R)—N-(7-fluoro-1,1-dimethyl-2,3-dihydro-1H-inden-5-yl)-2-methoxy-5,6,7,8-tetrahydro-1,6-naphthyridine-5-carboxamide (110 mg, 0.30 mmol), cis-3-(2-(tert-butoxy)-2-oxoethyl)cyclobutanecarboxylic acid (70.2 mg, 0.33 mmol) and DIEA (0.059 mL, 0.33 mmol) in DMF (2 mL) was stirred overnight at room temperature. To the reaction mixture was added water, and the mixture was extracted with ethyl acetate. The organic layer was dried over magnesium sulfate, and the solvent was evaporated under reduced pressure. The obtained residue was purified by silica gel column chromatography (solvent gradient; 3-*50% ethyl acetate/hexane) to give tert-butyl 2-(cis-3-((R)-5-((7-fluoro-1,1-dimethyl-2,3-dihydro-1H-inden-5-yl)carbamoyl)-2-methoxy-5,6,7,8-tetrahydro-1,6-naphthyridine-6-carbonyl)cyclobutyl)acetate (150 mg, 0.265 mmol, 89%) as a colorless oil.

MS(API): Calculated 565.7. Found 564.2 (M-H).
(Step 5)

tert-Butyl 2-(cis-3-((R)-5-((7-fluoro-1,1-dimethyl-2,3-dihydro-1H-inden-5-yl)carbamoyl)-2-methoxy-5,6,7,8-tetrahydro-1,6-naphthyridine-6-carbonyl)cyclobutyl)acetate (150 mg, 0.27 mmol) was dissolved in TFA (2 mL), and the solution was stirred at room temperature for 30 min. The reaction mixture was concentrated under reduced pressure, and the obtained residue was purified by silica gel column chromatography (solvent gradient; 30→100% ethyl acetate/hexane) to give the title compound (135 mg, 0.265 mmol, 100%) as a colorless amorphous solid.

$^1$H NMR (300 MHz, DMSO-d$_6$): δ1.29 (6H, s), 1.67-1.97 (4H, m), 2.16-2.41 (5H, m), 2.42-2.58 (1H, m), 2.76-3.06 (4H, m), 3.34-3.47 (1H, m), 3.68-3.87 (3H, m), 3.88-4.10 (1H, m), 5.39-5.77 (1H, m), 6.72 (1H, d, J=8.7 Hz), 7.09-7.34 (2H, m), 7.64-7.89 (1H, m), 10.37-10.68 (1H, m), 11.99 (1H, s). [α]$_D^{25}$+113.5 (c 0.2510, MeOH)

Example 17

(cis-3-(((1R)-1-((3,5-difluoro-4-(1-methoxy-2-methylpropan-2-yl)phenyl)carbamoyl)-6-ethoxy-3,4-dihydroisoquinolin-2(1H)-yl)carbonyl)cyclobutyl) acetic acid (Step 1)

Iodoethane (7.12 mL, 88.37 mmol) was added to a solution of 1-ethyl 2-tert-butyl 6-hydroxy-3,4-dihydroisoquinoline-1,2(1H)-dicarboxylate (14.2 g, 44.19 mmol) and cesium carbonate (18.72 g, 57.44 mmol) in DMF (100 mL), and the mixture was stirred at room temperature for 2.5 hr. To the reaction mixture was added water, and the mixture was extracted with ethyl acetate. The organic layer was washed with brine, and dried over magnesium sulfate, and the solvent was evaporated under reduced pressure to give 1-ethyl 2-tert-butyl 6-ethoxy-3,4-dihydroisoquinoline-1,2 (1H)-dicarboxylate (13.0 g, 37.2 mmol, 84%) as a colorless oil.

(Step 2) 2N Aqueous sodium hydroxide solution (55.8 mL, 111.61 mmol) was added to a solution of 1-ethyl 2-tert-butyl 6-ethoxy-3,4-dihydroisoquinoline-1,2(1H)-dicarboxylate (13.0 g, 37.20 mmol) in a mixed solvent of EtOH (100 mL) and THF (100 mL), and the mixture was stirred overnight at room temperature. To the reaction mixture was added ice water, and the mixture was washed with diethyl ether. The pH of the mixture was adjusted to 4 with 2N hydrochloric acid. Then, the mixture was extracted with ethyl acetate. The organic layer was washed with brine, and dried over magnesium sulfate, and the solvent was evaporated under reduced pressure to give 2-(tert-butoxycarbonyl)-6-ethoxy-1,2,3,4-tetrahydroisoquinoline-1-carboxylic acid (3.56 g, 11.08 mmol, 29.8%) as a colorless oil.
(Step 3)

T3P (9.88 mL, 16.80 mmol) was added to a solution of 2-(tert-butoxycarbonyl)-6-ethoxy-1,2,3,4-tetrahydroisoquinoline-1-carboxylic acid (1.8 g, 5.60 mmol), 3,5-difluoro-4-(1-methoxy-2-methylpropan-2-yl)aniline (1.206 g, 5.60 mmol), DIEA (4.89 mL, 28.01 mmol) and DMAP (0.684 g, 5.60 mmol) in ethyl acetate (5 mL), and the mixture was stirred overnight at 60° C. To the reaction mixture was added water, and the mixture was extracted with ethyl acetate. The organic layer was washed with 10% aqueous citric acid solution, aqueous sodium hydrogencarbonate solution and brine, and dried over magnesium sulfate, and the solvent was evaporated under reduced pressure. The obtained residue was purified by silica gel column chromatography (solvent gradient; 3→50% ethyl acetate/hexane) to give tert-butyl 1-((3,5-difluoro-4-(1-methoxy-2-methylpropan-2-yl)phenyl)carbamoyl)-6-ethoxy-3,4-dihydroisoquinoline-2(1H)-carboxylate (2.380 g, 4.59 mmol, 82%) as a white solid.

$^1$H NMR (300 MHz, CDCl$_3$): δ1.38-1.44 (9H, m), 1.51 (9H, s), 2.71-2.99 (2H, m), 3.30 (3H, s), 3.51 (2H, s), 3.54-3.76 (2H, m), 4.03 (2H, q, J=6.8 Hz), 5.55 (1H, brs), 6.72 (1H, s), 6.80 (1H, dd, J=8.5, 2.5 Hz), 7.03 (2H, d, J=12.5 Hz), 7.14 (1H, brs), 8.89 (1H, s).
(Step 4)

tert-Butyl 1-((3,5-difluoro-4-(1-methoxy-2-methylpropan-2-yl)phenyl)carbamoyl)-6-ethoxy-3,4-dihydroisoquinoline-2(1H)-carboxylate (2.20 g) was subjected to optical resolution by chiral column chromatography. The fraction having a shorter retention time was concentrated to give tert-butyl (R)-1-((3,5-difluoro-4-(1-methoxy-2-methylpropan-2-yl)phenyl)carbamoyl)-6-ethoxy-3,4-dihydroisoquinoline-2(1H)-carboxylate (1.02 g, >99% ee), and the fraction having a longer retention time was concentrated to give tert-butyl (S)-1-((3,5-difluoro-4-(1-methoxy-2-methylpropan-2-yl)phenyl)carbamoyl)-6-ethoxy-3,4-dihydroisoquinoline-2(1H)-carboxylate (1.03 g, 98.7% ee), as a white solid, respectively.
purification condition by chiral column chromatography
   column: CHIRALCEL OD(NL001) 50 mmID×500 mmL
   solvent: hexane/EtOH=900/100
   flow rate: 80 mL/min
   temperature: 30° C.
   detection method: UV 220 nm
(Step 5)

4N Hydrogen chloride/ethyl acetate (5 mL) was added to a solution of tert-butyl (R)-1-((3,5-difluoro-4-(1-methoxy-2-methylpropan-2-yl)phenyl)carbamoyl)-6-ethoxy-3,4-dihydroisoquinoline-2(1H)-carboxylate (1.02 g, 1.97 mmol) in ethyl acetate (2 mL), and the mixture was stirred overnight at room temperature. The reaction mixture was concentrated under reduced pressure, and the precipitate was collected by filtration with hexane to give (R)—N-(3,5-difluoro-4-(1-methoxy-2-methylpropan-2-yl)phenyl)-6-ethoxy-1,2,3,4-tetrahydroisoquinoline-1-carboxamide hydrochloride (0.917 g, 2.016 mmol, 102%) as a white solid.

MS(API): Calculated 454.9. Found 419.4 (M-HCl+H).
(Step 6)

HATU (113 mg, 0.30 mmol) was added to a solution of (R)—N-(3,5-difluoro-4-(1-methoxy-2-methylpropan-2-yl) phenyl)-6-ethoxy-1,2,3,4-tetrahydroisoquinoline-1-carboxamide hydrochloride (123 mg, 0.27 mmol), cis-3-(2-(tert-butoxy)-2-oxoethyl)cyclobutanecarboxylic acid (63.7 mg, 0.30 mmol) and DIEA (0.107 mL, 0.59 mmol) in DMF (2 mL) at room temperature, and the mixture was stirred overnight at room temperature. To the reaction mixture was added water, and the mixture was extracted with ethyl acetate. The organic layer was dried over magnesium sulfate, and the solvent was evaporated under reduced pressure. The obtained residue was purified by silica gel column chromatography (solvent gradient; 3→50% ethyl acetate/hexane) to give tert-butyl (cis-3-(((1R)-1-((3,5-difluoro-4-(1-methoxy-2-methylpropan-2-yl)phenyl)carbamoyl)-6-ethoxy-3,4-dihydroisoquinolin-2(1H)-yl)carbonyl)cyclobutyl)acetate (166 mg, 0.270 mmol, 100%).

MS(API): Calculated 614.7. Found 613.2 (M-H).
(Step 7)

Cooled TFA (2 mL) was added to tert-butyl (cis-3-(((1R)-1-((3,5-difluoro-4-(1-methoxy-2-methylpropan-2-yl)phenyl)carbamoyl)-6-ethoxy-3,4-dihydroisoquinolin-2(1H)-yl)carbonyl)cyclobutyl)acetate (166 mg, 0.27 mmol) at 0° C., and the mixture was stirred at 0° C. for 30 min. The reaction mixture was concentrated under reduced pressure, and the obtained residue was purified by silica gel column chromatography (solvent gradient; 50→100% ethyl acetate/hexane) to give the title compound (134 mg, 0.240 mmol, 89%) as a white solid.

$^1$H NMR (300 MHz, DMSO-d$_6$): δ1.29 (3H, t, J=7.0 Hz), 1.36 (6H, s), 1.73-1.93 (2H, m), 2.20-2.40 (5H, m), 2.67-2.84 (1H, m), 2.96-3.12 (1H, m), 3.19 (3H, s), 3.27-3.39 (1H, m), 3.40-3.53 (3H, m), 3.86-4.03 (3H, m), 5.30-5.62 (1H, m), 6.67-6.88 (2H, m), 7.06-7.28 (2H, m), 7.35-7.53 (1H, m), 10.48-10.77 (1H, m), 11.98 (1H, brs).

Example 18

(cis-3-(((1R)-6-ethoxy-1-((4-(1-ethoxy-2-methylpropan-2-yl)-3,5-difluorophenyl)carbamoyl)-3,4-dihydroisoquinolin-2(1H)-yl)carbonyl)cyclobutyl)acetic acid (Step 1)

Sodium hydride (60%, oil, 1.726 g, 43.15 mmol) was added to a solution of 2-(4-(bis(4-methoxybenzyl)amino)-2,6-difluorophenyl)-2-methylpropan-1-ol (7.62 g, 17.26 mmol) and iodoethane (3.49 mL, 43.15 mmol) in DMF (30 mL) at 5° C., and the mixture was stirred at room temperature for 14 hr. To the reaction mixture was added aqueous ammonium chloride solution, and the mixture was extracted with ethyl acetate (×2). The organic layer was washed with brine, and dried over magnesium sulfate, and the solvent was evaporated under reduced pressure. The obtained residue was purified by silica gel column chromatography (Diol, solvent gradient; 5→20% ethyl acetate/hexane) to give 4-(1-ethoxy-2-methylpropan-2-yl)-3,5-difluoro-N,N-bis(4-methoxybenzyl)aniline (8.51 g, 18.12 mmol, 105%) as a colorless oil.

$^1$H NMR (300 MHz, CDCl$_3$): δ1.14 (3H, t, J=7.0 Hz), 1.39 (6H, t, J=2.1 Hz), 3.47 (2H, d, J=7.2 Hz), 3.53 (2H, s), 3.79 (6H, s), 4.46 (4H, s), 6.17 (2H, d, J=14.4 Hz), 6.79-6.91 (4H, m), 7.11 (4H, d, J=8.7 Hz).
(Step 2)

A mixture of 4-(1-ethoxy-2-methylpropan-2-yl)-3,5-difluoro-N,N-bis(4-methoxybenzyl)aniline (8.51 g, 18.12 mmol), 1N hydrochloric acid (36.2 mL) and 10% palladium-carbon (1.929 g, 0.91 mmol, 50%, wet) in MeOH (164 mL) under hydrogen atmosphere (4 atm), and the mixture was stirred at room temperature for 1.5 hr. The catalyst was removed by filtration, and the filtrate was concentrated under reduced pressure. The obtained residue was dissolved in ethyl acetate, and the solution was washed with 1N aqueous sodium hydroxide solution and brine, and dried over magnesium sulfate, and the solvent was evaporated under reduced pressure. The obtained residue was purified by silica gel column chromatography (solvent gradient; 5→20% ethyl acetate/hexane) to give 4-(1-ethoxy-2-methylpropan-2-yl)-3,5-difluoroaniline (3.87 g, 16.88 mmol, 93%) as a white solid.

$^1$H NMR (300 MHz, CDCl$_3$): δ1.13 (3H, t, J=7.0 Hz), 1.40 (6H, t, J=2.5 Hz), 3.40-3.50 (2H, m, J=7.2, 7.2, 7.2 Hz), 3.53 (2H, s), 3.57-3.87 (2H, m), 6.09 (1H, s), 6.13 (1H, s).

(Step 3)

T3P (4.62 mL, 7.85 mmol) was added to a solution of 2-(tert-butoxycarbonyl)-6-ethoxy-1,2,3,4-tetrahydroisoquinoline-1-carboxylic acid (841 mg, 2.62 mmol), 4-(1-ethoxy-2-methylpropan-2-yl)-3,5-difluoroaniline (600 mg, 2.62 mmol), DIEA (2.285 mL, 13.09 mmol) and DMAP (320 mg, 2.62 mmol) in ethyl acetate (5 mL), and the mixture was stirred at 60° C. overnight. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 3→50% ethyl acetate/hexane), and crystallized from ethyl acetate/hexane to give tert-butyl 6-ethoxy-1-((4-(1-ethoxy-2-methylpropan-2-yl)-3,5-difluorophenyl)carbamoyl)-3,4-dihydroisoquinoline-2(1H)-carboxylate (700 mg, 1.314 mmol, 50.2%) as white crystals.

$^1$H NMR (300 MHz, CDCl$_3$): δ1.10 (3H, t, J=7.0 Hz), 1.36-1.45 (9H, m), 1.51 (9H, s), 2.76-2.98 (2H, m), 3.44 (2H, q, J=6.8 Hz), 3.54 (3H, s), 3.62-3.78 (1H, m), 4.03 (2H, q, J=6.8 Hz), 5.55 (1H, brs), 6.71 (1H, d, J=2.3 Hz), 6.80 (1H, dd, J=8.3, 2.6 Hz), 6.95-7.08 (2H, m, J=12.5 Hz), 7.10-7.22 (1H, m), 8.92 (1H, s).

(Step 4)

tert-Butyl 6-ethoxy-1-((4-(1-ethoxy-2-methylpropan-2-yl)-3,5-difluorophenyl)carbamoyl)-3,4-dihydroisoquinoline-2(1H)-carboxylate (0.70 g) was subjected to optical resolution by chiral column chromatography. The fraction having a shorter retention time was concentrated to give tert-butyl (R)-6-ethoxy-1-((4-(1-ethoxy-2-methylpropan-2-yl)-3,5-difluorophenyl)carbamoyl)-3,4-dihydroisoquinoline-2(1H)-carboxylate (0.32 g, >99% ee), and the fraction having a longer retention time was concentrated to give tert-butyl (S)-6-ethoxy-1-((4-(1-ethoxy-2-methylpropan-2-yl)-3,5-difluorophenyl)carbamoyl)-3,4-dihydroisoquinoline-2(1H)-carboxylate (0.32 g, 92.2% ee), as a white solid, respectively.

purification condition by chiral column chromatography
 column: CHIRALPAK IA(QK001) 50 mmID×500 mmL
 solvent: hexane/EtOH=850/150
 flow rate: 80 mL/min
 temperature: 30° C.
 detection method: UV 220 nm (Step 5)

4N Hydrogen chloride/ethyl acetate (4 mL) was added to a solution of tert-butyl (R)-6-ethoxy-1-((4-(1-ethoxy-2-methylpropan-2-yl)-3,5-difluorophenyl)carbamoyl)-3,4-dihydroisoquinoline-2(1H)-carboxylate (320 mg, 0.60 mmol) in ethyl acetate (2 mL), and the mixture was stirred overnight at room temperature. The reaction mixture was concentrated under reduced pressure, and the precipitate was collected by filtration with hexane to give (R)-6-ethoxy-N-(4-(1-ethoxy-2-methylpropan-2-yl)-3,5-difluorophenyl)-1,2,3,4-tetrahydroisoquinoline-1-carboxamide hydrochloride (273 mg, 0.582 mmol, 97%) as a white solid.

MS(API): Calculated 468.96. Found 433.4 (M-HCl+H).

(Step 6)

HATU (90 mg, 0.24 mmol) was added to a solution of (R)-6-ethoxy-N-(4-(1-ethoxy-2-methylpropan-2-yl)-3,5-difluorophenyl)-1,2,3,4-tetrahydroisoquinoline-1-carboxamide hydrochloride (101 mg, 0.22 mmol), cis-3-(2-(tert-butoxy)-2-oxoethyl)cyclobutanecarboxylic acid (50.8 mg, 0.24 mmol) and DIEA (0.085 mL, 0.47 mmol) in DMF (2 mL) at room temperature, and the mixture was stirred overnight at room temperature. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 3→50% ethyl acetate/hexane) to give tert-butyl 2-(cis-3-((R)-6-ethoxy-1-((4-(1-ethoxy-2-methylpropan-2-yl)-3,5-difluorophenyl)carbamoyl)-1,2,3,4-tetrahydroisoquinoline-2-carbonyl)cyclobutyl)acetate (135 mg, 0.215 mmol, quant.).

MS(API): Calculated 628.8. Found 627.2 (M-H).

(Step 7)

Cooled TFA (2 mL) was added to tert-butyl 2-(cis-3-((R)-6-ethoxy-1-((4-(1-ethoxy-2-methylpropan-2-yl)-3,5-difluorophenyl)carbamoyl)-1,2,3,4-tetrahydroisoquinoline-2-carbonyl)cyclobutyl)acetate (179 mg, 0.28 mmol) at 0° C., and the mixture was stirred at 0° C. for 30 min. The reaction mixture was concentrated under reduced pressure, and the obtained residue was purified by silica gel column chromatography (solvent gradient; 50→100% ethyl acetate/hexane) to give the title compound (108 mg, 0.189 mmol, 66.2%) as a white solid.

$^1$H NMR (300 MHz, DMSO-d$_6$): δ1.02 (3H, t, J=7.0 Hz), 1.29 (3H, t, J=7.0 Hz), 1.36 (6H, s), 1.71-1.92 (2H, m), 2.16-2.38 (5H, m), 2.50 (1H, dt, J=3.5, 1.8 Hz), 2.71-2.81 (1H, m), 2.95-3.13 (1H, m), 3.29-3.54 (5H, m), 3.82-4.10 (3H, m), 5.35-5.64 (1H, m), 6.70-6.88 (2H, m), 7.18 (2H, d, J=13.6 Hz), 7.35-7.50 (1H, m), 10.45-10.79 (1H, m), 12.00 (1H, brs).

$[α]_D^{25}$+11.0 (c 0.2520, MeOH)

Example 19

(cis-3-(((1R)-1-((7-fluoro-1,1-dimethyl-2,3-dihydro-1H-inden-5-yl)carbamoyl)-6-(methoxymethyl)-3,4-dihydroisoquinolin-2(1H)-yl)carbonyl)cyclobutyl) acetic acid (Step 1)

To a mixture of 1-ethyl 2-tert-butyl 6-hydroxy-3,4-dihydroisoquinoline-1,2(1H)-dicarboxylate (5 g, 15.56 mmol), DIEA (5.43 mL, 31.12 mmol), DMAP (0.190 g, 1.56 mmol) and THF (30 mL) was added 1,1,1-trifluoro-N-phenyl-N-((trifluoromethyl) sulfonyl)methanesulfonamide (8.34 g, 23.34 mmol) at room temperature, and the mixture was stirred at room temperature for 3 hr. To the reaction mixture was added ethyl acetate, the mixture was washed with water and brine, and dried over magnesium sulfate, and the solvent was evaporated under reduced pressure. The obtained residue was purified by silica gel column chromatography (solvent gradient; 3→50% ethyl acetate/hexane), and then silica gel column chromatography (NH, solvent gradient; 3→50% ethyl acetate/hexane) to give 1-ethyl 2-tert-butyl 6-(((trifluoromethyl)sulfonyl)oxy)-3,4-dihydroisoquinoline-1,2(1H)-dicarboxylate (7.44 g, 16.41 mmol, 105%) as a colorless oil.

$^1$H NMR (300 MHz, CDCl$_3$): δ1.21-1.31 (3H, m), 1.45-1.53 (9H, m), 2.82-2.99 (2H, m), 3.60-3.77 (1H, m), 3.80-3.99 (1H, m), 4.18 (2H, q, J=7.2 Hz), 5.28-5.69 (1H, m), 7.01-7.19 (2H, m), 7.60 (1H, dd, J=8.7, 3.8 Hz).

(Step 2)

A mixture of 1-ethyl 2-tert-butyl 6-(((trifluoromethyl)sulfonyl)oxy)-3,4-dihydroisoquinoline-1,2(1H)-dicarboxylate (7.44 g, 16.41 mmol), Pd(PPh$_3$)$_4$ (0.948 g, 0.82 mmol), zinc cyanide (2.119 g, 18.05 mmol) and DMF (100 mL) was stirred overnight at 100° C. The reaction mixture was diluted with ethyl acetate, and filtered. The filtrate was washed with water and brine, and dried over magnesium sulfate, and the solvent was evaporated under reduced pressure. The obtained residue was purified by silica gel column chromatography (solvent gradient; 3→60% ethyl acetate/hexane) to give 1-ethyl 2-tert-butyl 6-cyano-3,4-dihydroisoquinoline-1,2(1H)-dicarboxylate (4.92 g, 14.89 mmol, 91%) as a colorless oil.

$^1$H NMR (300 MHz, CDCl$_3$): δ1.18-1.33 (3H, m), 1.42-1.53 (9H, m), 2.78-3.03 (2H, m), 3.62-3.78 (1H, m), 3.80-3.99 (1H, m), 4.18 (2H, q, J=7.1 Hz), 5.38-5.71 (1H, m), 7.40-7.55 (2H, m), 7.58-7.69 (H, m).

(Step 3)

To a solution of 1-ethyl 2-tert-butyl 6-cyano-3,4-dihydroisoquinoline-1,2(1H)-dicarboxylate (0.5 g, 1.51 mmol) in acetic acid (5.00 mL) and pyridine (10 mL) was added a mixture of Raney-nickel (0.5 g, 1.51 mmol) and water (5 mL), and then sodium hypophosphite monohydrate (2.5 g, 23.59 mmol) was added thereto under argon atmosphere. The mixture was stirred at 60° C. for 3 hr, and then overnight at 100° C. The reaction mixture was filtered through Celite, and the filtrate was diluted with ethyl acetate. The mixture was washed with aqueous ammonium chloride solution, aqueous sodium hydrogencarbonate solution and brine, and dried over magnesium sulfate, and the solvent was evaporated under reduced pressure. The obtained residue was purified by silica gel column chromatography (solvent gradient; 5→70% ethyl acetate/hexane) to give 1-ethyl 2-tert-butyl 6-formyl-3,4-dihydroisoquinoline-1,2(1H)-dicarboxylate (0.430 g, 1.290 mmol, 85%) as a colorless oil.

$^1$H NMR (300 MHz, CDCl$_3$): δ1.26 (3H, t, J=7.2 Hz), 1.45-1.53 (9H, m), 2.80-3.13 (2H, m), 3.63-3.97 (2H, m), 4.18 (2H, q, J=7.2 Hz), 5.44-5.72 (1H, m), 7.61-7.80 (3H, m), 9.99 (1H, s).

(Step 4)

To a solution of 1-ethyl 2-tert-butyl 6-formyl-3,4-dihydroisoquinoline-1,2(1H)-dicarboxylate (430 mg, 1.29 mmol) in MeOH (10 mL) was added sodium borohydride (24.40 mg, 0.64 mmol) at 0° C., and the mixture was stirred for 20 min. To the reaction mixture was added aqueous ammonium chloride solution, and the mixture was extracted with ethyl acetate. The organic layer was washed with brine, and dried over magnesium sulfate, and the solvent was evaporated under reduced pressure to give 1-ethyl 2-tert-butyl 6-(hydroxymethyl)-3,4-dihydroisoquinoline-1,2(1H)-dicarboxylate (390 mg, 1.163 mmol, 90%) as a colorless oil.

$^1$H NMR (300 MHz, CDCl$_3$): δ1.23-1.30 (3H, m), 1.37-1.51 (9H, m), 1.67 (1H, brs), 2.70-3.05 (2H, m), 3.66-3.84 (2H, m), 4.11-4.21 (2H, m), 4.67 (2H, s), 5.28-5.64 (H, m), 7.13-7.25 (2H, m), 7.44-7.54 (1H, m).

(Step 5)

To a mixture of 1-ethyl 2-tert-butyl 6-(hydroxymethyl)-3,4-dihydroisoquinoline-1,2(1H)-dicarboxylate (390 mg, 1.16 mmol), methanesulfonyl chloride (0.135 mL, 1.74 mmol) and THF (10 mL) was added TEA (0.243 mL, 1.74 mmol) at 0° C., and the mixture was stirred for 1 hr. To the reaction mixture was added water, and the mixture was extracted with ethyl acetate. The organic layer was washed with brine, and dried over magnesium sulfate, and the solvent was evaporated under reduced pressure to give 1-ethyl 2-tert-butyl 6-(((methylsulfonyl)oxy)methyl)-3,4-dihydroisoquinoline-1,2(1H)-dicarboxylate (500 mg, 1.209 mmol, 104%) as a colorless oil.

$^1$H NMR (300 MHz, CDCl$_3$): δ1.20-1.30 (3H, m), 1.44-1.51 (9H, m), 2.78-3.05 (5H, m), 3.70-3.92 (2H, m), 4.16 (2H, q, J=7.2 Hz), 5.20 (2H, s), 5.37-5.65 (1H, m), 7.20-7.30 (2H, m), 7.49-7.59 (1H, m).

(Step 6)

To a solution of 1-ethyl 2-tert-butyl 6-(((methylsulfonyl)oxy)methyl)-3,4-dihydroisoquinoline-1,2(1H)-dicarboxylate (500 mg, 1.21 mmol) in MeOH (5 mL) was added TEA (0.337 mL, 2.42 mmol), and the mixture was stirred at 70° C. for 2 hr. The reaction mixture was concentrated under reduced pressure, and the obtained residue was purified by silica gel column chromatography (solvent gradient; 3→60% ethyl acetate/hexane) to give 1-ethyl 2-tert-butyl 6-(methoxymethyl)-3,4-dihydroisoquinoline-1,2(1H)-dicarboxylate (169 mg, 0.484 mmol, 40.0%) as a colorless oil.

$^1$H NMR (300 MHz, CDCl$_3$): δ1.20-1.30 (3H, m), 1.43-1.53 (9H, m), 2.73-3.06 (2H, m), 3.40 (3H, s), 3.67-3.84 (2H, m), 4.14 (2H, q, J=7.2 Hz), 4.42 (2H, s), 5.22-5.64 (1H, m), 7.05-7.22 (2H, m), 7.42-7.56 (1H, m).

(Step 7)

To a solution of 1-ethyl 2-tert-butyl 6-(methoxymethyl)-3,4-dihydroisoquinoline-1,2(1H)-dicarboxylate (160 mg, 0.0.46 mmol) in a mixture of MeOH (5 mL), THF (5.00 mL) and water (5.00 mL) was added lithium hydroxide (65.8 mg, 2.75 mmol), and the mixture was stirred at 60° C. for 1 hr. The reaction mixture was concentrated under reduced pressure. The obtained residue was dissolved in water, and the solution was washed with ethyl acetate. The pH of the aqueous layer was adjusted to 3 with 1M hydrochloric acid, and the mixture was extracted with ethyl acetate (×3). The organic layer was washed with brine, and dried over magnesium sulfate, and the solvent was evaporated under reduced pressure to give 2-(tert-butoxycarbonyl)-6-(methoxymethyl)-1,2,3,4-tetrahydroisoquinoline-1-carboxylic acid (148 mg, 0.461 mmol, 101%) as a colorless amorphous solid.

$^1$H NMR (300 MHz, CDCl$_3$): δ1.35-1.57 (9H, m), 2.77-3.02 (2H, m), 3.39 (3H, s), 3.60-3.90 (2H, m), 4.42 (2H, s), 5.23-5.66 (1H, m), 7.07-7.22 (2H, m), 7.45 (1H, d, J=7.6 Hz) (The exchangeable 1H was not observed).

(Step 8)

T3P (8.24 mL, 14.00 mmol) was added to a mixture of 2-(tert-butoxycarbonyl)-6-(methoxymethyl)-1,2,3,4-tetrahydroisoquinoline-1-carboxylic acid (1.5 g, 4.67 mmol), 7-fluoro-1,1-dimethyl-2,3-dihydro-1H-inden-5-amine (0.837 g, 4.67 mmol), DIEA (4.08 mL, 23.34 mmol), DMAP (0.570 g, 4.67 mmol) and ethyl acetate (5 mL) at 60° C., and the mixture was stirred at 60° C. for 2 days. To the reaction mixture was added ethyl acetate, and the mixture was washed with water and brine, and dried over magnesium sulfate, and the solvent was evaporated under reduced pressure. The obtained residue was purified by silica gel column chromatography (solvent gradient; 32→40% ethyl acetate/hexane) to give tert-butyl 1-((7-fluoro-1,1-dimethyl-2,3-dihydro-1H-inden-5-yl)carbamoyl)-6-(methoxymethyl)-3,4-dihydroisoquinoline-2 (1H)-carboxylate (1.600 g, 3.32 mmol, 71.0%) as a white solid.

MS(API): Calculated 482.6. Found 481.3 (M-H).

(Step 9)

tert-Butyl 1-((7-fluoro-1,1-dimethyl-2,3-dihydro-1H-inden-5-yl)carbamoyl)-6-(methoxymethyl)-3,4-dihydroisoquinoline-2(1H)-carboxylate (1.60 g) was subjected to optical resolution by chiral column chromatography. The fraction having a shorter retention time was concentrated to give tert-butyl (R)-1-((7-fluoro-1,1-dimethyl-2,3-dihydro-1H-inden-5-yl)carbamoyl)-6-(methoxymethyl)-3,4-dihydroisoquinoline-2(1H)-carboxylate (0.77 g, >99% ee), and the fraction having a longer retention time was concentrated to give tert-butyl (S)-1-((7-fluoro-1,1-dimethyl-2,3-dihydro-1H-inden-5-yl)carbamoyl)-6-(methoxymethyl)-3,4-dihydroisoquinoline-2(1H)-carboxylate (0.73 g, >99% ee), respectively.

purification condition by chiral column chromatography
- column: CHIRALCEL OD(NL001) 50 mmID×500 mmL
- solvent: hexane/EtOH-900/100
- flow rate: 80 mL/min
- temperature: 30° C.
- detection method: UV 220 nm (Step 10)

4N Hydrogen chloride/ethyl acetate (4 mL) was added to a solution of tert-butyl (R)-1-((7-fluoro-1,1-dimethyl-2,3-dihydro-1H-inden-5-yl)carbamoyl)-6-(methoxymethyl)-3,4-dihydroisoquinoline-2(1H)-carboxylate (0.77 g, 1.60 mmol) in ethyl acetate (2 mL), and the mixture was stirred overnight at room temperature. The reaction mixture was concentrated, and the obtained precipitate was washed with ethyl acetate/hexane to give (R)—N-(7-fluoro-1,1-dimethyl-2,3-dihydro-1H-inden-5-yl)-6-(methoxymethyl)-1,2,3,4-tetrahydroisoquinoline-1-carboxamide hydrochloride (0.730 g, 1.743 mmol, 109%) as a white solid.

MS(API): Calculated 418.9. Found 381.2 (M-HCl-H).

(Step 11)

A mixture of HATU (100 mg, 0.26 mmol), (R)—N-(7-fluoro-1,1-dimethyl-2,3-dihydro-1H-inden-5-yl)-6-(methoxymethyl)-1,2,3,4-tetrahydroisoquinoline-1-carboxamide hydrochloride (100 mg, 0.24 mmol), cis-3-(2-(tert-butoxy)-2-oxoethyl)cyclobutanecarboxylic acid (56.3 mg, 0.26 mmol), DIEA (0.094 mL, 0.53 mmol) and DMF (2 mL) was stirred overnight at room temperature. To the reaction mixture was added water, and the mixture was extracted with ethyl acetate. The organic layer was dried over magnesium sulfate, and the solvent was evaporated under reduced pressure. The obtained residue was purified by silica gel column chromatography (solvent gradient; 3→50% ethyl acetate/hexane) to give tert-butyl 2-(cis-3-((R)-1-((7-fluoro-1,1-dimethyl-2,3-dihydro-1H-inden-5-yl)carbamoyl)-6-(methoxymethyl)-1,2,3,4-tetrahydroisoquinoline-2-carbonyl)cyclobutyl)acetate (130 mg, 0.225 mmol, 94%) as a colorless oil.

MS(API): Calculated 578.7. Found 577.2 (M-H).

(Step 12)

tert-Butyl 2-(cis-3-((R)-1-((7-fluoro-1,1-dimethyl-2,3-dihydro-1H-inden-5-yl)carbamoyl)-6-(methoxymethyl)-1,2,3,4-tetrahydroisoquinoline-2-carbonyl)cyclobutyl)acetate (130 mg, 0.22 mmol) was dissolved in TFA (2 mL) at 0° C., and the solution was stirred for 30 min. The reaction mixture was concentrated under reduced pressure, and the obtained residue was purified by silica gel column chromatography (solvent gradient; 50→400% ethyl acetate/hexane) to give the title compound (106 mg, 0.203 mmol, 90%) as a colorless amorphous solid.

$^1$H NMR (300 MHz, DMSO-$d_6$): δ1.28 (3H, s), 1.28 (3H, s), 1.70-1.94 (4H, m), 2.12-2.40 (4H, m), 2.76-2.91 (3H, m), 2.96-3.14 (1H, m), 3.22-3.28 (3H, m), 3.29-3.41 (1H, m), 3.49-3.53 (1H, m), 3.85-4.01 (1H, m), 4.35 (2H, s), 5.44-5.84 (1H, m), 7.01-7.31 (4H, m), 7.51 (1H, d, J=8.7 Hz), 10.21-10.61 (1H, m), 11.98 (1H, s).

$[α]_D^{25}$+31.5 (c 0.2530, MeOH)

Example 20

(trans-3-(((5R)-5-((7-fluoro-1,1-dimethyl-2,3-dihydro-1H-inden-5-yl)carbamoyl)-2-methoxy-7,8-dihydro-1,6-naphthyridin-6(5H)-yl)carbonyl)cyclobutyl)acetic acid (Step 1)

A mixture of (S)-1-phenylethyl trans-3-(2-(tert-butoxy)-2-oxoethyl)cyclobutanecarboxylate (0.4 g, 1.26 mmol) and 10% palladium-carbon (0.134 g, 1.26 mmol, 50%, wet) in MeOH (20 mL) was stirred at room temperature for 1.5 hr under hydrogen atmosphere (1 atm). The catalyst was removed by filtration, and the filtrate was concentrated under reduced pressure to give trans-3-(2-(tert-butoxy)-2-oxoethyl)cyclobutanecarboxylic acid (0.261 g, 1.218 mmol, 97%) as a colorless oil.

$^1$H NMR (300 MHz, CDCl$_3$): δ1.36-1.47 (9H, m), 1.96-2.11 (2H, m), 2.39 (2H, d, J=7.6 Hz), 2.43-2.57 (2H, m), 2.69-2.88 (1H, m), 3.03-3.26 (1H, m) (The peak derived from COOH was not observed).

(Step 2)

HATU (113 mg, 0.30 mmol) was added to a solution of (R)—N-(7-fluoro-1,1-dimethyl-2,3-dihydro-1H-inden-5-yl)-2-methoxy-5,6,7,8-tetrahydro-1,6-naphthyridine-5-carboxamide (100 mg, 0.27 mmol), trans-3-(2-(tert-butoxy)-2-oxoethyl)cyclobutanecarboxylic acid (63.8 mg, 0.30 mmol) and DIEA (0.053 mL, 0.30 mmol) in DMF (2 mL) at room temperature, and the mixture was stirred overnight at room temperature. To the reaction mixture was added water, and the mixture was extracted with ethyl acetate. The organic layer was dried over magnesium sulfate, and the solvent was evaporated under reduced pressure. The obtained residue was purified by silica gel column chromatography (solvent gradient; 3→50% ethyl acetate/hexane) to give tert-butyl 2-(trans-3-((R)-5-((7-fluoro-1,1-dimethyl-2,3-dihydro-1H-inden-5-yl)carbamoyl)-2-methoxy-5,6,7,8-tetrahydro-1,6-naphthyridine-6-carbonyl)cyclobutyl)acetate (150 mg, 0.27 mmol, 98%) as a colorless oil.

MS(API): Calculated 565.7. Found 564.2 (M-H).

(Step 3)

Cooled TFA (2 mL) was added to tert-butyl 2-(trans-3-((R)-5-((7-fluoro-1,1-dimethyl-2,3-dihydro-1H-inden-5-yl)carbamoyl)-2-methoxy-5,6,7,8-tetrahydro-1,6-naphthyridine-6-carbonyl)cyclobutyl)acetate (150 mg, 0.27 mmol) at 0° C., and the mixture was stirred at 0° C. for 30 min. The reaction mixture was concentrated under reduced pressure, and the obtained residue was purified by silica gel column chromatography (solvent gradient; 50→100% ethyl acetate/hexane) to give the title compound (113 mg, 0.222 mmol, 84%) as a white solid.

$^1$H NMR (300 MHz, DMSO-$d_6$): δ1.11-1.38 (7H, m), 1.74-2.07 (4H, m), 2.22-2.47 (4H, m), 2.68-3.06 (4H, m), 3.55 (1H, d, J=8.7 Hz), 3.62-3.75 (1H, m), 3.83 (3H, d, J=1.9 Hz), 3.85-4.11 (1H, m), 5.36-5.82 (1H, m), 6.72 (1H, d, J=8.7 Hz), 7.10-7.32 (2H, m), 7.78 (1H, d, J=8.3 Hz), 10.36-10.65 (1H, m), 12.03 (1H, brs).

$[α]_D^{25}$+109.0 (c 0.2515, MeOH)

Example 23

(cis-3-(((5R)-5-((3,5-difluoro-4-(trimethylsilyl)phenyl)carbamoyl)-2-methoxy-7,8-dihydro-1,6-naphthyridin-6(5H)-yl) carbonyl)cyclobutyl)acetic acid (Step 1)

HATU (107 mg, 0.28 mmol) was added to a solution of (R)—N-(3,5-difluoro-4-(trimethylsilyl)phenyl)-2-methoxy- 5,6,7,8-tetrahydro-1,6-naphthyridine-5-carboxamide (100 mg, 0.26 mmol), cis-3-(2-(tert-butoxy)-2-oxoethyl)cyclobutanecarboxylic acid (60.2 mg, 0.28 mmol) and DIEA (0.050 mL, 0.28 mmol) in DMF (2 mL) at room temperature, and the mixture was stirred overnight at room temperature. To the reaction mixture was added water, and the mixture was extracted with ethyl acetate. The organic layer was dried over magnesium sulfate, and the solvent was evaporated under reduced pressure. The obtained residue was purified by silica gel column chromatography (solvent gradient; 3→50% ethyl acetate/hexane) to give tert-butyl 2-(cis-3-((R)-5-((3,5-difluoro-4-(trimethylsilyl)phenyl)carbamoyl)-2-methoxy-5,6,7,8-tetrahydro-1,6-naphthyridine-6-carbonyl)cyclobutyl)acetate (100 mg, 0.170 mmol, 66.6%) as a colorless oil.

MS(API): Calculated 587.7. Found 586.1 (M-H).

(Step 2)

Cooled TFA (2 mL) was added to tert-butyl 2-(cis-3-((R)-5-((3,5-difluoro-4-(trimethylsilyl)phenyl)carbamoyl)-2-methoxy-5,6,7,8-tetrahydro-1,6-naphthyridine-6-carbonyl)cyclobutyl)acetate (100 mg, 0.17 mmol) at 0° C., and the mixture was stirred at 0° C. for 30 min. The pH of the reaction mixture was adjusted to 6 with cooled aqueous sodium hydrogencarbonate solution, and the mixture was extracted with ethyl acetate. The organic layer was dried over magnesium sulfate, and the solvent was evaporated under reduced pressure. The obtained residue was purified by silica gel column chromatography (solvent gradient; 50→100% ethyl acetate/hexane) to give the title compound (67.0 mg, 0.126 mmol, 74.1%) as a white solid.

$^1$H NMR (300 MHz, DMSO-$d_6$): δ0.30 (9H, s), 1.74-1.97 (2H, m), 2.21-2.38 (5H, m), 2.75-2.90 (1H, m), 2.91-3.05 (1H, m), 3.36-3.47 (1H, m), 3.64-3.79 (1H, m), 3.82 (3H, s), 3.86-4.08 (1H, m), 5.48-5.76 (1H, m), 6.73 (1H, d, J=8.3 Hz), 7.14-7.37 (2H, m), 7.63-7.85 (1H, m), 10.61-10.97 (1H, m), 11.97 (1H, brs).

$[\alpha]_D^{25}$+108.8 (c 0.2515, MeOH)

Example 24

(trans-3-(((1R)-1-((7-fluoro-1,1-dimethyl-2,3-dihydro-1H-inden-5-yl)carbamoyl)-6-(methoxymethyl)-3,4-dihydroisoquinolin-2(1H)-yl)carbonyl)cyclobutyl)acetic acid (Step 1)

HATU (49.9 mg, 0.13 mmol) was added to a solution of (R)—N-(7-fluoro-1,1-dimethyl-2,3-dihydro-1H-inden-5-yl)-6-(methoxymethyl)-1,2,3,4-tetrahydroisoquinoline-1-carboxamide hydrochloride (50 mg, 0.12 mmol), trans-3-(2-(tert-butoxy)-2-oxoethyl)cyclobutanecarboxylic acid (26.9 mg, 0.13 mmol) and DIEA (0.024 mL, 0.13 mmol) in DMF (2 mL) at room temperature, and the mixture was stirred overnight at room temperature. To the reaction mixture was added water, and the precipitate was collected by filtration, and washed with water to give tert-butyl 2-(trans-3-((R)-1-((7-fluoro-1,1-dimethyl-2,3-dihydro-1H-inden-5-yl)carbamoyl)-6-(methoxymethyl)-1,2,3,4-tetrahydroisoquinoline-2-carbonyl)cyclobutyl)acetate (74.0 mg, 0.128 mmol, 107%) as a white solid.

MS(API): Calculated 578.7. Found 577.2 (M-H).

(Step 2)

Cooled TFA (2 mL) was added to tert-butyl 2-(trans-3-((R)-1-((7-fluoro-1, 1-dimethyl-2,3-dihydro-1H-inden-5-yl)carbamoyl)-6-(methoxymethyl)-1,2,3,4-tetrahydroisoquinoline-2-carbonyl)cyclobutyl)acetate (74 mg, 0.13 mmol) at 0° C., and the mixture was stirred at 0° C. for 30 min. The pH of the reaction mixture was adjusted to 6 with cooled aqueous sodium hydrogencarbonate solution, and the mixture was extracted with ethyl acetate. The organic layer was dried over magnesium sulfate, and the solvent was evaporated under reduced pressure. The obtained residue was purified by silica gel column chromatography (solvent gradient; 50→100% ethyl acetate/hexane) to give the title compound (51.0 mg, 0.098 mmol, 76%) as a pale-yellow solid.

$^1$H NMR (300 MHz, DMSO-$d_6$): δ1.28 (6H, d, J=1.5 Hz), 1.78-2.00 (4H, m), 2.29-2.47 (5H, m), 2.75-2.93 (3H, m), 2.97-3.15 (1H, m), 3.24-3.28 (3H, m), 3.38-3.61 (2H, m), 3.72-4.01 (1H, m), 4.35 (2H, s), 5.71 (1H, s), 7.06-7.30 (4H, m), 7.39-7.67 (1H, m), 10.36-10.36-10.65 (1H, m), 12.02 (1H, s).

$[\alpha]_D^{25}$+28.3 (c 0.2510, MeOH)

Example 25

(cis-3-(((1R)-1-((3,5-difluoro-4-(trimethylsilyl)phenyl)carbamoyl)-6-methoxy-3,4-dihydroisoquinolin-2(1H)-yl)carbonyl)cyclobutyl)acetic acid (Step 1)

HATU (92 mg, 0.24 mmol) was added to a solution of (R)—N-(3,5-difluoro-4-(trimethylsilyl)phenyl)-6-methoxy-1,2,3,4-tetrahydroisoquinoline-1-carboxamide (86 mg, 0.22 mmol), cis-3-(2-(tert-butoxy)-2-oxoethyl)cyclobutanecarboxylic acid (51.9 mg, 0.24 mmol) and DIEA (0.043 mL, 0.24 mmol) in DMF (2 mL) at room temperature, and the mixture was stirred overnight at room temperature. To the reaction mixture was added water, and the mixture was extracted with ethyl acetate. The organic layer was dried over magnesium sulfate, and the solvent was evaporated under reduced pressure. The obtained residue was purified by silica gel column chromatography (solvent gradient; 3→50% ethyl acetate/hexane) to give tert-butyl 2-(cis-3-((R)-1-((3,5-difluoro-4-(trimethylsilyl)phenyl)carbamoyl)-6-methoxy-1,2,3,4-tetrahydroisoquinoline-2-carbonyl)cyclobutyl)acetate (86 mg, 0.22 mmol) as a colorless oil.

MS(API): Calculated 586.7. Found 585.1 (M-H).

(Step 2)

Cooled TFA (2 mL) was added to tert-butyl 2-(cis-3-((R)-1-((3,5-difluoro-4-(trimethylsilyl)phenyl)carbamoyl)-6-methoxy-1, 2,3,4-tetrahydroisoquinoline-2-carbonyl)cyclobutyl)acetate (130 mg, 0.22 mmol) at 0° C., and the mixture was stirred at 0° C. for 30 min. The pH of the reaction mixture was adjusted to 6 with cooled aqueous sodium hydrogencarbonate solution, and the mixture was extracted with ethyl acetate. The organic layer was dried over magnesium sulfate, and the solvent was evaporated under reduced pressure. The obtained residue was purified by silica gel column chromatography (solvent gradient; 50→100% ethyl acetate/hexane) to give the title compound (78 mg, 0.146 mmol, 65.9%) as a white solid.

$^1$H NMR (300 MHz, DMSO-$d_6$): δ0.30 (9H, s), 1.70-1.94 (2H, m), 2.20-2.41 (5H, m), 2.67-2.84 (1H, m), 2.97-3.13 (1H, m), 3.27-3.38 (1H, m), 3.45 (1H, ddd, J=12.2, 8.4, 4.0 Hz), 3.72 (3H, s), 3.82-4.03 (1H, m), 5.40-5.67 (1H, m), 6.74-6.94 (2H, m), 7.11-7.33 (2H, m), 7.36-7.54 (1H, m), 10.59-10.94 (H, m), 11.99 (1H, s).

$[\alpha]_D^{25}$+14.8 (c 0.2000, MeOH)

Example 27

(trans-3-(((1R)-1-((3,5-difluoro-4-(trimethylsilyl) phenyl)carbamoyl)-6-methoxy-3, 4-dihydroisoquinolin-2(1H)-yl)carbonyl)cyclobutyl)acetic acid (Step 1)
HATU (55.7 mg, 0.15 mmol) was added to a solution of (R)—N-(3,5-difluoro-4-(trimethylsilyl)phenyl)-6-methoxy-1,2,3,4-tetrahydroisoquinoline-1-carboxamide (52 mg, 0.13 nmol), trans-3-(2-(tert-butoxy)-2-oxoethyl)cyclobutanecarboxylic acid (30.0 mg, 0.14 mmol) and DIEA (0.026 mL, 0.15 mmol) in DMF (2 mL) at room temperature, and the mixture was stirred overnight at room temperature. To the reaction mixture was added water, and the precipitate was collected by filtration, and washed with water to give tert-butyl 2-(trans-3-((R)-1-((3,5-difluoro-4-(trimethylsilyl) phenyl)carbamoyl)-6-methoxy-1,2,3,4-tetrahydroisoquinoline-2-carbonyl)cyclobutyl)acetate (64.0 mg, 0.109 mmol, 82%) as a white solid.
MS(API): Calculated 586.7. Found 585.1 (M-H).

(Step 2)
Cooled TFA (2 mL) was added to tert-butyl 2-(trans-3-((R)-1-((3,5-difluoro-4-(trimethylsilyl)phenyl)carbamoyl)-6-methoxy-1,2,3,4-tetrahydroisoquinoline-2-carbonyl)cyclobutyl)acetate (64 mg, 0.11 mmol) at 0° C., and the mixture was stirred at 0° C. for 30 min. The pH of the reaction mixture was adjusted to 6 with cooled aqueous sodium hydrogencarbonate solution, and the mixture was extracted with ethyl acetate. The organic layer was dried over magnesium sulfate, and the solvent was evaporated under reduced pressure. The obtained residue was purified by silica gel column chromatography (solvent gradient; 50→100% ethyl acetate/hexane) to give the title compound (41.5 mg, 0.078 mmol, 71.7%) as a white solid.
$^1$H NMR (300 MHz, DMSO-$d_6$): δ0.30 (9H, s), 1.80-2.01 (2H, m), 2.27-2.39 (2H, m), 2.41-2.48 (3H, m), 2.67-2.84 (1H, m), 2.96-3.14 (1H, m), 3.40 (1H, ddd, J=12.3, 8.5, 4.2 Hz), 3.45-3.58 (1H, m), 3.72 (3H, s), 3.78-3.97 (1H, m), 5.32-5.68 (1H, m), 6.72-6.90 (2H, m), 7.08-7.33 (2H, m), 7.37-7.52 (1H, m), 10.59-10.91 (1H, m), 12.03 (1H, s).

Example 28

(trans-3-(((5R)-5-((3,5-difluoro-4-(trimethylsilyl) phenyl)carbamoyl)-2-methoxy-7,8-dihydro-1,6-naphthyridin-6(5H)-yl)carbonyl)cyclobutyl)acetic acid (Step 1)
HATU (64.1 mg, 0.17 mmol) was added to a solution of (R)—N-(3,5-difluoro-4-(trimethylsilyl)phenyl)-2-methoxy-5,6,7,8-tetrahydro-1,6-naphthyridine-5-carboxamide (60 mg, 0.15 mmol), trans-3-(2-(tert-butoxy)-2-oxoethyl)cyclobutanecarboxylic acid (32.8 mg, 0.15 mmol) and DIEA (0.030 mL, 0.17 mmol) in DMF (2 mL) at room temperature, and the mixture was stirred overnight at room temperature. To the reaction mixture was added water, and the precipitate was collected by filtration, and washed with water to give tert-butyl 2-(trans-3-((R)-5-((3,5-difluoro-4-(trimethylsilyl) phenyl)carbamoyl)-2-methoxy-5,6,7,8-tetrahydro-1,6-naphthyridine-6-carbonyl)cyclobutyl)acetate (60.0 mg, 0.102 mmol, 66.6%) as a white solid.
MS(API): Calculated 587.7. Found 586.1 (M-H).

(Step 2)
Cooled TFA (2 mL) was added to tert-butyl 2-(trans-3-((R)-5-((3,5-difluoro-4-(trimethylsilyl)phenyl)carbamoyl)-2-methoxy-5, 6,7,8-tetrahydro-1,6-naphthyridine-6-carbonyl)cyclobutyl)acetate (60 mg, 0.10 mmol) at 0° C., and the mixture was stirred at 0° C. for 30 min. The pH of the reaction mixture was adjusted to 6 to 7 with cooled aqueous sodium hydrogencarbonate solution, and the mixture was extracted with ethyl acetate. The organic layer was dried over magnesium sulfate, and the solvent was evaporated under reduced pressure. The obtained residue was purified by silica gel column chromatography (solvent gradient; 50→100% ethyl acetate/hexane) to give the title compound (36.0 mg, 0.068 mmol, 66.3%) as a white solid.
$^1$H NMR (300 MHz, DMSO-$d_6$): δ0.30 (9H, s), 1.82-1.99 (2H, m), 2.29-2.48 (5H, m), 2.75-2.90 (1H, m), 2.92-3.07 (1H, m), 3.47-3.61 (1H, m), 3.61-3.74 (1H, m), 3.83 (3H, s), 3.91 (1H, ddd, J=12.8, 8.3, 4.5 Hz), 5.41-5.76 (1H, m), 6.62-6.81 (1H, m), 7.11-7.29 (2H, m), 7.78 (1H, d, J=8.7 Hz), 10.61-10.97 (1H, m), 12.03 (1H, s).
$[α]_D^{25}$+104.6 (c 0.2525, MeOH)

Example 29

((1R,2S)-2-(((1R)-1-((3,5-difluoro-4-(trimethylsilyl) phenyl)carbamoyl)-6-methoxy-3,4-dihydroisoquinolin-2(1H)-yl)carbonyl)cyclopropyl)acetic acid (Step 1)
HATU (137 mg, 0.36 mmol) was added to a solution of (R)—N-(3,5-difluoro-4-(trimethylsilyl)phenyl)-6-methoxy-1,2,3,4-tetrahydroisoquinoline-1-carboxamide (128 mg, 0.33 mmol), trans-2-(2-(benzyloxy)-2-oxoethyl)cyclopropanecarboxylic acid (84 mg, 0.36 mmol) and DIEA (0.065 mL, 0.36 mmol) in DMF (2 mL) at room temperature, and the mixture was stirred at room temperature for 2 hr. To the reaction mixture was added water, and the mixture was extracted with ethyl acetate. The organic layer was washed with water, and dried over magnesium sulfate, and the solvent was evaporated under reduced pressure. The obtained residue was purified by silica gel column chromatography (solvent gradient; 30→100% ethyl acetate/hexane to give a mixture (147 mg) of two diastereomeric isomers.

The obtained mixture (147 mg) of diastereomeric isomers was resolved by chiral column chromatography. The fraction having a shorter retention time was concentrated to give benzyl 2-((1R,2S)-2-((R)-1-((3,5-difluoro-4-(trimethylsilyl) phenyl)carbamoyl)-6-methoxy-1,2,3,4-tetrahydroisoquinoline-2-carbonyl)cyclopropyl)acetate (55.4 mg, 0.091 mmol, 28%, >99% de), and the fraction having a longer retention time was concentrated to give benzyl 2-((1S,2R)-2-((R)-1-((3,5-difluoro-4-(trimethylsilyl)phenyl)carbamoyl)-6-methoxy-1,2,3,4-tetrahydroisoquinoline-2-carbonyl)cyclopropyl)acetate (63 mg, 0.104 mmol, 32%, >99% de), respectively.
MS spectrum of benzyl 2-((1R,2S)-2-((R)-1-((3,5-difluoro-4-(trimethylsilyl)phenyl)carbamoyl)-6-methoxy-1,2,3,4-tetrahydroisoquinoline-2-carbonyl)cyclopropyl)acetate
MS(API): Calculated 606.7. Found 605.1 (M-H).
MS spectrum of benzyl 2-((1S,2R)-2-((R)-1-((3,5-difluoro-4-(trimethylsilyl)phenyl)carbamoyl)-6-methoxy-1,2,3,4-tetrahydroisoquinoline-2-carbonyl)cyclopropyl)acetate
MS(API): Calculated 606.7. Found 605.2 (M-H).
purification condition by chiral column chromatography
  column: CHIRALPAK AD(NF001) 50 mmID×500 mmL
  solvent: EtOH
  flow rate: 80 mL/min
  temperature: 30° C.
  detection method: UV 220 nm (Step 2)

A mixture of benzyl 2-((1R,2S)-2-((R)-1-((3,5-difluoro-4-(trimethylsilyl)phenyl)carbamoyl)-6-methoxy-1,2,3,4-tetrahydroisoquinoline-2-carbonyl)cyclopropyl)acetate (55 mg, 0.09 mmol) and 10% palladium-carbon (9.65 mg, 0.09 mmol, 50%, wet) in MeOH (2 mL) was stirred at room temperature for 2 hr under hydrogen atmosphere (1 atm). The catalyst was removed by filtration, and the filtrate was concentrated under reduced pressure. The obtained residue was purified by silica gel column chromatography (solvent gradient; 50→100% ethyl acetate/hexane) to give the title compound (43.8 mg, 0.085 mmol, 94%) as a white solid.

$^1$H NMR (300 MHz, DMSO-d$_6$): δ0.29 (9H, s), 0.67-0.81 (1H, m, J=4.5 Hz), 0.86-1.08 (1H, m, J=4.5 Hz), 1.32-1.49 (1H, m), 1.94-2.06 (1H, m, J=3.4 Hz), 2.17-2.30 (H, m), 2.31-2.42 (1H, m), 2.78-2.94 (1H, m, J=15.1 Hz), 3.06-3.22 (1H, m), 3.66-3.80 (4H, m), 4.16-4.31 (1H, m), 5.65 (1H, s), 6.76-6.87 (2H, m), 7.19 (2H, d, J=9.4 Hz), 7.45 (1H, d, J=7.9 Hz), 10.76 (1H, s), 12.12 (1H, brs).

$[\alpha]_D^{25}$+30.8 (c 0.2515, MeOH)

Example 30

((1S,2R)-2-(((1R)-1-((3,5-difluoro-4-(trimethylsilyl)phenyl)carbamoyl)-6-methoxy-3,4-dihydroisoquinolin-2 (1H)-yl)carbonyl)cyclopropyl) acetic acid A mixture of benzyl 2-((1S,2R)-2-((R)-1-((3,5-difluoro-4-(trimethylsilyl)phenyl)carbamoyl)-6-methoxy-1,2,3,4-tetrahydroisoquinoline-2-carbonyl)cyclopropyl)acetate (63 mg, 0.10 mmol) and 10% palladium-carbon (11.1 mg, 0.10 mmol, 50%, wet) in MeOH (20 mL) was stirred at room temperature for 2 hr under hydrogen atmosphere (1 atm). The catalyst was removed by filtration, and the filtrate was concentrated under reduced pressure. The obtained residue was purified by silica gel column chromatography (solvent gradient; 50-*100% ethyl acetate/hexane) to give the title compound (40.0 mg, 0.077 mmol, 74.6%) as a white solid.

$^1$H NMR (300 MHz, DMSO-d$_6$): δ0.29 (9H, s), 0.57-0.74 (1H, m), 1.00-1.11 (H, m), 1.31 (1H, brs), 1.93-2.04 (1H, m), 2.34 (2H, dd, J=6.8, 4.2 Hz), 2.79-2.91 (1H, m), 3.20 (1H, t, J=9.4 Hz), 3.64-3.78 (4H, m), 4.19-4.39 (1H, m), 5.51-5.68 (1H, m), 6.72-6.92 (2H, m), 7.10-7.32 (2H, m), 7.39-7.52 (1H, m), 10.67-10.83 (1H, m), 12.17 (1H, brs).

Example 31 cis-3-(((5R)-5-((3,5-difluoro-4-(trimethylsilyl)phenyl)carbamoyl)-2-methoxy-7,8-dihydro-1,6-naphthyridin-6(5H)-yl)carbonyl)cyclobutanecarboxylic acid HATU (82 mg, 0.21 mmol) was added to a solution of (R)—N-(3,5-difluoro-4-(trimethylsilyl)phenyl)-2-methoxy-5,6,7,8-tetrahydro-1,6-naphthyridine-5-carboxamide (70 mg, 0.18 mmol), DIEA (0.061 mL, 0.36 mmol) and cis-cyclobutane-1,3-dicarboxylic acid (38.7 mg, 0.27 mmol) in DMF (2.0 mL) at room temperature, and the mixture was stirred at room temperature for 5 hr. To the reaction mixture was added aqueous sodium hydrogencarbonate solution, and the mixture was extracted with ethyl acetate. The organic layer was washed with water, and dried over magnesium sulfate, and the solvent was evaporated under reduced pressure. The obtained residue was purified by silica gel column chromatography (solvent gradient; 20→90% ethyl acetate/hexane), and then preparative HPLC (C18, mobile phase: water/acetonitrile (containing 0.1% TFA)) to give the title compound (35.6 mg, 0.069 mmol, 38.5%) as a white solid.

$^1$H NMR (300 MHz, DMSO-d$_6$): δ0.30 (9H, s), 2.22-2.43 (4H, m), 2.76-2.92 (1H, m), 2.92-3.08 (2H, m), 3.39-3.52 (1H, m), 3.66-3.79 (1H, m), 3.82 (3H, s), 3.88-4.01 (1H, m), 5.67 (1H, s), 6.66-6.78 (1H, m), 7.14-7.27 (2H, m), 7.66-7.88 (1H, m), 10.88 (1H, s), 12.21 (1H, brs)

$[\alpha]_D^{25}$+101.5 (c 0.2510, MeOH)

Example 32 cis-3-(((1R)-1-((3-fluoro-4-(trimethylsilyl)phenyl)carbamoyl)-6-methoxy-3,4-dihydroisoquinolin-2 (1H)-yl) carbonyl)cyclobutanecarboxylic acid (Step 1)

A solution of 1-chloro-2-fluoro-4-nitrobenzene (2.63 g, 15 mmol), HMDS (8.12 g, 55.50 mmol) and Pd(PPh$_3$)$_4$ (0.433 g, 0.38 mmol) in xylene (6.5 mL) was stirred at 200° C. for 1 hr under microwave irradiation. To the reaction mixture was added ethyl acetate (about 150 mL), and the insoluble substance was removed by filtration. The filtrate was concentrated under reduced pressure, and the obtained residue was purified by NH-silica gel column chromatography (solvent gradient; 2→5% ethyl acetate/hexane) to give (2-fluoro-4-nitrophenyl)trimethylsilane (3.22 g, 15.10 mmol, 101%) a yellow oil.

$^1$H NMR (300 MHz, CDCl$_3$): δ0.36 (9H, d, J=1.1 Hz), 7.57 (1H, dd, J=8.1, 5.5 Hz), 7.82 (1H, dd, J=8.1, 2.1 Hz), 7.99 (1H, dd, J=8.1, 2.1 Hz).

(Step 2)

A mixture of (2-fluoro-4-nitrophenyl)trimethylsilane (3.22 g, 15.10 mmol) and 10% palladium-carbon (1.0 g, 0.47 mmol, 50%, wet) in MeOH (65 mL) was stirred at room temperature for 3.5 hr under hydrogen atmosphere (1 atm). The catalyst was removed by filtration, and the filtrate was concentrated under reduced pressure. The obtained residue was purified by silica gel column chromatography (solvent gradient; 2→15% MeOH/ethyl acetate) to give 3-fluoro-4-(trimethylsilyl)aniline (1.89 g, 10.31 mmol, 68.3%) as a colorless oil.

$^1$H NMR (300 MHz, CDCl$_3$): δ0.26 (9H, d, J=0.8 Hz), 3.79 (2H, brs), 6.31 (1H, dd, J=10.6, 2.3 Hz), 6.44 (1H, dd, J=7.9, 1.9 Hz), 7.13 (1H, dd, J=7.9, 6.8 Hz).

(Step 3)

T3P (4.46 mL, 7.50 mmol) was added to a solution of 2-(tert-butoxycarbonyl)-6-methoxy-1,2,3,4-tetrahydroisoquinoline-1-carboxylic acid (1.537 g, 5 mmol), 3-fluoro-4-(trimethylsilyl)aniline (0.916 g, 5.00 mmol), DIEA (4.35 mL, 25.00 mmol) and DMAP (0.672 g, 5.50 mmol) in ethyl acetate (35 mL), and the mixture was stirred at 70° C. for 18 hr. To the reaction mixture was added water, and the mixture was extracted with ethyl acetate (×3). The organic layer was washed with brine, and dried over magnesium sulfate, and the solvent was evaporated under reduced pressure. The obtained residue was purified by silica gel column chromatography (solvent gradient; 2→20% ethyl acetate/hexane), and the precipitate was washed with IPE/hexane to give tert-butyl 1-((3-fluoro-4-(trimethylsilyl)phenyl)carbamoyl)-6-methoxy-3,4-dihydroisoquinoline-2(1H)-carboxylate (1.85 g, 3.91 mmol, 78%) as white crystals.

$^1$H NMR (300 MHz, CDCl$_3$): δ0.27 (9H, s), 1.52 (9H, s), 2.80-2.96 (2H, m), 3.55-3.76 (2H, m), 3.80 (3H, s), 5.61 (1H, brs), 6.72 (1H, d, J=2.3 Hz), 6.81 (1H, dd, J=8.3, 2.6 Hz), 7.09 (1H, d, J=7.9 Hz), 7.24-7.30 (2H, m), 7.39 (1H, dd, J=10.6, 1.9 Hz), 9.00 (1H, brs).

(Step 4)

tert-Butyl 1-((3-fluoro-4-(trimethylsilyl)phenyl)carbamoyl)-6-methoxy-3,4-dihydroisoquinoline-2(1H)-carboxylate (1.10 g) was subjected to optical resolution by chiral column chromatography. The fraction having a shorter retention time was concentrated to give tert-butyl (R)-1-((3-fluoro-4-(trimethylsilyl)phenyl)carbamoyl)-6-methoxy-3,4-dihydroisoquinoline-2(1H)-carboxylate (0.53 g, >99% ee), and the fraction having a longer retention time was concentrated to give tert-butyl (S)-1-((3-fluoro-4-(trimethylsilyl)phenyl)carbamoyl)-6-methoxy-3,4-dihydroisoquinoline-2(1H)-carboxylate (0.51 g, 96.7% ee), as a white solid, respectively.

purification condition by chiral column chromatography column: CHIRALCEL OD(NL001) 50 mmID×500 mmL solvent: hexane/EtOH=900/100 flow rate: 80 mL/min temperature: 30° C.

detection method: UV 220 nm (Step 5)

Cooled TFA (5.0 mL) was added to tert-butyl (R)-1-((3-fluoro-4-(trimethylsilyl)phenyl)carbamoyl)-6-methoxy-3,4-dihydroisoquinoline-2(1H)-carboxylate (526 mg, 1.11 mmol), and the mixture was stirred at room temperature for 2 min. The reaction mixture was poured into ice and aqueous sodium hydrogencarbonate solution, and the mixture was extracted with ethyl acetate. The organic layer was washed with brine, and dried over magnesium sulfate, and the solvent was evaporated under reduced pressure. The obtained residue was purified by NH-silica gel column chromatography (solvent gradient; 20→50% ethyl acetate/hexane) to give (R)—N-(3-fluoro-4-(trimethylsilyl)phenyl)-6-methoxy-1,2,3,4-tetrahydroisoquinoline-1-carboxamide (350.3 mg, 0.940 mmol, 84%) as a white solid.

$^1$H NMR (300 MHz, CDCl$_3$): δ0.28 (9H, d, J=0.8 Hz), 2.68-2.82 (1H, m), 2.83-2.97 (1H, m), 3.10-3.19 (2H, m), 3.79 (3H, s), 4.64 (1H, s), 6.65 (1H, d, J=2.6 Hz), 6.79 (1H, dd, J=8.5, 2.6 Hz), 7.18 (1H, dd, J=7.9, 1.9 Hz), 7.27 (1H, s), 7.46 (1H, dd, J=10.6, 1.9 Hz), 7.53 (1H, d, J=8.6 Hz), 9.46 (1H, s)

(Step 6)

HATU (147 mg, 0.39 mmol) was added to a solution of (R)—N-(3-fluoro-4-(trimethylsilyl)phenyl)-6-methoxy-1,2,3,4-tetrahydroisoquinoline-1-carboxamide (120 mg, 0.32 mmol), DIEA (0.110 mL, 0.64 mmol) and cis-cyclobutane-1,3-dicarboxylic acid (69.6 mg, 0.48 mmol) in DMF (2.0 mL) at room temperature, and the mixture was stirred at room temperature for 5 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 20→90% ethyl acetate/hexane, 0→10% MeOH/ethyl acetate), and then preparative HPLC (C18, mobile phase: water/acetonitrile (containing 0.1% TFA)) to give the title compound (47.0 mg, 0.094 mmol, 29.3%) as a white solid.

$^1$H NMR (300 MHz, DMSO-d$_6$): δ0.30 (9H, s), 2.22-2.43 (4H, m), 2.76-2.92 (1H, m), 2.92-3.08 (2H, m), 3.39-3.52 (1H, m), 3.66-3.79 (1H, m), 3.82 (3H, s), 3.88-4.01 (1H, m), 5.67 (1H, s), 6.66-6.78 (1H, m), 7.14-7.27 (2H, m), 7.66-7.88 (1H, m), 10.88 (1H, s), 12.21 (1H, brs)

$[α]_D^{25}$+19.8 (c 0.2545, MeOH)

Example 33

(cis-3-(((1R)-1-((3-fluoro-4-(trimethylsilyl)phenyl)carbamoyl)-6-methoxy-3,4-dihydroisoquinolin-2(1H)-yl) carbonyl)cyclobutyl) acetic acid (Step 1)

HATU (147 mg, 0.39 mmol) was added to a solution of (R)—N-(3-fluoro-4-(trimethylsilyl)phenyl)-6-methoxy-1,2,3,4-tetrahydroisoquinoline-1-carboxamide (120 mg, 0.32 mmol), DIEA (0.110 mL, 0.64 mmol) and cis-3-(2-(tert-butoxy)-2-oxoethyl)cyclobutanecarboxylic acid (72.5 mg, 0.34 mmol) in DMF (2.0 mL) at room temperature, and the mixture was stirred at room temperature for 5 hr. To the reaction mixture was added water, and the mixture was extracted with ethyl acetate. The organic layer was washed with water, and dried over-magnesium sulfate, and the solvent was evaporated under reduced pressure. The obtained residue was purified by silica gel column chromatography (solvent gradient; 20→50% ethyl acetate/hexane) to give tert-butyl 2-(cis-3-((R)-1-((3-fluoro-4-(trimethylsilyl)phenyl)carbamoyl)-6-methoxy-1,2,3,4-tetrahydroisoquinoline-2-carbonyl)cyclobutyl)acetate (162.1 mg, 0.285 mmol, 88%) as a white solid.

MS(API): Calculated 568.8. Found 567.2 (M-H).

(Step 2)

Cooled TFA (2.0 mL) was added to tert-butyl 2-(cis-3-((R)-1-((3-fluoro-4-(trimethylsilyl)phenyl)carbamoyl)-6-methoxy-1,2,3,4-tetrahydroisoquinoline-2-carbonyl)cyclobutyl)acetate (160 mg, 0.28 mmol) at 0° C., and the mixture was stirred at 0° C. for 1 hr. The reaction mixture was neutralized with ice and aqueous sodium hydrogencarbonate solution, and the mixture was extracted with ethyl acetate. The organic layer was dried over magnesium sulfate, and the solvent was evaporated under reduced pressure. The obtained residue was purified by silica gel column chromatography (solvent gradient; 20→90% ethyl acetate/hexane), and then preparative HPLC (C18, mobile phase: water/acetonitrile (containing 0.1% TFA)) to give the title compound (46.9 mg, 0.091 mmol, 32.5%) as a white solid.

$^1$H NMR (300 MHz, DMSO-d$_6$): δ0.25 (9H, d, J=0.8 Hz), 1.73-1.93 (2H, m), 2.20-2.39 (4H, m), 2.42-2.58 (1H, m), 2.68-2.84 (1H, m), 2.97-3.14 (1H, m), 3.22-3.39 (1H, m), 3.40-3.54 (1H, m), 3.72 (3H, s), 3.84-3.98 (1H, m), 5.63 (1H, s), 6.72-6.89 (2H, m), 7.23-7.39 (2H, m), 7.40-7.56 (2H, m), 10.64 (1H, s), 12.02 (1H, brs)

$[α]_D^{25}$+20.7 (c 0.2505, MeOH)

Example 34

(trans-3-(((1R)-1-((3-fluoro-4-(trimethylsilyl)phenyl)carbamoyl)-6-methoxy-3,4-dihydroisoquinolin-2(1H)-yl)carbonyl)cyclobutyl)acetic acid (Step 1)

HATU (86 mg, 0.23 mmol) was added to a solution of (R)—N-(3-fluoro-4-(trimethylsilyl)phenyl)-6-methoxy-1,2,3,4-tetrahydroisoquinoline-1-carboxamide (70 mg, 0.19 mmol), DIEA (0.064 mL, 0.38 mmol) and trans-3-(2-(tert-butoxy)-2-oxoethyl)cyclobutanecarboxylic acid (42.3 mg, 0.20 mmol) in DMF (2.0 mL) at room temperature, and the mixture was stirred at room temperature for 5 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 20→50% ethyl acetate/hexane) to give tert-butyl 2-(trans-3-((R)-1-((3-fluoro-4-(trimethylsilyl)phenyl)carbamoyl)-6-methoxy-1,2,3,4-tetrahydroisoquinoline-2-carbonyl)cyclobutyl)acetate (92.3 mg, 0.162 mmol, 86%) as a white solid.

MS(API): Calculated 568.8. Found 567.1 (M-H).

(Step 2)

Cooled TFA (2.0 mL) was added to tert-butyl 2-(trans-3-((R)-1-((3-fluoro-4-(trimethylsilyl)phenyl)carbamoyl)-6-methoxy-1,2,3,4-tetrahydroisoquinoline-2-carbonyl)cyclobutyl)acetate (90 mg, 0.16 mmol) at 0° C., and the mixture was stirred at 0° C. for 1 hr. The reaction mixture was neutralized with ice and aqueous sodium hydrogencarbonate solution, and the mixture was extracted with ethyl acetate. The organic layer was dried over magnesium sulfate, and the solvent was evaporated under reduced pressure. The obtained residue was purified by silica gel column chromatography (solvent gradient; 20→90% ethyl acetate/hexane), and then preparative HPLC (C18, mobile phase: water/acetonitrile (containing 0.1% TFA)) to give the title compound (29.8 mg, 0.058 mmol, 36.7%) as a white solid.

$^1$H NMR (300 MHz, DMSO-d$_6$): δ0.25 (9H, s), 1.80-1.99 (2H, m), 2.24-2.40 (2H, m), 2.40-2.47 (3H, m), 2.69-2.85 (H, m), 2.98-3.14 (1H, m), 3.37-3.57 (2H, m), 3.72 (3H, s), 3.79-3.96 (1H, m), 5.65 (1H, s), 6.72-6.90 (2H, m), 7.22-7.39 (2H, m), 7.39-7.53 (2H, m), 10.65 (1H, s), 12.03 (1H, brs)

Example 35

(cis-3-(((1R)-1-((3,5-difluoro-4-(1-methoxy-2-methylpropan-2-yl)phenyl)carbamoyl)-6-methoxy-3,4-dihydroisoquinolin-2(1H)-yl)carbonyl)cyclobutyl) acetic acid (Step 1)

Diethyl malonate (44.8 g, 280 mmol) was added to a suspension of sodium hydride (60%, oil, 28.0 g, 700 mmol) in THF (280 mL) at 0° C., and the mixture was stirred at room temperature for 1 hr. Then, 1,2,3-trifluoro-5-nitrobenzene (24.79 g, 140 mmol) was added thereto at 0° C., and the mixture was stirred at room temperature for 2 hr. To the reaction mixture was added aqueous ammonium chloride solution, and the mixture was extracted with ethyl acetate (×2). The organic layer was washed with brine, and dried over magnesium sulfate, and the solvent was evaporated under reduced pressure to give diethyl 2,6-difluoro-4-nitrophenylmalonate (42 g) as a colorless oil.

A solution of the obtained diethyl 2,6-difluoro-4-nitrophenylmalonate (42 g) in a mixed solvent of acetic acid (200 mL), water (150 mL) and conc. sulfuric acid (50 mL) was heated under reflux for 18 hr, and the reaction mixture was concentrated under reduced pressure. To the residue was added water, and the mixture was extracted with ethyl acetate (×2). The organic layer was back-extracted with 10% sodium carbonate aqueous solution, and the aqueous layer was acidified with 2N hydrochloric acid. The precipitate was collected by filtration to give 2-(2,6-difluoro-4-nitrophenyl) acetic acid (27.90 g, 128 mmol, 92.0%) as white crystals.

$^1$H NMR (300 MHz, DMSO-d$_6$): δ3.79 (2H, s), 7.81-8.24 (2H, m), 12.93 (1H, brs).

(Step 2)

A solution of 2-(2,6-difluoro-4-nitrophenyl)acetic acid (27.90 g, 128.5 mmol) and conc. sulfuric acid (1.0 mL) in MeOH (260 mL) was heated under reflux for 18 hr. The reaction mixture was neutralized with aqueous sodium hydrogencarbonate solution, and ethyl acetate and water were added thereto. The organic layer was dried over magnesium sulfate, and the solvent was evaporated under reduced pressure. The obtained residue was purified by silica gel column chromatography (solvent gradient; 0→100% ethyl acetate/hexane) to give methyl 2-(2,6-difluoro-4-nitrophenyl)acetate (28.71 g, 128.5 mmol, 97.0%) as a yellow solid.

$^1$H NMR (300 MHz, CDCl$_3$): δ3.75 (3H, s), 3.80 (2H, s), 7.80-7.85 (2H, m).

(Step 3)

To a solution of methyl 2-(2,6-difluoro-4-nitrophenyl) acetate (10.7 g, 50.20 mmol) and iodomethane (12.55 mL, 200.79 mmol) in DMF (100 mL) was added sodium hydride (60%, oil, 5.02 g, 125.49 mmol) at 0° C., and the mixture was stirred at 0° C. for 4 hr. To the reaction mixture was added aqueous ammonium chloride solution, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 5→20% ethyl acetate/hexane) to give methyl 2-(2,6-difluoro-4-nitrophenyl)-2-methylpropanoate (12.10 g, 50.2 mmol, 100%) as yellow crystals.

(Step 4)

A mixture of methyl 2-(2,6-difluoro-4-nitrophenyl)-2-methylpropanoate (3.2 g, 12.35 mmol) and 10% palladium-carbon (1.314 g, 0.617 mmol, 50%, wet) in MeOH (30 mL) was stirred overnight at room temperature under hydrogen atmosphere (1 atm). The catalyst was removed by filtration, and the filtrate was concentrated under reduced pressure. The obtained residue was purified by silica gel column chromatography (solvent gradient; 3→50% ethyl acetate/hexane) to give methyl 2-(4-amino-2, 6-difluorophenyl)-2-methylpropanoate (2.87 g, 12.52 mmol, 101%) as a colorless oil.

$^1$H NMR (300 MHz, CDCl$_3$): δ1.59 (6H, t, J=1.7 Hz), 3.69 (3H, s), 3.77 (2H, brs), 6.00-6.25 (2H, m).

(Step 5)

To a solution of methyl 2-(4-amino-2,6-difluorophenyl)-2-methylpropanoate (2.8 g, 12.22 mmol) and α-chloro-4-methoxytoluene (3.48 mL, 25.65 mmol) in DMF (50 mL) was added sodium hydride (60%, oil, 1.075 g, 26.87 mmol) at 0° C., and the mixture was stirred at 0° C. for 4 hr. To the reaction mixture was added aqueous ammonium chloride solution, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 3→50% ethyl acetate/hexane) to give methyl 2-(4-(bis(4-methoxybenzyl)amino)-2,6-difluorophenyl)-2-methylpropanoate (2.470 g, 5.26 mmol, 43.1%) as an orange oil.

(Step 6)

To a solution of methyl 2-(4-(bis(4-methoxybenzyl) amino)-2,6-difluorophenyl)-2-methylpropanoate (2.17 g, 4.62 mmol) in THF (30 mL) was added 1M DIBAL-H/THF solution (13.87 mL, 13.87 mmol) at 0° C., and the mixture was stirred at 0° C. for 5 hr. 1M DIBAL-H/THF solution (1.0 mL, 1.0 mmol) was added again thereto at 0° C., and the mixture was stirred at 0° C. for 1.5 hr. To the reaction mixture were added 1N hydrochloric acid and water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 3→50% ethyl acetate/hexane), and then silica gel column chromatography (NH, solvent gradient; 3→50% ethyl acetate/hexane) to give 2-(4-(bis(4-methoxybenzyl)amino)-2,6-difluorophenyl)-2-methylpropan-1-ol (1.310 g, 2.97 mmol, 64.2%) as a colorless oil.

(Step 7)

To a solution of 2-(4-(bis(4-methoxybenzyl)amino)-2,6-difluorophenyl)-2-methylpropan-1-ol (1.31 g, 2.97 mmol) and iodomethane (0.278 mL, 4.45 mmol) in DMF (10 mL) was added sodium hydride (60%, oil, 0.154 g, 3.86 mmol) at 0° C., and the mixture was stirred at 0° C. for 4 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 3→40% ethyl acetate/hexane) to give 3,5-difluoro-4-(1-methoxy-2-methylpropan-2-yl)-N,N-bis(4-methoxybenzyl)aniline (1.000 g, 2.195 mmol, 74.0%) a yellow oil.

$^1$H NMR (300 MHz, CDCl$_3$): δ1.37-1.42 (6H, m), 3.33 (3H, s), 3.50 (2H, s), 3.80 (6H, s), 4.46 (4H, s), 6.08-6.24 (2H, m), 6.86 (4H, d, J=8.3 Hz), 7.11 (4H, d, J=8.7 Hz).

(Step 8)

A solution of 3,5-difluoro-4-(1-methoxy-2-methylpropan-2-yl)-N,N-bis(4-methoxybenzyl)aniline (1 g, 2.20 mmol) in TFA (10 mL) was stirred at room temperature for 1 hr. The reaction mixture was concentrated under reduced pressure, and to the obtained residue was added ethyl acetate. The organic layer was washed with brine, and dried over magnesium sulfate, and the solvent was evaporated under reduced pressure. The obtained residue was purified by silica gel column chromatography (solvent gradient; 3→50% ethyl acetate/hexane) to give 3,5-difluoro-4-(1-methoxy-2-methylpropan-2-yl)aniline (0.470 g, 2.184 mmol, 99%) as a pale-yellow oil.

$^1$H NMR (300 MHz, CDCl$_3$): δ1.40 (6H, t, J=2.5 Hz), 3.32 (3H, s), 3.50 (2H, s), 3.69 (2H, brs), 6.07-6.16 (2H, m).

(Step 9)

To a solution of 2-(tert-butoxycarbonyl)-6-methoxy-1,2,3,4-tetrahydroisoquinoline-1-carboxylic acid (671 mg, 2.18 mmol), 3,5-difluoro-4-(1-methoxy-2-methylpropan-2-yl)aniline (470 mg, 2.18 mmol), DIEA (1.907 mL, 10.92 mmol) and DMAP (267 mg, 2.18 mmol) in ethyl acetate (30 mL) was added T3P (3.85 mL, 6.55 mmol) at room temperature, and the mixture was stirred overnight at 60° C. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 5→60% ethyl acetate/hexane), and then silica gel column chromatography (NH, solvent gradient; 5→60% ethyl acetate/hexane), and the precipitate was washed with ethyl acetate/hexane to give tert-butyl 1-((3,5-difluoro-4-(1-methoxy-2-methylpropan-2-yl)phenyl)carbamoyl)-6-methoxy-3,4-dihydroisoquinoline-2(1H)-carboxylate (440 mg, 0.872 mmol, 39.9%) as white crystals.

$^1$H NMR (300 MHz, CDCl$_3$): δ1.42 (6H, t, J=2.3 Hz), 1.51 (9H, s), 2.72-2.99 (2H, m), 3.30 (3H, s), 3.46-3.75 (4H, m), 3.80 (3H, s), 5.57 (1H, brs), 6.73 (1H, s), 6.81 (1H, dd, J=8.5, 2.8 Hz), 6.94-7.11 (2H, m), 7.10-7.20 (1H, m), 8.93 (1H, brs).

(Step 10)

tert-Butyl 1-((3,5-difluoro-4-(1-methoxy-2-methylpropan-2-yl)phenyl)carbamoyl)-6-methoxy-3,4-dihydroisoquinoline-2(1H)-carboxylate (440 mg) was subjected to optical resolution by chiral column chromatography. The fraction having a shorter retention time was concentrated to give tert-butyl (R)-1-((3,5-difluoro-4-(1-methoxy-2-methylpropan-2-yl)phenyl)carbamoyl)-6-methoxy-3,4-dihydroisoquinoline-2(1H)-carboxylate (200 mg, >99.9% ee) as a white solid.

purification condition by chiral column chromatography
    column: CHIRALCEL OD(NF001) 50 mmID×500 mmL
    solvent: hexane/EtOH-900/100
    flow rate: 80 mL/min
    temperature: 30° C.
    detection method: UV 220 nm (Step 11)

To a solution of tert-butyl (R)-1-((3,5-difluoro-4-(1-methoxy-2-methylpropan-2-yl)phenyl)carbamoyl)-6-methoxy-3,4-dihydroisoquinoline-2(1H)-carboxylate (200 mg, 0.40 mmol) in ethyl acetate (3 mL) was added 4M hydrogen chloride/ethyl acetate (4 mL) at room temperature, and the mixture was stirred overnight. The reaction mixture was concentrated under reduced pressure to give (R)—N-(3,5-difluoro-4-(1-methoxy-2-methylpropan-2-yl)phenyl)-6-methoxy-1,2,3,4-tetrahydroisoquinoline-1-carboxamide hydrochloride (175 mg, 0.397 mmol, 100%) as white crystals.

(Step 12)

HATU (114 mg, 0.30 mmol) was added to a solution of (R)—N-(3,5-difluoro-4-(1-methoxy-2-methylpropan-2-yl)phenyl)-6-methoxy-1,2,3,4-tetrahydroisoquinoline-1-carboxamide hydrochloride (120 mg, 0.27 mmol), cis-3-(2-(tert-butoxy)-2-oxoethyl)cyclobutanecarboxylic acid (61.2 mg, 0.29 mmol) and DIEA (0.107 mL, 0.60 mmol) in DMF (2 mL) at room temperature, and the mixture was stirred overnight at room temperature. To the reaction mixture was added water, and the mixture was extracted with ethyl acetate. The organic layer was dried over magnesium sulfate, and the solvent was evaporated under reduced pressure. The obtained residue was purified by silica gel column chromatography (solvent gradient; 3→50% ethyl acetate/hexane) to give tert-butyl 2-(cis-3-((R)-1-((3,5-difluoro-4-(1-methoxy-2-methylpropan-2-yl)phenyl)carbamoyl)-6-methoxy-1,2,3,4-tetrahydroisoquinoline-2-carbonyl)cyclobutyl)acetate (120 mg, 0.200 mmol, 73.4%) as a colorless oil.

MS(API): Calculated 600.7. Found 599.2 (M-H).

(Step 13)

Cooled TFA (4 mL) was added to tert-butyl 2-(cis-3-((R)-1-((3,5-difluoro-4-(1-methoxy-2-methylpropan-2-yl)phenyl)carbamoyl)-6-methoxy-1,2,3,4-tetrahydroisoquinoline-2-carbonyl)cyclobutyl)acetate (120 mg, 0.20 mmol) at 0° C., and the mixture was stirred for 45 min. The reaction mixture was concentrated under reduced pressure, and the obtained residue was purified by silica gel column chromatography (solvent gradient; 50→100% ethyl acetate/hexane) to give the title compound (106 mg, 0.195 mmol, 97%) as a white solid.

1H NMR (300 MHz, DMSO-d$_6$): δ1.35 (6H, s), 1.71-1.92 (3H, m), 2.20-2.36 (5H, m), 2.73-2.83 (1H, m), 2.98-3.12 (1H, m), 3.19 (3H, s), 3.40-3.53 (3H, m), 3.69-3.77 (3H, m), 3.83-4.02 (1H, m), 5.41-5.62 (1H, m), 6.72-6.91 (2H, m), 7.07-7.27 (2H, m), 7.34-7.56 (1H, m), 10.51-10.77 (1H, m), 11.99 (1H, brs).

The compounds described in Examples 1 to 35 are below (Table 1-1-Table 1-7).

TABLE 1-1

| Ex. | IUPAC NAME | Structure | SALT | MS |
|---|---|---|---|---|
| 1 | trans-2-(((1R)-1-((3,5-difluoro-4-(trimethylsilyl)phenyl)carbamoyl)-6-methoxy-3,4-dihydroisoquinolin-2(1H)-yl)carbonyl)cyclopropanecarboxylic acid (a mixture of two diastereomers) | 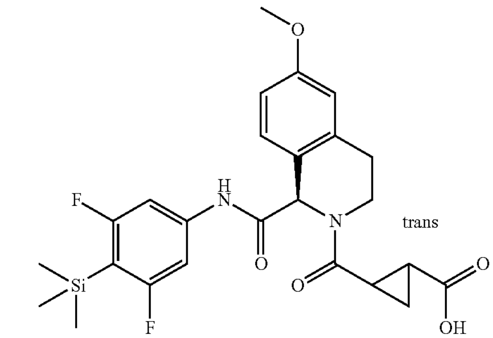 [SMILES: COc1ccc2c(c1)CCN(C(=O)C1CC1C(=O)O)[C@H]2C(=O)Nc1cc(F)c([Si](C)(C)C)c(F)c1] | | 503.2 (M + H) |
| 2 | trans-2-(((1R)-1-((3,5-difluoro-4-(trimethylsilyl)phenyl)carbamoyl)-6-methoxy-3,4-dihydroisoquinolin-2(1H)-yl)carbonyl)cyclopropanecarboxylic acid (single stereoisomer, shorter retention time) | 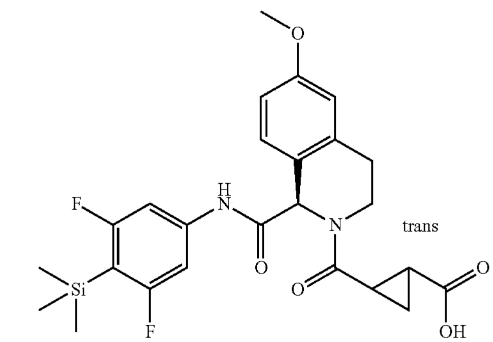 [SMILES: COc1ccc2c(c1)CCN(C(=O)C1CC1C(=O)O)[C@H]2C(=O)Nc1cc(F)c([Si](C)(C)C)c(F)c1] | | 503.1 (M + H) |
| 3 | trans-2-(((1R)-1-((3,5-difluoro-4-(trimethylsilyl)phenyl)carbamoyl)-6-methoxy-3,4-dihydroisoquinolin-2(1H)-yl)carbonyl)cyclopropanecarboxylic acid (single stereoisomer, longer retention time) | 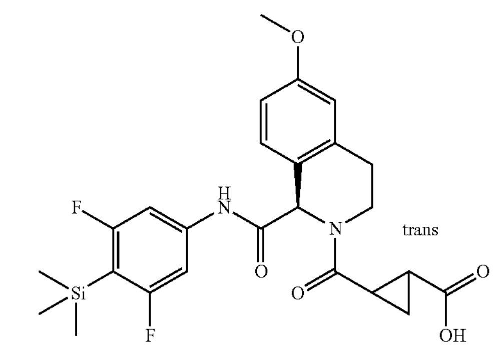 [SMILES: COc1ccc2c(c1)CCN(C(=O)C1CC1C(=O)O)[C@H]2C(=O)Nc1cc(F)c([Si](C)(C)C)c(F)c1] | | 501.2 (M − H) |
| 4 | (3-(((1R)-1-((3,5-difluoro-4-(trimethylsilyl)phenyl)carbamoyl)-6-methoxy-3,4-dihydroisoquinolin-2(1H)-yl)carbonyl)cyclobutyl)acetic acid | 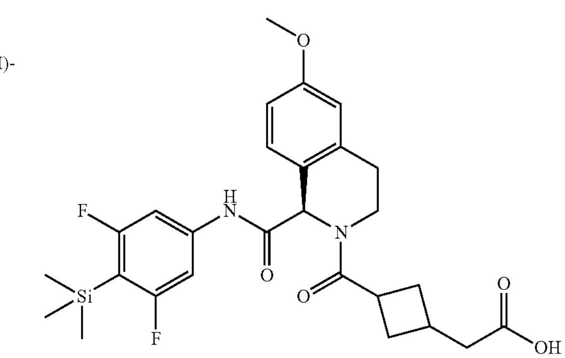 | | 531.2 (M + H) |

TABLE 1-1-continued

| Ex. | IUPAC NAME | Structure | SALT | MS |
|---|---|---|---|---|
| 5 | cis-3-(((1R)-1-((3,5-difluoro-4-(trimethylsilyl)phenyl)carbamoyl)-6-methoxy-3,4-dihydroisoquinolin-2(1H)-yl)carbonyl)cyclobutanecarboxylic acid | 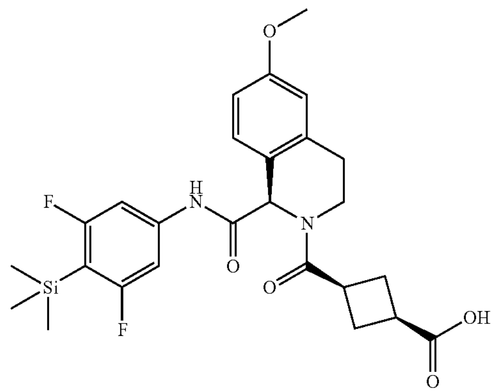 [SMILES: COc1ccc2c(c1)CCN(C(=O)[C@H]1C[C@@H](C(=O)O)C1)[C@H]2C(=O)Nc1cc(F)c([Si](C)(C)C)c(F)c1] | | 515.1 (M − H) |

TABLE 1-2

| Ex. | IUPAC NAME | Structure | SALT | MS |
|---|---|---|---|---|
| 6 | ((1R,2S)-2-(((5R)-5-((7-fluoro-1,1-dimethyl-2,3-dihydro-1H-inden-5-yl)carbamoyl)-2-methoxy-7,8-dihydro-1,6-naphthyridin-6(5H)-yl)carbonyl)cyclopropyl)acetic acid | 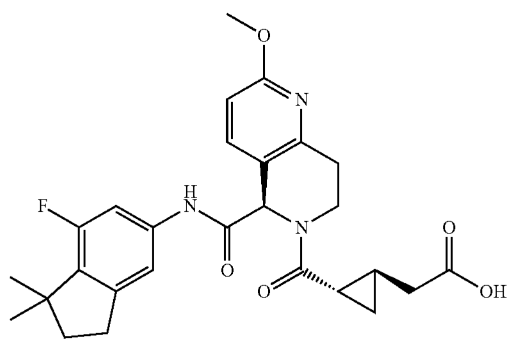 [SMILES: COc1ccc2c(n1)CCN(C(=O)[C@H]1C[C@@H]1CC(=O)O)[C@H]2C(=O)Nc1cc(F)c2c(c1)CCC2(C)C] | | 496.1 (M + H) |
| 7 | ((1S,2R)-2-(((5R)-5-((7-fluoro-1,1-dimethyl-2,3-dihydro-1H-inden-5-yl)carbamoyl)-2-methoxy-7,8-dihydro-1,6-naphthyridin-6(5H)-yl)carbonyl)cyclopropyl)acetic acid | 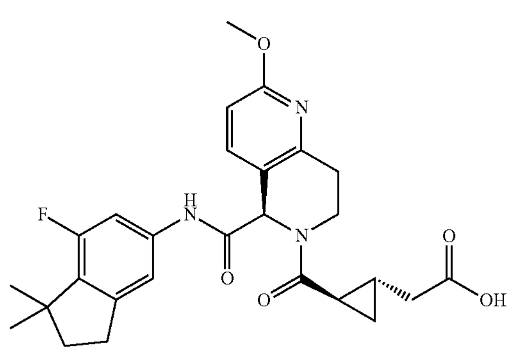 [SMILES: COc1ccc2c(n1)CCN(C(=O)[C@@H]1C[C@H]1CC(=O)O)[C@H]2C(=O)Nc1cc(F)c2c(c1)CCC2(C)C] | | 496.2 (M + H) |

TABLE 1-2-continued

| Ex. | IUPAC NAME | Structure | SALT | MS |
|---|---|---|---|---|
| 8 | cis-3-(((1R)-1-((3,5-difluoro-4-(trimethylsilyl)phenyl)carbamoyl)-6-ethoxy-3,4-dihydroisoquinolin-2(1H)-yl)carbonyl)cyclobutanecarboxylic acid | 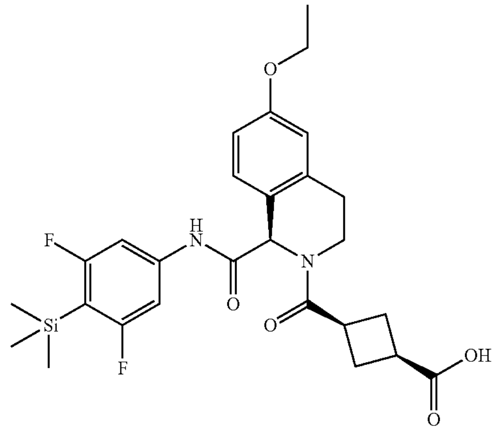 [SMILES: CCOc1ccc2c(c1)CCN(C(=O)[C@H]1C[C@@H](C(=O)O)C1)[C@H]2C(=O)Nc1cc(F)c([Si](C)(C)C)c(F)c1] | | 531.2 (M + H) |
| 9 | trans-3-(((1R)-1-((3,5-difluoro-4-(trimethylsilyl)phenyl)carbamoyl)-6-ethoxy-3,4-dihydroisoquinolin-2(1H)-yl)carbonyl)cyclobutanecarboxylic acid | 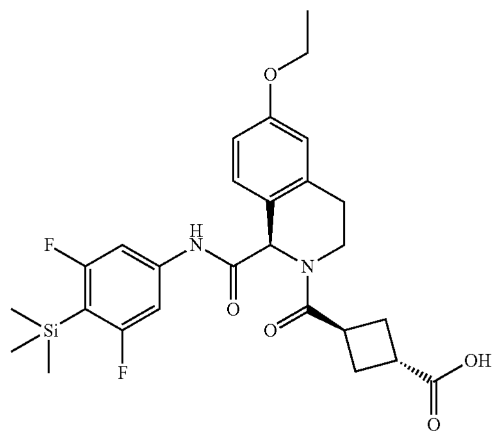 [SMILES: CCOc1ccc2c(c1)CCN(C(=O)[C@H]1C[C@H](C(=O)O)C1)[C@H]2C(=O)Nc1cc(F)c([Si](C)(C)C)c(F)c1] | | 531.2 (M + H) |
| 10 | cis-3-(((5R)-5-((7-fluoro-1,1-dimethyl-2,3-dihydro-1H-inden-5-yl)carbamoyl)-2-methoxy-7,8-dihydro-1,6-naphthyridin-6(5H)-yl)carbonyl)cyclobutanecarboxylic acid | 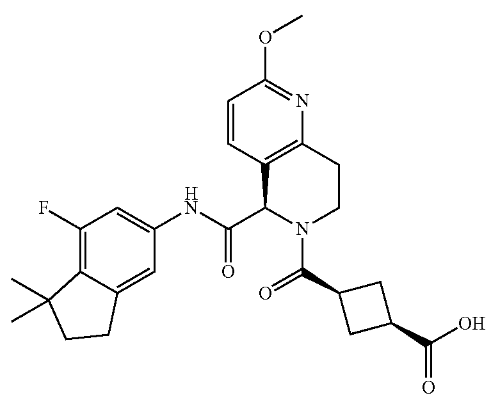 [SMILES: COc1ccc2c(n1)CCN(C(=O)[C@H]1C[C@@H](C(=O)O)C1)[C@H]2C(=O)Nc1cc(F)c2c(c1)CCC2(C)C] | | 496.0 (M + H) |

TABLE 1-3

| Ex. | IUPAC NAME | Structure | SALT | MS |
|---|---|---|---|---|
| 11 | trans-3-(((5R)-((7-fluoro-1,1-dimethyl-2,3-dihydro-1H-inden-5-yl)carbamoyl)-2-methoxy-7,8-dihydro-1,6-naphthyridin-6(5)-yl)carbonyl)cyclobutanecarboxylic acid | 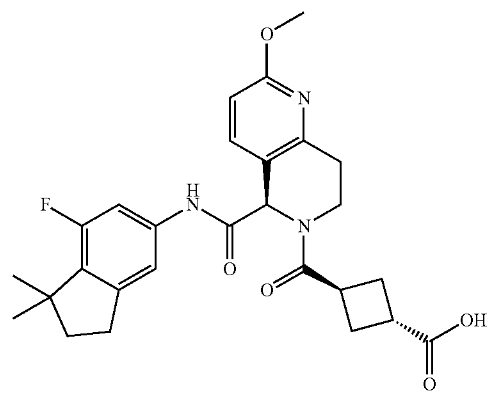 [SMILES: COc1ccc2c(n1)CCN(C(=O)[C@H]1C[C@H](C(=O)O)C1)[C@H]2C(=O)Nc1cc(F)c2c(c1)CCC2(C)C] | | 496.1 (M + 1) |
| 12 | trans-3-(((1R)-1-((3,5-difluoro-4-(trimethylsilyl)phenyl)carbamoyl)-6-methoxy-3,4-dihydroisoquinolin-2(1H)-yl)carbonyl)cyclobutanecarboxylic acid | 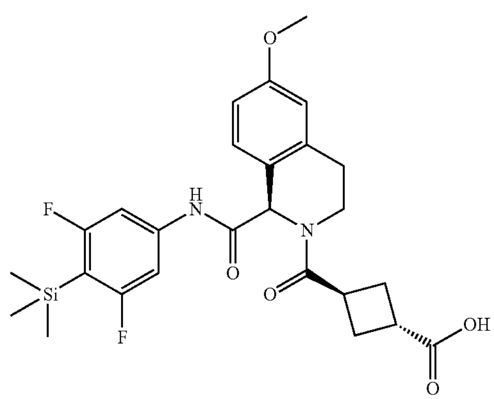 [SMILES: COc1ccc2c(c1)CCN(C(=O)[C@H]1C[C@H](C(=O)O)C1)[C@H]2C(=O)Nc1cc(F)c([Si](C)(C)C)c(F)c1] | | 517.2 (M + H) |
| 13 | ((1R,2S)-2-(((5R)-5-((3,5-difluoro-4-(trimethylsilyl)phenyl)carbamoyl)-2-methoxy-7,8-dihydro-1,6-naphthyridin-6(5H)-yl)carbonyl)cyclopropyl)acetic acid | 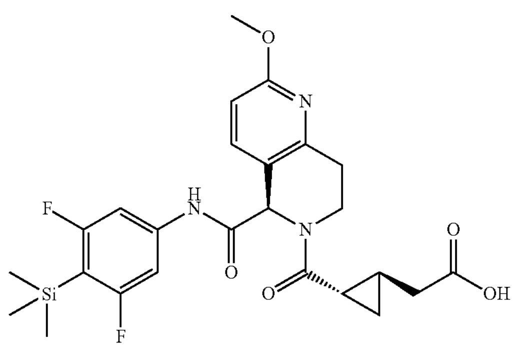 [SMILES: COc1ccc2c(n1)CCN(C(=O)[C@H]1C[C@@H]1CC(=O)O)[C@H]2C(=O)Nc1cc(F)c([Si](C)(C)C)c(F)c1] | | 518.1 (M + H) |
| 14 | ((1S,2R)-2-(((5R)-5-((3,5-difluoro-4-(trimethylsilyl)phenyl)carbamoyl)-2-methoxy-7,8-dihydro-1,6-naphthyridin-6(5H)-yl)carbonyl)cyclopropyl)acetic acid | 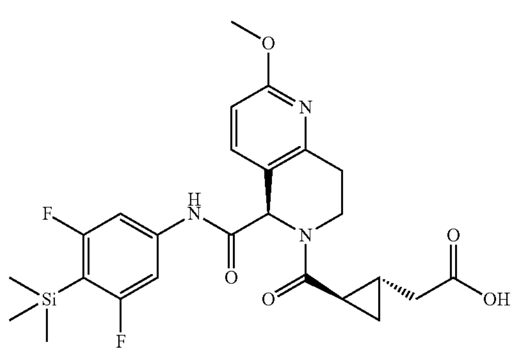 [SMILES: COc1ccc2c(n1)CCN(C(=O)[C@@H]1C[C@H]1CC(=O)O)[C@H]2C(=O)Nc1cc(F)c([Si](C)(C)C)c(F)c1] | | 518.2 (M + H) |

TABLE 1-3-continued

| Ex. | IUPAC NAME | Structure | SALT | MS |
|---|---|---|---|---|
| 15 | (cis-3-(((5R)-5-((7-fluoro-1,1-dimethyl-2,3-dihydro-1H-inden-5-yl)carbamoyl)-2-methoxy-7,8-dihydro-1,6-naphthyridin-6(5)-yl)carbonyl)cyclobutyl)acetic acid | 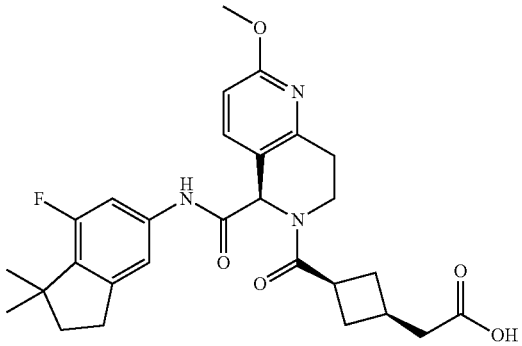 [SMILES: COc1ccc2c(n1)CCN(C(=O)[C@H]1C[C@@H](CC(=O)O)C1)[C@H]2C(=O)Nc1cc(F)c2c(c1)CCC2(C)C] | | 510.2 (M + H) |

TABLE 1-4

| Ex. | IUPAC NAME | Structure | SALT | MS |
|---|---|---|---|---|
| 16 | (cis-3-(((1R)-6-ethoxy-1-((7-fluoro-1,1-dimethyl-2,3-dihydro-1H-inden-5-yl)carbamoyl)-3,4-dihydroisoquinolin-2(1H)-yl)carbonyl)cyclobutyl)acetic acid | 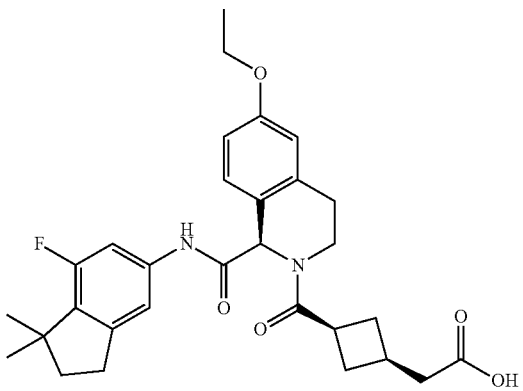 [SMILES: CCOc1ccc2c(c1)CCN(C(=O)[C@H]1C[C@@H](CC(=O)O)C1)[C@H]2C(=O)Nc1cc(F)c2c(c1)CCC2(C)C] | | 523.3 (M + H) |
| 17 | (cis-3-(((1R)-1-((3,5-difluoro-4-(1-methoxy-2-methylpropan-2-yl)phenyl)carbamoyl)-6-ethoxy-3,4-dihydroisoquinolin-2(1H)-yl)carbonyl)cyclobutyl)acetic acid | 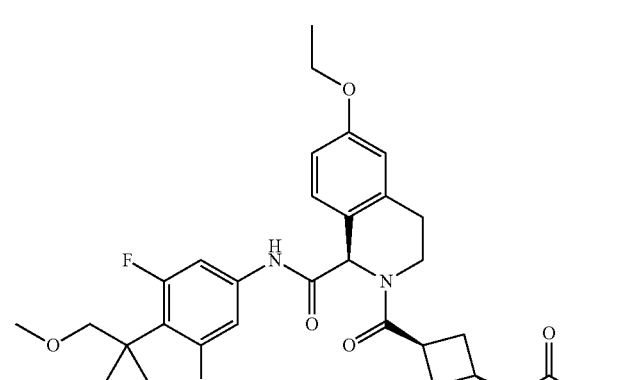 | | 559.2 (M + H) |

TABLE 1-4-continued

| Ex. | IUPAC NAME | Structure | SALT | MS |
|---|---|---|---|---|
| 18 | (cis-3-(((1R)-6-ethoxy-1-((4-(1-ethoxy-2-methylpropan-2-yl)-3,5-difluorophenyl)carbamoyl)-3,4-dihydroisoquinolin-2(1H)-yl)carbonyl)cyclobutyl)acetic acid | 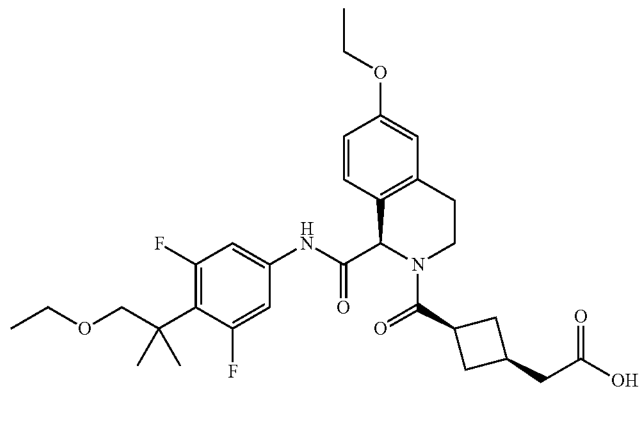 [SMILES: CCOCC(C)(C)c1c(F)cc(NC(=O)[C@H]2c3ccc(OCC)cc3CCN2C(=O)[C@H]2C[C@@H](CC(=O)O)C2)cc1F] | | 573.3 (M + H) |
| 19 | (cis-3-(((1R)-1-((7-fluoro-1,1-dimethyl-2,3-dihydro-1H-inden-5-yl)carbamoyl)-6-(methoxymethyl)-3,4-dihydroisoquinolin-2(1H)-yl)carbonyl)cyclobutyl)acetic acid | 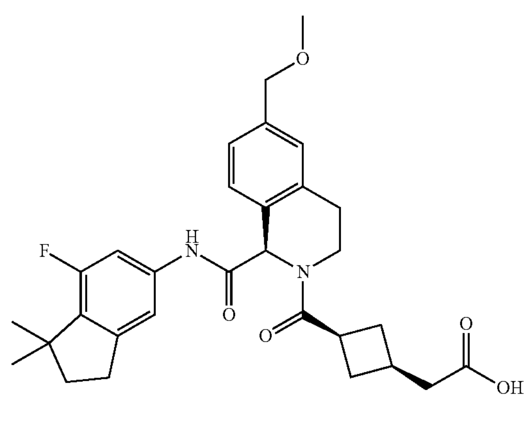 [SMILES: COCc1ccc2c(c1)CCN(C(=O)[C@H]1C[C@@H](CC(=O)O)C1)[C@H]2C(=O)Nc1cc(F)c2c(c1)CCC2(C)C] | | 523.1 (M + H) |
| 20 | (trans-3-(((5R)-5-((7-fluoro-1,1-dimethyl-2,3-dihydro-1H-inden-5-yl)carbamoyl)-2-methoxy-7,8-dihydro-1,6-naphthyridin-6(5H)-yl)carbonyl)cyclobutyl)acetic acid | 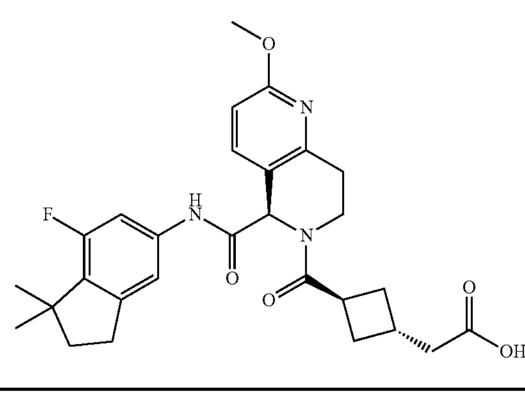 | | 510.3 (M + H) |

TABLE 1-5

| Ex. | IUPAC NAME | Structure | SALT | MS |
|---|---|---|---|---|
| 21 | (cis-3-(((6R)-6-((7-fluoro-1,1-dimethyl-2,3-dihydro-1H-inden-5-yl)carbamoyl)-3,6,8,9-tetrahydrofuro[2,3-f]isoquinolin-7(2H)-yl)carbonyl)cyclobutyl)acetic acid | 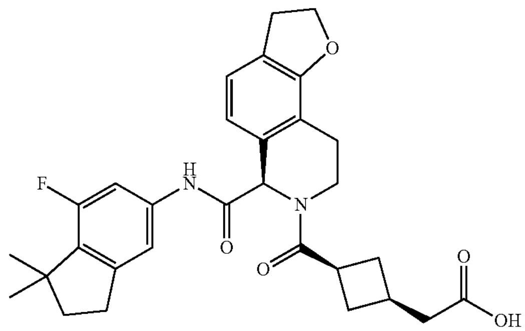 [SMILES: CC1(C)CCc2cc(NC(=O)[C@H]3c4ccc5c(c4CCN3C(=O)[C@H]3C[C@@H](CC(=O)O)C3)OCC5)cc(F)c21] | | 521.3 (M + H) |
| 22 | (cis-3-(((7R)-7-((7-fluoro-1,1-dimethyl-2,3-dihydro-1H-inden-5-yl)carbamoyl)-2,3,9,10-tetrahydro[1,4]dioxino[2,3-f]isoquinolin-8(7H)-yl)carbonyl)cyclobutyl)acetic acid | 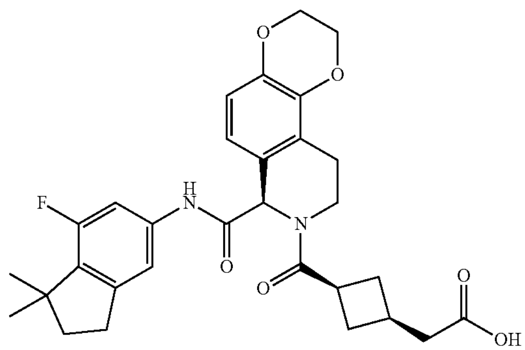 [SMILES: CC1(C)CCc2cc(NC(=O)[C@H]3c4ccc5c(c4CCN3C(=O)[C@H]3C[C@@H](CC(=O)O)C3)OCCO5)cc(F)c21] | | 537.2 (M + H) |
| 23 | (cis-3-(((5R)-5-((3,5-difluoro-4-(trimethylsilyl)phenyl)carbamoyl)-2-methoxy-7,8-dihydro-1,6-naphthyridin-6(5H)-yl)carbonyl)cyclobutyl)acetic acid | 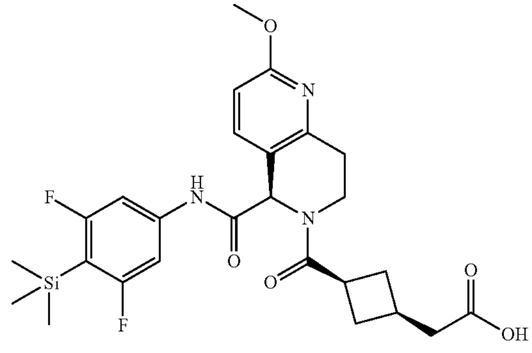 [SMILES: COc1ccc2c(n1)CCN(C(=O)[C@H]1C[C@@H](CC(=O)O)C1)[C@H]2C(=O)Nc1cc(F)c([Si](C)(C)C)c(F)c1] | | 532.1 (M + H) |
| 24 | (trans-3-(((1R)-1-((7-fluoro-1,1-dimethyl-2,3-dihydro-1H-inden-5-yl)carbamoyl)-6-(methoxymethyl)-3,4-dihydroisoquinolin-2(1H)-yl)carbonyl)cyclobutyl)acetic acid | 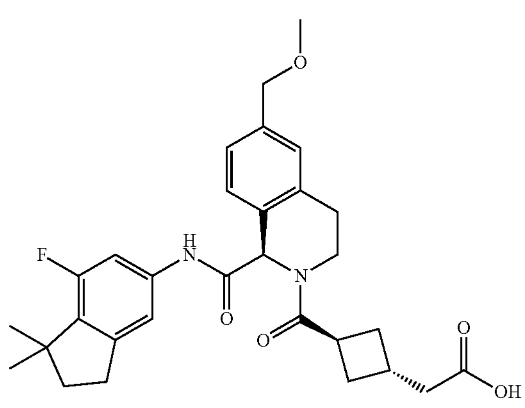 [SMILES: COCc1ccc2c(c1)CCN(C(=O)[C@H]1C[C@H](CC(=O)O)C1)[C@H]2C(=O)Nc1cc(F)c2c(c1)CCC2(C)C] | | 523.3 (M + H) |

TABLE 1-5-continued

| Ex. | IUPAC NAME | Structure | SALT | MS |
|---|---|---|---|---|
| 25 | (cis-3-(((1R)-1-((3,5-difluoro-4-(trimethylsilyl)phenyl)carbamoyl)-6-methoxy-3,4-dihydroisoquinolin-2(1H)-yl)carbonyl)cyclobutyl)acetic acid | 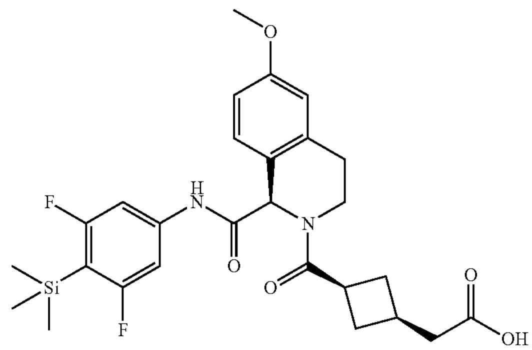 [SMILES: COc1ccc2c(c1)CCN(C(=O)[C@H]1C[C@@H](CC(=O)O)C1)[C@H]2C(=O)Nc1cc(F)c([Si](C)(C)C)c(F)c1] | | 531.2 (M + H) |

TABLE 1-6

| Ex. | IUPAC NAME | Structure | SALT | MS |
|---|---|---|---|---|
| 26 | (trans-3-(((1R)-1-((3,5-difluoro-4-(1-methoxy-2-methylpropan-2-yl)phenyl)carbamoyl)-6-ethoxy-3,4-dihydroisoquinolin-2(1H)-yl)carbonyl)cyclobutyl)acetic acid | 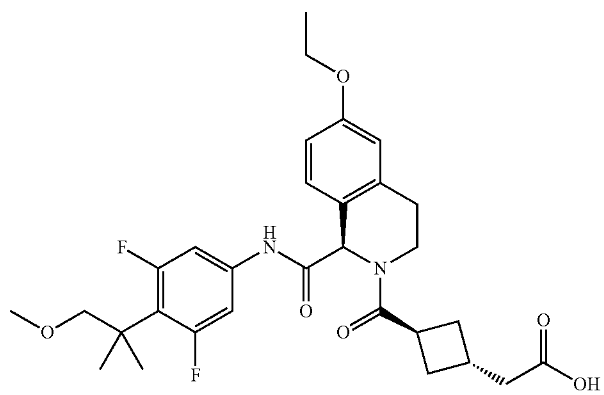 [SMILES: CCOc1ccc2c(c1)CCN(C(=O)[C@H]1C[C@H](CC(=O)O)C1)[C@H]2C(=O)Nc1cc(F)c(C(C)(C)COC)c(F)c1] | | 559.3 (M + H) |
| 27 | (trans-3-(((1R)-1-((3,5-difluoro-4-(trimethylsilyl)phenyl)carbamoyl)-6-methoxy-3,4-dihydroisoquinolin-2(1H)-yl)carbonyl)cyclobutyl)acetic acid | 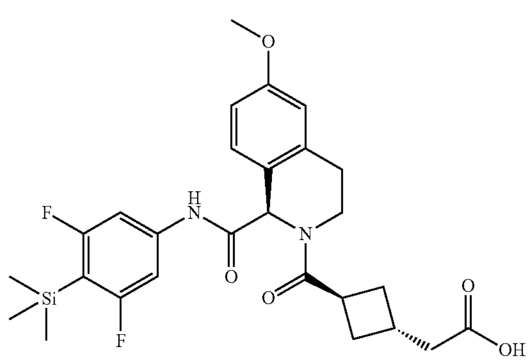 [SMILES: COc1ccc2c(c1)CCN(C(=O)[C@H]1C[C@H](CC(=O)O)C1)[C@H]2C(=O)Nc1cc(F)c([Si](C)(C)C)c(F)c1] | | 531.2 (M + H) |

TABLE 1-6-continued

| Ex. | IUPAC NAME | Structure | SALT | MS |
|---|---|---|---|---|
| 28 | (trans-3-(((5R)-5-((3,5-difluoro-4-(trimethylsilyl)phenyl)carbamoyl)-2-methoxy-7,8-dihydro-1,6-naphthyridin-6(5H)-yl)carbonyl)cyclobutyl)acetic acid | 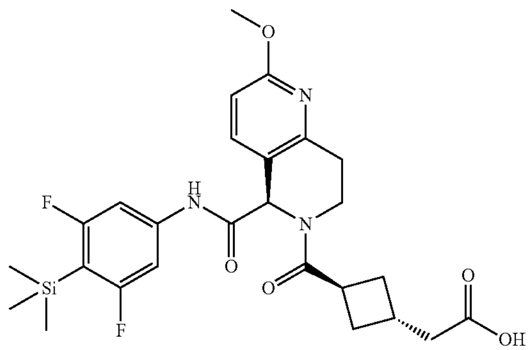 [SMILES: COc1ccc2c(n1)CCN(C(=O)[C@H]1C[C@H](CC(=O)O)C1)[C@H]2C(=O)Nc1cc(F)c([Si](C)(C)C)c(F)c1] | | 532.1 (M + 1) |
| 29 | ((1R,2S)-2-(((1R)-1-((3,5-difluoro-4-(trimethylsilyl)phenyl)carbamoyl)-6-methoxy-3,4-dihydroisoquinolin-2(1H)-yl)carbonyl)cyclopropyl)acetic acid | 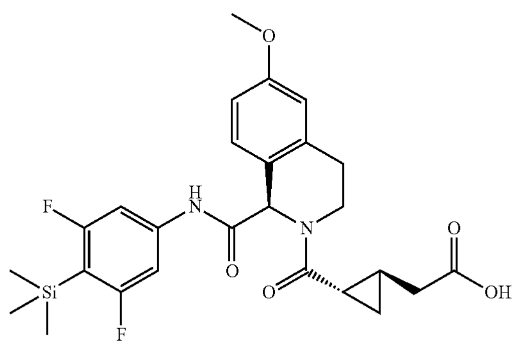 [SMILES: COc1ccc2c(c1)CCN(C(=O)[C@H]1C[C@@H]1CC(=O)O)[C@H]2C(=O)Nc1cc(F)c([Si](C)(C)C)c(F)c1] | | 517.2 (M + H) |
| 30 | ((1S,2R)-2-(((1R)-1-((3,5-difluoro-4-(trimethylsilyl)phenyl)carbamoyl)-6-methoxy-3,4-dihydroisoquinolin-2(1H)-yl)carbonyl)cyclopropyl)acetic acid | 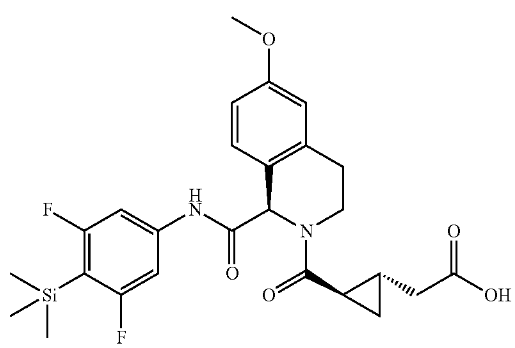 [SMILES: COc1ccc2c(c1)CCN(C(=O)[C@@H]1C[C@H]1CC(=O)O)[C@H]2C(=O)Nc1cc(F)c([Si](C)(C)C)c(F)c1] | | 517.2 (M + H) |

TABLE 1-7

| Ex. | IUPAC NAME | Structure | SALT | MS |
|---|---|---|---|---|
| 31 | cis-3-(((5R)-5-((3,5-difluoro-4-(trimethylsilyl)phenyl)carbamoyl)-2-methoxy-7,8-dihydro-1,6-naphthyridin-6(5H)-yl)carbonyl)cyclobutanecarboxylic acid | 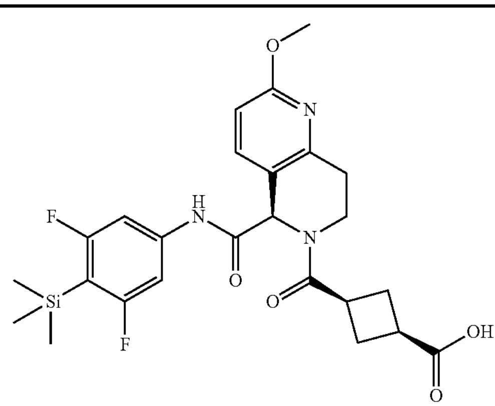 | | 518.1 (M + H) |

TABLE 1-7-continued

| Ex. | IUPAC NAME | Structure | SALT | MS |
|---|---|---|---|---|
| 32 | cis-3-(((1R)-1-((3-fluoro-4-(trimethylsilyl)phenyl)carbamoyl)-6-methoxy-3,4-dihydroisoquinolin-2(1H)-yl)carbonyl)cyclobutanecarboxylic acid | 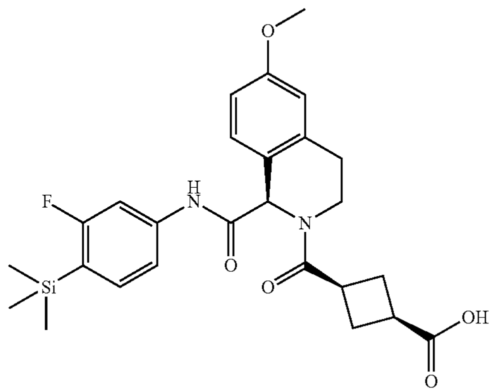 [SMILES: COc1ccc2c(c1)CCN(C(=O)[C@H]1C[C@@H](C(=O)O)C1)[C@H]2C(=O)Nc1ccc([Si](C)(C)C)c(F)c1] | | 499.2 (M + H) |
| 33 | (cis-3-(((1R)-1-((3-fluoro-4-(trimethylsilyl)phenyl)carbamoyl)-6-methoxy-3,4-dihydroisoquinolin-2(1H)-yl)carbonyl)cyclobutyl)acetic acid | 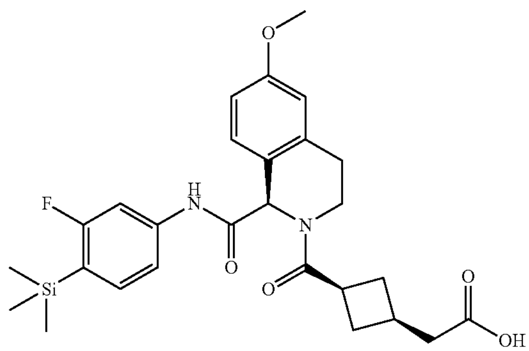 [SMILES: COc1ccc2c(c1)CCN(C(=O)[C@H]1C[C@@H](CC(=O)O)C1)[C@H]2C(=O)Nc1ccc([Si](C)(C)C)c(F)c1] | | 513.1 (M + H) |
| 34 | (trans-3-(((1R)-1-((3-fluoro-4-(trimethylsilyl)phenyl)carbamoyl)-6-methoxy-3,4-dihydroisoquinolin-2(1H)-yl)carbonyl)cyclobutyl)acetic acid | 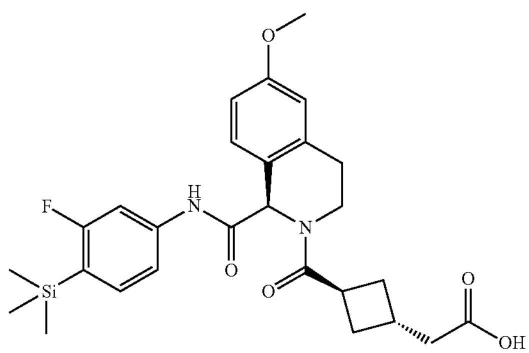 [SMILES: COc1ccc2c(c1)CCN(C(=O)[C@H]1C[C@H](CC(=O)O)C1)[C@H]2C(=O)Nc1ccc([Si](C)(C)C)c(F)c1] | | 513.2 (M + H) |
| 35 | (cis-3-(((1R)-1-((3,5-difluoro-4-(1-methoxy-2-methylpropan-2-yl)phenyl)carbamoyl)-6-methoxy-3,4-dihydroisoquinolin-2(1H)-yl)carbonyl)cyclobutyl)acetic acid | 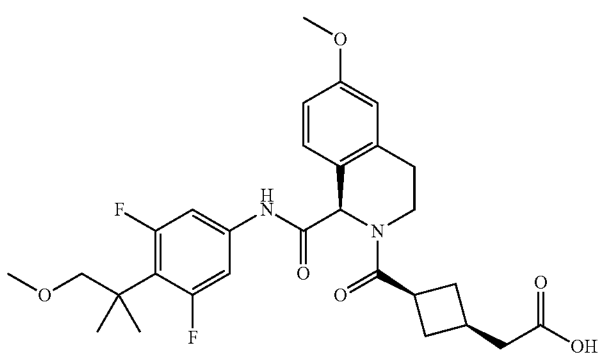 [SMILES: COCC(C)(C)c1c(F)cc(NC(=O)[C@H]2c3ccc(OC)cc3CCN2C(=O)[C@H]2C[C@@H](CC(=O)O)C2)cc1F] | | 545.2 (M + H) |

The compounds described in Examples 7, 16, 21, 22 and 26 were synthesized in the same manner as in the reaction and purification described in the above-mentioned Examples.

Example 36 benzyl cis-3-(((5R)-5-((7-fluoro-1, 1-dimethyl-2,3-dihydro-1H-inden-5-yl)carbamoyl)-2-methoxy-7,8-dihydro-1,6-naphthyridin-6(5H)-yl)carbonyl)cyclobutanecarboxylate (Step 1)
To a solution of cis-cyclobutane-1,3-dicarboxylic acid (4.00 g, 27.75 mmol), benzyl alcohol (2.87 mL, 27.75 mmol) and DMAP (0.339 g, 2.78 mmol) in DMF (80 mL) was added WSC (5.59 mL, 30.53 mmol) at room temperature, and the mixture was stirred overnight. The reaction mixture was poured into water, and the pH of the mixture was adjusted to 2 to 3 with 1N hydrochloric acid. The mixture was extracted with ethyl acetate, and the organic layer was washed with water and brine, and dried over magnesium sulfate, and the solvent was evaporated under reduced pressure to give crude cis-3-((benzyloxy)carbonyl)cyclobutanecarboxylic acid (5.93 g, 25.3 mmol, 91%) as a colorless oil. This compound was used for the next step without purification.

(Step 2)
HATU (9.88 g, 25.99 mmol) was added to a solution of (R)—N-(7-fluoro-1, 1-dimethyl-2,3-dihydro-1H-inden-5-yl)-2-methoxy-5,6,7,8-tetrahydro-1,6-naphthyridine-5-carboxamide (8.0 g, 21.65 mmol), DIEA (7.40 mL, 43.31 mmol) and the crude cis-3-((benzyloxy) carbonyl)cyclobutanecarboxylic acid (6.59 g, 28.15 mmol) in DMF (150 mL) at room temperature, and the mixture was stirred at room temperature for 5 hr. To the reaction mixture was added water, and the mixture was extracted with ethyl acetate. The organic layer was washed with water and brine, and dried over magnesium sulfate, and the solvent was evaporated under reduced pressure. The obtained residue was purified by silica gel column chromatography (solvent gradient; 20→50% ethyl acetate/hexane). The obtained solid was recrystallized from ethyl acetate/hexane to give the title compound (5.50 g, 9.39 mmol, 43.4%) as white crystals.
$[\alpha]_D^{25}$+109.5 (c 0.2500, MeOH)
$^1$H NMR (300 MHz, CDCl$_3$): δ1.34 (6H, s), 1.91 (2H, t, J=7.4 Hz), 2.45-2.62 (2H, m), 2.63-2.78 (2H, m), 2.86 (2H, t, J=7.4 Hz), 2.91-3.03 (2H, m), 3.11-3.26 (H, m), 3.25-3.41 (H, m), 3.57-3.70 (1H, m), 3.76-3.87 (1H, m), 3.92 (3H, s), 5.14 (2H, s), 5.98 (1H, s), 6.66 (1H, d, J=8.7 Hz), 7.04-7.10 (1H, m), 7.12-7.20 (1H, m), 7.35 (5H, s), 7.41 (1H, d, J=8.3 Hz), 9.00 (1H, s)

Example 38

(5-methyl-2-oxo-1,3-dioxol-4-yl)methyl (cis-3-(((5R)-5-((7-fluoro-1,1-dimethyl-2,3-dihydro-1H-inden-5-yl)carbamoyl)-2-methoxy-7,8-dihydro-1,6-naphthyridin-6(5H)-yl)carbonyl)cyclobutyl)acetate 4-(Chloromethyl)-5-methyl-1,3-dioxol-2-one (77 μL, 0.71 mmol) was added to a mixture of 2-(cis-3-(((5R)-5-((7-fluoro-1,1-dimethyl-2,3-dihydro-1H-inden-5-yl)carbamoyl)-2-methoxy-7,8-tetrahydro-1,6-naphthyridin-6(5H)-yl)carbonyl)cyclobutyl)acetic acid (300 mg, 0.59 mmol) and potassium carbonate (98 mg, 0.71 mmol) in DMF (5 mL) at room temperature, and the mixture was stirred at room temperature for 4 hr. To the reaction mixture was added water (60 mL), and the mixture was extracted with ethyl acetate (×3). The organic layer was washed with brine, and dried over magnesium sulfate, and the solvent was evaporated under reduced pressure. The obtained residue was purified by silica gel column chromatography (solvent gradient; 50→71% ethyl acetate/hexane) to give the title compound (258.0 mg, 0.415 mmol, 70.5%) as a colorless amorphous solid.
$^1$H NMR (300 MHz, CDCl$_3$): δ1.32 (6H, s), 1.89 (2H, t, J=7.4 Hz), 2.11 (2H, d, J=10.6 Hz), 2.17 (3H, s), 2.42-2.53 (4H, m), 2.62-2.77 (1H, m), 2.85 (2H, t, J=7.4 Hz), 2.91-3.03 (2H, m), 3.31 (1H, quin, J=8.9 Hz), 3.61-3.72 (1H, m), 3.84 (1H, dt), 3.91 (3H, s), 4.82 (2H, s), 5.96 (1H, s), 6.64 (1H, d, J=8.7 Hz), 7.05 (1H, s), 7.10 (1H, d, J=11.7 Hz), 7.43 (1H, d, J=8.7 Hz), 9.09 (1H, s)

Example 39 ethyl (cis-3-(((5R)-5-((7-fluoro-1, 1-dimethyl-2,3-dihydro-1H-inden-5-yl)carbamoyl)-2-methoxy-7,8-dihydro-1,6-naphthyridin-6(5H)-yl)carbonyl)cyclobutyl)acetate Iodoethane (57 μL, 0.71 mmol) was added to a mixture of 2-(cis-3-(((5R)-5-((7-fluoro-1,1-dimethyl-2,3-dihydro-1H-inden-5-yl)carbamoyl)-2-methoxy-7,8-tetrahydro-1,6-naphthyridin-6(5H)-yl) carbonyl)cyclobutyl)acetic acid (300 mg, 0.59 mmol) and potassium carbonate (98 mg, 0.71 mmol) in DMF (5 mL) at room temperature, and the mixture was stirred at room temperature for 3.5 hr. To the reaction mixture was added water (60 mL), and the mixture was extracted with ethyl acetate (×3). The organic layer was washed with brine, and dried over magnesium sulfate, and the solvent was evaporated under reduced pressure. The obtained residue was purified by silica gel column chromatography (solvent gradient; 25→46% ethyl acetate/hexane) to give the title compound (256.8 mg, 0.478 mmol, 81%) as a colorless amorphous solid.
$^1$H NMR (300 MHz, CDCl$_3$): δ1.24 (3H, t, J=7.2 Hz), 1.32 (6H, s), 1.89 (2H, t, J=7.4 Hz), 2.04-2.17 (2H, m), 2.40-2.54 (4H, m), 2.62-2.78 (1H, m), 2.84 (2H, t, J=7.4 Hz), 2.89-3.05 (2H, m), 3.31 (1H, quin, J=8.9 Hz), 3.64-3.75 (1H, m), 3.81-3.89 (1H, m), 3.91 (3H, s), 4.11 (2H, q, J=7.2 Hz), 5.98 (1H, s), 6.64 (1H, d, J=8.7 Hz), 7.02 (1H, s), 7.10 (1H, d, J=11.7 Hz), 7.47 (1H, d, J=8.7 Hz), 9.22 (1H, s)

Example 40-A monopotassium (cis-3-(((1R)-1-((7-fluoro-1,1-dimethyl-2,3-dihydro-1H-inden-5-yl)carbamoyl)-6-(methoxymethyl)-3,4-dihydroisoquinolin-2(1H)-yl)carbonyl)cyclobutyl)acetate acetonitrile solvate To a mixture of (cis-3-(((1R)-1-((7-fluoro-1,1-dimethyl-2,3-dihydro-1H-inden-5-yl)carbamoyl)-6-(methoxymethyl)-3,4-dihydroisoquinolin-2(1H)-yl)carbonyl)cyclobutyl)acetic acid (580 mg, 1.11 mmol) in acetonitrile (40 mL) was added 0.1N aqueous potassium hydroxide solution (11.10 mL, 1.11 mmol) at room temperature, and the solvent was evaporated under reduced pressure. To the obtained residue was added acetonitrile (40 mL), and the mixture was stirred at room temperature for 14 hr. The precipitate was collected by filtration, and washed with acetonitrile to give the title compound (586.6 mg, 1.046 mmol, 94%) as white crystals.

¹H NMR (300 MHz, CD₃OD): δ1.33 (6H, s), 2.03 (4H, s), 2.18-2.34 (2H, m), 2.34-2.52 (2H, m), 2.56-2.74 (1H, m), 2.79-2.94 (3H, m), 3.10-3.23 (1H, m), 3.36 (4H, s), 3.54-3.68 (1H, m), 3.92-4.07 (1H, m), 4.43 (2H, s), 5.51-5.75 (1H, m), 7.06-7.16 (2H, m), 7.18-7.28 (2H, m), 7.45 (1H, d, J=8.3 Hz)

$[\alpha]_D^{25}$+39.7 (c 0.2515, MeOH)

The crystallinity by powder X-RAY diffraction was 64.3%.

The peaks by powder X-RAY diffraction were below.

TABLE 2

| No. | 2θ | d value | peak search-set width | intensity (cps) | relative intensity |
|---|---|---|---|---|---|
| 1 | 5.080 | 17.3812 | 0.2118 | 635 | 100 |
| 2 | 7.200 | 12.2675 | 0.2353 | 275 | 44 |
| 3 | 13.900 | 6.3658 | 0.2118 | 354 | 56 |
| 4 | 15.340 | 5.7713 | 0.2353 | 395 | 63 |
| 5 | 16.160 | 5.4803 | 0.2118 | 182 | 29 |
| 6 | 17.300 | 5.1216 | 0.3294 | 202 | 32 |
| 7 | 18.020 | 4.9186 | 0.2118 | 407 | 65 |
| 8 | 18.440 | 4.8075 | 0.2118 | 148 | 24 |
| 9 | 18.840 | 4.7063 | 0.3294 | 133 | 21 |
| 10 | 19.540 | 4.5392 | 0.2824 | 155 | 25 |
| 11 | 20.140 | 4.4054 | 0.2353 | 304 | 48 |
| 12 | 21.160 | 4.1952 | 0.1882 | 159 | 26 |
| 13 | 22.080 | 4.0225 | 0.3529 | 160 | 26 |
| 14 | 22.640 | 3.9242 | 0.2353 | 321 | 51 |
| 15 | 22.960 | 3.8703 | 0.1647 | 246 | 39 |
| 16 | 24.360 | 3.6509 | 0.3529 | 198 | 32 |
| 17 | 25.720 | 3.4609 | 0.2118 | 126 | 20 |
| 18 | 26.520 | 3.3582 | 0.3059 | 123 | 20 |
| 19 | 26.980 | 3.3020 | 0.2588 | 155 | 25 |
| 20 | 28.940 | 3.0827 | 0.2353 | 133 | 21 |
| 21 | 30.340 | 2.9436 | 0.2353 | 135 | 22 |

Example 40-B monopotassium (cis-3-(((1R)-1-((7-fluoro-1,1-dimethyl-2,3-dihydro-1H-inden-5-yl)carbamoyl)-6-(methoxymethyl)-3,4-dihydroisoquinolin-2(1H)-yl)carbonyl)cyclobutyl)acetate methyl ethyl ketone solvate Monopotassium (cis-3-((1R)-1-((7-fluoro-1,1-dimethyl-2,3-dihydro-1H-inden-5-yl)carbamoyl)-6-(methoxymethyl)-3,4-dihydroisoquinolin-2(1H)-yl)carbonyl)cyclobutyl)acetate acetonitrile solvate (30 mg, 0.05 mmol) was dissolved in MEK (2 mL), and the solution was stood to give the title compound (21.2 mg, 0.038 mmol, 71%) as white crystals.

¹H NMR (300 MHz, CD₃OD): δ1.36 (s, 6H), 1.87-2.11 (m, 4H), 2.20-2.39 (m, 2H), 2.38-2.58 (m, 2H), 2.60-2.77 (m, 1H), 2.91 (t, J=7.36 Hz, 3H), 3.12-3.27 (m, 1H), 3.36-3.50 (m, 4H), 3.55-3.77 (m, 1H), 3.93-4.11 (m, 1H), 4.46 (s, 2H), 5.75 (s, 1H), 7.12 (s, 2H), 7.23 (s, 2H), 7.48 (d, J=8.31 Hz, 1H) (The exchangeable 1H was not observed. The signals of MEK were omitted).

The crystallinity by powder X-RAY diffraction was 62.5%.

The peaks by powder X-RAY diffraction were below.

TABLE 3

| No. | 2θ | d value | peak search-set width | intensity (cps) | relative intensity |
|---|---|---|---|---|---|
| 1 | 4.940 | 17.8735 | 0.2118 | 1885 | 100 |
| 2 | 6.720 | 13.1426 | 0.2118 | 421 | 23 |
| 3 | 7.420 | 11.9042 | 0.2353 | 488 | 26 |
| 4 | 10.900 | 8.1102 | 0.2118 | 284 | 16 |
| 5 | 14.880 | 5.9487 | 0.2118 | 623 | 34 |
| 6 | 15.360 | 5.7638 | 0.2118 | 1335 | 71 |
| 7 | 15.680 | 5.6469 | 0.1647 | 309 | 17 |
| 8 | 17.260 | 5.1334 | 0.2118 | 506 | 27 |
| 9 | 17.580 | 5.0407 | 0.2118 | 253 | 14 |
| 10 | 18.060 | 4.9078 | 0.1882 | 232 | 13 |
| 11 | 18.440 | 4.8075 | 0.1882 | 301 | 16 |
| 12 | 19.000 | 4.6670 | 0.2118 | 219 | 12 |
| 13 | 20.440 | 4.3414 | 0.2588 | 285 | 16 |
| 14 | 20.700 | 4.2874 | 0.1647 | 315 | 17 |
| 15 | 21.000 | 4.2268 | 0.1882 | 239 | 13 |
| 16 | 21.560 | 4.1183 | 0.3529 | 369 | 20 |
| 17 | 22.020 | 4.0333 | 0.4235 | 422 | 23 |
| 18 | 22.480 | 3.9518 | 0.2118 | 279 | 15 |
| 19 | 23.240 | 3.8243 | 0.2118 | 695 | 37 |
| 20 | 23.700 | 3.7511 | 0.1882 | 310 | 17 |
| 21 | 27.340 | 3.2594 | 0.2118 | 258 | 14 |
| 22 | 29.740 | 3.0016 | 0.2118 | 215 | 12 |

Example 42-A (cis-3-(((5R)-5-((7-fluoro-1,1-dimethyl-2,3-dihydro-1H-inden-5-yl)carbamoyl)-2-methoxy-7,8-dihydro-1,6-naphthyridin-6(5H)-yl)carbonyl)cyclobutyl)acetic acid monosulfate hemihydrate 0.126M Sulfuric acid/THF (13.24 mL, 1.67 mmol) solution was added to a solution of (cis-3-(((5R)-5-((7-fluoro-1,1-dimethyl-2,3-dihydro-1H-inden-5-yl)carbamoyl)-2-methoxy-7,8-dihydro-1,6-naphthyridin-6(5H)-yl)carbonyl)cyclobutyl)acetic acid (850 mg, 1.67 mmol) in THF (20 mL) at room temperature. The mixture was concentrated under reduced pressure to dryness, and the solid was collected by filtration with ethyl acetate (20 mL) to give (cis-3-(((5R)-5-((7-fluoro-1,1-dimethyl-2,3-dihydro-1H-inden-5-yl)carbamoyl)-2-methoxy-7,8-dihydro-1,6-naphthyridin-6(5H)-yl)carbonyl)cyclobutyl)acetic acid monosulfate (980.1 mg, 1.613 mmol, 97%) as a white solid.

The obtained (cis-3-(((5R)-5-((7-fluoro-1,1-dimethyl-2,3-dihydro-1H-inden-5-yl)carbamoyl)-2-methoxy-7,8-dihydro-1,6-naphthyridin-6(5H)-yl)carbonyl)cyclobutyl)acetic acid monosulfate (300 mg, 0.49 mmol) was dissolved in MEK (600 μL) while warming at water-bath (60° C.). After changing to an oil, the oil was stood overnight at room temperature. The precipitated white crystals were stood at refrigerator for several weeks to give the title compound.

The crystallinity by powder X-RAY diffraction was 49.1%.

The peaks by powder X-RAY diffraction were below.

TABLE 4

| No. | 2θ | d value | peak search-set width | intensity (cps) | relative intensity |
|---|---|---|---|---|---|
| 1 | 4.040 | 21.8530 | 0.4471 | 432 | 41 |
| 2 | 8.620 | 10.2495 | 0.2353 | 435 | 41 |
| 3 | 11.060 | 7.9932 | 0.2353 | 421 | 40 |
| 4 | 13.820 | 6.4025 | 0.1882 | 292 | 28 |
| 5 | 16.600 | 5.3360 | 0.2588 | 558 | 53 |
| 6 | 17.240 | 5.1393 | 0.2118 | 1063 | 100 |
| 7 | 18.240 | 4.8597 | 0.4000 | 475 | 45 |
| 8 | 18.900 | 4.6915 | 0.1882 | 262 | 25 |
| 9 | 19.340 | 4.5857 | 0.2588 | 407 | 39 |
| 10 | 19.880 | 4.4624 | 0.2118 | 372 | 35 |
| 11 | 20.380 | 4.3540 | 0.1882 | 475 | 45 |

TABLE 4-continued

| No. | 2θ | d value | peak search-set width | intensity (cps) | relative intensity |
|---|---|---|---|---|---|
| 12 | 21.100 | 4.2070 | 0.2588 | 587 | 56 |
| 13 | 21.860 | 4.0625 | 0.2588 | 483 | 46 |
| 14 | 22.200 | 4.0010 | 0.2118 | 848 | 80 |
| 15 | 22.540 | 3.9414 | 0.2118 | 597 | 57 |
| 16 | 23.560 | 3.7730 | 0.2118 | 476 | 45 |
| 17 | 23.960 | 3.7109 | 0.2118 | 433 | 41 |
| 18 | 24.440 | 3.6391 | 0.1882 | 310 | 30 |
| 19 | 25.280 | 3.5201 | 0.2118 | 332 | 32 |
| 20 | 25.720 | 3.4609 | 0.1647 | 535 | 51 |
| 21 | 25.940 | 3.4320 | 0.1882 | 778 | 74 |
| 22 | 26.340 | 3.3808 | 0.4000 | 298 | 29 |
| 23 | 28.880 | 3.0890 | 0.2118 | 344 | 33 |

Example 42-B (cis-3-(((5R)-5-((7-fluoro-1,1-dimethyl-2,3-dihydro-1H-inden-5-yl)carbamoyl)-2-methoxy-7,8-dihydro-1,6-naphthyridin-6(5H)-yl)carbonyl)cyclobutyl)acetic acid monosulfate monohydrate To a solution of (cis-3-(((5R)-5-((7-fluoro-1,1-dimethyl-2,3-dihydro-1H-inden-5-yl)carbamoyl)-2-methoxy-7,8-dihydro-1,6-naphthyridin-6(5H)-yl) carbonyl)cyclobutyl) acetic acid (5 g, 9.81 mmol) in MEK (50.0 mL) was added a mixture of sulfuric acid (0.575 mL, 10.79 mmol) and acetic acid (2.292 mL, 40.03 mmol). To the mixture were added acetonitrile (25.00 mL) and the seed crystals obtained in Example 42-A, and the mixture was stirred at 60° C. for 1 hr. Then, cyclopropylmethyl ether (50.0 mL) was added thereto, and the mixture was stirred at 60° C. for 2 hr, and then at room temperature for 16 hr. The mixture was cooled in ice bath, and the precipitate was collected by filtration, and washed with MEK (30 mL). The crystals were dried to give a pale-brown solid (4.82 g, 7.93 mmol, 81%). To the obtained solid was added MEK (96 mL), and the mixture was suspended at 60° C. for 1 hr, and cooled, and the precipitate was collected by filtration, and washed with MEK (20 mL). The crystals were dried at 50° C. under reduced pressure to give the title compound (4.30 g, 6.87 mmol, 70.0%) as white crystals.

$^1$H NMR (300 MHz, DMSO-d$_6$): δ1.29 (6H, s), 1.75-1.95 (4H, m), 2.24-2.40 (4H, m), 2.43-2.49 (1H, m), 2.53-2.59 (1H, m), 2.77-2.91 (3H, m), 2.98 (1H, dt, J=16.7, 4.8 Hz), 3.37 (1H, quin, J=8.8 Hz), 3.77 (1H, dt, J=13.0, 5.4 Hz), 3.83 (3H, s), 3.96 (1H, ddd, J=12.9, 8.6, 4.5 Hz), 5.72 (1H, s), 6.73 (1H, d, J=8.7 Hz), 7.19 (1H, s), 7.23 (1H, d, J=12.5 Hz), 7.79 (1H, d, J=8.7 Hz), 8.43 (4H, brs), 10.51 (1H, s).
[α]$_D^{25}$+86.2 (c 0.2520, MeOH)
The crystallinity by powder X-RAY diffraction was 57.7%.
The peaks by powder X-RAY diffraction were below.

TABLE 5

| No | 2θ | d value | peak search-set width | intensity (cps) | relative intensity |
|---|---|---|---|---|---|
| 1 | 4.060 | 21.7454 | 0.2118 | 887 | 84 |
| 2 | 8.620 | 10.2495 | 0.2118 | 571 | 54 |
| 3 | 8.980 | 9.8394 | 0.1882 | 368 | 35 |
| 4 | 11.000 | 8.0367 | 0.2353 | 463 | 44 |
| 5 | 13.780 | 6.4210 | 0.2118 | 332 | 32 |
| 6 | 15.500 | 5.7121 | 0.1647 | 267 | 26 |
| 7 | 15.800 | 5.6043 | 0.3059 | 270 | 26 |
| 8 | 16.600 | 5.3360 | 0.2118 | 731 | 70 |
| 9 | 17.200 | 5.1512 | 0.2118 | 1059 | 100 |
| 10 | 18.060 | 4.9078 | 0.2353 | 435 | 42 |
| 11 | 18.300 | 4.8439 | 0.2353 | 399 | 38 |
| 12 | 19.240 | 4.6093 | 0.2588 | 348 | 33 |
| 13 | 19.760 | 4.4892 | 0.2588 | 326 | 31 |
| 14 | 20.340 | 4.3625 | 0.2118 | 352 | 34 |
| 15 | 21.060 | 4.2149 | 0.2118 | 594 | 57 |
| 16 | 21.440 | 4.1411 | 0.1647 | 323 | 31 |
| 17 | 21.820 | 4.0698 | 0.2353 | 614 | 58 |
| 18 | 22.160 | 4.0081 | 0.1882 | 780 | 74 |
| 19 | 22.440 | 3.9588 | 0.1647 | 514 | 49 |
| 20 | 23.660 | 3.7573 | 0.2353 | 531 | 51 |
| 21 | 24.400 | 3.6450 | 0.1882 | 314 | 30 |
| 22 | 25.240 | 3.5256 | 0.2118 | 314 | 30 |
| 23 | 25.720 | 3.4609 | 0.2118 | 567 | 54 |
| 24 | 28.900 | 3.0869 | 0.2824 | 314 | 30 |

Example 43 cis-3-(((5R)-5-((7-fluoro-1,1-dimethyl-2,3-dihydro-1H-inden-5-yl)carbamoyl)-2-methoxy-7,8-dihydro-1,6-naphthyridin-6(5H)-yl)carbonyl)cyclobutanecarboxylic acid monosulfate 0.126M Sulfuric acid/THF (8.01 mL, 1.01 mmol) solution was added to a solution of cis-3-(((5R)-5-((7-fluoro-1,1-dimethyl-2,3-dihydro-1H-inden-5-yl)carbamoyl)-2-methoxy-7,8-dihydro-1,6-naphthyridin-6(5H)-yl)carbonyl) cyclobutanecarboxylic acid (500 mg, 1.01 mmol) in THF (10 mL) at room temperature. The mixture was concentrated under reduced pressure to dryness, and the solid was collected by filtration with ethyl acetate (10 mL) to give the title compound (548.3 mg, 0.924 mmol, 92%) as a white solid.

$^1$H NMR (300 MHz, DMSO-d$_6$): δ1.25-1.32 (6H, m), 1.87 (2H, t, J=7.4 Hz), 2.20-2.44 (4H, m), 2.76-2.91 (3H, m), 2.92-3.09 (2H, m), 3.35-3.51 (1H, m), 3.69-3.80 (1H, m), 3.82 (3H, s), 3.90-4.02 (1H, m), 5.46-5.79 (1H, m), 6.72 (1H, d, J=8.3 Hz), 7.13-7.31 (2H, m), 7.69-7.86 (1H, m), 10.39-10.62 (1H, m), 12.13 (1H, brs) (The exchangeable 2H was not observed).

Example 44

(5-methyl-2-oxo-1,3-dioxol-4-yl)methyl cis-3-(((5R)-5-((7-fluoro-1,1-dimethyl-2,3-dihydro-1H-inden-5-yl)carbamoyl)-2-methoxy-7,8-dihydro-1,6-naphthyridin-6(5H)-yl)carbonyl) cyclobutanecarboxylate 4-Chloromethyl-5-methyl-1,3-dioxolan-2-one (0.026 mL, 0.24 mmol) was added to a mixture of cis-3-(((5R)-5-((7-fluoro-1,1-dimethyl-2,3-dihydro-1H-inden-5-yl)carbamoyl)-2-methoxy-7,8-dihydro-1,6-naphthyridin-6(5H)-yl)carbonyl)cyclobutanecarboxylic acid (100 mg, 0.20 mmol) and potassium carbonate (33.5 mg, 0.24 mmol) in DMF (2.0 mL) at room temperature, and the mixture was stirred at room temperature for 5 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 20→50% ethyl acetate/hexane) to give the title compound (58.2 mg, 0.096 mmol, 47.5%) as a white amorphous solid.

$^1$H NMR (300 MHz, DMSO-d$_6$): δ1.29 (6H, s), 1.87 (2H, t, J=7.2 Hz), 2.14 (3H, s), 2.24-2.47 (4H, m), 2.77-2.91 (3H, m), 2.92-3.04 (1H, m), 3.08-3.25 (1H, m), 3.36-3.66 (1H, m), 3.69-3.80 (1H, m), 3.82 (3H, s), 3.88-4.02 (1H, m), 4.94

(2H, s), 5.49-5.73 (H, m), 6.72 (H, d, J=8.3 Hz), 7.12-7.29 (2H, m), 7.72-7.84 (1H, m), 10.38-10.59 (H, m)

Example 45 methyl (cis-3-(((5R)-5-((7-fluoro-1,1-dimethyl-2,3-dihydro-1H-inden-5-yl)carbamoyl)-2-methoxy-7,8-dihydro-1,6-naphthyridin-6 (5H)-yl) carbonyl)cyclobutyl)acetate (Diazomethyl)trimethylsilane (0.6M hexane solution) (0.392 mL, 0.24 mmol) was added to a mixture of (cis-3-(((5R)-5-((7-fluoro-1,1-dimethyl-2,3-dihydro-1H-inden-5-yl)carbamoyl)-2-methoxy-7,8-dihydro-1,6-naphthyridin-6 (5H)-yl)carbonyl)cyclobutyl)acetic acid (60 mg, 0.12 mmol) in THF (1 mL) and MeOH (1 mL) at 5° C., and the mixture was stirred at room temperature for 2 hr. To the reaction mixture were added water and ethyl acetate, the organic layer was separated, and the aqueous layer was extracted with ethyl acetate. The organic layer was washed with brine, and dried over magnesium sulfate, and the solvent was evaporated under reduced pressure. The obtained residue was purified by silica gel column chromatography (solvent gradient; 5→50% ethyl acetate/hexane) to give the title compound (50 mg, 0.095 mmol, 81%) as a colorless oil.

$^1$H NMR (300 MHz, CDCl$_3$): δ1.31 (s, 6H), 1.83-1.93 (m, 2H), 2.05-2.18 (m, 2H), 2.36-2.57 (m, 4H), 2.61-3.09 (m, 5H), 3.24-3.42 (m, 1H), 3.65 (s, 3H), 3.71-3.87 (m, 2H), 3.91 (s, 3H), 5.99 (s, 1H), 6.62 (d, J=8.69 Hz, 1H), 6.99 (s, 1H), 7.04-7.13 (m, 1H), 7.54 (d, J=8.31 Hz, 1H), 9.40 (s, 1H)

Example 46 methyl cis-3-(((5R)-5-((7-fluoro-1,1-dimethyl-2,3-dihydro-1H-inden-5-yl)carbamoyl)-2-methoxy-7,8-dihydro-1,6-naphthyridin-6(5H)-yl) carbonyl)cyclobutanecarboxylate (Diazomethyl)trimethylsilane (0.6M hexane solution) (0.404 mL, 0.24 mmol) was added to a mixture of cis-3-(((5R)-5-((7-fluoro-1,1-dimethyl-2,3-dihydro-1H-inden-5-yl)carbamoyl)-2-methoxy-7,8-dihydro-1,6-naphthyridin-6 (5H)-yl)carbonyl)cyclobutanecarboxylic acid (60 mg, 0.12 mmol) in THF (1 mL) and MeOH (1 mL) at 5° C., and the mixture was stirred at room temperature for 2 hr. To the reaction mixture were added water and ethyl acetate, the organic layer was separated, and the aqueous layer was extracted with ethyl acetate. The organic layer was washed with brine, and dried over magnesium sulfate, and the solvent was evaporated under reduced pressure. The obtained residue was purified by silica gel column chromatography (solvent gradient; 5→50% ethyl acetate/hexane) to give the title compound (50 mg, 0.098 mmol, 81%) as a colorless oil.

$^1$H NMR (300 MHz, CDCl$_3$): δ1.31 (s, 6H), 1.82-1.94 (m, 2H), 2.44-2.75 (m, 4H), 2.77-3.23 (m, 5H), 3.27-3.43 (m, 1H), 3.66 (brs, 1H), 3.71-3.85 (m, 2H), 3.91 (s, 3H), 5.99 (s, 1H), 6.66 (d, J=8.69 Hz, 1H), 6.97-7.05 (m, 1H), 7.06-7.17 (m, 1H), 7.51 (d, J=8.31 Hz, 1H), 9.24 (s, 1H)

Example 47 benzyl (cis-3-(((5R)-5-((7-fluoro-1, 1-dimethyl-2,3-dihydro-1H-inden-5-yl)carbamoyl)-2-methoxy-7,8-dihydro-1,6-naphthyridin-6(5H)-yl)carbonyl)cyclobutyl)acetate Benzyl bromide (84 μL, 0.71 mmol) was added to a mixture of (cis-3-(((5R)-5-((7-fluoro-1,1-dimethyl-2,3-dihydro-1H-inden-5-yl)carbamoyl)-2-methoxy-7,8-dihydro-1,6-naphthyridin-6(5H)-yl)carbonyl)cyclobutyl)acetic acid (300 mg, 0.59 mmol) and potassium carbonate (98 mg, 0.71 mmol) in DMF (5 mL) at room temperature, and the mixture was stirred at room temperature for 2.5 hr. To the reaction mixture was added water (60 mL), and the mixture was extracted with ethyl acetate (×3). The organic layer was washed with water and brine, and dried over magnesium sulfate, and the solvent was evaporated under reduced pressure. The obtained residue was purified by silica gel column chromatography (solvent so gradient; 20→41% ethyl acetate/hexane) to give the title compound (282.3 mg, 0.471 mmol, 80%) as a colorless amorphous solid.

$^1$H NMR (300 MHz, CDCl$_3$): δ1.31 (6H, s), 1.88 (2H, t, J=7.4 Hz), 2.04-2.17 (2H, m), 2.41-2.53 (4H, m), 2.63-2.79 (1H, m), 2.83 (2H, t, J=7.2 Hz), 2.87-3.04 (2H, m), 3.30 (1H, quin, J=8.9 Hz), 3.69 (1H, ddd), 3.84 (1H, dt), 3.91 (3H, s), 5.09 (2H, s), 5.97 (1H, s), 6.63 (1H, d, J=8.7 Hz), 7.01 (1H, s), 7.10 (1H, d, J=11.7 Hz), 7.28-7.38 (5H, m), 7.46 (1H, d, J=8.7 Hz), 9.22 (H, s)

The compounds described in Examples 36 to 48 are below (Table 6-1 to Table 6-3).

TABLE 6-1

| Ex. | IUPAC NAME | Structure | SALT ADDITIVE | MS |
|---|---|---|---|---|
| 36 | benzyl cis-3-(((5R)-5-((7-fluoro-1,1-dimethyl-2,3-dihydro-1H-inden-5-yl)carbamoyl)-2-methoxy-7,8-dihydro-1,6-naphthyridin-6(5H)-yl)carbonyl)cyclobutanecarboxylate | 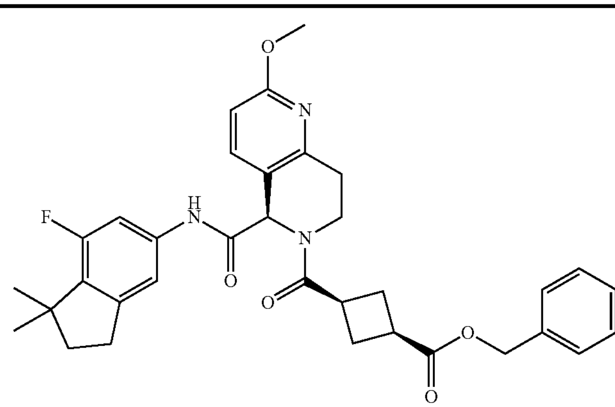 | | 584.3 (M − H) |

TABLE 6-1-continued

| Ex. | IUPAC NAME | Structure | SALT ADDITIVE | MS |
|---|---|---|---|---|
| 37 | tert-butyl (cis-3-(((5R)-5-((7-fluoro-1,1-dimethyl-2,3-dihydro-1H-inden-5-yl)carbamoyl)-2-methoxy-7,8-dihydro-1,6-naphthyridin-6(5H)-yl)carbonyl)cyclobutyl)acetate | 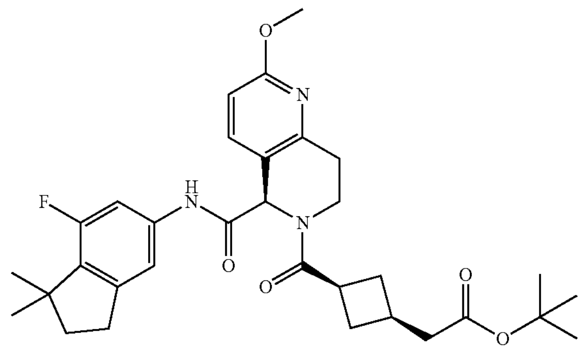 [SMILES: COc1ccc2c(n1)CCN(C(=O)[C@H]1C[C@@H](CC(=O)OC(C)(C)C)C1)[C@H]2C(=O)Nc1cc(F)c2c(c1)CCC2(C)C] | | 566.2 (M + H) |
| 38 | (5-methyl-2-oxo-1,3-dioxol-4-yl)methyl(cis-3-((5R)-5-((7-fluoro-1,1-dimethyl-2,3-dihydro-1H-inden-5-yl)carbamoyl)-2-methoxy-7,8-dihydro-1,6-naphthyridin-6(5H)-yl)carbonyl)cyclobutyl)acetate | 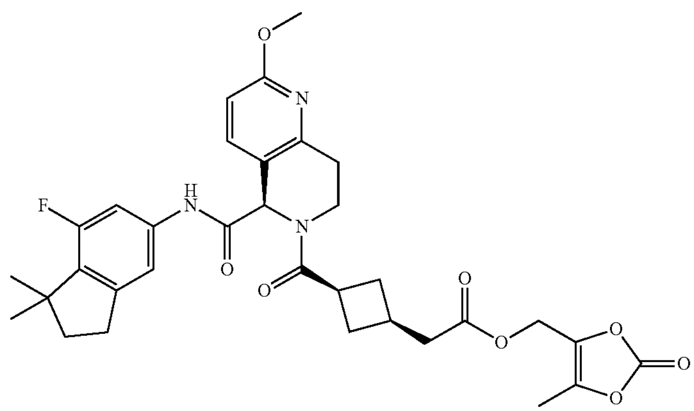 [SMILES: COc1ccc2c(n1)CCN(C(=O)[C@H]1C[C@@H](CC(=O)OCc3oc(=O)oc3C)C1)[C@H]2C(=O)Nc1cc(F)c2c(c1)CCC2(C)C] | | 622.1 (M + H) |
| 39 | ethyl (cis-3-(((5R)-5-((7-fluoro-1,1-dimethyl-2,3-dihydro-1H-inden-5-yl)carbamoyl)-2-methoxy-7,8-dihydro-1,6-naphthyridin-6(5H)-yl)carbonyl)cyclobutyl)acetate | 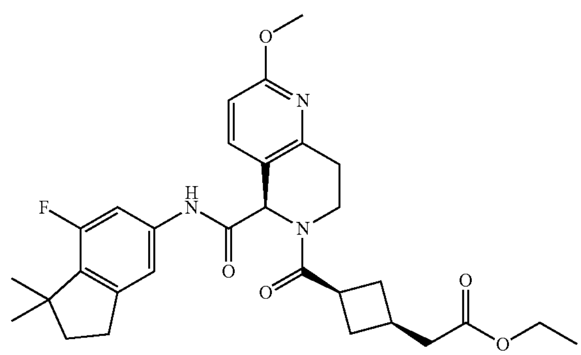 [SMILES: CCOC(=O)C[C@H]1C[C@@H](C(=O)N2CCc3nc(OC)ccc3[C@@H]2C(=O)Nc2cc(F)c3c(c2)CCC3(C)C)C1] | | 536.2 (M − H) |
| 40A | monopotassium (cis-3-(((1R)-1-((7-fluoro-1,1-dimethyl-2,3-dihydro-1H-inden-5-yl)carbamoyl)-6-(methoxymethyl)-3,4-dihydroisoquinolin-2(1H)-yl)carbonyl)cyclobutyl)acetate acetonitrile solvate | 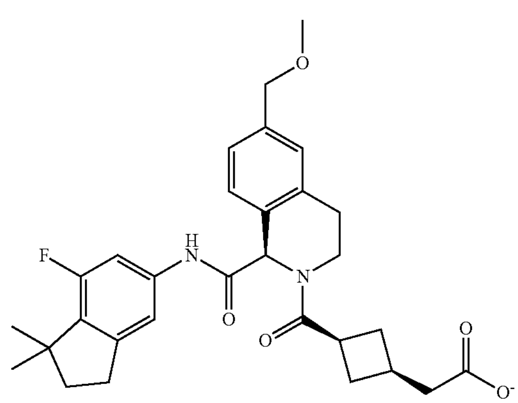 [SMILES: COCc1ccc2c(c1)CCN(C(=O)[C@H]1C[C@@H](CC(=O)[O-])C1)[C@H]2C(=O)Nc1cc(F)c2c(c1)CCC2(C)C] | K | 521.2 (M − H) |

TABLE 6-1-continued

| Ex. | IUPAC NAME | Structure | SALT ADDITIVE | MS |
|---|---|---|---|---|
| 40B | monopotassium (cis-3-(((1R)-1-((7-fluoro-1,1-dimethyl-2,3-dihydro-1H-inden-5-yl)carbamoyl)-6-(methoxymethyl)-3,4-dihydroisoquinolin-2(1H)-yl)carbonyl)cyclobutyl)acetate methyl ethyl ketone solvate | 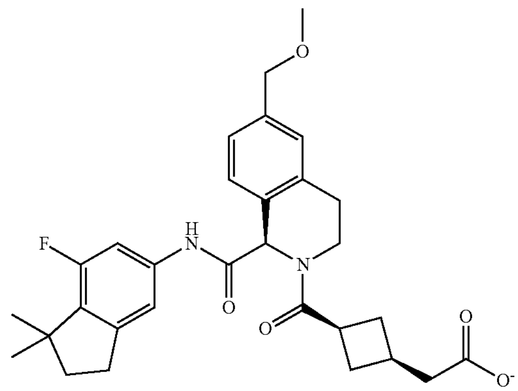 [SMILES: COCc1ccc2c(c1)CCN(C(=O)[C@H]1C[C@@H](CC(=O)[O-])C1)[C@H]2C(=O)Nc1cc(F)c2c(c1)CCC2(C)C] | K | Not tested |

TABLE 6-2

| Ex. | IUPAC NAME | Structure | SALT ADDITIVE | MS |
|---|---|---|---|---|
| 41 | tert-butyl (cis-3-(((1R)-1-((7-fluoro-1,1-dimethyl-2,3-dihydro-1H-inden-5-yl)carbamoyl)-6-(methoxymethyl)-3,4-dihydroisoquinolin-2(1H)-yl)carbonyl)cyclobutyl)acetate | 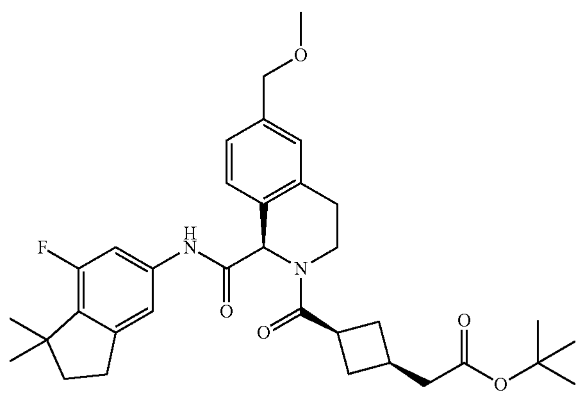 [SMILES: COCc1ccc2c(c1)CCN(C(=O)[C@H]1C[C@@H](CC(=O)OC(C)(C)C)C1)[C@H]2C(=O)Nc1cc(F)c2c(c1)CCC2(C)C] | | 579.2 (M + H) |
| 42A | (cis-3-(((5R)-5-((7-fluoro-1,1-dimethyl-2,3-dihydro-1H-inden-5-yl)carbamoyl)-2-methoxy-7,8-dihydro-1,6-naphthyridin-6(5H)-yl)carbonyl)cyclobutyl)acetic acid monosulfate hemihydrate | 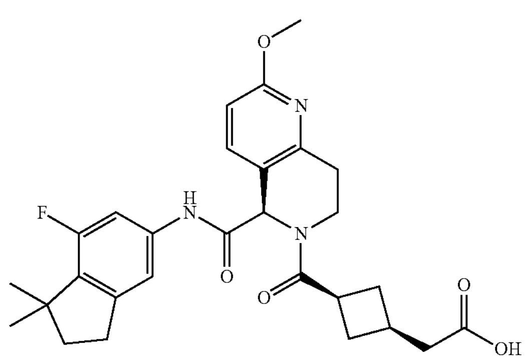 [SMILES: COc1ccc2c(n1)CCN(C(=O)[C@H]1C[C@@H](CC(=O)O)C1)[C@H]2C(=O)Nc1cc(F)c2c(c1)CCC2(C)C] | $H_2SO_4$ 1/2$H_2O$ | 510.3 (M + H) |

TABLE 6-2-continued

| Ex. | IUPAC NAME | Structure | SALT ADDITIVE | MS |
|---|---|---|---|---|
| 42B | (cis-3-(((5R)-5-((7-fluoro-1,1-dimethyl-2,3-dihydro-1H-inden-5-yl)carbamoyl)-2-methoxy-7,8-dihydro-1,6-naphthyridin-6(5H)-yl)carbonyl)cyclobutyl)acetic acid monosulfate monohydrate | 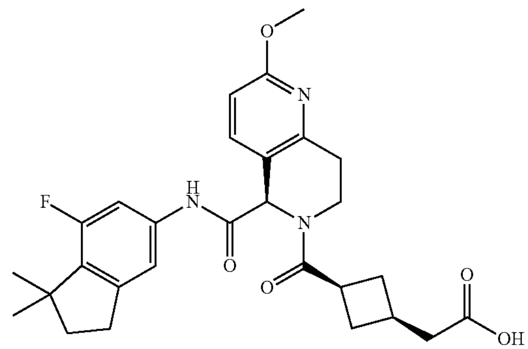 [SMILES: COc1ccc2c(n1)CCN(C(=O)[C@H]1C[C@@H](CC(=O)O)C1)[C@H]2C(=O)Nc1cc(F)c2c(c1)CCC2(C)C] | $H_2SO_4$ $H_2O$ | 510.3 (M + H) |
| 43 | cis-3-(((5R)-5-((7-fluoro-1,1-dimethyl-2,3-dihydro-1H-inden-5-yl)carbamoyl)-2-methoxy-7,8-dihydro-1,6-naphthyridin-6(5H)-yl)carbonyl)cyclobutanecarboxylic acid monosulfate | 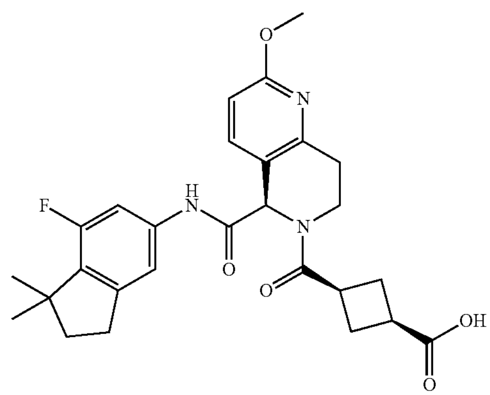 [SMILES: COc1ccc2c(n1)CCN(C(=O)[C@H]1C[C@@H](C(=O)O)C1)[C@H]2C(=O)Nc1cc(F)c2c(c1)CCC2(C)C] | $H_2SO_4$ | 494.2 (M − H) |
| 44 | (5-methyl-2-oxo-1,3-dioxol-4-yl)methyl cis-3-(((5R)-5-((7-fluoro-1,1-dimethyl-2,3-dihydro-1H-inden-5-yl)carbamoyl)-2-methoxy-7,8-dihydro-1,6-naphthyridin-6(5H)-yl)carbonyl)cyclobutanecarboxylate | 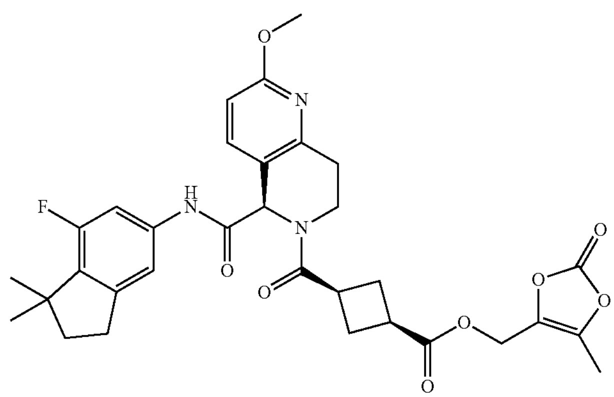 [SMILES: COc1ccc2c(n1)CCN(C(=O)[C@H]1C[C@@H](C(=O)OCc3oc(=O)oc3C)C1)[C@H]2C(=O)Nc1cc(F)c2c(c1)CCC2(C)C] | | 608.1 (M + H) |
| 45 | methyl (cis-3-(((5R)-5-((7-fluoro-1,1-dimethyl-2,3-dihydro-1H-inden-5-yl)carbamoyl)-2-methoxy-7,8-dihydro-1,6-naphthyridin-6(5H)-yl)carbonyl)cyclobutyl)acetate | 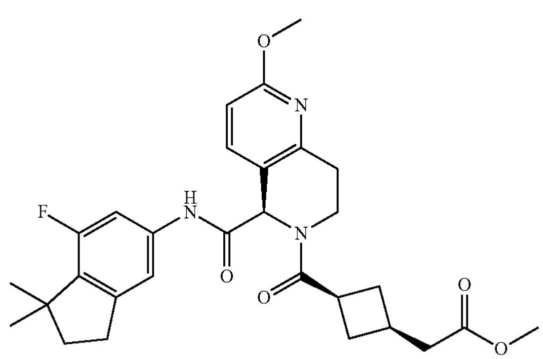 | | 524.2 (M + H) |

TABLE 6-3

| Ex. | IUPAC NAME | Structure | SALT ADDITIVE | MS |
|---|---|---|---|---|
| 46 | methyl cis-3-(((5R)-5-((7-fluoro-1,1-dimethyl-2,3-dihydro-1H-inden-5-yl)carbamoyl)-2-methoxy-7,8-dihydro-1,6-naphthyridin-6(5H)-yl)carbonyl)cyclobutanecarboxylate | 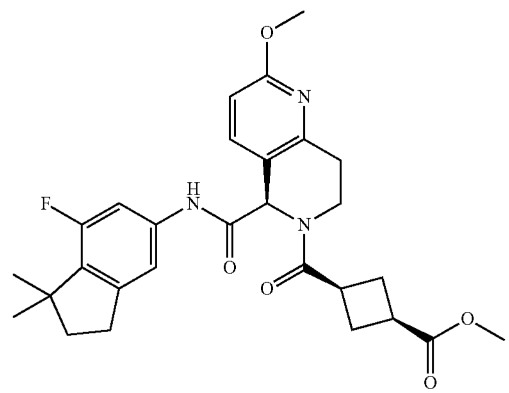 | | 508.2 (M − H) |
| 47 | benzyl (cis-3-(((5R)-5-((7-fluoro-1,1-dimethyl-2,3-dihydro-1H-inden-5-yl)carbamoyl)-2-methoxy-7,8-dihydro-1,6-naphthyridin-6(5H)-yl)carbonyl)cyclobutyl)acetate | 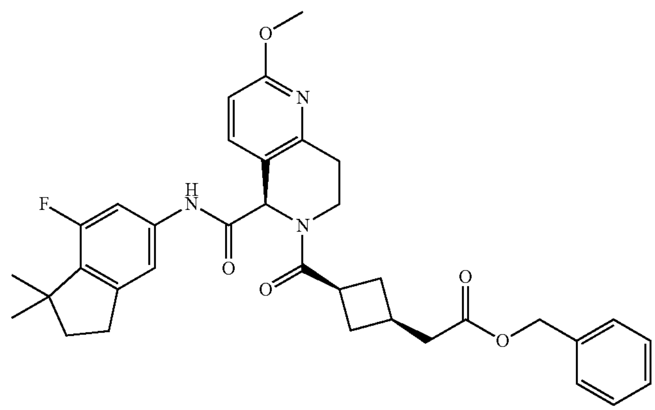 [SMILES: COc1ccc2c(n1)CCN(C(=O)[C@H]1C[C@@H](CC(=O)OCc3ccccc3)C1)[C@H]2C(=O)Nc1cc(F)c2c(c1)CCC2(C)C] | | 600.2 (M + H) |
| 48 | methyl (cis-3-(((1R)-1-((7-fluoro-1,1-dimethyl-2,3-dihydro-1H-inden-5-yl)carbamoyl)-6-(methoxymethyl)-3,4-dihydroisoquinolin-2(1H)-yl)carbonyl)cyclobutyl)acetate | 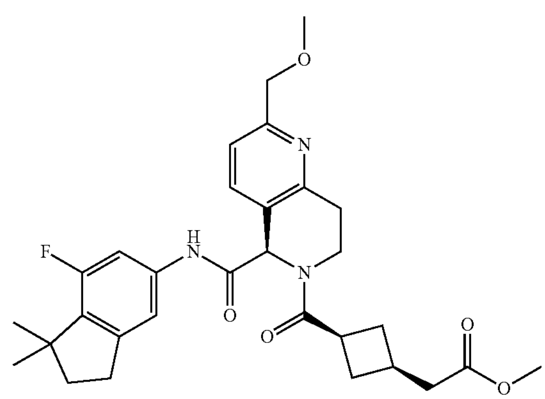 | | 537.3 (M + H) |

The compounds described in Examples 37, 41 and 48 were synthesized in the same manner as in the reaction and purification described in the above-mentioned Examples.

Experimental Example 1

RORγt Binding Test Using Fluorescent-Labeled Synthetic Ligand

The fluorescent-labeled synthetic ligand was synthesized as follows.
(Step 1)
A solution of (4-(methoxymethyl)phenyl)boronic acid (999 mg, 6.02 mmol), glyoxylic acid monohydrate (554 mg, 6.02 mmol) and diallylamine (0.741 mL, 6.02 mmol) in acetonitrile (12 mL) was stirred at 60° C. for 5 hr. The reaction mixture was concentrated under reduced pressure. The obtained residue was purified by silica gel column chromatography (Diol, solvent; ethyl acetate), and crystallized from ethyl acetate/hexane to give 2-(diallylamino)-2-(4-(methoxymethyl)phenyl)acetic acid (200 mg, 0.726 mmol, 12.07%) as crystals.
$^1$H NMR (300 MHz, DMSO-d$_6$): δ 3.04-3.46 (7H, m), 4.39 (2H, s), 4.43 (1H, s), 5.04-5.23 (4H, m), 5.78 (2H, ddt, J=16.9, 10.5, 6.3 Hz), 7.23-7.40 (4H, m).
(Step 2)
To a solution of 3,5-difluoro-4-(trimethylsilyl)aniline (5 g, 24.84 mmol), 2-(diallylamino)-2-(4-(methoxymethyl)

phenyl)acetic acid (8.21 g, 29.81 mmol), DMAP (3.34 g, 27.32 mmol) and DIEA (21.69 mL, 124.20 mmol) in ethyl acetate (150 mL) was added T3P (29.2 mL, 49.68 mmol), and the mixture was stirred at 80° C. for 2 hr. To the reaction mixture were added water and ethyl acetate, and the organic layer was separated. The organic layer was washed with water and brine, and dried over magnesium sulfate, and the solvent was evaporated under reduced pressure. The obtained residue was purified by silica gel column chromatography (solvent gradient; 0→10% ethyl acetate/hexane) to give 2-(diallylamino)-N-(3,5-difluoro-4-(trimethylsilyl)phenyl)-2-(4-(methoxymethyl)phenyl)acetamide (6.79 g, 14.81 mmol, 59.6%) as a pale-yellow oil. This compound was used for the next step without further purification.

(Step 3)

To a solution of 2-(diallylamino)-N-(3,5-difluoro-4-(trimethylsilyl)phenyl)-2-(4-(methoxymethyl)phenyl)acetamide (6.79 g, 14.81 mmol) and 1,3-dimethylbarbituric acid (4.85 g, 31.09 mmol) in THF (120 mL) was added Pd(PPh$_3$)$_4$ (0.684 g, 0.59 mmol), and the mixture was stirred overnight at room temperature under argon atmosphere. The reaction solution was concentrated, and the obtained residue was purified by silica gel column chromatography (NH, solvent gradient; 50→100% ethyl acetate/hexane) to give crude 2-amino-N-(3,5-difluoro-4-(trimethylsilyl)phenyl)-2-(4-(methoxymethyl)phenyl)acetamide (4.00 g) as a colorless oil.

(Step 4)

To a solution of the crude 2-amino-N-(3,5-difluoro-4-(trimethylsilyl)phenyl)-2-(4-(methoxymethyl)phenyl)acetamide (9.07 mg, 0.02 mmol) in DMF (0.5 mL) was added 1-((5-((2Z)-2-((1-(difluoroboryl)-3,5-dimethyl-1H-pyrrol-2-yl)methylene)-2H-pyrrol-5-yl)pentanoyl)oxy)pyrrolidine-2,5-dione (BODIPY (registered trademark) FL-C5 succinimidyl ester) (5.0 mg, 0.01 mmol) at room temperature, and the mixture was stirred at room temperature for 3 hr. To the reaction mixture was added water, and the mixture was extracted with ethyl acetate. The organic layer was washed with water and brine, and dried over magnesium sulfate, and the solvent was evaporated under reduced pressure. The obtained residue was purified by silica gel column chromatography (solvent; ethyl acetate/hexane), and then preparative HPLC (C18, mobile phase: water/acetonitrile (containing 0.1% TFA)) to give 5-((2Z)-2-((1-(difluoroboryl)-3,5-dimethyl-1H-pyrrol-2-yl)methylene)-2H-pyrrol-5-yl)-N-(2-((3,5-difluoro-4-(trimethylsilyl)phenyl)amino)-1-(4-(methoxymethyl)phenyl)-2-oxoethyl)pentanamide (3.8 mg, 5.58 μmol, 46.6%) as an orange solid, which is a fluorescent-labeled synthetic ligand.

$^1$H NMR (300 MHz, CDCl$_3$): δ0.31 (9H, t, J=1.3 Hz), 1.71-1.87 (4H, m), 2.25 (3H, s), 2.32-2.42 (2H, m), 2.53 (3H, s), 2.91-3.03 (2H, m), 3.35 (3H, s), 4.40 (2H, s), 5.71 (1H, d, J=7.2 Hz), 6.09 (1H, s), 6.23 (1H, d, J=4.2 Hz), 6.80-6.90 (2H, m), 6.90-6.99 (2H, m), 7.06 (1H, s), 7.23-7.31 (2H, m), 7.33-7.42 (2H, m), 8.63 (1H, s).

MS(API): Calculated 680.6. Found 679.4 (M-H).

The binding activity of the test compound to RORγt was measured by a time resolved fluorescence resonance energy transfer method (TR-FRET) utilizing histidine-tagged RORγt, fluorescent-labeled synthetic ligand and terbium-labeled anti-histidine tag antibody (Invitrogen). First, a test compound diluted with an assay buffer (20 mM Tris-HCl (pH 7.5), 100 mM NaCl, 1 mM DTT, 0.1% BSA) was added to a 384 well plate by 3 L. Then, RORγt diluted with an assay buffer to 240 nM was added by 3 μL, after which fluorescent-labeled synthetic ligand diluted with the assay buffer to 12 μM was added by 3 μL, and the mixture was stood at room temperature for 20 min. Thereafter, a terbium-labeled anti-histidine tag antibody diluted with the assay buffer to 8 nM was added by 3 μL. The mixture was stood at room temperature for 20 min, and fluorescence intensity (excitation wavelength 320 nm, fluorescence wavelength 520 nm, delay time 100 microseconds) was measured by Envision (PerkinElmer).

The results (binding inhibitory rate of fluorescent-labeled synthetic ligand to RORγt at test compound 1 μM) measured by the above-mentioned method are shown in Table 7.

Experimental Example 2

Cofactor Recruitment Test

Cofactor recruitment test was performed by Alpha Screen (Histidine Detection Kit, PerkinElmer) method. First, a test compound was diluted with an assay buffer (50 mM Tris-HCl (pH 7.5), 50 mM KCl, 1 mM DTT, 0.1% BSA) and added to a 384 well plate by 5 μL. Then, RORγt diluted with an assay buffer to 125 nM was added by 10 μL each, after which solutions of 25 nM biotinylated SRC-1 peptide (biotin-CLTARHKILHRLLQEGSPSD), 12.5 μg/mL acceptor beads and 12.5 μg/mL donor beads prepared with the assay buffer were added by 10 μL each. The mixture was stood in a dark place for 1 hr, and the signal value was measured by Envision (PerkinElmer).

The results (signal value inhibitory rate at test compound 1 μM) measured by the above-mentioned method are shown in Table 7.

Experimental Example 3

Jurkat Reporter Test

The Jurkat cells used for the reporter test were cultured in a culture medium (RPMI (Invitrogen), 10% FCS (AusGeneX), 100 U/mL penicillin, 100 μg/mL streptomycin). On the day of the test, 4×10$^7$ cells were recovered by a centrifugal operation (1000 rpm, 5 min.) and suspended in PBS (phosphate buffered saline) (Invitrogen). Thereafter, the cells were recovered again by a centrifugal operation, and suspended in 2 mL of R buffer (NEON transfection kit, Invitrogen). Then, a reporter vector (53 μg) wherein a human IL-17 ROR response element was inserted into the upstream of luciferase of pGL 4.28 (Promega), and a vector (27 μg) wherein RORγt sequence was inserted into the downstream of CMV promoter were added to the cell suspension. Gene transfer was performed by Electroporation apparatus (NEON, Invitrogen) under the conditions of pulse voltage 1350 V, interval 10 milliseconds, number of times 3. The cells after gene transfer were suspended in 40 mL of a reaction medium (RPMI, 10% Lipid reduced FCS (HyClone), 10 mM HEPES (pH 7.5), 100 U/mL penicillin, 100 μg/mL streptomycin, 5 μM lovastatin), and plated in a 96 well plate by 90 μL. A test compound diluted with the reaction medium was added by 10 μL, and the cells were cultured overnight in an incubator. Bright-Glo (Promega) was added by 100 μL, and the mixture was stirred at room temperature for 10 min, and the luminescence level was measured by Envision (PerkinElmer).

The results (luminescence level inhibitory rate at test compound 3 μM) measured by the above-mentioned method are shown in Table 7.

TABLE 7

| Ex. No. | Experimental Example 1 binding inhibitory rate of fluorescent-labeled synthetic ligand to RORγt at test compound 1 μM (%) | Experimental Example 2 signal value inhibitory rate at test compound 1 μM (%) | Experimental Example 3 luminescence level inhibitory rate at test compound 3 μM (%) |
|---|---|---|---|
| 3 | 102% | 84% | 97% |
| 4 | 102% | 94% | 100% |
| 5 | 102% | 93% | 100% |
| 6 | 102% | 54% | 97% |
| 8 | 102% | 90% | 100% |
| 9 | 102% | 88% | 99% |
| 10 | 102% | 62% | 98% |
| 11 | 102% | 58% | 98% |
| 12 | 102% | 91% | 99% |
| 13 | 102% | 83% | 104% |
| 14 | 101% | 86% | 100% |
| 15 | 102% | 60% | 99% |
| 17 | 101% | 85% | 99% |
| 18 | 101% | 70% | 97% |
| 19 | 101% | 82% | 99% |
| 20 | 101% | 54% | 98% |
| 23 | 102% | 87% | 101% |
| 24 | 101% | 80% | 101% |
| 25 | 102% | 93% | 101% |
| 27 | 102% | 91% | 103% |
| 28 | 102% | 87% | 101% |
| 29 | 102% | 91% | 102% |
| 30 | 101% | 90% | 100% |
| 31 | 102% | 86% | 102% |
| 32 | 102% | 91% | 101% |
| 33 | 102% | 92% | 102% |
| 34 | 102% | 88% | 100% |
| 35 | 102% | 83% | 99% |
| 36 | 102% | 72% | 102% |
| 38 | 102% | 61% | 102% |
| 39 | 101% | 63% | 103% |
| 40-A | 102% | 87% | 104% |
| 43 | 102% | 62% | 102% |
| 44 | 102% | 61% | 102% |
| 45 | 101% | 66% | 101% |
| 46 | 102% | 69% | 102% |

Experimental Example 4

Effect on IL-17 Production in Human Blood

The inhibitory effect of the test compound on IL-17 production in human blood was evaluated as follows. First, 150 μL of peripheral blood collected from healthy individuals using heparinized vacuum blood collection tubes was dispensed into each well of a 96-well plate (Corning), and 45 μL of RPMI 1640 medium (Gibco) containing 10% fetal bovine serum (FBS, Hyclone) and 30 μL of the test compound diluted with the medium were added to each well. The plate was then cultured for 30 min at 37° C. The cells were subsequently stimulated by adding 30 μL of 100 ng/mL human IL-23 (R&D) and 45 μL of Dynabeads Human (Invitrogen) to each well and culturing the plate for 3 days at 37° C. In wells without stimulation, 75 μL of RPMI 1640 medium containing 10% FBS was added instead of the IL-23 and Dynabeads solution. After culturing for 3 days, the culture supernatant was collected, and the amount of IL-17 in the supernatant was measured using an IL-17 ELISA kit (R&D).

The results (percent inhibition of IL-17 production with 10 μM of the test compound) measured by the above-mentioned method are shown in Table 8.

TABLE 8

| Example number | percent inhibition at 10 μM |
|---|---|
| 4 | 88.3% |
| 5 | 88.6% |
| 6 | 86.6% |
| 8 | 82.9% |
| 9 | 93.5% |
| 10 | 89.7% |
| 15 | 94.0% |
| 18 | 80.0% |
| 19 | 94.1% |
| 23 | 85.9% |
| 24 | 92.7% |
| 28 | 89.1% |
| 29 | 74.9% |
| 31 | 89.8% |
| 33 | 78.5% |

The results above showed that the example compounds inhibited IL-17 production in human blood.

Experimental Example 5

Effect on IL-23-Induced Cytokine Expression in Mice

A mouse IL-23 solution (500 ng/10 μL, prepared by Takeda Pharmaceutical Company Limited) or PBS (10 μL, negative control group) was administered intradermally in the ear of Balb/c mice (Charles River Japan, male, 7 weeks old). Twenty-four hr after administration, the ear was resected under isoflurane anesthesia. The test compound was suspended in 0.5% methylcellulose and administered orally 30 min before and 8 hr after IL-23 administration.

RNA extraction from the ear tissue and quantitative PCR were performed as follows. Specifically, ear tissue 5 mm in diameter was punched from an area of the resected ear centering on the IL-23 injection site, and the tissue was immersed in RNAlater (QIAGEN) for at least 18 hr. The RNAlater-treated ear tissue was homogenized in 350 μL of RLT buffer (RNeasy mini kit, QIAGEN) and treated (55° C., 10 min) with Proteinase K (QIAGEN). Total RNA was then extracted according to the RNeasy mini kit protocol. The RNA thus obtained was then reverse transcribed into cDNA using the High-Capacity RNA-to-cDNA kit (Applied Biosystems), and the amount of each gene expressions was measured by real-time PCR (Viia7™, Applied Biosystems). The PCR buffer used was TaqMan Fast Advanced Master Mix (Applied Biosystems), and TaqMan Gene Expression Assays (Applied Biosystems) Mm00439618_m1 (IL-17A) and 4352341E (β-actin) were used for each gene detection. The IL-17A gene expression level was normalized to the β-actin gene expression level, and the percent inhibition of IL-17A gene expression with the test compound was then calculated.

The results (percent inhibition of IL-17A gene expression with oral administration of the test compound) measured by the above-mentioned method are shown in Table 9.

TABLE 9

| Example number | Dose mg/kg | percent inhibition of IL-17A gene expression* |
|---|---|---|
| 4 | 10 | 86% |
| 5 | 10 | 57% |
| 6 | 10 | 95% |
| 8 | 10 | 72% |

TABLE 9-continued

| Example number | Dose mg/kg | percent inhibition of IL-17A gene expression* |
|---|---|---|
| 9 | 10 | 57% |
| 10 | 10 | 87% |
| 13 | 10 | 91% |
| 15 | 3 | 99% |
| 18 | 10 | 72% |
| 19 | 10 | 90% |
| 20 | 10 | 99% |
| 23 | 10 | 96% |
| 24 | 10 | 74% |
| 25 | 10 | 92% |
| 28 | 10 | 91% |
| 29 | 10 | 73% |
| 31 | 10 | 85% |
| 32 | 10 | 83% |
| 33 | 10 | 94% |
| 36 | 10 | 78% |

*versus the negative control group

The results above showed that oral administration of the example compounds inhibited IL-17A gene expression in vivo.

Experimental Example 6

Effect in an IL-23-Induced Mouse Psoriasis Model

Mouse IL-23 (500 ng/15 μL, R&D) or PBS (15 μL, negative control group) was administered intradermally in the ear of Balb/c mice (Charles River Japan, male, 7 weeks old) 5 times every other days. Seven hr after IL-23 administration at 8 days after the initial administration (final administration), the mice were anesthetized with isoflurane, and ear thickness was measured with calipers. After the ear thickness was measured, the ear was resected, tissue 8 mm in diameter was punched from an area centering on the IL-23 injection site, and the tissue was weighed. The punched ear tissue was cut in half, and one half was immersion-fixed in 10% neutral buffer formalin solution for use in histopathological evaluation. The other half was immersed in RNAlater (QIAGEN) for at least 18 hr for use in an evaluation of the IL-17A mRNA expression level. The test compound was suspended in 0.5% methylcellulose and administered orally twice daily on consecutive days from 30 min before the initial IL-23 administration to 30 min before the final IL-23 administration.

The change in ear thickness in this model was evaluated by calculating the difference in measured thickness between before IL-23 administration and 7 hr after the final IL-23 administration. In addition, the formalin-fixed tissue was embedded and sectioned, then stained with hematoxylin-eosin. The degree of acanthosis was then evaluated qualitatively by microscopy (classified with a score of 0 to 4). RNA extraction from the ear tissue and quantitative PCR were performed as follows. As described above, ear tissue treated with RNAlater (QIAGEN) was homogenized in 350 μL of RLT buffer (RNeasy mini kit, QIAGEN) and treated (55° C., 10 min) with Proteinase K (QIAGEN). Total RNA was then extracted according to the RNeasy mini kit protocol. The RNA thus obtained was reverse transcribed into cDNA using the High-Capacity RNA-to-cDNA kit (Applied Biosystems), and the expression of each gene was measured by real-time PCR (Viia7™, Applied Biosystems). The PCR buffer used was TaqMan Fast Advanced Master Mix (Applied Biosystems), and TaqMan Gene Expression Assays (Applied Biosystems) Mm00439618_m1 (IL-17A) and 4352341E (β-actin) were used to detect the genes. The IL-17A gene expression level was normalized to the β-actin gene expression level, and the percent inhibition of IL-17A gene expression with the test compound was then calculated.

The results (percent inhibition of ear thickness, acanthosis score and IL-17A gene expression with oral administration of the test compound) measured by the above-mentioned method are shown in Table 10.

TABLE 10

| Ex. No. | Dose mg/kg | percent inhibition of ear thickness* | percent inhibition of acanthosis score* | percent inhibition of IL-17A expression* |
|---|---|---|---|---|
| 6 | 10 | 64% | 39% | 111% |
| 10 | 1 | 52% | 47% | 91% |
| 15 | 3 | 61% | 53% | 93% |
| 19 | 10 | 40% | 29% | 94% |

*versus the negative control group

Experimental Example 7

Effect in a T Cell-Transferred Mouse Colitis Model

Balb/c mice (Charles River Japan, female, 8 weeks old) were euthanized, and the spleens were resected, mashed in mesh, and passed through cell strainer to prepare a suspension of splenic cells. The mononuclear cell fraction in the splenic cells was isolated by density-gradient centrifugation, and subjected to hemolysis treatment with ammonium chloride buffer solution (Immuno-Biological Laboratories, Co., Ltd.). The naive T-cells were purified using CD4+CD62L+ T Cell Isolation Kit II (Miltenyi Biotec). The naive T-cells ($2\times10^5$ cells/mouse) were intravenously transferred into SCIDmice (CLEA Japan, female, 8 weeks old). The compound was suspended in 0.5% methyl cellulose, and the suspension was orally administered twice daily on consecutive days from the same evening of the cell transfer. The mice were blinded 20 days after the cell transfer, and the symptom of the stool on floorcloth under blind was evaluated by scores of 1 to 4 (1: normal, 2: loose stool, 3: diarrhea (formed), 4: diarrhea (unformed)) 21 days after the cell transfer. The large intestine was resected under isoflurane anesthesia, and the feces were removed. The large intestine was washed with saline, and the weight was measured.

The results (percent inhibition of intestinal tract weight and diarrhea score with oral administration of the test compound) measured by the above-mentioned method are shown in Table 11.

TABLE 11

| Ex. No. | Dose mg/kg | percent inhibition of intestinal tract weight* | percent inhibition of diarrhea score* |
|---|---|---|---|
| 15 | 3 | 58% | 81% |

*versus the negative control group

Experimental Example 8

Effect in a Mouse EAE Model

A solution of $MOG_{35-55}$ (2 mg/mL, BEX, synthesized by commissioning) was mixed in equal amount with FCA (DIFCO) wherein H37Ra (5 mg/mL, DIFCO) was suspended, and the mixture was emulsified using sonicator to give an emulsion. C57BL/6J mice (10 weeks old, female, Charles River Japan) were grouped based on the body weight, and the MOG emulsion was intradermally administered at two point of the joint of dorsal hindlimb so that the dose was 100 μL/site, 200 μL/mouse. In addition, Pertussis toxin (Merck) was intraperitoneally administered twice on the sensitization day and 2 days thereafter in the dose of 400 ng/200 μL/mouse. The body weight was measured twice a week before onset and everyday (excluding holiday) after onset from the sensitization day. The clinical score was evaluated by the following standard scores of 0 to 5 (0: normal, 0.5: partial paralysis of tail, 1: complete paralysis of tail, 2: partial paralysis of hindlimb, 3: paralysis of lower body, 4: partial paralysis of forelimb, 5: paralysis of both forelimbs or death) by observation everyday (excluding holiday) after the beginning of onset.

The percent inhibition of the clinical score of the test compound administration group relative to that of the control group was calculated using integration value of the clinical score for 28 days.

The results (percent inhibition of clinical score with oral administration of the test compound) measured by the above-mentioned method are shown in Table 12.

TABLE 12

| Ex. No. | Dose mg/kg | percent inhibition of clinical score* |
|---|---|---|
| 15 | 3 | 64% |

*versus the negative control group

The results above showed that oral administration of the example compounds inhibited the increase in ear thickness, acanthosis, and IL-17A gene expression in the mouse model of psoriasis.

Formulation Example 1

| (1) the compound of Example 1 | 10.0 g |
|---|---|
| (2) lactose | 70.0 g |
| (3) cornstarch | 50.0 g |
| (4) soluble starch | 7.0 g |
| (5) magnesium stearate | 3.0 g |

The compound of Example 1 (10.0 g) and magnesium stearate (3.0 g) are granulated in aqueous solution (70 mL) of soluble starch (7.0 g as soluble starch) and then dried, the resulting mixture is mixed with lactose (70.0 g) and cornstarch (50.0 g) (lactose, cornstarch, soluble starch and magnesium stearate are all products in compliance with Japanese Pharmacopoeia $14^{th}$ Edition). The mixture compressed to give tablets.

INDUSTRIAL APPLICABILITY

The compound of the present invention has a superior RORγt inhibitory action, and useful as an agent for the prophylaxis or treatment of psoriasis, inflammatory bowel disease (IBD), ulcerative colitis (UC), Crohn's disease (CD), rheumatoid arthritis, multiple sclerosis, uveitis, asthma, ankylopoietic spondylarthritis, systemic lupus erythematosus (SLE) and the like.

This application is based on patent application Nos. 2014-136359 and 2014-262775 filed in Japan, the contents of which are encompassed in full herein.

The invention claimed is:

1. ((1R,2S)-2-(((5R)-5-((7-Fluoro-1,1-dimethyl-2,3-dihydro-1H-inden-5-yl)carbamoyl)-2-methoxy-7,8-dihydro-1,6-naphthyridin-6(5H)-yl)carbonyl)cyclopropyl)acetic acid or a salt thereof.

2. A method of inhibiting RORγt in a mammal, which comprises administering an effective amount of the compound or salt of claim 1 to the mammal.

* * * * *